US011821036B2

(12) United States Patent
Yoffe et al.

(10) Patent No.: US 11,821,036 B2
(45) Date of Patent: Nov. 21, 2023

(54) METHODS FOR IDENTIFYING AND MONITORING PREGNANT WOMEN AT RISK OF PREECLAMPSIA

(71) Applicants: RAMOT AT TEL-AVIV UNIVERSITY LTD., Tel Aviv (IL); MOR RESEARCH APPLICATIONS LTD., Tel Aviv (IL)

(72) Inventors: Liron Yoffe, Tel Aviv (IL); Noam Shomron, Herzelia (IL); Moshe Hod, Herzelia (IL)

(73) Assignees: RAMOT AT TEL-AVIV UNIVERSITY LTD., Tel Aviv (IL); MOR RESEARCH APPLICATIONS LTD., Ramat Gan (IL)

( * ) Notice: Subject to any disclaimer, the term of this patent is extended or adjusted under 35 U.S.C. 154(b) by 81 days.

(21) Appl. No.: 16/493,874

(22) PCT Filed: Mar. 15, 2018

(86) PCT No.: PCT/IL2018/050301
§ 371 (c)(1),
(2) Date: Sep. 13, 2019

(87) PCT Pub. No.: WO2018/167790
PCT Pub. Date: Sep. 20, 2018

(65) Prior Publication Data

US 2021/0116444 A1 Apr. 22, 2021

Related U.S. Application Data

(60) Provisional application No. 62/471,976, filed on Mar. 16, 2017.

(51) Int. Cl.
*C12Q 1/6883* (2018.01)
*C12Q 1/6851* (2018.01)
*C12Q 1/6834* (2018.01)
*G01N 33/53* (2006.01)

(52) U.S. Cl.
CPC ......... *C12Q 1/6883* (2013.01); *C12Q 1/6834* (2013.01); *C12Q 1/6851* (2013.01); *G01N 33/5308* (2013.01); *C12Q 2600/178* (2013.01); *G01N 2496/00* (2013.01); *G01N 2800/368* (2013.01)

(58) Field of Classification Search
None
See application file for complete search history.

(56) References Cited

U.S. PATENT DOCUMENTS 8,580,503 B2 11/2013 Goren
9,334,540 B2 5/2016 Goren
2013/0245135 A1 9/2013 Winger
2014/0017227 A1* 1/2014 Chew .................... G16B 25/10 424/130.1
2015/0157666 A1* 6/2015 Katakowski .......... C12N 15/111 424/450
2019/0055605 A1* 2/2019 Choudhury ............ A44B 11/00

FOREIGN PATENT DOCUMENTS

CN 106480037 A * 3/2017 ......... A61K 31/7105
CN 106520771 A * 3/2017 ......... A61K 31/7105
CN 106754914 A * 5/2017 ......... A61K 31/7105
WO 2009093254 A2 7/2009
WO 2015128836 A1 9/2015
WO 2015165779 A2 11/2015

OTHER PUBLICATIONS

Tritten et al. Detection of Circulating Parasite-Derived MicroRNAs in Filarial Infections, 2014, PLOS Neglected Tropical Diseases, vol. 8, No. 7, e2971 (Year: 2014).*
Gunel et al. Expression profiling of maternal plasma and placenta microRNAs in preeclamptic pregnancies by microarray technology. Feb. 22, 2017, Placenta, vol. 52, pp. 77-85. (Year: 2017).*
Hromadnikova et al. First trimester screening of circulating C19MC microRNAs and the evaluation of their potential to predict the onset of preeclampsia and IUGR. Feb. 9, 2017, PLoS ONE, vol. 12, No. 2, e0171756. (Year: 2017).*
Sun and Manley (1995) A novel U2-U6 snRNA structure is necessary for mammalian mRNA splicing. Genes Dev. 9(7): 843-854.
Svecova et al., (2015) P40. MIR-21 and mir-221 overexpression in placental tissue of preeclamptic patients. Pregnancy Hypertension: An International Journal of Women's Cardiovascular Health 5(3): 245.
Swinkels et al., (2002) Hemolysis, elevated liver enzymes, and low platelet count (HELLP) syndrome as a complication of preeclampsia in pregnant women increases the amount of cell-free fetal and maternal DNA in maternal plasma and serum. Clin Chem 48(4): 650-653.
Tal (2012) The Role of Hypoxia and Hypoxia-Inducible Factor-1Alpha in Preeclampsia Pathogenesis. Biology of Reproduction 87(6): 134; 8 pages.
Ura et al., (2014) Potential role of circulating microRNAs as early markers of preeclampsia. Taiwan J Obstet Gynecol 53(2): 232-234.
Wang and Walsh (1998) Placental mitochondria as a source of oxidative stress in pre-eclampsia. Placenta. 19(8): 581-586.

(Continued)

*Primary Examiner* — Samuel C Woolwine
(74) *Attorney, Agent, or Firm* — BROWDY AND NEIMARK, PLLC

(57) ABSTRACT

Methods and kits for identifying an increased risk of developing preeclampsia in a pregnant woman based on expression pattern of non-coding RNAs in body fluids are provided. In particular, the methods provide information for identifying a pregnant woman as being at risk of developing preeclampsia by analyzing the pattern of non-coding RNAs in body fluids during early stages of pregnancy.

18 Claims, 6 Drawing Sheets

Specification includes a Sequence Listing.

(56) References Cited

OTHER PUBLICATIONS

Wang et al., (2012) Preeclampsia Up-Regulates Angiogenesis-Associated MicroRNA (i.e., miR-17, -20a, and -20b) That Target Ephrin-B2 and EPHB4 in Human Placenta. J Clin Endocrinol Metab 97(6): E1051-E1059.
Watanabe et al., (2011) Role for piRNAs and noncoding RNA in de novo DNA methylation of the imprinted mouse Rasgrf1 locus. Science. 332(6031): 848-852.
Widschwendter et al., (1998) Pre-eclampsia: a disorder of placental mitochondria? Mol Med Today. 4(7): 286-291.
Williams et al., (2013) Comprehensive profiling of circulating microRNA via small RNA sequencing of cDNA libraries reveals biomarker potential and limitations. Proc Natl Acad Sci U S A 110(11): 4255-4260.
Wu et al., (2012) Circulating microRNAs are elevated in plasma from severe preeclamptic pregnancies. Reproduction. 143(3): 389-397.
Xu et al., (2014) Variations of microRNAs in human placentas and plasma from preeclamptic pregnancy. Hypertension 63(6): 1276-1284.
Yang et al., (2011) Application of next-generation sequencing technology to profile the circulating microRNAs in the serum of preeclampsia versus normal pregnant women. Clin Chim Acta. 412(23-24): 2167-2173.
Yoffe et al., (2018) Early Detection of Preeclampsia Using Circulating Small non-coding RNA. Sci Rep 8(1): 3401; 11 pages.
Zhang et al., (2010) MicroRNA-155 contributes to preeclampsia by down-regulating CYR61. Am J Obstet Gynecol 202(5): 466.e1-466.e7.
Zhong et al., (2001) Elevation of both maternal and fetal extracellular circulating deoxyribonucleic acid concentrations in the plasma of pregnant women with preeclampsia. Am J Obstet Gynecol 184(3): 414-419.
Zhu et al., (2009) Differential expression profile of microRNAs in human placentas from preeclamptic pregnancies vs hormal pregnancies. Am J Obstet Gynecol 200(6): 661.e1-661.e7.
Hromadnikova et al., (2017) First trimester screening of circulating C19MC microRNAs and the evaluation of their potential to predict the onset of preeclampsia and IUGR. PLoS ONE 12(2): e0171756; 17 pages.
Yang et al., (2013) ChIPBase: a database for decoding the transcriptional regulation of long non-coding RNA and microRNA genes from ChIP-Seq data. Nucleic Acids Res 41(Database issue): D177-D187.
Alexander et al., (2010) Annotating non-coding regions of the genome. Nat Rev Genet. 11(8): 559-571.
Ashur-Fabian et al., (2012) Cell free expression of hif1α and p21 in maternal peripheral blood as a marker for preeclampsia and fetal growth restriction. PLOS One 7(5): e37273; 6 pages.
Calcagno and de Mazancourt (2010) glmulti: An R Package for Easy Automated Model Selection with (Generalized) Linear Models. Journal of Statistical Software 34(12): 29 pages.
Caniggia and Winter (2002) Adriana and Luisa Castellucci Award lecture 2001. Hypoxia inducible factor-1: oxygen regulation of trophoblast differentiation in normal and pre-eclamptic pregnancies—a review. Placenta 23 Suppl A: S47-S57.
Caniggia et al, (1999) Inhibition of TGF-β3 restores the invasive capability of extravillous trophoblasts in preeclamptic pregnancies. J Clin Invest 103(12): 1641-1650.
Caniggia et al., (2000) Hypoxia-inducible factor-1 mediates the biological effects of oxygen on human trophoblast differentiation through TGFβ3. J Clin Invest 105(5): 577-587.
Croce (2009) Causes and consequences of microRNA dysregulation in cancer. Nat Rev Genet. 10(10): 704-714.
Chen et al., (2013) Human Placental MicroRNAs and Preeclampsia. Biology of Reproduction 88(5): 130; 11 pages.
Crick (1968) The origin of the genetic code. J Mol Biol. 38(3): 367-379.
Enquobahrie et al., (2011) Placental microRNA expression in pregnancies complicated by preeclampsia. Am J Obstet Gynecol 204(2): 178.e12-178.e21.
Esquela-Kerscher and Slack (2006) Oncomirs—microRNAs with a role in cancer. Nat Rev Cancer. 6(4): 259-269.
Esteller (2011) Non-coding RNAs in human disease. Nat Rev Genet. 12(12): 861-874.
Flicek et al., (2014) Ensembl 2014. Nucleic Acids Res 42(Database issue): D749-D755.
Guay et al., (2011) Diabetes mellitus, a microRNA-related disease? Transl Res. 157(4): 253-264.
Hammond (2007) MicroRNAs as tumor suppressors. Nat Genet. 39(5): 582-583.
He and Hannon (2004) MicroRNAs: small RNAs with a big role in gene regulation. Nat Rev Genet. 5(7): 522-531.
Hu et al., (2009) Differential expression of microRNAs in the placentae of Chinese patients with severe pre-eclampsia. Clin Chem Lab Med 47(8): 923-929.
Hulsmans et al., (2012) Decrease of miR-146b-5p in monocytes during obesity is associated with loss of the anti-inflammatory but not insulin signaling action of adiponectin. PLOS One 7(2): e32794; 10 pages.
Jairajpuri and Almawi (2016) MicroRNA expression pattern in pre-eclampsia (Review). Mol Med Rep 13(3): 2351-2358.
Johnson et al., (2007) Adjusting batch effects in microarray expression data using empirical Bayes methods. Biostatistics 8(1): 118-127.
King et al., (2003) Ribosome structure and activity are altered in cells lacking snoRNPs that form pseudouridines in the peptidyl transferase center. Mol Cell. 11(2): 425-435.
Kinzler and Vintzileos (2008) Fetal growth restriction: a modern approach. Curr Opin Obstet Gynecol. 20(2): 125-131.
Kwek et al., (2002) U1 snRNA associates with TFIIH and regulates transcriptional initiation. Nat Struct Biol. 9(11): 800-805.
Lee et al., (2003) Neutrophil activation and production of reactive oxygen species in pre-eclampsia. J Hypertens 21(2): 395-402.
Leek et al., (2012) The sva package for removing batch effects and other unwanted variation in high-throughput experiments. Bioinformatics 28(6): 882-883.
Li and Durbin (2009) Fast and accurate short read alignment with Burrows-Wheeler transform. Bioinformatics 25(14): 1754-1760.
Li et al., (2013) Maternal Plasma miRNAs Expression in Preeclamptic Pregnancies. Biomed Res Int 2013: 970265; 9 pages.
Lo et al., (1999) Quantitative abnormalities of fetal DNA in maternal serum in preeclampsia. Clin Chem 45(2): 184-188.
Love et al., (2014) Moderated estimation of fold change and dispersion for RNA-seq data with DESeq2. Genome Biol 15(12): 550; 21 pages.
Luque et al., (2014) Usefulness of circulating microRNAs for the prediction of early preeclampsia at first-trimester of pregnancy. Sci Rep 4: 4882; 8 pages.
Matsubara et al., (2010) Role of nitric oxide and reactive oxygen species in the pathogenesis of preeclampsia. J Obstet Gynaecol Res 36(2): 239-247.
Maynard et al., (2003) Excess placental soluble fms-like tyrosine kinase 1 (sFlt1) may contribute to endothelial dysfunction, hypertension, and proteinuria in preeclampsia. J Clin Invest. 111(5): 649-658.
Mayor-Lynn et al., (2011) Expression profile of microRNAs and mRNAs in human placentas from pregnancies complicated by preeclampsia and preterm labor. Reprod Sci 18(1): 46-56.
Murphy et al., (2017) Maternal Circulating microRNAs and Pre-Eclampsia: Challenges for Diagnostic Potential. Mol Diagn Ther 21(1): 23-30.
Ng et al., (2003) The concentration of circulating corticotropin-releasing hormone mRNA in maternal plasma is increased in preeclampsia. Clin Chem 49(5): 727-731.
Ni et al., (1997) Small nucleolar RNAs direct site-specific synthesis of pseudouridine in ribosomal RNA. Cell. 89(4): 565-573.
Nicoloso et al., (2009) MicroRNAs—the micro steering wheel of tumour metastases. Nat Rev Cancer. 9(4): 293-302.

(56) References Cited

OTHER PUBLICATIONS

Padmini et al., (2009) Preeclamptic placental stress and over expression of mitochondrial HSP70. Clin Chem Lab Med. 47(9): 1073-1080.
Pallotto and Kilbride (2006) Perinatal outcome and later implications of intrauterine growth restriction. Clin Obstet Gynecol. 49(2): 257-269.
Pavon-Eternod et al., (2009) tRNA over-expression in breast cancer and functional consequences. Nucleic Acids Res. 37(21): 7268-7280.
Pineles et al., (2007) Distinct subsets of microRNAs are expressed differentially in the human placentas of patients with preeclampsia. Am J Obstet Gynecol 196(3): 261.e1-261.e6.
Poon et al., (2000) Presence of fetal RNA in maternal plasma. Clin Chem 46(11): 1832-1834.
Rajakumar et al., (2004) Evidence for the functional activity of hypoxia-inducible transcription factors overexpressed in preeclamptic placentae. Placenta 25(10): 763-769.
Roman et al., (2008) 237: Microrna expression in placenta of patients with preeclampsia. American Journal of Obstetrics and Gynecology 199 (6 Supplement A): S78.
Shen and Temple (2009) Fine control: microRNA regulation of adult neurogenesis. Nat Neurosci. 12(4): 369-370.
Shi et al., (2013) Comparative Proteomics Analysis Suggests that Placental Mitochondria are Involved in the Development of Pre-Eclampsia. PLOS One 8(5): e64351; 8 pages.
Shibata et al., (2003) Enhancement of mitochondrial oxidative stress and up-regulation of antioxidant protein peroxiredoxin III/SP-22 in the mitochondria of human pre-eclamptic placentae. Placenta. 24(6): 698-705.
Smets et al., (2006) Novel biomarkers in preeclampsia. Clin Chim Acta 364(1-2): 22-32.
Steegers et al., (2010) Pre-eclampsia. Lancet. 376(9741): 631-644.
Hromadnikova et al., First trimester screening of circulating C19MC microRNAs can predict subsequent onset of gestational hypertension. PLoS One, Dec. 15, 2014, 9(12): e113735; 18 pages.
Mattick, Non-coding RNAs: the architects of eukaryotic complexity. EMBO Rep., 2001, 2(11): 986-991.

* cited by examiner

METHODS FOR IDENTIFYING AND MONITORING PREGNANT WOMEN AT RISK OF PREECLAMPSIA

The Sequence Listing in ASCII text file format of 296,708 bytes in size, created on May 25, 2021, with the file name "2019-09-13seq_listing_YOFFE1," filed in the U.S. Patent and Trademark Office on Sep. 13, 2019, is hereby incorporated herein by reference.

FIELD OF THE INVENTION

The present invention relates to identifying and monitoring the risk of a pregnant woman to develop preeclampsia by analyzing circulating non-coding RNAs (ncRNAs).

BACKGROUND OF THE INVENTION

Preeclampsia is one of the most dangerous pregnancy complications and is the leading cause of maternal and perinatal morbidity and mortality. It typically occurs in the second or third trimester and is characterized by the development of concurrent hypertension and proteinuria, sometimes progressing into a multi-organ cluster of varying clinical features affecting the kidneys, liver, brain and heart of the pregnant woman. Preeclampsia can develop either gradually or suddenly, and may remain mild throughout the pregnancy or become severe. Common symptoms in addition to high blood pressure and proteinuria include elevated uric acid, vision problems such as blinking lights or blurry vision, persistent headaches, extreme swelling of hands and feet, fluid retention and pain in the upper right abdomen.

The cause of preeclampsia is unclear. Current theory of preeclampsia pathogenesis states that it begins with poor placentation in the first trimester of pregnancy, and evidence show that it involves inadequate blood supply to the placenta leading to an hypoxic environment. It has also been suggested that placental mitochondria are involved in the development of preeclampsia. Currently there is no test that can effectively predict or diagnose preeclampsia prior to its clinical presentation, and diagnosis is typically made only after increased blood pressure and protein in the urine are detected, for example in routine physician tests following the $20^{th}$ week of pregnancy.

Cell-free fetal (cff) DNA and RNA were previously identified in the maternal blood (Poon et al., 2000, *Clin. Chem.* 46:1832-1834). Additionally, in pregnancies complicated by preeclampsia, expression levels of cff DNA and cff RNA in maternal plasma were reported to be increased (Lo et al., 1999, *Clin. Chem.* 45:184-188; Ng et al., 2003, *Clin. Chem.* 49:727-731; Swinkels et al., 2002, *Clin. Chem.* 48:650-653; Zhong et al., *Am. J. Obstet. Gynecol.* 184:414-419). A few potential messenger RNA (mRNA) markers of preeclampsia were found in maternal plasma (Ng et al., 2003, ibid; Ashur-Fabian et al., 2012, *PLoS ONE* 7:e37273), though they were all identified at late stages of the pregnancy.

In addition to mRNA, small non-coding RNAs (ncRNAs) have been investigated. Small non-coding RNAs (ncRNAs) are a diverse family of untranslated RNA molecules (<200 nucleotides) that are part of the transcribed genomic output. Some of these molecules were reported to have a functional role in cells. Small ncRNAs include microRNAs (miRNA), which are about 22 nucleotides long RNA molecules that in animals regulate gene expression post-transcriptionally in a sequence-specific manner, by facilitating messenger RNA (mRNA) degradation or by controlling translation. Other small ncRNAs include: PIWI-interacting RNA (piRNA), about 28 nucleotides long RNA molecules involved in transposon repression and DNA methylation; small nucleolar RNA (snoRNA), about 60-300 nucleotides long, components of small nucleolar ribonucleoproteins, which modulate biogenesis and activity of ribosomes by post-transcriptional modifications of ribosomal RNA (rRNA); small nuclear RNA (snRNA), about 150 nucleotides long RNA molecules that facilitate mRNA splicing and regulate transcription factors; and transfer RNA (tRNA), typically 73-94 nucleotides long, which are the most abundant small ncRNA and play a role in translation.

Small ncRNAs, particularly miRNAs typically have tissue-specific expression patterns. Tissue-specific small ncRNAs are sometimes shed into the circulation where they may be detected using e.g., reverse transcription PCR—based techniques. Williams et al., 2013, *Proc Natl Acad Sci USA.* 110(11):4255-60 studied the presence of placenta-specific miRNAs in the blood.

The role of small ncRNAs in human diseases has been investigated mainly in the context of regulating gene expression via miRNAs, and has been well studied in several systems, especially in cancer, neurogenesis and diabetes. Recent studies have shown that dysregulation of other small ncRNAs, besides miRNAs, have functional relevance in cancer and other diseases as well.

In recent years, abundantly and differentially expressed miRNA species in placental samples from women with preeclampsia versus healthy women have been reported (Enquobahrie et al., 2011 *Am. J. Obstet. Gynecol.* 204:178.e12-178.e21; Hu et al., 2009, *Clin. Chem. Lab. Med.* 47:923-929; Pineles et al., 2007, *Am. J. Obstet. Gynecol.* 196:261.e1-261.e6; Roman et al., 2008, *Am. J. Obstet. Gynecol.* 199:S78; Zhu et al., 2009 *Am. J. Obstet. Gynecol.* 200:661.e1-661.e7; Mayor-Lynn et al., 2011, *Reprod. Sci. Thousand Oaks Calif* 18:46-56).

Smets et al., 2006, *Clin. Chim. Acta* 364:22-32 describe RNA biomarkers for pre-symptomatic detection of pregnancy-associated diseases with placental origin and/or dysfunction, identified by reviewing genes with placental expression in the Human SymAtlas and comparison with proven qualifiers.

U.S. Pat. Nos. 9,334,540 and 8,580,503 disclose methods and compositions for identifying subjects at risk of developing a complication of pregnancy, such as preeclampsia or preterm labor. The compositions are microRNAs and associated nucleic acids. Among others, microRNA 10b is disclosed as having an increased expression level in serum samples from pregnant women with severe preeclampsia (measured just before they were delivered by Caesarean section) compared to control women with no pregnancy complication.

Luque et al., 2014, *Sci Rep.* 4:4882 studied the usefulness of circulating miRNAs for the prediction of early preeclampsia at the first-trimester of pregnancy by collecting and analyzing pooled sera from early preeclampsia patients and uncomplicated pregnancies. However, statistical analysis of the identified miRNAs showed that none of them was differentially abundant in serum from preeclamptic pregnancies compared with serum from normal pregnancies. It was therefore concluded that maternal serum miRNA assessment at first-trimester of pregnancy does not appear to have any predictive value for early preeclampsia.

There still remains a need for efficient diagnostic methods and kits for detection of preeclampsia risk at early stages of pregnancy, and for monitoring pregnant women at risk of developing preeclampsia.

SUMMARY OF THE INVENTION

The present invention provides, according to some aspects, methods and kits for identification and monitoring of pregnant women at risk of developing preeclampsia by analyzing circulating non-coding RNAs (ncRNAs), mainly small ncRNAs. More particularly, the present invention is directed to a set of ncRNAs whose expression pattern in body fluids at early stages of the pregnancy is indicative of an increased risk to develop preeclampsia at later stages of the pregnancy.

The present invention is based in part on the surprising finding that plasma samples taken at a pre-symptomatic stage (e.g., at the end of the first trimester) from pregnant women that developed preeclampsia show altered levels of a set of ncRNAs compared to the levels of these ncRNAs in plasma samples of pregnant women that did not develop preeclampsia during their pregnancy. These ncRNAs were found to include a subset of molecules characterized by increased expression levels in samples from women that developed preeclampsia, and another subset of molecules characterized by decreased expression levels in samples from women that developed preeclampsia.

The methods and kits of the present invention are particularly advantageous as they provide minimally-invasive means for early detection of preeclampsia risk and, as a consequence, closer and better monitoring of women at risk. To date there has been no method of predicting a risk of developing preeclampsia at such an early stage of pregnancy when no symptoms of this type of complication are evinced. The methods and kits of the present invention are therefore useful for determining whether a pregnant woman is in need of monitoring for development of preeclampsia.

The methods and kits disclosed herein are further useful for aiding, or confirming, the diagnosis of preeclampsia in pregnant women suspected of having preeclampsia, for example, in pregnant women that show elevated blood pressure without further symptoms characteristics of preeclampsia.

According to one aspect, the present invention provides a method for determining whether a pregnant woman is at risk of developing preeclampsia, the method comprising:

(i) measuring the levels of a plurality of non-coding RNAs (ncRNAs) selected from ncRNAs corresponding to SEQ ID NOs: 1-25 in a body fluid sample from the pregnant woman to thereby obtain a ncRNA expression pattern of said pregnant woman;

(ii) comparing the ncRNA expression pattern of the pregnant woman to a non-preeclampsia reference pattern;

(iii) characterizing the pregnant woman as being at risk of developing preeclampsia wherein the ncRNA expression pattern of the pregnant woman is determined to be different from the non-preeclampsia reference pattern, by detecting at least one of: increased expression levels of one or more ncRNA corresponding to SEQ ID NOs: 1-2, 5, 7-10, 13, 16-17, 19-23 and 25 compared to non-preeclampsia reference values; and decreased expression levels of one or more ncRNA corresponding to SEQ ID NOs: 3-4, 6, 11-12, 14-15, 18 and 24 compared to the non-preeclampsia reference values.

In some embodiments, there is provided herein a method for determining whether a pregnant woman is at risk of developing preeclampsia, the method comprising:

(i) measuring the levels of a plurality of ncRNAs selected from ncRNAs corresponding to SEQ ID NOs: 1-25 in a body fluid sample from the pregnant woman to thereby obtain a ncRNA expression pattern of said pregnant woman;

(ii) providing preeclampsia and non-preeclampsia reference values of each of said plurality of ncRNAs corresponding to SEQ ID NOs: 1-25;

(iii) comparing the ncRNA expression pattern of the pregnant woman to the reference values to determine if said ncRNA expression pattern of the pregnant woman is a preeclampsia or a non-preeclampsia pattern; and (vi) characterizing the woman as being at risk of developing preeclampsia wherein the ncRNA expression pattern of the pregnant woman is a preeclampsia pattern, wherein said preeclampsia pattern is characterized by at least one of: increased expression levels of one or more ncRNA corresponding to SEQ ID NOs: 1-2, 5, 7-10, 13, 16-17, 19-23 and 25 compared to a non-preeclampsia pattern; and decreased expression levels of one or more ncRNA corresponding to SEQ ID NOs: 3-4, 6, 11-12, 14-15, 18 and 24 compared to the non-preeclampsia pattern.

In some embodiments, the pregnant woman is in the first trimester of the pregnancy. In some particular embodiments, the pregnant woman is in weeks 10 to 12 of the pregnancy. In some embodiments, the pregnant woman is in weeks 10 to 14 of the pregnancy.

In some embodiments, the body fluid sample is selected from the group consisting of peripheral blood, plasma and serum samples. Each possibility represents a separate embodiment of the present invention.

In some particular embodiments, the body fluid sample is a plasma sample.

In some embodiments, said measuring levels of a plurality of ncRNAs comprises extracting RNA from the body fluid sample, reverse transcribing said RNA into cDNA, and measuring the amount of said cDNA using quantitative-PCR.

In some embodiments, said measuring levels of a plurality of ncRNAs comprises applying a plurality of detectably labeled oligonucleotides, each capable of specifically hybridizing to one of said ncRNAs. In some embodiments, said detectably labeled oligonucleotides are immobilized to a solid surface.

In some embodiments, said plurality comprises at least five ncRNAs. In some embodiments, said plurality comprises at least ten ncRNAs. In additional embodiments, said plurality comprises at least fifteen ncRNAs. In yet additional embodiments, said plurality comprises at least twenty ncRNAs. In yet additional embodiments, said plurality comprises the set of ncRNAs corresponding to SEQ ID NOs: 1-25.

In some embodiments, characterizing the woman as being at risk of developing preeclampsia further comprises characterizing the woman as requiring monitoring for development of preeclampsia symptoms.

In some embodiments, said comparing is carried out using a computer software employing a pattern analyzing algorithm.

According to a further aspect, the present invention provides a kit for determining whether a pregnant woman is at risk of developing preeclampsia, the kit comprising:

(a) probes for measuring the levels of a plurality of ncRNAs selected from ncRNAs corresponding to SEQ ID NOs: 1-25 in a body fluid sample obtained from a pregnant woman in need for assessment of risk of preeclampsia;

(b) written material specifying non-preeclampsia reference values for each of said plurality of ncRNAs corresponding to in SEQ ID NOs: 1-25; and (c) manual instructions for characterizing the pregnant woman as being at an increased risk of developing preeclampsia wherein the ncRNA expression pattern of said pregnant woman is determined to be different from the non-preeclampsia reference values by detecting at least one of: increased expression levels of the or more ncRNA corresponding to SEQ ID NOs: 1-2, 5, 7-10, 13, 16-17, 19-23 and 25 compared to corresponding non-preeclampsia reference values; and decreased expression levels of one or more ncRNA corresponding to SEQ ID NOs: 3-4, 6, 11-12, 14-15, 18 and 24 compared to corresponding non-preeclampsia reference values.

In some embodiments, said written material is further specifying preeclampsia reference values for each of said plurality of ncRNAs corresponding to SEQ ID NOs: 1-25.

In some embodiments, at least one of said written material and instruction manual is in an electronic form.

In some embodiments, the kit further comprises a computer software for carrying out a comparison between the ncRNA expression pattern of the pregnant woman and the reference values.

In some embodiments, the computer software: (i) compares a ncRNA expression pattern of a pregnant woman in question to a non-preeclampsia reference pattern, preeclampsia reference pattern or both; and (ii) based on the comparison, outputs an indication whether the pregnant woman is at an increased risk of developing preeclampsia.

In some embodiments, the computer software outputs a score indicative of the risk of the pregnant woman to develop preeclampsia. In some embodiments, a score above a predefined threshold is indicative of an increased risk of developing preeclampsia requiring regular monitoring and frequent prenatal checkups.

In some embodiments, the computer software employs a pattern analyzing algorithm.

In some embodiments, said probes for measuring levels of a plurality of ncRNAs comprise oligonucleotide primer pairs for reverse transcribing RNA of said plurality of ncRNAs from the body fluid sample into cDNA, and measuring the amount of said cDNA using quantitative-PCR.

In some embodiments, said oligonucleotide primer pairs are detectably-labeled.

In some embodiments, the kit comprises detectably-labeled oligonucleotides for detecting amplification products in the quantitative-PCR.

In some embodiments, said probes for measuring levels of a plurality of ncRNAs comprise a plurality of detectably-labeled oligonucleotides that specifically hybridize to said ncRNAs.

In some embodiments, said detectably-labeled oligonucleotides are immobilized to a surface.

In some embodiments, the kit further comprises means for extracting RNA from the body fluid sample.

According to a further aspect, there is provided a method for identifying and treating a pregnant woman at risk of developing preeclampsia, the method comprising:

(i) measuring the levels of a plurality of non-coding RNAs (ncRNAs) selected from ncRNAs corresponding to SEQ ID NOs: 1-25 in a body fluid sample from the pregnant woman to thereby obtain a ncRNA expression pattern of said pregnant woman;

(ii) comparing the ncRNA expression pattern of the pregnant woman to a non-preeclampsia reference pattern;

(iii) characterizing the pregnant woman as being at risk of developing preeclampsia wherein the ncRNA expression pattern of the pregnant woman is determined to be different from the non-preeclampsia reference pattern by detecting at least one of: increased expression levels of one or more ncRNA corresponding to SEQ ID NOs: 1-2, 5, 7-10, 13, 16-17, 19-23 and 25 compared to non-preeclampsia reference values; and decreased expression levels of one or more ncRNA corresponding to SEQ ID NOs: 3-4, 6, 11-12, 14-15, 18 and 24 compared to the non-preeclampsia reference values; and iv) treating the pregnant woman characterized as being at risk of developing preeclampsia to decrease the pregnant woman's risk of developing preeclampsia.

These and further aspects and features of the present invention will become apparent from the detailed description, examples and claims which follow.

DETAILED DESCRIPTION OF THE INVENTION

Figure 1A:
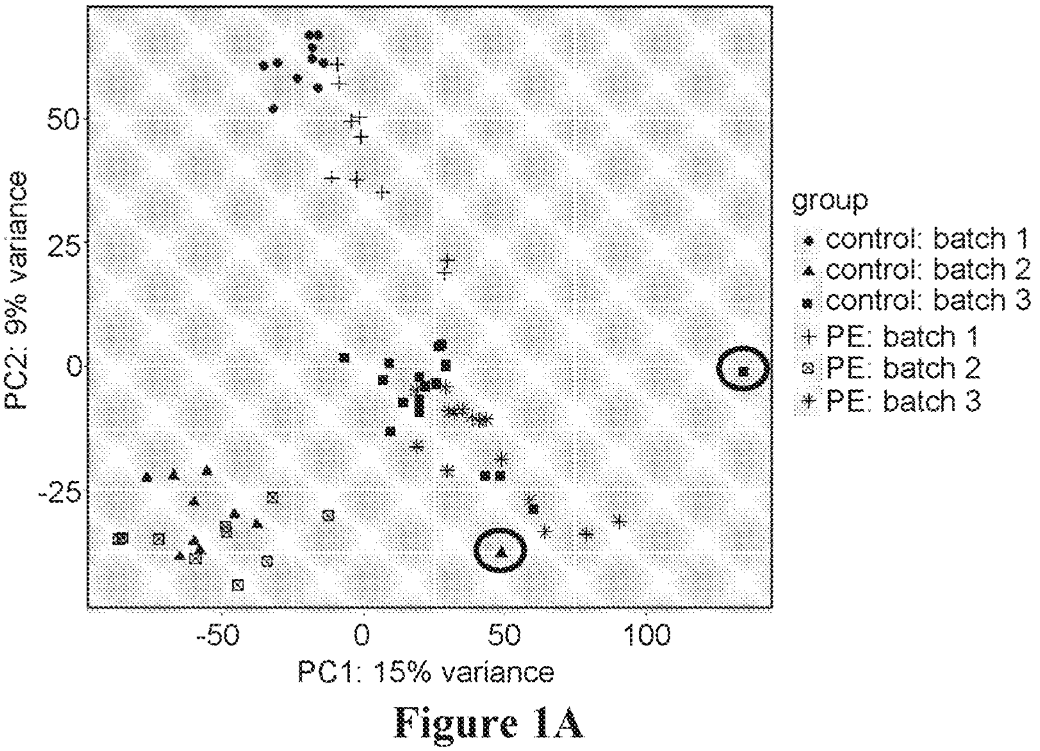
FIG. 1. Principal component analysis (PCA) plot. The samples are shown in the 2D plane spanned by their first two principal components. (A) Samples before batch effects removal and (B) after batch effects removal. Outlier samples are highlighted by a circle. "control"—samples from healthy women; "PE"—samples from women that developed preeclampsia.

The present invention provides, according to some aspects, methods and kits for identification and monitoring of pregnant women having an increased risk of developing preeclampsia.

The present invention proposes a unique marker of preeclampsia—an expression pattern of a set of ncRNAs that were found to be differentially expressed in first trimester body fluid samples of pregnant women that developed preeclampsia compared to similar samples of women that did not develop preeclampsia.

In certain embodiments of the present invention, preeclampsia is defined as hypertension (systolic blood pressure ≥140 mmHg or diastolic blood pressure ≥90 mmHg on at least two occasions, 6 hours apart), and proteinuria (>300 milligrams in a 24 hour urine collection or one dipstick measurement >2+).

In some embodiments, the woman to be tested by the methods and kits of the present invention is asymptomatic and the method/kit is applied for evaluating the risk of said woman to develop preeclampsia.

In other embodiments, the woman shows one or more signs characteristic of preeclampsia (e.g., increased blood pressure) and the method/kit is applied for confirming the diagnosis, or for aiding the diagnosis of preeclampsia in said woman.

The woman to be tested according to the present invention is at early stages of the pregnancy, up to week 15. In some embodiments, the woman to be tested is in the first trimester of the pregnancy, which is typically defined as week 1 through week 12. In some embodiments, the woman to be tested is in weeks 12-14. In additional embodiments, for example when the method is applied for confirming or aiding the diagnosis of a woman showing some symptoms of preeclampsia, the woman may be in a more advanced stage of the pregnancy.

As used herein, the term "increased", when referring to a risk of developing preeclampsia, refers to increased risk compared to the normal risk in the population.

According to some embodiments, the method of the present invention comprises the following steps: (i) measuring the levels of a plurality of ncRNAs (small ncRNAs according to some embodiments) selected from ncRNAs corresponding to SEQ ID NOs: 1-25 in a body fluid sample from said pregnant woman, thereby obtaining a ncRNA pattern of the pregnant woman; (ii) comparing the ncRNA pattern of the pregnant woman to a non-preeclampsia reference pattern; and (iii) characterizing the pregnant woman as being at an increased risk of developing preeclampsia wherein the ncRNA pattern of the pregnant woman is determined to be different from the non-preeclampsia reference pattern by detecting at least one of: increased levels of the one or more ncRNA set forth in SEQ ID NOs: 1-2, 5, 7-10, 13, 16-17, 19-23 and 25 compared to non-preeclampsia reference values; and decreased values of the one or more ncRNA corresponding to SEQ ID NOs: 3-4, 6, 11-12, 14-15, 18 and 24 compared to non-preeclampsia reference values.

In some embodiments, the method further comprises informing the pregnant woman characterized as being at risk of developing preeclampsia, or a health care professional involved in the prenatal care of said pregnant woman, that said pregnant woman must be monitored for development of symptoms of preeclampsia. A health care professional may include, for example, a gynecologist, a family doctor or a nurse.

In some embodiments, a method is provided for determining a ncRNA expression pattern in the plasma of a pregnant woman in the first trimester of the pregnancy, the method comprising:

(i) obtaining a plasma sample from the pregnant woman in the first trimester of the pregnancy;
(ii) measuring levels of a plurality of ncRNAs selected from ncRNAs corresponding to SEQ ID NOs: 1-25 in the plasma sample from said pregnant woman;
(iii) determining whether the level of the one or more ncRNA corresponding to SEQ ID NOs: 1-2, 5, 7-10, 13, 16-17, 19-23 and 25 is increased compared to corresponding non-preeclampsia reference values, and whether the level of the one or more ncRNA corresponding to SEQ ID NOs: 3-4, 6, 11-12, 14-15, 18 and 24 is decreased compared to corresponding non-preeclampsia reference values, thereby determining the ncRNA expression pattern in the plasma of the pregnant woman in the first trimester of the pregnancy.

In additional embodiments, a method is provided for identifying and treating a pregnant woman at risk of developing preeclampsia, the method comprising:

(i) measuring levels of a plurality of ncRNAs selected from ncRNAs corresponding to SEQ ID NOs: 1-25 in a body fluid sample from the pregnant woman to obtain a ncRNA expression pattern of said pregnant woman;
(ii) comparing the ncRNA expression pattern of the pregnant woman to a non-preeclampsia reference pattern;
(iii) characterizing the pregnant woman as being at risk of developing preeclampsia wherein the ncRNA expression pattern of the pregnant woman is determined to be different from the non-preeclampsia reference pattern by detecting at least one of: increased expression levels of the one or more ncRNA corresponding to SEQ ID NOs: 1-2, 5, 7-10, 13, 16-17, 19-23 and 25 compared to non-preeclampsia reference values; and decreased expression levels of the one or more ncRNA corresponding to SEQ ID NOs: 3-4, 6, 11-12, 14-15, 18 and 24 compared to the non-preeclampsia reference values; and
iv) treating the pregnant woman to decrease the pregnant woman's risk of developing preeclampsia.

Treatment to reduce the risk of developing preeclampsia, or to reduce the severity of preeclampsia, may include rest, close monitoring and diet changes. Close monitoring may include blood tests, urine tests and monitoring of blood pressure more frequently than what is typically recommended for pregnancy.

In some embodiments, a kit is provided for determining whether a pregnant woman is at risk of developing preeclampsia, the kit comprising:

(a) probes for measuring levels of a plurality of ncRNAs selected from ncRNAs corresponding to SEQ ID NOs: 1-25 in a body fluid sample obtained from a pregnant woman in need for assessment of risk of preeclampsia;
(b) written material specifying non-preeclampsia reference values for each of said plurality of ncRNAs corresponding to SEQ ID NOs: 1-25; and
(c) instruction manual for characterizing the pregnant woman as being at risk of developing preeclampsia wherein the ncRNAs expression pattern of the pregnant woman is determined to be different from the non-preeclampsia reference values by detecting at least one of: increased expression levels of the one or more ncRNA corresponding to SEQ ID NOs: 1-2, 5, 7-10, 13, 16-17, 19-23 and 25 compared to corresponding non-preeclampsia reference values; and decreased expression levels of the one or more ncRNA corresponding to SEQ ID NOs: 3-4, 6, 11-12, 14-15, 18 and 24 compared to corresponding non-preeclampsia reference values.

In some embodiments, the kit further including, in at least one of said written material and instruction manual, a recommendation for a pregnant woman found to be at risk of developing preeclampsia to be monitored for symptoms of preeclampsia.

As used herein, a "plurality" indicates at least two. In some embodiments, a plurality refers to at least three ncRNAs, for example at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four or twenty-five ncRNAs. Each possibility represents a separate embodiment of the present invention.

As referred to herein, the terms "polynucleotide molecules", "oligonucleotide", "polynucleotide", "nucleic acid" and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded (ss), double stranded (ds), triple stranded (ts), or hybrids thereof. The term also encompasses RNA/DNA hybrids. The polynucleotides may be, for example, sense and antisense oligonucleotide or polynucleotide sequences of DNA or RNA. The DNA or RNA molecules may be, for example, but are not limited to: complementary DNA (cDNA), genomic DNA, synthesized DNA, recombinant DNA, or a hybrid thereof or an RNA molecule such as miRNA. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions.

The terms "non-coding RNA" (typically abbreviated "ncRNA") refers to untranslated RNA molecules that are part of the transcribed genomic output. Some of these molecules were reported to have functional roles in cells, for example, in regulation of gene expression. Non-coding RNAs include long non-coding RNA molecules (typically more than 200 nucleotides in length), such as long intergenic non-coding RNAs (lincRNAs), and small non-coding RNA molecules. Small ncRNAs include microRNAs (miRNA), which are about 22 nucleotides long RNA molecules that in animals regulate gene expression post-transcriptionally in a sequence-specific manner by facilitating messenger RNA (mRNA) degradation or by controlling translation. Other small ncRNAs include: PIWI-interacting RNA (piRNA), which are about 28 nucleotides long RNA molecules involved in transposon repression and DNA methylation; small nucleolar RNA (snoRNA), which are about 60-300 nucleotides long, components of small nucleolar ribonucleoproteins that modulate biogenesis and activity of ribosomes by post-transcriptional modifications of ribosomal RNA (rRNA); small nuclear RNA (snRNA), which are about 150 nucleotides long RNA molecules that facilitate mRNA splicing and regulate transcription factors; and transfer RNA (tRNA), typically 73-94 nucleotides long, which are the most abundant small ncRNA and play a role in translation.

The term "complementary DNA", abbreviated "cDNA", refers to a DNA sequence complementary to a mature RNA molecule, and is therefore a copy of the intron-free biologically active RNA. The term also encompasses a DNA molecule produced by reverse transcription of an RNA molecule.

The present invention is based on determining the level of at least two non-coding RNA molecules selected from ncRNAs corresponding to SEQ ID NOs: 1-25. SEQ ID NOs: 1-25 are cDNA sequences of the transcripts listed in Table 1 (see the Examples section below). It is understood that in a body fluid sample that is analyzed according to the methods of the present invention the polynucleotide molecules are RNA molecules, in which the sequences are identical to the cDNA sequences except for T nucleotides being replaced with U nucleotides. The term "ncRNA corresponding to" therefore encompasses both the RNA molecules themselves, which can be detected by known methods such as array-based methods, and cDNA generated based on the ncRNA molecules having sequences as set forth in SEQ ID NOs: 1-25. The latter can be detected, for example, using array-based methods as well as quantitative PCR methods.

The ncRNAs analyzed according to the methods of the present invention originate from a body fluid sample. According to some embodiments, the body fluid sample is selected from the group consisting of: whole blood, plasma and serum. Each possibility represents a separate embodiment of the present invention. Thus, according to some embodiments, the ncRNA molecules analyzed according to the methods of the present invention are "circulating" ncRNA molecules, namely, present in circulating blood (in the plasma/serum fractions)

The body fluid sample may be obtained or collected from a subject by conventional methods. The body fluid sample may be treated prior to being subjected to the methods of the present invention. For example, according to some embodiments, the sample is treated to remove cells and cell debris. For removing cells or debris of cells from a bodily fluid sample, the cells or debris of cells may be precipitated by centrifugation and the supernatant is taken for determining the levels of the ncRNAs as disclosed herein. Alternatively, cells can be removed by filtration.

According to embodiments of the present invention, the body fluid samples are collected from women at the first trimester of the pregnancy, typically between weeks 10-15, for example between weeks 10-14, or 10-13.

Measuring Levels of ncRNAs:

As used herein, determination of a "level" of a particular small ncRNA or long ncRNA may refer to determining concentration, expressed, for example, as nanograms/milliliter (ng/ml). In some embodiments, determination of a "level" refers to determining intensity of a signal collected from a probe that represents the amount or concentration of the ncRNA in the sample. In additional embodiments, determination of a "level" refers to calculating an index that represents the amount or concentration of the ncRNA in the sample (for example, determining a Ct value of a real-time PCR reaction). Measuring the levels of the RNA molecules described herein can be performed by any method known in the art. Non-limiting examples include reverse-transcription and quantitative amplification, microarray, NGS (deep sequencing) and Northern blot. Each possibility represents a separate embodiment of the present invention. In some embodiments, measuring a level of a certain ncRNA refers to measuring a level of a fragment thereof, for example a fragment of between 100-200 bps, such as between 140-160 bps. Primers, probes or other molecules may be designed for the detection and measurement of a single fragment or a plurality of fragments of a certain ncRNA, or tiled across the ncRNA such that all of the ncRNA can be detected and measured.

As used herein, "comparing", when referring to expression levels of a tested sample versus reference pattern/values includes comparison of values such as concentrations, or Ct values or other indices indicating expression levels. For example, in some embodiments, a pattern of Ct values is generated for a tested sample and compared to a reference pattern of Ct values. As another example, a reference pattern of fluorescence units is generated for a tested sample and compared to a reference pattern of fluorescence units.

Typically, the method initially includes extracting total RNA from the body fluid sample.

In some embodiments, the method includes reverse-transcribing the RNA into cDNA, either specifically (e.g., using primers specific to each ncRNA to be measured) or non-specifically (e.g., using poly-A tailing and universal oligo-d(T) primer). Each possibility represents a separate embodiment of the present invention.

In some embodiments, the method further includes quantitatively-amplifying from the cDNA each of the plurality of ncRNA (i.e., DNA sequences corresponding to those of the RNA).

In some embodiment, the quantitative amplification is carried out using labeled primers, e.g., fluorescently labeled primer, to enable detection and quantification of the amplification product, and accordingly the level of the ncRNA in the body fluid sample.

In additional embodiments, detection and quantification of the amplification product is carried out by adding fluorescently labeled oligonucleotide probes to the amplification reaction.

In some embodiment, the method includes fluorescently-labeling the ncRNAs following extraction from the body fluid sample, or the corresponding cDNA, and hybridizing the fluorescently-labeled molecules to an array comprising a plurality of oligonucleotide probes. In some embodiments, the method further includes scanning the array to detect binding of the oligonucleotide probes, and accordingly determining the level of the ncRNA in the original sample. In some embodiments, the method includes comparing the test sample hybridization profile to a reference hybridization profile representing preeclampsia and/or to a reference hybridization profile representing non-preeclampsia. In some embodiments, the method further comprises reverse-transcribing and amplifying the target ncRNAs prior to hybridization with the microarray.

In some embodiments, the method includes separating the ncRNAs following extraction from the body fluid sample, or their corresponding DNA amplification products by gel electrophoresis, transferring to a membrane, probing with oligonucleotide probes capable of specific hybridization to each ncRNA and detecting and quantifying the hybridization to determine the level of the ncRNAs in the original body fluid sample.

As used herein, a "primer" defines an oligonucleotide which is capable of annealing to (hybridizing with) a target sequence, thereby creating a double stranded region which can serve as an initiation point for DNA synthesis under suitable conditions. The terminology "primer pair" refers to a pair of oligonucleotides which are used together in amplifying a selected nucleic acid sequence by PCR. As commonly known in the art, the primers may be designed to bind to a complementary sequence under selected conditions.

In some embodiments, the methods disclosed herein involve simultaneous amplification of more than one target sequence (e.g., more than one ncRNA) in the same reaction mixture, a process known as multiplex amplification or co-amplification. This process requires simultaneous use of a plurality of primer pairs. As known in the art, the primers may be designed such that they can work at the same annealing temperature during amplification. In some embodiments, primers with similar melting temperature (Tm) are used in the method disclosed herein. A Tm variation of between about 3°-5° C. is considered acceptable for primers used in a pool.

In other embodiments, each ncRNA is amplified in a separate reaction mixture.

In some embodiments, the methods of the present invention employ quantitative amplification to measure the levels of ncRNAs. Quantitative amplification typically involves the use of fluorescent probes for detection of the amplification product. The fluorescent signal emitted from the probe correlates with the amount of the amplification product, i.e., the signal increases as the amplification product accumulates.

"Probes" according to the present invention encompass probes for detection of amplification products in quantitative amplification such as real-time PCR, as well as probes for detection of polynucleotide sequences of interest in an array-based assay. In the context of quantitative amplification, "probes" encompass fluorophores such as SYBR® Green, which generally bind the amplification product in a sequence-independent manner, as well as oligonucleotide probes. In the context of array-based quantification of ncRNAs of interest, "probes" typically refers to oligonucleotide probes. As used herein, the term "oligonucleotide probes" refers to oligonucleotides which are complementary to specific sub-sequences within a nucleic acid sequence of interest, for example, within the sequence of a ncRNA or a corresponding cDNA, and which facilitate the detection and quantification of the nucleic acid of interest. In some embodiments, the oligonucleotide probes are detectably-labeled. The oligonucleotide probes typically selectively hybridize to their target sequences.

As used herein, "selectively hybridize to" (as well as "selective hybridization," "specifically hybridize to," and "specific hybridization") refers to the binding, duplexing, or hybridizing of a nucleic acid molecule (such as a primer or a probe) preferentially to a particular complementary nucleotide sequence under stringent conditions. The term "stringent conditions" refers to conditions under which a nucleic acid molecule will hybridize preferentially to its target sequence and to a lesser extent to, or not at all to, other non-target sequences. A "stringent hybridization" in the context of nucleic acid hybridization is sequence-dependent, and differs under different conditions, as known in the art.

Polynucleotide probes may vary in length. In some embodiments, the polynucleotide probes may include between 15-30 bases. In additional embodiments, the polynucleotide probes may include between 25-30 bases. In some embodiments, the polynucleotide probes may include between 20-30 bases.

For quantitative PCR amplification, polynucleotide probes may be designed to bind to either strand of the template. Additional considerations include the Tm of the polynucleotide probes, which should preferably be compatible to that of the primers. Computer software may be used for designing the primers and probes.

The methods of the present invention comprise according to some embodiments measuring levels of at least two non-coding RNAs selected from ncRNAs corresponding to SEQ ID NOs: 1-25 in a body fluid sample from a pregnant woman in the first trimester of the pregnancy.

In some embodiments, the methods of the present invention comprise measuring the level of the ncRNA corresponding to SEQ ID NO: 1 and at least one more ncRNA corresponding to SEQ ID NOs: 2-25.

In some embodiments, the methods of the present invention comprise measuring the level of the ncRNA corresponding to SEQ ID NO: 2 and at least one more ncRNA corresponding to SEQ ID NOs: 1, 3-25.

In some embodiments, the methods of the present invention comprise measuring the level of the ncRNA corresponding to SEQ ID NO: 3 and at least one more ncRNA corresponding to SEQ ID NOs: 1-2, 4-25.

In some embodiments, the methods of the present invention comprise measuring the level of the ncRNA corresponding to SEQ ID NO: 4 and at least one more ncRNA corresponding to SEQ ID NOs: 1-3, 5-25.

In some embodiments, the methods of the present invention comprise measuring the level of the ncRNA corresponding to SEQ ID NO: 5 and at least one more ncRNA corresponding to SEQ ID NOs: 1-4, 6-25.

In some embodiments, the methods of the present invention comprise measuring the level of the ncRNA corresponding to SEQ ID NO: 6 and at least one more ncRNA corresponding to SEQ ID NOs: 1-5, 7-25.

In some embodiments, the methods of the present invention comprise measuring the level of the ncRNA corresponding to SEQ ID NO: 7 and at least one more ncRNA corresponding to SEQ ID NOs: 1-6, 8-25.

In some embodiments, the methods of the present invention comprise measuring the level of the ncRNA corresponding to SEQ ID NO: 8 and at least one more ncRNA corresponding to SEQ ID NOs: 1-7, 9-25.

In some embodiments, the methods of the present invention comprise measuring the level of the ncRNA corresponding to SEQ ID NO: 9 and at least one more ncRNA corresponding to SEQ ID NOs: 1-8, 10-25.

In some embodiments, the methods of the present invention comprise measuring the level of the ncRNA corresponding to SEQ ID NO: 10 and at least one more ncRNA corresponding to SEQ ID NOs: 1-9, 11-25.

In some embodiments, the methods of the present invention comprise measuring the level of the ncRNA corresponding to SEQ ID NO: 11 and at least one more ncRNA corresponding to SEQ ID NOs: 1-10, 12-25.

In some embodiments, the methods of the present invention comprise measuring the level of the ncRNA corresponding to SEQ ID NO: 12 and at least one more ncRNA corresponding to SEQ ID NOs: 1-11, 13-25.

In some embodiments, the methods of the present invention comprise measuring the level of the ncRNA corresponding to SEQ ID NO: 13 and at least one more ncRNA corresponding to SEQ ID NOs: 1-12, 14-25.

In some embodiments, the methods of the present invention comprise measuring the level of the ncRNA corresponding to SEQ ID NO: 14 and at least one more ncRNA corresponding to SEQ ID NOs: 1-13, 15-25.

In some embodiments, the methods of the present invention comprise measuring the level of the ncRNA corresponding to SEQ ID NO: 15 and at least one more ncRNA corresponding to SEQ ID NOs: 1-14, 16-25.

In some embodiments, the methods of the present invention comprise measuring the level of the ncRNA corresponding to SEQ ID NO: 16 and at least one more ncRNA corresponding to SEQ ID NOs: 1-15, 17-25.

In some embodiments, the methods of the present invention comprise measuring the level of the ncRNA corresponding to SEQ ID NO: 17 and at least one more ncRNA corresponding to SEQ ID NOs: 1-16, 18-25.

In some embodiments, the methods of the present invention comprise measuring the level of the ncRNA corresponding to SEQ ID NO: 18 and at least one more ncRNA corresponding to SEQ ID NOs: 1-17, 19-25.

In some embodiments, the methods of the present invention comprise measuring the level of the ncRNA corresponding to SEQ ID NO: 19 and at least one more ncRNA corresponding to SEQ ID NOs: 1-18, 20-25.

In some embodiments, the methods of the present invention comprise measuring the level of the ncRNA corresponding to SEQ ID NO: 20 and at least one more ncRNA corresponding to SEQ ID NOs: 1-19, 21-25.

In some embodiments, the methods of the present invention comprise measuring the level of the ncRNA corresponding to SEQ ID NO: 21 and at least one more ncRNA corresponding to SEQ ID NOs: 1-20, 22-25.

In some embodiments, the methods of the present invention comprise measuring the level of the ncRNA corresponding to SEQ ID NO: 22 and at least one more ncRNA corresponding to SEQ ID NOs: 1-21, 23-25.

In some embodiments, the methods of the present invention comprise measuring the level of the ncRNA corresponding to SEQ ID NO: 23 and at least one more ncRNA corresponding to SEQ ID NOs: 1-22, 24-25.

In some embodiments, the methods of the present invention comprise measuring the level of the ncRNA corresponding to SEQ ID NO: 24 and at least one more ncRNA corresponding to SEQ ID NOs: 1-23, 25.

In some embodiments, the methods of the present invention comprise measuring the level of the ncRNA corresponding to SEQ ID NO: 25 and at least one more ncRNA corresponding to SEQ ID NOs: 1-24.

In some embodiments, the methods of the present invention comprise measuring the level of a plurality of ncRNAs corresponding to SEQ ID NO: 11 (microRNA 99b), SEQ ID NO: 14 (microRNA 151a), SEQ ID NO: 15 (microRNA 191), SEQ ID NO: 18 (microRNA 146b) and SEQ ID NO: 19 (microRNA 221), and optionally measuring the levels of at least one more ncRNA selected from ncRNAs corresponding to SEQ ID NOs: 1-10, 12-13, 16-17, 20-25.

In some embodiments, the methods of the present invention comprise measuring the level of at least three, at least four or the five ncRNAs corresponding to SEQ ID NO: 11, SEQ ID NO: 14, SEQ ID NO: 15, SEQ ID NO: 18 and SEQ ID NO: 19, and optionally measuring the levels of at least one more ncRNA selected from ncRNAs corresponding to SEQ ID Nos: 1-10, 12-13, 16-17, 20-25.

Non-coding RNAs having a sequence identity of at least 80-90% with the ncRNAs corresponding to SEQ ID Nos; 1-25 are also encompassed by the methods of the present invention.

Reference Values/Patterns

Preeclampsia and non-preeclampsia reference values are typically compiled from data obtained from a plurality of pregnant women. To generate the reference values, samples (e.g. plasma samples) are preferably taken from a large set of women during the first trimester of their pregnancy or up to week 14-15. Each woman is followed-up until the end of the pregnancy for preeclampsia development. Samples originating from women who did not develop preeclampsia during their pregnancy are classified as "non-preeclampsia" and the levels measured for the set of ncRNAs disclosed herein are stored as non-preeclampsia values. Samples originating from women that developed preeclampsia are classified as “preeclampsia” and the levels measured for the set of ncRNAs disclosed herein are stored as preeclampsia values.

The data from the large set of women is analyzed to generate reference values (reference pattern) for preeclampsia, non-preeclampsia or both. Reference values may be represented in a number of ways. For example, reference values may be statistic values, such as mean values determined in each group. As another example, reference values may be threshold, or cutoff, values, differentiating between preeclampsia and non-preeclampsia.

Thus, in some embodiments, preeclampsia reference pattern and/or preeclampsia reference values are determined from expression levels of the different ncRNAs in a subset of body fluid samples of pregnant women who developed preeclampsia out of a set of plasma samples of pregnant women collected at the first trimester of the pregnancy.

When comparing an expression pattern of a tested sample to a reference pattern, for example to a preeclampsia pattern, each of the ncRNAs that are increased in preeclampsia may be indeed detected at elevated levels, but in some embodiments only a portion of the ncRNAs that are increased in preeclampsia is elevated in the tested sample. A pattern analyzing algorithm is typically used in order to determine whether an expression pattern of a tested sample as a whole correlates, or is different from, a reference pattern.

In some embodiment, comparing comprises determining for each ncRNA if its expression level is above or below a predetermined cutoff that differentiates preeclampsia from non-preeclampsia. In some embodiments, detecting an expression level of a ncRNA above a preeclampsia cutoff identifies this ncRNA as representing preeclampsia or risk of preeclampsia. In some embodiments, comparing comprises allocating a score for each ncRNA identified as representing preeclampsia or risk of preeclampsia. In some embodiments, comparing comprises calculating a total score for each sample based on the number of ncRNAs identified as representing preeclampsia, and characterizing the woman as having preeclampsia wherein said total score is above a predefined threshold.

Example of a score-based classification method can be carried out as follows: (i) For each marker, find the best split point to minimize the number of misclassified subjects. The split point defines two intervals: one for normal pregnancy and another for pregnancy destined to be complicated by preeclampsia. A score of 0 is assigned to a subject if its related observation falls in the normal interval; otherwise, a score of 1 is assigned. (ii) Overall, a subject is assigned a score as the sum of these assigned scores from m different markers. Therefore, the range of such score is between 0 and m. (iii) A given threshold (t) is used to predict the disease status for a given subject, e.g., a given woman with a total score equal or less than t is predicted to have normal status (e.g., pregnancy not destined to be complicated by preeclampsia), whereas a woman with a score higher than t will be diagnosed to have disease or likely to develop a disease (e.g., pregnancy destined to be complicated by preeclampsia).

Typically, determining that an expression level is “different” from that of a reference level, for example increased or decreased compared to a reference level, indicates a statistically significant difference, for example a statistically significant increase or a statistically significant decrease compared to the reference level. As used herein, the term “statistically significant difference”, or simply “significant difference”, is well within the knowledge of a skilled artisan and can be determined empirically with reference to each particular biomarker or panel of biomarkers. For example, a significant difference in the body fluid level of a biomarker in a woman at risk of developing preeclampsia as compared to one not at risk of developing preeclampsia is any difference that is statistically significant (for example, level=$p<0.05$).

Advantageously, the methods of the invention may employ the use of learning and pattern recognition analyzers, clustering algorithms and the like, in order to discriminate between expression patterns of samples obtained from pregnant woman that developed preeclampsia to control samples.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Example 1—Detecting Differentially Expressed ncRNAs Between Preeclampsia and Control Samples Methods:

Non-coding RNA extraction and sequencing. Total RNA was extracted from plasma samples via miRNeasy™ Serum/Plasma Kit, and quantified using a NanoDrop spectrophotometer (ND-1000). The spectrophotometric absorbance parameters of the samples were: 260/280 nm~1.8 and 260/230 nm~1.8. Small RNA libraries were prepared for deep sequencing using Illumina's TruSeq® small RNA sample preparation kit. During this process, RNA molecules from each sample were ligated with 3' and 5' adapters, reverse-transcribed and then amplified using a PCR. Libraries of cDNA were prepared from 140-160 bp PCR products (representing 20-50 nt RNA molecules) and sequenced in separate lanes on an Illumina HiSeq® 2500 instrument. The plasma samples were processed in three batches (i.e., RNA extraction, library preparation and sequencing).

Sequence reads profiling and differential expression analysis. Sequence reads were analyzed as follows:

1. Fastq-mcf tool was used for adapter sequences clipping, low quality (i.e., quality 30) bases trimming and filtering out short reads (i.e., reads with less than 16 nt).
2. Reads were mapped against Ensembl database for human ncRNAs (Flicek et al., 2014, *Nucleic Acids Res.* 42:D749-D755) using Burrows—Wheeler transform based alignment tool (BWA) (Li and Durbin, 2009, *Bioinformatics* 25:1754-1760).
3. Read counts were summarized in a counts matrix that contained the number of reads mapped to each transcript in each sample. Only uniquely mapped reads with no mismatches were considered.
4. Data normalization was performed using DESeq2 package in R to the effective library size (Love et al., 2014, *Genome Biol.* 15(12):550). Each column was divided by the geometric means of the rows. The median of these ratios (skipping the genes with a geometric mean of zero) was used as the size factor for this column. Each column of the count table was divided by the size factor for this column. This normalization brings all samples to a common scale and allows the comparison between samples.

5. Principal component analysis (PCA) and samples clustering were performed in R using prcomp and heatmap2 methods respectively to discover batch effects and outlier samples.
6. Differential expression analysis: DESeq2 (in R) was applied to obtain a list of differentially expressed transcripts between control and preeclampsia samples. Only transcripts with p-value<=0.05 after false discovery rate (FDR) adjustment were considered.

Results:

RNA was extracted and non-coding RNAs (mainly small ncRNAs but also degradation products of long ncRNAs) were sequenced from plasma samples taken from 75 pregnant women at the end of the first trimester: 35 women that developed preeclampsia (these women showed no signs of preeclampsia at the time of collecting the sample but developed preeclampsia afterwards) and 40 healthy women that did not develop preeclampsia during their pregnancy (a control set).

Figure 1B:
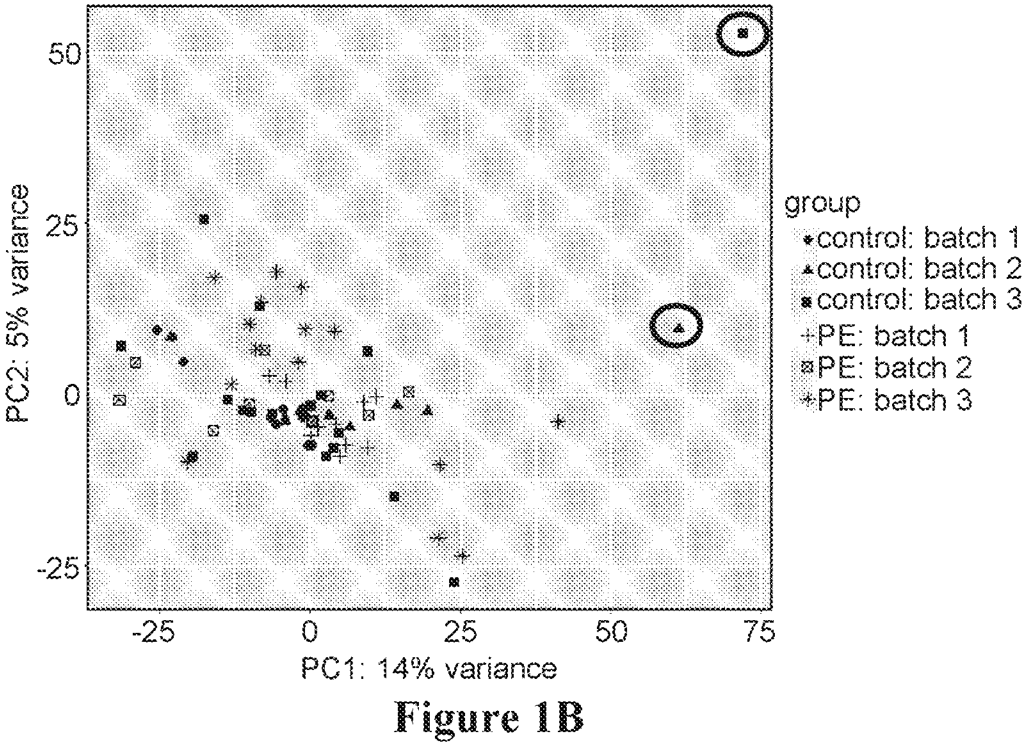

Sequence reads were analyzed to obtain a counts matrix. In the matrix, a cell in the $i^{th}$ row and the $j^{th}$ column holds the number of reads mapped uniquely to gene i in sample j. As noted above, the samples were processed in three batches (i.e., RNA extraction, library preparation and sequencing), which inserted technical noise to the results. To examine the batch effect, principal component analysis (PCA) was performed. FIG. 1A shows the PCA plot displaying a clear batch effect that is captured in the first principal component. To remove this unwanted effect, ComBat method from sva package in R was used, which adjusts for known batches using an empirical Bayesian framework (Leek et al, 2012, *Bioinformatics* 28:882-883; and Johnson et al., 2007, *Biostat. Oxf. Engl.* 8:118-127). FIG. 1B shows the PCA plot after batch effect removal. The PCA plot also indicates the existence of two outlier samples (marked with a circle), which were removed from downstream analysis.

Next, each transcript from the 100 most highly abundant transcripts was tested for differential expression in the preeclampsia/control group via DESeq2 package in R (Love et al., *ibid*). Twenty-five (25) transcripts were found to be differentially expressed between preeclampsia and control samples after correction for multiple testing (adjusted p-value<0.05, see Table 1): 16 transcripts were found to be up-regulated and 9 were down-regulated in preeclampsia compared to control. Of these, 7 transcripts were transfer RNAs (tRNAs) and ribosomal RNAs (rRNAs) encoded in the mitochondria, 12 transcripts were microRNAs, 4 transcripts were long non-coding RNAs (linc), one transcript was ribosomal RNA and one transcript was processed transcript (i.e., a non-coding transcript that does not belong to any of the categories in Ensembl database).

TABLE 1

Differentially expressed ncRNAs in preeclampsia vs. control samples

| Transcript ID[a] | Description | *Base mean count | **Fold change | P-value | Adjusted P-value |
|---|---|---|---|---|---|
| ENST00000387461 (SEQ ID NO: 1) | mitochondrially encoded tRNA proline | 489.86 | 4.25 | 1.65E−16 | 1.57E−14 |
| ENST00000387421 (SEQ ID NO: 2) | mitochondrially encoded tRNA lysine | 433.25 | 2.27 | 3.43E−06 | 1.63E−04 |
| ENST00000385255 (SEQ ID NO: 3) | microRNA 182 | 1325.43 | 0.54 | 5.45E−06 | 1.73E−04 |
| ENST00000385011 (SEQ ID NO: 4) | microRNA 10b | 7115.29 | 0.50 | 8.96E−06 | 2.13E−04 |
| ENST00000361558 (SEQ ID NO: 5) | mucin 2, oligomeric mucus/gel-forming (processed transcript) | 900.99 | 2.34 | 1.68E−05 | 3.19E−04 |
| ENST00000384816 (SEQ ID NO: 6) | microRNA 25 | 5584.66 | 0.61 | 5.38E−05 | 6.39E−04 |
| ENST00000514519 (SEQ ID NO: 7) | RP11-259O2.3-001 (lincRNA) | 408.71 | 2.97 | 4.92E−05 | 6.39E−04 |
| ENST00000581329 (SEQ ID NO: 8) | microRNA 4433b | 473.02 | 1.71 | 4.98E−05 | 6.39E−04 |
| ENST00000387441 (SEQ ID NO: 9) | mitochondrially encoded tRNA histidine | 246.72 | 1.95 | 9.21E−05 | 9.72E−04 |
| ENST00000626826 (SEQ ID NO: 10) | HELLP associated long non-coding RNA (macro_lncRNA) | 729.26 | 2.02 | 1.08E−04 | 1.03E−03 |
| ENST00000384819 (SEQ ID NO: 11) | microRNA 99b | 344.45 | 0.65 | 1.57E−04 | 1.31E−03 |
| ENST00000385300 (SEQ ID NO: 12) | microRNA 143 | 1631.94 | 0.62 | 1.66E−04 | 1.31E−03 |
| ENST00000387342 (SEQ ID NO: 13) | mitochondrially encoded tRNA valine | 664.18 | 1.99 | 2.11E−04 | 1.54E−03 |
| ENST00000521276 (SEQ ID NO: 14) | microRNA 151a | 10020.95 | 0.75 | 5.68E−04 | 3.85E−03 |
| ENST00000384873 (SEQ ID NO: 15) | microRNA 191 | 31187.05 | 0.75 | 6.26E−04 | 3.97E−03 |

TABLE 1-continued

Differentially expressed ncRNAs in preeclampsia vs. control samples

| Transcript ID[a] | Description | *Base mean count | **Fold change | P-value | Adjusted P-value |
|---|---|---|---|---|---|
| ENST00000365096 (SEQ ID NO: 16) | RNA, 5.8S ribosomal pseudogene 4 (rRNA) | 1652.37 | 1.68 | 1.65E−03 | 9.21E−03 |
| ENST00000387449 (SEQ ID NO: 17) | mitochondrially encoded tRNA serine 2 (AGU/C) | 1249.73 | 1.72 | 1.61E−03 | 9.21E−03 |
| ENST00000365699 (SEQ ID NO: 18) | microRNA 146b | 1322.69 | 0.75 | 2.67E−03 | 1.41E−02 |
| ENST00000385135 (SEQ ID NO: 19) | microRNA 221 | 587.31 | 1.44 | 3.97E−03 | 1.98E−02 |
| ENST00000387409 (SEQ ID NO: 20) | mitochondrially encoded tRNA tyrosine | 173.20 | 1.53 | 4.41E−03 | 2.09E−02 |
| ENST00000387347 (SEQ ID NO: 21) | mitochondrially encoded 16S RNA | 6217.70 | 1.63 | 4.82E−03 | 2.18E−02 |
| ENST00000362280 (SEQ ID NO: 22) | microRNA let-7g | 1072.71 | 1.27 | 9.85E−03 | 4.26E−02 |
| ENST00000315707 (SEQ ID NO: 23) | long intergenic non-protein coding RNA 324 (lincRNA) | 1086.88 | 1.50 | 1.03E−02 | 4.27E−02 |
| ENST00000612171 (SEQ ID NO: 24) | AC113133.1-201 (miRNA-486) | 17568.81 | 0.70 | 1.11E−02 | 4.38E−02 |
| ENST00000614316 (SEQ ID NO: 25) | AC020956.3-001 (lincRNA) | 901.99 | 1.71 | 1.18E−02 | 4.47E−02 |

Figure 2:
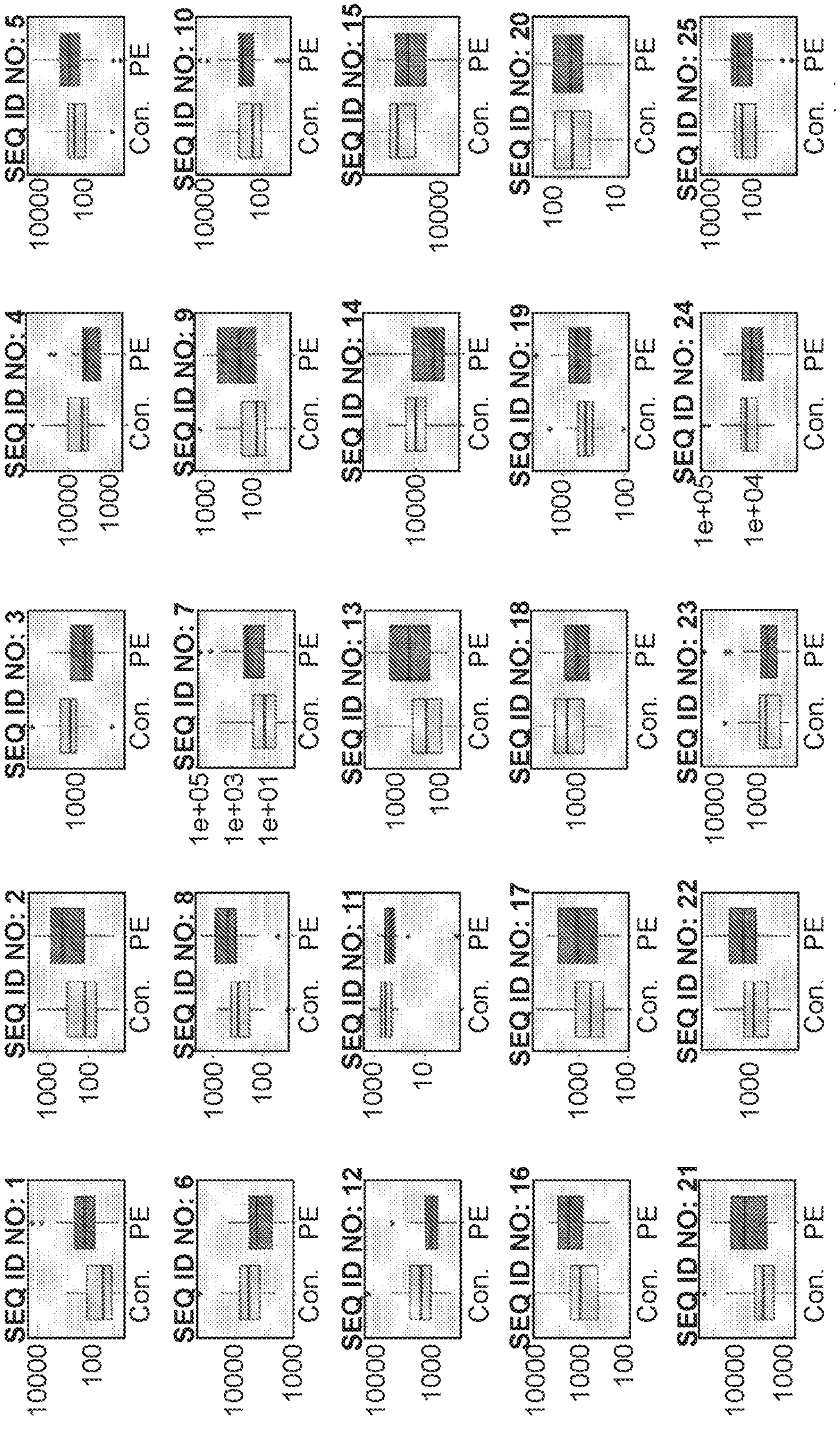
FIG. 2. Plots of normalized counts for the 25 differentially expressed transcripts in the top 100 most abundant transcripts in preeclampsia (marked as PE) and control samples. The Y axis represents normalized counts.

[a]The transcript ID is the accession number in Ensembl database. The sequences are cDNA sequences corresponding to the RNA transcripts.
*mean of normalized counts for all samples
preeclampsia compared to control FIG. 2** demonstrates the count differences in both conditions (preeclampsia—"PE", and control) for the significant differentially expressed transcripts listed in Table 1.

Figure 3A:
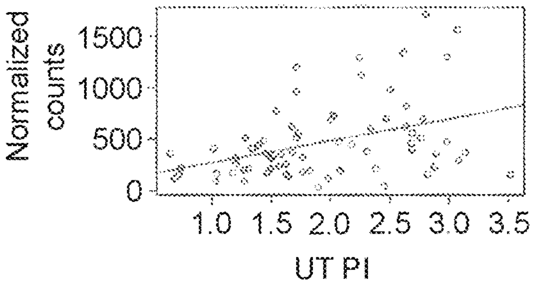
FIG. 3. Correlation between microRNA 4433b (SEQ ID NO: 8) and maternal clinical characteristics. Plots of mir-4433b normalized counts obtained by RNA-Seq of circulating non-coding RNA extracted from first trimester pregnant women plasma, versus clinical features of these women: (A) uterine artery pulsatility index (UT PI, r=0.395, p-value=0.016); (B) mean arterial pressure (MAP, r=0.442, p-value=0.003).
Figure 3B:
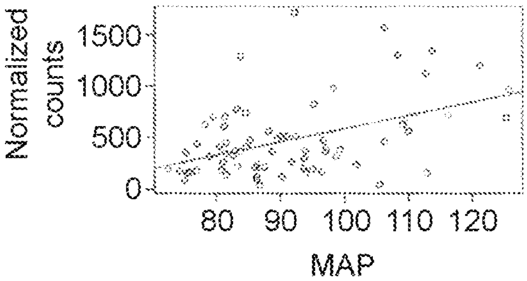

Next, the correlation of each of the differentially expressed transcripts and maternal clinical features (as measured during the first trimester, at the time of taking the blood sample for the RNA analyses) was analyzed. The analysis has shown moderate yet significant correlations between miR-4433b (SEQ ID NO: 8) and two maternal clinical features (FIGS. 3A+B): the uterine artery pulsatility index (UT PI; r=0.395, adjusted p-value=0.016), and the mean arterial pressure (MAP; r=0.442, adjusted p-value=0.003).

In order to validate the expression data obtained by sequencing, the expression of five microRNAs was examined using qPCR in 14 samples: 6 preeclampsia samples and 8 control samples, and the correlation between the expression of these microRNAs obtained by sequencing and by qPCR in the relevant samples was analyzed. Pearson's product moment correlation coefficients were calculated between normalized counts obtained by sequencing and qPCR normalized values ($2^{-C_t}$). The analysis has shown a significant correlation for all tested microRNAs (see Table 2), which confirms the microRNA counts obtained by sequencing.

TABLE 2

Expression of microRNAs - sequencing vs. qPCR

| miRNA | Fold change | P-value | Correlation between sequencing and qPCR ($r^2$) | P-value |
|---|---|---|---|---|
| microRNA 99b (SEQ ID NO: 11) | 0.65 | 1.57E−04 | 0.83 | 0.017 |

TABLE 2-continued

Expression of microRNAs - sequencing vs. qPCR

| miRNA | Fold change | P-value | Correlation between sequencing and qPCR ($r^2$) | P-value |
|---|---|---|---|---|
| microRNA 151a (SEQ ID NO: 14) | 0.75 | 5.68E−04 | 0.73 | 0.011 |
| microRNA 191 (SEQ ID NO: 15) | 0.75 | 6.26E−04 | 0.7 | 0.016 |
| microRNA 146b (SEQ ID NO: 18) | 0.75 | 2.67E−03 | 0.85 | 0.00099 |
| microRNA 221 (SEQ ID NO: 19) | 1.44 | 3.97E−03 | 0.83 | 0.0015 |

Example 2—Preeclampsia/Control Sample Classification

Methods:

As noted above, counts were normalized and transformed using DESeq2 by normalization to the effective library size and variance stabilizing transformations (VST) to estimate the mean-dispersion relationship of data (Love et al., ibid). Next, for the purpose of building a generalized classifier and estimating its performance when applied on new samples, logistic regression in a k-fold cross validation (CV) procedure was used.

In order to obtain more generalizable models, the cross validation concept was applied 100 times (cycles). In each cycle, the data was divided to training and test sets, and 5-fold cross validation was applied on the training set, i.e., the training set was divided to 5 non-overlapping and equally sized subsets, a logistic regression model was trained on 4 subsets and tested in the remaining subset. This process was repeated 5 times, thus all subsets were used as a test set in each step. For model selection glmulti package in R was used (Calcagno and de Mazancourt, 2010, *J. Stat. Softw.* 34:29), which performs an exhaustive search over all possible models, fit each model to the current set using glm and ranks them by Akaike information criterion (AIC). A feature selection procedure was applied in each CV cycle and the list of transcripts was narrowed down to differentially expressed transcripts that have substantial expression (i.e., in the top 100 most abundant transcripts). Highly correlated transcripts (i.e., Pearson correlation >0.7) were then collapsed. Best model (i.e., with the highest AIC calculated by glmulti) was tested in each CV step on the reaming subset (i.e., the inner test set), and misclassification error was calculated. The model that got the lowest CV error in all CV steps was then selected, fitted on the complete training set and tested on the outer test set. After 100 repeats, the average error rate and related statistics was calculated.

Figure 4:
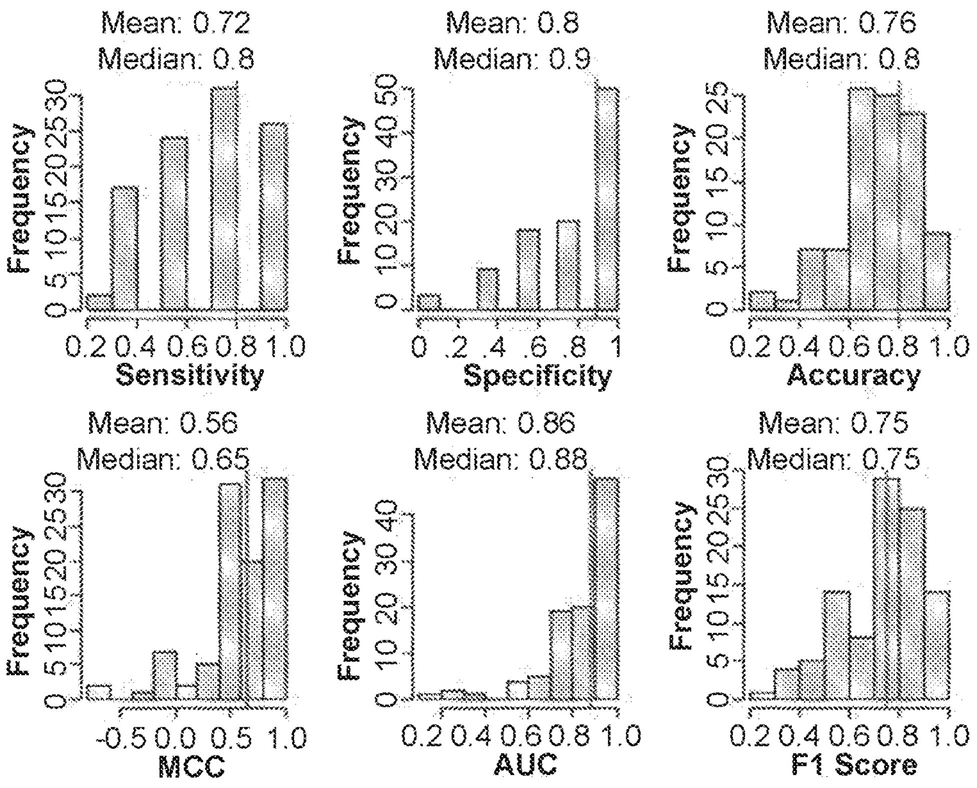
FIG. 4. Statistic histograms obtained by 100 repeats of the classification procedure described in Example 2 (i.e., on 100 random test sets). Means and medians are indicated.

Results:

K-fold cross validation was applied in 100 repeats to obtain a generalizable logistic regression model that includes feature selection pre-processing step. Using this technique, the goodness of the procedure was estimated on a new blind data set. FIG. 4 displays summary statistic histograms, mean and medians calculated in each of the 100 repeats. All measures imply that the procedure can classify blind samples with preeclampsia/control conditions in a relatively good manner.

Example 3—Expression of the Differentially Expressed Transcripts Over Trimesters To assess the expression of the 25 differentially expressed transcripts later in the pregnancy, after the appearance of preeclampsia symptoms, small ncRNAs were sequenced in the plasma of a subset of 40 women (out of the 75) at weeks 20-22 (second trimester): 20 women who developed preeclampsia and 20 control women. The sequencing data from the second trimester samples were compared to those of the first trimester samples.

Before the comparison was made, the first trimester samples of this subset of 40 women were analyzed again. As this subset is half the size of the original size and thus insufficiently powered, out of the 25 differentially expressed transcripts, only 9 transcripts were significantly differentially expressed between preeclampsia and control samples in the limited set of 40 first trimester samples (adjusted p-value<0.05). In the second trimester samples, 4 transcripts out of the 25 were differentially expressed (adjusted p-value<0.05).

Figure 5:
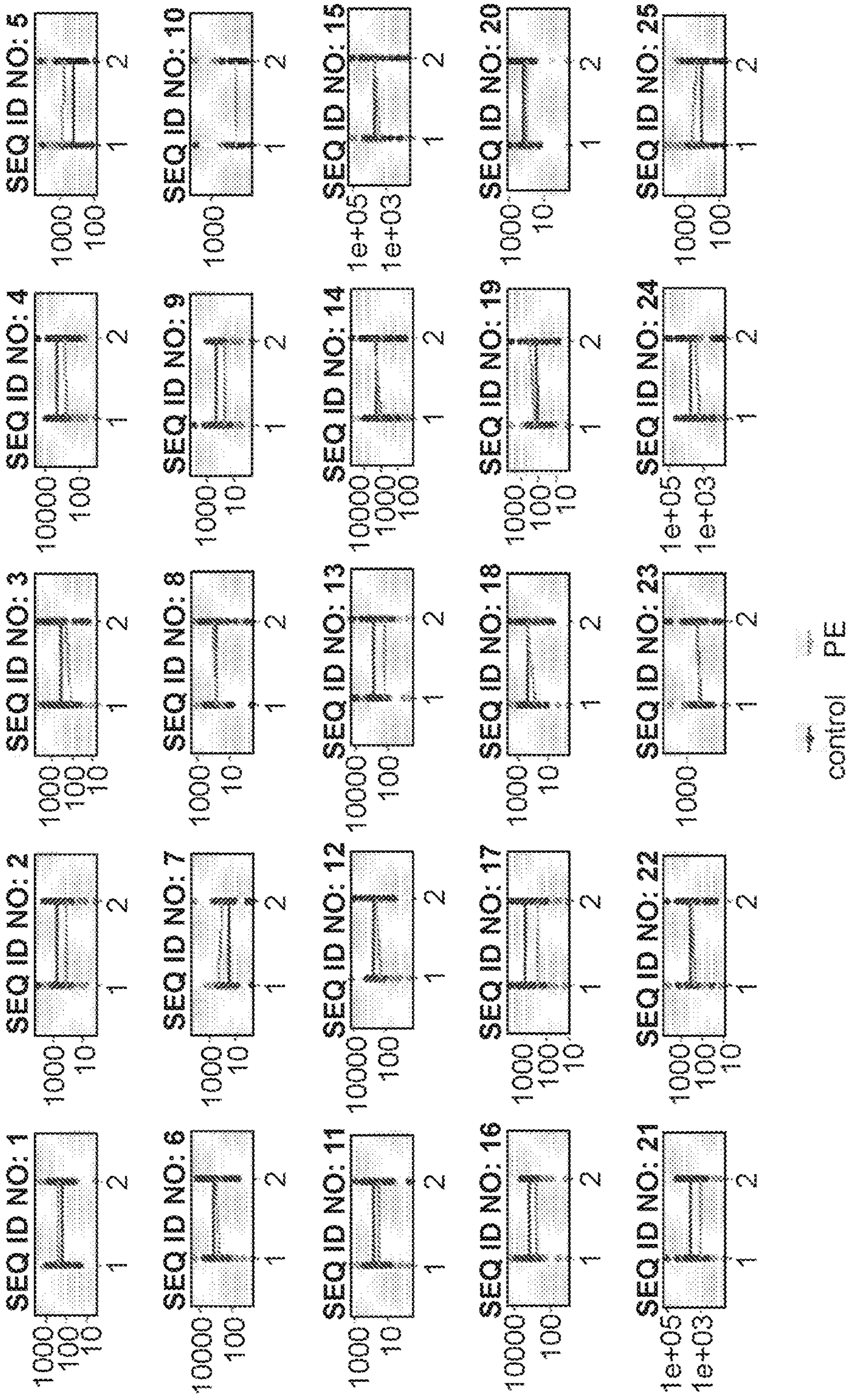
FIG. 5. Normalized counts for the 25 differentially expressed transcripts in preeclampsia (PE) vs. control samples in the first and second trimesters. Regression lines for both groups are indicated, to display expression trend between the two trimesters. The X axis represents the different trimesters (1 and 2). The Y axis represents normalized counts.

The first and second trimester samples were then combined and a design formula was used, which models the condition-specific (i.e., preeclampsia or control) difference at the first trimester, the difference over trimesters, and any condition-specific differences over trimesters (i.e., an interaction term condition:trimester). A likelihood ratio test was performed with a reduced model which does not contain the interaction term, to test whether the condition induces a change in gene expression at the second trimester compared to the first trimester. Only transcripts with p-value<0.05 after false discovery rate (FDR) adjustment were considered. Applying this test, none of the transcripts displayed significant preeclampsia-dependent change in expression over the trimesters (preeclampsia/trimester interaction test, see Table 3 and FIG. 5. These results suggest that fold changes in expression observed in the first trimester are maintained during the second trimester as well, after the appearance of preeclampsia symptoms, though more samples from both gestational ages are required to further investigate this matter.

TABLE 3

Comparison of first and second trimesters

| Transcript ID | Description | Base mean count | *Fold change | P-value | Adjusted P-value |
|---|---|---|---|---|---|
| ENST00000521276 (SEQ ID NO: 14) | microRNA 151a | 4,514.08 | 0.27 | 0.04 | 0.40 |
| ENST00000384873 (SEQ ID NO: 15) | microRNA 191 | 12,546.19 | 0.28 | 0.06 | 0.40 |
| ENST00000384819 (SEQ ID NO: 11) | microRNA 99b | 129.85 | 0.31 | 0.07 | 0.40 |
| ENST00000362280 (SEQ ID NO: 22) | microRNA let-7g | 653.84 | 0.36 | 0.08 | 0.40 |
| ENST00000387342 (SEQ ID NO: 13) | mitochondrially encoded tRNA valine | 1,517.16 | 0.31 | 0.09 | 0.40 |
| ENST00000385135 (SEQ ID NO: 19) | microRNA 221 | 446.48 | 0.36 | 0.10 | 0.40 |
| ENST00000626826 (SEQ ID NO: 10) | HELLP associated long non-coding RNA | 497.67 | 1.30 | 0.14 | 0.49 |
| ENST00000365699 (SEQ ID NO: 18) | microRNA 146b | 413.93 | 0.42 | 0.17 | 0.52 |
| ENST00000385300 (SEQ ID NO: 12) | microRNA 143 | 861.77 | 0.45 | 0.19 | 0.52 |
| ENST00000385255 (SEQ ID NO: 3) | microRNA 182 | 617.00 | 0.47 | 0.23 | 0.52 |
| ENST00000612171 (SEQ ID NO: 24) | AC113133.1-201 | 10,420.59 | 0.48 | 0.24 | 0.52 |
| ENST00000387461 (SEQ ID NO: 1) | mitochondrially encoded tRNA proline | 315.89 | 1.74 | 0.25 | 0.52 |

TABLE 3-continued

| Comparison of first and second trimesters | | | | | |
|---|---|---|---|---|---|
| Transcript ID | Description | Base mean count | *Fold change | P-value | Adjusted P-value |
| ENST00000385011 (SEQ ID NO: 4) | microRNA 10b | 2,488.02 | 0.53 | 0.27 | 0.53 |
| ENST00000514519 (SEQ ID NO: 7) | RP11-259O2.3-001 | 209.70 | 0.60 | 0.39 | 0.63 |
| ENST00000384816 (SEQ ID NO: 6) | microRNA 25 | 2,728.09 | 0.59 | 0.40 | 0.63 |
| ENST00000387441 (SEQ ID NO: 9) | mitochondrially encoded tRNA histidine | 356.59 | 1.70 | 0.40 | 0.63 |
| ENST00000387449 (SEQ ID NO: 17) | mitochondrially encoded tRNA serine 2 (AGU/C) | 1,106.02 | 1.44 | 0.52 | 0.74 |
| ENST00000614316 (SEQ ID NO: 25) | AC020956.3-001 | 568.39 | 0.80 | 0.54 | 0.74 |
| ENST00000315707 (SEQ ID NO: 23) | long intergenic non-protein coding RNA 324 | 651.28 | 0.83 | 0.57 | 0.74 |
| ENST00000387421 (SEQ ID NO: 2) | mitochondrially encoded tRNA lysine | 926.67 | 0.71 | 0.60 | 0.74 |
| ENST00000387409 (SEQ ID NO: 20) | mitochondrially encoded tRNA tyrosine | 207.66 | 1.27 | 0.64 | 0.74 |
| ENST00000387347 (SEQ ID NO: 21) | mitochondrially encoded 16S RNA | 6,306.61 | 1.28 | 0.68 | 0.74 |
| ENST00000365096 (SEQ ID NO: 16) | RNA, 5.8S ribosomal pseudogene 4 | 1,782.07 | 0.81 | 0.69 | 0.74 |
| ENST00000581329 (SEQ ID NO: 8) | microRNA 4433b | 200.30 | 0.79 | 0.72 | 0.75 |
| ENST00000361558 (SEQ ID NO: 5) | mucin 2, oligomeric mucus/gel-forming | 792.728 | 0.94 | 0.87 | 0.87 |

*fold changes are a ratio of first trimester fold change divided by second trimester fold change.

Figure 6:
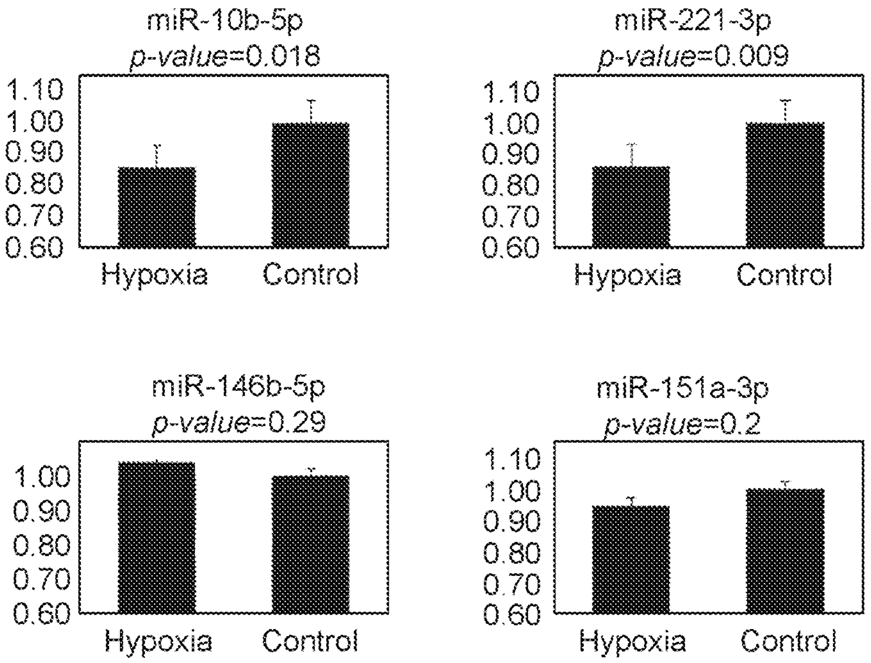
FIG. 6. Relative expression of miR-22, miR-10b, miR-146b, and miR-151a in human first trimester cytotrophoblast cell line (HTR8/SVneo cells) cultured under both hypoxic (PE model) and normal (control) conditions. Expressions were measured by RT-qPCR. Control expressions were set to 1.

Example 4—Expression of the Differentially Expressed Transcripts in the Placenta Although the cause of preeclampsia is unclear, it is known that it involves inadequate blood supply to the placenta, leading to a hypoxic environment. To evaluate the effect of hypoxic conditions on the expression level of the differentially expressed transcripts, four (4) microRNAs out of the 25 differentially expressed transcripts were tested for their expression in human first-trimester cytotrophoblast cell line (HTR8/SVneo cells) cultured for 48 hours under hypoxic or normal conditions. Out of the four tested microRNAs, 2 microRNAs, miR-10b and miR-221, displayed significant differential expression, similar to the differential expression identified in the plasma (FIG. 6). These results suggest that their observed expression changes in the plasma originated in the placenta.

To further inspect this matter, the expression of the 25 differentially expressed transcripts was tested in preeclampsia and control placenta biopsies. Placenta segments were collected from 15 different locations in the placenta, from 6 different placentas: 3 from preeclampsia patients and 3 from healthy pregnant women. Small ncRNA from all locations was extracted and sequenced, and the expression of all 25 transcripts was examined. In this sample set, none of the transcripts displayed differential expression in those samples between preeclampsia and control groups.

The foregoing description of the specific embodiments will so fully reveal the general nature of the invention that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the invention.

The invention claimed is:

1. A method for determining a non-coding RNA (ncRNA) expression pattern in plasma or serum, the method comprising:

(i) obtaining a plasma or serum sample from a pregnant woman in the first trimester of the pregnancy or in weeks 10-14 of the pregnancy; and (ii) measuring the levels of a at least ten non-coding RNAs (ncRNAs) selected from ncRNAs corresponding to SEQ ID NOs: 1-25 in the plasma or serum sample from the pregnant woman.

2. The method of claim 1, wherein said measuring levels of at least ten ncRNAs comprises extracting RNA from the plasma or serum sample, reverse transcribing said RNA into cDNA, and measuring the amount of said cDNA using quantitative-PCR.

3. The method of claim 1, wherein said measuring levels of at least ten ncRNAs comprises applying at least ten detectably labeled oligonucleotides, each capable of specifically hybridizing to one of said ncRNAs.

4. The method of claim 3, wherein said detectably labeled oligonucleotides are immobilized to a solid surface.

5. The method of claim 1, wherein said at least ten ncRNAs comprises all 25 of the ncRNAs corresponding to SEQ ID NOs: 1-25.

6. A system for determining whether a pregnant woman is at risk of developing preeclampsia, the system comprising:

detectably-labeled probes for measuring the levels of a plurality of ncRNAs selected from ncRNAs corresponding to SEQ ID NOs: 1-25 in a plasma or serum sample obtained from the pregnant woman, wherein the pregnant woman is in the first trimester of the pregnancy or in week 10 to 14 of the pregnancy; and a computer software embodied on a computer readable storage medium, the computer software employing a pattern analyzing algorithm for carrying out a comparison between the ncRNA expression pattern of the pregnant woman and reference values, wherein the computer software: (i) compares the ncRNA expression pattern of the pregnant woman to non-preeclampsia reference pattern, preeclampsia reference pattern or both; and (ii) based on the comparison, outputs an indication whether the pregnant woman is at risk of developing preeclampsia, by detecting at least one of: increased expression levels of one or more ncRNA corresponding to SEQ ID NOs: 1-2, 5, 7-10, 13, 16-17, 19-23 and 25 compared to non-preeclampsia reference values; and decreased expression levels of one or more ncRNA corresponding to SEQ ID NOs: 3-4, 6, 11-12, 14-15, 18 and 24 compared to non-preeclampsia reference values.

7. The system of claim 6, wherein the computer software outputs a score indicative of the risk of the pregnant woman to develop preeclampsia, wherein a score above a predefined threshold is indicative of risk of developing preeclampsia.

8. The system of claim 6, further comprising oligonucleotide primer pairs for reverse transcribing RNA of said plurality of ncRNAs from the plasma or serum sample into cDNA, and performing quantitative-PCR of the cDNA.

9. The system of claim 6, wherein said detectably-labeled probes comprise oligonucleotides for detecting amplification products in quantitative-PCR.

10. The system of claim 6, wherein said detectably-labeled probes for measuring levels of a plurality of ncRNAs comprise a plurality of detectably-labeled oligonucleotides that specifically hybridize to said ncRNAs.

11. The system of claim 10, wherein said detectably-labeled oligonucleotides are immobilized to a surface.

12. The system of claim 6, further comprising means for extracting RNA from the plasma or serum sample.

13. The system of claim 6, wherein said plurality of ncRNAs comprises at least five ncRNAs.

14. The system of claim 6, wherein said plurality of ncRNAs comprises at least ten ncRNAs.

15. A method for identifying and managing a pregnant woman at risk of developing preeclampsia, the method comprising:

(i) measuring the levels of a plurality of non-coding RNAs (ncRNAs) selected from ncRNAs corresponding to SEQ ID NOs: 1-25 in a plasma or serum sample from the pregnant woman, wherein the pregnant woman is in the first trimester of the pregnancy or in week 10 to 14 of the pregnancy, to thereby obtain a ncRNA expression pattern of said pregnant woman;

(ii) comparing the ncRNA expression pattern of the pregnant woman to a non-preeclampsia reference pattern;

(iii) characterizing the pregnant woman as being at risk of developing preeclampsia when the ncRNA expression pattern of the pregnant woman is determined to be different from the non-preeclampsia reference pattern by detecting at least one of: increased expression levels of one or more ncRNA corresponding to SEQ ID NOs: 1-2, 5, 7-10, 13, 16-17, 19-23 and 25 compared to non-preeclampsia reference values, and decreased expression levels of one or more ncRNA corresponding to SEQ ID NOs: 3-4, 6, 11-12, 14-15, 18 and 24 compared to the non-preeclampsia reference values;

iv) optionally conducting preeclampsia follow-up testing comprising one or more of blood tests, urine tests and blood pressure measurements; and v) administering to the pregnant woman characterized as being at risk of developing preeclampsia a therapy to manage preeclampsia comprising at least one of bed rest and diet changes.

16. The method of claim 15, wherein said plurality of ncRNAs comprises at least five ncRNAs.

17. The method of claim 15, wherein said plurality of ncRNAs comprises at least ten ncRNAs.

18. The method of claim 15, wherein said plurality of ncRNAs comprises all 25 of the ncRNAs corresponding to SEQ ID NOs: 1-25.

* * * * *

SEQUENCE LISTING

```
<160> NUMBER OF SEQ ID NOS: 25

<210> SEQ ID NO 1
<211> LENGTH: 68
```

<212> TYPE: DNA
<213> ORGANISM: Homo sapiens

<400> SEQUENCE: 1
cagagaatag tttaaattag aatcttagct ttgggtgcta atggtggagt taaagacttt 60
ttctctga 68

<210> SEQ ID NO 2
<211> LENGTH: 70
<212> TYPE: DNA
<213> ORGANISM: Homo sapiens

<400> SEQUENCE: 2
cactgtaaag ctaacttagc attaaccttt taagttaaag attaagagaa ccaacacctc 60
tttacagtga 70

<210> SEQ ID NO 3
<211> LENGTH: 112
<212> TYPE: DNA
<213> ORGANISM: Homo sapiens

<400> SEQUENCE: 3
gctgcttgcc tccccccgtt tttggcaatg gtagaactca cactggtgag gtaacaggat 60
ccggtggttc tagacttgcc aactatgggg cgaggactca gccggcaccc tg 112

<210> SEQ ID NO 4
<211> LENGTH: 110
<212> TYPE: DNA
<213> ORGANISM: Homo sapiens

<400> SEQUENCE: 4
ccagaggttg taacgttgtc tatatatacc ctgtagaacc gaatttgtgt ggtatccgta 60
tagtcacaga ttcgattcta ggggaatata tggtcgatgc aaaaacttca 110

<210> SEQ ID NO 5
<211> LENGTH: 12667
<212> TYPE: DNA
<213> ORGANISM: Homo sapiens

<400> SEQUENCE: 5
caacccacac cgcccctgcc agccaccatg gggctgccac tagcccgcct ggcggctgtg 60
tgcctggccc tgtctttggc agggggctcg gagctccaga cagagggcag aacccgaaac 120
cacggccaca acgtctgcag cacctggggc aacttccact acaagacctt cgacggggac 180
gtcttccgct tccccggccc ctgcgactac aacttcgcct ccgactgccg aggctcctac 240
aaggaatttg ctgtgcacct gaagcggggt ccgggccagg ctgaggcccc cgccggggtg 300
gagtccatcc tgctgaccat caaggatgac accatctacc tcacccgcca cctggctgtg 360
cttaacgggg ccgtggtcag caccccgcac tacagccccg ggctgctcat tgagaagagc 420
gatgcctaca ccaaagtcta ctcccgcgcc ggcctcaccc tcatgtggaa ccgggaggat 480
gcactcatgc tggagctgga cactaagttc cggaaccaca cctgtggcct ctgcggggac 540
tacaacggcc tgcagagcta ttcagaattc ctctctgacg gcgtgctctt cagtcccctg 600
gagtttggga acatgcagaa gatcaaccag cccgatgtgg tgtgtgagga tcccgaggag 660
gaggtggccc ccgcatcctg ctccgagcac cgcgccgagt gtgagaggct gctgaccgcc 720
gaggccttcg cggactgtca ggacctggtg ccgctggagc cgtatctgcg cgcctgccag 780

-continued

```
caggaccgct gccggtgccc gggcggtgac acctgcgtct gcagcaccgt ggccgagttc    840
tcccgccagt gctcccacgc cggcggccgg cccgggaact ggaggaccgc cacgctctgc    900
cccaagacct gccccgggaa cctggtgtac ctggagagcg gctcgccctg catggacacc    960
tgctcacacc tggaggtgag cagcctgtgc gaggagcacc gcatggacgg ctgtttctgc   1020
ccagaaggca ccgtatatga cgacatcggg gacagtggct gcgttcctgt gagccagtgc   1080
cactgcaggc tgcacggaca cctgtacaca ccgggccagg agatcaccaa tgactgcgag   1140
cagtgtgtct gtaacgctgg ccgctgggtg tgcaaagacc tgccctgccc cggcacctgt   1200
gccctggaag gcggctccca catcaccacc ttcgatggga agacgtacac cttccacggg   1260
gactgctact atgtcctggc caagggtgac cacaacgatt cctacgctct cctgggcgag   1320
ctggcccccct gtggctccac agacaagcag acctgcctga agacggtggt gctgctggct   1380
gacaagaaga agaatgtggt ggtcttcaag tccgatggca gtgtactgct caacgagctg   1440
caggtgaacc tgccccacgt gaccgcgagc ttctctgtct tccgcccgtc ttcctaccac   1500
atcatggtga gcatggccat tggcgtccgg ctgcaggtgc agctggcccc agtcatgcaa   1560
ctctttgtga cactggacca ggcctcccag gggcaggtgc agggcctctg cgggaacttc   1620
aacggcctgg aaggtgacga cttcaagacg gccagcgggc tggtggaggc cacgggggcc   1680
ggctttgcca acacctggaa ggcacagtca acctgccatg acaagctgga ctggttggac   1740
gatccctgct ccctgaacat cgagagcgcc aactacgccg agcactggtg ctccctcctg   1800
aagaagacag agacccccctt tggcaggtgc cactcggctg tggaccctgc tgagtattac   1860
aagaggtgca aatatgacac gtgtaactgt cagaacaatg aggactgcct gtgcgccgcc   1920
ctgtcctcct acgcgcgcgc ctgcaccgcc aagggcgtca tgctgtgggg ctggcgggag   1980
catgtctgca acaaggatgt gggctcctgc cccaactcgc aggtcttcct gtacaacctg   2040
accacctgcc agcagacctg ccgctccctc tccgaggccg acagccactg tctcgagggc   2100
tttgcgcctg tggacggctg cggctgccct gaccacacct tcctggacga gaagggccgc   2160
tgcgtacccc tggccaagtg ctcctgttac caccgcggtc tctacctgga ggcgggggac   2220
gtggtcgtca ggcaggaaga acgatgtgtg tgccgggatg ggcggctgca ctgtaggcag   2280
atccggctga tcggccagag ctgcacggcc ccaaagatcc acatggactg cagcaacctg   2340
actgcactgg ccacctcgaa gccccgagcc ctcagctgcc agacgctggc cgccggctat   2400
taccacacag agtgtgtcag tggctgtgtg tgccccgacg ggctgatgga tgacggccgg   2460
ggtggctgcg tggtggagaa ggaatgccct tgcgtccata acaacgacct gtattcttcc   2520
ggcgccaaga tcaaggtgga ctgcaatacc tgcacctgca agagaggacg ctgggtgtgc   2580
acccaggctg tgtgccatgg cacctgctcc atttacggga gtggccacta catcaccttt   2640
gacgggaagt actacgactt tgacggacac tgctcctacg tggctgttca ggactactgc   2700
ggccagaact cctcactggg ctcattcagc atcatcaccg agaacgtccc ctgtggcact   2760
acgggcgtca cctgctccaa ggccatcaag atcttcatgg ggaggacgga gctgaagttg   2820
gaagacaagc accgtgtggt gatccagcgt gatgagggtc accacgtggc ctacaccacg   2880
cgggaggtgg gccagtacct ggtggtggag tccagcacgg gcatcatcgt catctgggac   2940
aagaggacca ccgtgttcat caagctggct ccctcctaca agggcaccgt gtgtggcctg   3000
tgtgggaact ttgaccaccg ctccaacaac gacttcacca cgcgggacca catggtggtg   3060
agcagcgagc tggacttcgg gaacagctgg aaggaggccc ccacctgccc agatgtgagc   3120
accaaccccg agccctgcag cctgaacccg caccgccgct cctgggccga gaagcagtgc   3180
```

-continued

```
agcatcctca aaagcagcgt gttcagcatc tgccacagca aggtggaccc caagcccttc   3240
tacgaggcct gtgtgcacga ctcgtgctcc tgtgacacgg gtggggactg tgagtgcttc   3300
tgctctgccg tggcctccta cgcccaggag tgtaccaaag agggggcctg cgtgttctgg   3360
aggacgccgg acctgtgccc catattctgc gactactaca accctccgca tgagtgtgag   3420
tggcactatg agccatgtgg gaaccggagc ttcgagacct gcaggaccat caatggcatc   3480
cactccaaca tctccgtgtc ctacctggag ggctgctacc cccggtgccc caaggacagg   3540
cccatctatg aggaggatct gaagaagtgt gtcactgcag acaagtgtgg ctgctatgtc   3600
gaggacaccc actacccacc tggagcatcg gttcccaccg aggagacctg caagtcctgc   3660
gtgtgtacca actcctccca agtcgtctgc aggccggagg aaggaaagat tcttaaccag   3720
acccaggatg gcgccttctg ctactgggag atctgtggcc ccaacgggac ggtggagaag   3780
cacttcaaca tctgttccat tacgacacgc ccgtccaccc tgaccacctt caccaccatc   3840
accctcccca ccacccccac caccttcacc actaccacca ccaccaccac cccgacctcc   3900
agcacagttt tatcaacaac tccgaagctg tgctgcctct ggtctgactg gatcaatgag   3960
gaccacccca gcagtggcag cgacgacggt gaccgagaaa catttgatgg ggtctgcggg   4020
gcccctgagg acatcgagtg caggtcggtc aaggatcccc acctcagctt ggagcagcta   4080
ggccagaagg tgcagtgtga tgtctctgtt gggttcattt gcaagaatga agaccagttt   4140
ggaaatggac catttggact gtgttacgac tacaagatac gtgtcaattg ttgctggccc   4200
atggataagt gtatcaccac tcccagccct ccaactacca ctcccagccc tccaccaacc   4260
agcacgacca cccttccacc aaccaccacc cccagccctc caaccaccac cacaaccacc   4320
cctccaccaa ccaccacccc cagccctcca ataaccacca cgaccacccc tccaccaacc   4380
accactccca gccctccaat aagcaccaca accacccctc caccaaccac cactcccagc   4440
cctccaacca ccactcccag ccctccaacc accactccca gccctccaac aaccaccaca   4500
accacccctc caccaaccac cactcccagc cctccaacga ctacgcccat cactccacca   4560
gccagcacta ccacccttcc accaaccacc actcccagcc ctccaacaac caccacaacc   4620
acccctccac caaccaccac tcccagtcct ccaacgacta cgcccatcac tccaccaacc   4680
agcactacta cccttccacc aaccaccact cccagccctc caccaaccac cacaaccacc   4740
cctccaccaa ccaccactcc cagccctcca acaaccacca ctcccagtcc tccaacaatc   4800
accacaacca cccctccacc aaccaccact cccagccctc caacaaccac cacgaccacc   4860
cttccaccaa ccaccacttc cagccctcta acaactactc ctctacctcc atcaataact   4920
cctcctacat tttcaccatt ctcaacgaca acccctacta ccccatgcgt gcctctctgc   4980
aattggactg gctggctgga ttctggaaaa cccaactttc acaaaccagg tggagacaca   5040
gaattgattg gagacgtctg tggaccaggc tgggcagcta acatctcttg cagagccacc   5100
atgtatcctg atgttcccat tggacagctt ggacaaacag tggtgtgtga tgtctctgtg   5160
gggctgatat gcaaaaatga agaccaaaag ccaggtgggg tcatccctat ggccttctgc   5220
ctcaactacg agatcaacgt tcagtgctgt gagtgtgtca cccaacccac caccatgaca   5280
accaccacca cagagaaccc aactccgaca ccaatcacca ccaccactac ggtgacccca   5340
accccaacac ccaccagcac acagagtaca acaccaacac ccatcaccac caccaatacg   5400
gtaaccccaa ccccaacccc cactggcaca cagaccccaa ccccgacacc catcaccacc   5460
accaccacta tggtgacccc aacaccaaca atcaccagca cacagacccc aaccccgaca   5520
```

-continued

```
cccatcacca ccactacggt gaccccaacc ccaacaccca ccagcacaca gagaacaaca   5580
ccgacatcca tcaccaccac caccacggtg accccaaccc caacacccac cggcacacag   5640
accccaacca cgacacccat caccaccacc accacggtga ccccaacccc aacacccacc   5700
ggcacacaga ccccaacaac gacacccatc accaccacca ccatggtgac cccaacccca   5760
acacccactg gaacacagac ccaaacccca acacccatca ccaccaccac tacggtgacc   5820
ccaaccccta cacccaccgg cacacagacc ccaacatcga cacccatcag caccaccact   5880
acggtgaccc caacaccaac acccaccggc acacagaccc caaccctgac acccatcacc   5940
accaccacta cggtgacccc aaccccaaca cccaccggca cacagacccc aaccacgaca   6000
cccatcacca ccaccactac ggtgacccca accccaacac ccaccggcac aaagagtaca   6060
accccgacat ccatcaccac caccactatg gtgaccccaa ccccaccacc cactggcaca   6120
cagaccccaa ccacgacacc catcaccacc accactacgg tgaccccaac cccaacaccc   6180
accggcacac agaccccaac cccgacaccc atcaccacca ccaccacggt gaccccaacc   6240
ccaacaccca ccggcacaca gaccccaaca tcgacaccca tcaccaccaa cactacggtg   6300
accccaaccc caacaccaac cggcacaccg agtacaaccc tgacacccat caccaccacc   6360
actatggtga ccccaacccc aacacccacc ggcacacaga ccccaacatc gacacccatc   6420
agcaccacca ctacggtgac cccaacctca acacccaccg gcacacagac cccaaccccg   6480
acacccatct ccaccaccac tacggtgacc ccaaccccga cacccatctc caccaccact   6540
acagtgaccc caaccccaac acccaccggc acacagaccc caaccatgac acccatcacc   6600
accaccacca cggtgacccc aaccccaaca cccaccggca cacagacccc aacaacgaca   6660
cccatcagca ccaccaccac agtgacccca accccaacac ccaccggcac acagacccca   6720
acatcgacac ccatcaccac caccactacg gtgaccccaa ccccaacacc caccggcaca   6780
cagaccccaa ccacgacacc catcaccacc accaccacgg tgaccccaac cccaacaccc   6840
accggcacac agagtacaac cctgacaccc atcaccacca ccaccacggt gacaccaacc   6900
ccaacaccca ccggcacaca gaccccaacc ccgacaccca tctccaccac cactacggtg   6960
accccaaccc caacacccac cggcacacag accccaacca cgacacccat caccaccacc   7020
accacggtga ccccaacccc aacacccacc ggcacacaga ccccaacaac gacacccatc   7080
agcaccacca ccacggtgac cccaacccca acacccaccg gcacacagac cccaacatcg   7140
acacccatca ccaccaccac tacggtgacc ccaaccccaa cacccaccgg cacacagacc   7200
ccaaccacga cacccatcac caccaccacc acggtgaccc caaccccaac acccactggc   7260
acacaggccc caaccccaac agccatcacc accaccacta cggtgacccc aaccccaaca   7320
cccaccggca cacagacccc aacaacgaca cccatcacca ccaccaccat ggtgacccca   7380
accccaacac ccaccggcac acagacccca acatcgacac ccatcaccac caccactacg   7440
gtgaccccaa ccccaacacc caccggcaca cagaccccaa ccccgacacc catctccacc   7500
accactacgg tgaccccaac cccaacaccc accggcacac agaccccaac catgacaccc   7560
atcaccacca ccaccacggt gaccccaacc ccaacaccca ccggcacaca gaccccaaca   7620
acgacaccca tcagcaccac caccacggtg accccaaccc caacacccac cggcacacag   7680
accccaacat cgacacccat caccaccacc actacggtga ccccaacccc aacacccacc   7740
ggcacacaga ccccaacccc gacacccatc accaccacca ccacggtgac cccaacccca   7800
acacccaccg gcacacagac cccaacatcg acacccatca ccaccaccac tacggtgacc   7860
ccaaccccaa cacccaccgg cacacagacc ccaaccacga cacccatcac caccaccacc   7920
```

-continued

```
acggtgaccc caaccccaac acccaccggc acacagagta caaccctgac acccatcacc   7980
accaccacca cggtgaacac caacccccaa cacccaccgg cacacaaaac cccaacatca   8040
acacccatca ccacccacca ctacggttga ccccaacccc caaaacccac cggcacacag   8100
accccaaccc caacacccat tctccaccac caataacggg tgaccccaac cccaacaacc   8160
caccggcaca cagaccccaa ccatgacacc catcaccacc accaccacgg tgaccccaac   8220
cccaacaccc accggcacac agaccccaac atcgacaccc atcaccacca ccactacggt   8280
gaccccaacc ccaacaccca ccggcacaca gaccccaacc atgacaccca tcaccaccac   8340
caccacggtg accccaaccc caacacccac tggcacacag gccccaaccc caacagccat   8400
caccaccacc actacggtga ccccaacccc aacacccacc ggcacacaga ccccaaccac   8460
gacacccatc accaccacca ccacggtgac cccaacccca acacccaccg gcacacagag   8520
tacaaccctg acacccatca ccaccaccac cacggtgaca ccaaccccaa cacccaccgg   8580
cacacagacc ccaaccccga cacccatctc caccaccact acggtgaccc caaccccaac   8640
acccaccggc acacagaccc caaccatgac acccatcacc accaccacca cggtgacccc   8700
aaccccaaca cccaccggca cacagacccc aacaacgaca cccatcagca ccaccaccac   8760
ggtgacccca accccaacac ccaccggcac acagacccca acatcgacac ccatcaccac   8820
caccactacg gtgaccccaa ccccaacacc caccggcaca cagaccccaa ccacgacacc   8880
catcaccacc accaccacgg tgaccccaac cccaacaccc actggcacac aggccccaac   8940
cccaacagcc atcaccacca ccagtacggt gaccccaacc ccaacaccca ccggcacaca   9000
gaccccaacc acgacaccca tcaccaccac cactacggtg acaccaaccc caacacccac   9060
cggcacacag tccccaaccc caacagccat caccaccacc actacggtga ccccaacccc   9120
aacacccacc ggcacacaga ccccaacatt gacgcccatc accaccacca ctacggtgac   9180
cccaacccca acacccaccg gcacacagac cccaaccccg acacccatct ccaccaccac   9240
tacggtgacc ccaaccccaa cacccaccgg cacacagacc ccaaccacga cacccatcac   9300
caccaccacc acggtgaccc caaccccgac acccaccggc acacagaccc caaccacggt   9360
actcatcacc accaccacta cgatgacccc aaccccaaca cccaccagca caaagagtac   9420
aaccgtgaca cccatcacca ccacaactac ggtgaccgca accccaacac ccaccggcac   9480
acagacccca accatgatac ccatcagcac caccactacg gtgaccccaa ccccaacacc   9540
caccactgga agcacggggc cccccaccca cacaagcaca gcaccgattg ctgagttgac   9600
cacatccaat cctccgcctg agtcctcaac ccctcagacc tctcggtcca cctcttcccc   9660
tctcacggag tcaaccaccc ttctgagtac cctaccacct gccattgaga tgaccagcac   9720
ggccccaccc tccacaccca cggcacccac gaccacgagc ggaggccaca cactgtctcc   9780
accgcccagc accaccacgt cccctccagg cacccccact cgcggtacca cgactgggtc   9840
atcttcagcc cccaccccca gcactgtgca gacgaccacc accagtgcct ggaccccccac   9900
gccgacccca ctctccacac ccagcatcat caggaccaca ggcctgaggc cctacccttc   9960
ctctgtgctt atctgctgtg tcctgaacga cacctactac gcaccaggtg aggaggtgta  10020
caacggcaca tacggagaca cctgttattt cgtcaactgc tcactgagct gtacgttgga  10080
gttctataac tggtcctgcc catccacgcc ctccccaaca cccacgccct ccaagtcgac  10140
gcccacgcct tccaagccat cgtccacgcc ctccaagccg acgcccggca ccaagccccc  10200
cgagtgccca gactttgatc ctcccagaca ggagaacgag acttggtggc tgtgcgactg  10260
```

-continued

```
cttcatggcc acgtgcaagt acaacaacac ggtggagatc gtgaaggtgg agtgtgagcc  10320
gccgcccatg cccacctgct ccaacggcct ccaacccgtg cgcgtcgagg accccgacgg  10380
ctgctgctgg cactgggagt gcgactgcta ctgcacgggc tggggcgacc cgcactatgt  10440
caccttcgac ggactctact acagctacca gggcaactgc acctacgtgc tggtggagga  10500
gatcagcccc tccgtggaca acttcggagt ttacatcgac aactaccact gcgatcccaa  10560
cgacaaggtg tcctgccccc gcaccctcat cgtgcgccac gagacccagg aggtgctgat  10620
caagaccgtg catatgatgc ccatgcaggt gcaggtgcag gtgaacaggc aggcggtggc  10680
actgccctac aagaagtacg ggctggaggt gtaccagtct ggcatcaact acgtggtgga  10740
catccccgag ctgggtgtcc tcgtctccta caatggcctg tccttctccg tcaggctgcc  10800
ctaccaccgg tttggcaaca acaccaaggg ccagtgtggc acctgcacca acaccacctc  10860
cgacgactgc attctgccca gcggggagat cgtctccaac tgtgaggctg cggctgacca  10920
gtggctggtg aacgacccct ccaagccaca ctgcccccac agcagctcca cgaccaagcg  10980
cccggccgtc actgtgcccg ggggcggtaa aacgacccca cacaaggact gcaccccatc  11040
tcccctctgc cagctcatca aggacagcct gtttgcccag tgccacgcac tggtgccccc  11100
gcagcactac tacgatgcct gcgtgttcga cagctgcttc atgccgggct cgagcctgga  11160
gtgcgccagt ctgcaggcct acgcagccct ctgtgcccag cagaacatct gcctcgactg  11220
gcggaaccac acgcatgggg cctgcttggt ggagtgccca tctcacaggg agtaccaggc  11280
ctgtggccct gcagaagagc ccacgtgcaa atccagctcc tcccagcaga acaacacagt  11340
cctggtggaa ggctgcttct gtcctgaggg caccatgaac tacgctcctg gctttgatgt  11400
ctgcgtgaag acctgcggct gtgtgggacc tgacaatgtg cccagagagt ttggggagca  11460
cttcgagttc gactgcaaga actgtgtctg cctggagggt ggaagtggca tcatctgcca  11520
acccaagagg tgcagccaga agcccgttac ccactgcgtg gaagacggca cctacctcgc  11580
cacggaggtc aaccctgccg acacctgctg caacattacc gtctgcaagt gcaacaccag  11640
cctgtgcaaa gagaagccct ccgtgtgccc gctgggattc gaagtgaaga gcaagatggt  11700
gcctggaagg tgctgtcctt tctactggtg tgagtccaag gggtgtgtg ttcacgggaa  11760
tgctgagtac cagcccggtt ctccagttta ttcctccaag tgccaggact gcgtgtgcac  11820
ggacaaggtg gacaacaaca ccctgctcaa cgtcatcgcc tgcacccacg tgccctgcaa  11880
cacctcctgc agccctggct tcgaactcat ggaggccccc ggggagtgct gtaagaagtg  11940
tgaacagacg cactgtatca tcaaacggcc cgacaaccag cacgtcatcc tgaagcccgg  12000
ggacttcaag agcgacccga agaacaactg cacattcttc agctgcgtga agatccacaa  12060
ccagctcatc tcgtccgtct ccaacatcac ctgccccaac tttgatgcca gcatttgcat  12120
cccgggctcc atcacattca tgcccaatgg atgctgcaag acctgcaccc ctcgcaatga  12180
gaccagggtg ccctgctcca ccgtccccgt caccacggag gtttcgtacg ccggctgcac  12240
caagaccgtc ctcatgaatc attgctccgg gtcctgcggg acatttgtca tgtactcggc  12300
caaggcccag gccctggacc acagctgctc ctgctgcaaa gaggagaaaa ccagccagcg  12360
tgaggtggtc ctgagctgcc ccaatggcgg ctcgctgaca cacacctaca cccacatcga  12420
gagctgccag tgccaggaca ccgtctgcgg gctccccacc ggcacctccc gccgggcccg  12480
gcgctcccct aggcatctgg ggagcgggtg agcggggtgg gcacagcccc cttcactgcc  12540
ctcgacagct ttacctcccc cggaccctct gagcctccta agctcggctt cctctcttca  12600
gatatttatt gtctgagtct ttgttcagtc cttgctttcc aataataaac tcagggggac  12660
```

atgctgt 12667

<210> SEQ ID NO 6
<211> LENGTH: 84
<212> TYPE: DNA
<213> ORGANISM: Homo sapiens

<400> SEQUENCE: 6
ggccagtgtt gagaggcgga gacttgggca attgctggac gctgccctgg gcattgcact 60
tgtctcggtc tgacagtgcc ggcc 84

<210> SEQ ID NO 7
<211> LENGTH: 560
<212> TYPE: DNA
<213> ORGANISM: Homo sapiens

<400> SEQUENCE: 7
atgatgctgt tgtggctgtt ggcaggaagc ttcctcacat tttcagttta aatgcattcc 60
tcctgatctt tccaaaagac ggaggcagaa cagctggttg ccatactccg cataaagtcc 120
tttgggtaaa ttgaaggcat ttagtgctat aaatttccct ctacacacag aaatacaaac 180
taccatcaga gaatactaca aacacctcta cgcaaataaa ctagaaaatc tagaagaaat 240
ggatacattc ctcgacacat acactctccc aagactaaac caggaagaag ttgaatctct 300
gaatcgacca ataacaggct ctgaaattgt ggcaataatc aatagtttac caaccaaaaa 360
gagtccagga ccagatggat tcacagccga attctaccag aggtacaagg aggaactggt 420
accattcctt ctgaaactat tccaatcaat agaaaaagag ggaatcctcc ctaactcatt 480
ttatgaggcc agcatcattc tgataccaaa gccgggcaga gacacaacca aaaaagagaa 540
ttttagacca atatccttga 560

<210> SEQ ID NO 8
<211> LENGTH: 102
<212> TYPE: DNA
<213> ORGANISM: Homo sapiens

<400> SEQUENCE: 8
tgtgttccct atcctcctta tgtcccaccc ccactcctgt ttgaatattt caccagaaac 60
aggagtgggg ggtgggacgt aaggaggatg ggggaaagaa ca 102

<210> SEQ ID NO 9
<211> LENGTH: 69
<212> TYPE: DNA
<213> ORGANISM: Homo sapiens

<400> SEQUENCE: 9
gtaaatatag tttaaccaaa acatcagatt gtgaatctga caacagaggc ttacgacccc 60
ttatttacc 69

<210> SEQ ID NO 10
<211> LENGTH: 205012
<212> TYPE: DNA
<213> ORGANISM: Homo sapiens

<400> SEQUENCE: 10
ggaaggagca ataactgatt tttctgcagt gtcttccttc tgaaagcctt tccccaacct 60
gaatgtatta aataccatgt catcatctaa atttcttatg gacttggatg ctgaaagtaa 120

-continued aataccttga gaaaacaaag aaaaagttag tattaatata taggaagaga gattcatttt 180
tgccattctt agtttgatgt ttgcatacag tcaaacaaga aagaaaatga aaaatttctc 240
tgtcagcctg cttggtaaac gattctgtat ctttatatat tttctagctt gaatagaaag 300
cacttcaaag aattatactt ttcatcattt tagaaatgac tcattagatt gaggctaacc 360
tttatgcagc tgctaatacc tacattgttt tggttttagt gacacattgt ttattttgag 420
tgtgaatttt ctcagaatct gactaagatc cttggtagaa tgctttctgt tgagtagatt 480
atagtctctt gaaaatgggt tgttattaag gaagaccaca ggacatcagg ctctctctat 540
attattgttt ccttttgtgt attttctgat taagtaaaga tattaaaact caagttattt 600
cactcaagga tgataaggat aaagttttat ttccttttaa tcctgattaa actgaaataa 660
tcctcaaaag agactttctt ttataaatac ttgatatagt ttttggtgat taaagtacat 720
atgcctgtca gtgtgaacaa aaagccattc atgctatatc aaaaattgac ctgtcaggtg 780
tattttatct ctgcatttac aaaaggataa tatgtacaaa tatttattaa tgaatttaga 840
aattaatgaa ttagtccatg aaaagaatat ttatgtgccc ataaacatta cttttggatg 900
atgagtttat gttgtatgac ttttaattaa acatttcaga gttaatttct aattttgacc 960
ccaatgaata agataataca ttcttttata tgtcttctgg tacatatatg taagaatttt 1020
tctagagtat atttctcagt atggaattac tggatcatgg agtatgtata tgttcagctt 1080
tactaatgcc aaaatgtttt ccaacatagt tgtaagcgat ttgtgccctc gataagcagg 1140
gtatgagaat ttccattgtt ccatgtccta gctgactctt gtgtctcatt gtccttttaa 1200
tttgtatttt cctaattacc aaagaggtta agtgtcttcc catatgtttc tgagccattt 1260
atgtttcctc ttatgttaaa tgcttttttt tttttctttt tttggctttg tccatttttc 1320
tattgggttg tctttttcta atttatttat gggagttctt tatatattct ggatattaat 1380
tgttagttat atatgtttca attattttcg ctcagtttgt gacatatttt caacccctct 1440
ggtgtctttt ggtgaaccaa actgattaat tttaatgttt aaatattttt ctttttttctt 1500
tatggcaact acttttaatg tgttgttttt ttttagaaat ccttctcaat ccttagatta 1560
ttaacgtgtt ttcatatatt ttcttctaaa agtttaaata ttttgacttt catgtttagg 1620
tttgtaattc atctgtaatt ttgtgtatga tataagatag agatgtaatt ttactttttc 1680
caatgtcctt atatatttct tgaagaagtc atcctgtccc cactaatctg cagtgccatc 1740
tctacagtat atcagatttc tatatatgtg tgggctcctt tcagaacgtt ctattccaca 1800
gccaaatcta cagtattaat ataactttaa aataattttt aatatctggt caaatttccc 1860
agccctctac ttacccacat gtttttcttt tacagcagtt ccttagctat tcttagtcat 1920
ttcttttcca tataaatctt aaaatcagct tttcaagttc cgtaagaaca cttgacagga 1980
tattaaggtt ctagttaggt atcccttatc tgaaatgctt aggaccagaa gtatttttgg 2040
atttgggata tttttttcag aatttggaac atttgcatta tatcagttaa gtatcccaaa 2100
atctgaaatc tgaaatgctt caatgaatat atatttttta gcatattgtt aatgcttaac 2160
aagtttcaga ttttggagca tttttggatt ttggcttttc agatttggga tgctcaactt 2220
ataatcacat tggttttata gatttataga ttaattttgg agaagaactg atatcctgaa 2280
ggtaatttat tatctatgag catgacattt ttctgtattt gcttagatct tctttaatct 2340
tttttcttc tttaatcttt taatgacatt ttcttttctt cataaaggtc ttgcatacct 2400
ttgttgagag aattataatt ctttataatt taattgaatt tcttattttt ggttattata 2460
aattgtattt tgaaatgatc tttctaacat tattgctggt atgtgcatgt gcatttggct 2520

```
tgtgcatagt aatttgataa cagaaaaaaa ctttctaaac tcttattttt ttttcttttt   2580
aattgtttat aaatgtatag attctttggg attttgtatg aagacaattg atataaatga   2640
taaaataatg gcattttatc tctttctcct aacttcatct atattgtgta tacatgtctt   2700
tgtgtctgtt catgtgttca tacacactgg ccaaagcctc cagtaaatac tgaaaatgga   2760
gagaagagat atctttacag tgttactgat tttacagata atgattttaa tgcttcacca   2820
ctgagcgtaa tgtttgctgt aggtttctta tagatacttg ctataaagta caggatgttc   2880
tcttttgttt ctggcttact aatagttttt atcatgaatt gttgttgaat attattgaat   2940
gctttttttg catatattga gatgaccaga tcattttctc cttcagtctt tggaaatatt   3000
aacagatttt tctaatgtta aactaaccat gtgttcatga agaaaccttt aaattatcgg   3060
attcaatttg gcaatatttg atttagtaca ttttacattt attatgagta agattgattt   3120
gtaattttcc tttttatat tgactttggt ttgatattaa gtttgtacca atttcttaca   3180
ttgagggcaa gatttatcct tctttctttt ctctcttgtt agactttggg tttggtgttt   3240
tcttggtagg atttttgttg ttaagaattg atgtactttc ttcagtagct gtagtaacat   3300
ttagcttctc tgtttctttt ttagtttgtt ttaggaattt acattattgt ataatttgtc   3360
catttcactt aagtactttt tatctgaggt agacttaact gctgattttc tcggggacta   3420
ttaagatctt tctcagtaaa tgttttgtga ttataattat aaacaaagga ctctgacatc   3480
ccttgacttc tttgatctta gagcttcctt atctttttaa tgttgttagt tgtgccctac   3540
tttgtttccc ttggtttgaa cctggtttgg atgtgcctgt ttaatctata aaagtccttg   3600
ttaggctggg cacggtggct cacgcctgta accccagcac catgggaggc cgaggtgggt   3660
ggatcacctg aggtcaggag tttgtgacca gcctggccaa catggtgaaa ccccatctct   3720
actaaaaata taaaaattag ctgggcatgg tggtgggtgc ctgtaattcc agctactgga   3780
gaggctgagg caggagaatt gcttgaaccc aggagacgga ggttgcagtg aaccaaacat   3840
ggtgccattg cactccagcc caggcgacag agcgagactc tgtctggaaa aaaaaaaaaa   3900
aaaaaaaaaa aaagtccttg ttaatggaaa tcttttttct tagatgctgt tgtgggaggg   3960
taataaatat taataattat gtactttgtt ttaaatttcc actggatgaa ttggcttggc   4020
tgatcttcac tcaaaattgg gaccaaatcc aaatgatttt gacggtttag agaagttaat   4080
gttttatttt gtttaaactg tcatagcctc tgagcattat gaggttttgc cataaccatt   4140
taattatgga gatagtttcc aatttttta atgataactt tttttaaaaa aaactttggt   4200
tactgtgatg tgcagtggag catagtagac ttctttttca ttgatgctga aaatggtatg   4260
tccccaagta gtagaaggga actttggaga agtaaaacta ttgccagatg ggcttgggtg   4320
gttcagtaaa ccttacaaag gcaaaaggct tatataaaat atgatcttca ttttctgttg   4380
aactactgct aacactgtat atttgcaagt cactttatta aatttctctt tgttccaatt   4440
aacacatctt tgctatgtgt caccagtaaa ttaaatggca attggccatt ggcttactga   4500
gaatcatcaa tttcttagtg gctaattgta tgagtgtaaa aacaagattg ctcacttata   4560
taaattatca aaagatataa gaaaacttaa aattccttct cagatttcta tagtaaacaa   4620
cccatacact ttcacctagc gtttaccatt aacgttttac ttctatccct tcatcccttt   4680
attaatcatc ttattctttt aatgcatttc aaaggatatt gcatatatca gtatgctttt   4740
catgaaatac ttcaacatac gtatcattaa ctggaattta atagttgttt acagcttttt   4800
tttgaagtaa aatttatgga aagtaaaatg cataaactat aagtgcatat ttgctaattt   4860
```

-continued

```
ttgacaaatg tgtttgctta tgaaacccaa agtcctttca agatacaaga cattgccatc   4920
accccagaaa gttatgtctt accttgttag agtttacatg taccaccatt ttccccactc   4980
ccacccgtca ttccaactct gctcttagac aatcactgtt ctaatttctt ctgctgtgaa   5040
ttagttttgc ctattttgga aatatacagt atgacgtctt ttatggaagg cctctttcac   5100
tcagcatgtt tgacattcat ctttaatgtt gtaagaagca gtagttcctt ccttttttat   5160
taccgttgta taaatatact acaattgact tgtctctttt cctgttaatg gactcttgaa   5220
ttgtatccag tttttggcta ttacgaataa cactatctac attcttgcac aagtcttttt   5280
gtggacatgt gtttttattt ctcttgggta aatatatagg aatggaattg ctaggatata   5340
agatagatgt atctttaatt ttgtaagaaa ttgttagatt attttccaaa gtgattgtac   5400
cattttatac ttcaacaaag actgtattag agctttggtt gctccacatc ctcaccagca   5460
tttgatgttg tcagtcttaa tcttagccat tctggtagat gagtagtgat atcgtgtttt   5520
aattacattt tcctaataac taatgatgtt gagcactttt tcatgtgctt gttagctatt   5580
catatatttt cttttgtgaa gtgtctgttt agatcttttg ttcattttgt tgggcgaggg   5640
atgtttcttt ttattactga gttgtaagag ttatatatat tacatatata ttcctcccac   5700
cccagaaatt ccccccaacc ccagaatttt cttctcttta tctatgtttc caactggagt   5760
gggccacatg agacattcct gtataagatt ggagagcaga agtgaagcag atgtcacgta   5820
cggttcacac atgatgtcgc ttatctgctg gctcatgtcg ttggctctgc agcagtcaga   5880
cctgcgactg ctccactttc gctggatcca ctttcagttt ctctgactcc tgggacacat   5940
gtgtgcagtt ctgtgacaaa ggagactagc tgtcctgagg acatccatac cattgaggtc   6000
agatgcagca agatatgata tgagtttcag tctatcctca tgggtttcag ctcatgctgg   6060
tgaattccag tatgttcttc ttcttcccta ctttacatcc atctttcctt cctggcagcc   6120
tgccctgtgg actccagcat tagatggaat gatctgctta atattgctta attagctttc   6180
acaattgcat gagacagatt tatgtaacaa attgtgtata tatttctgta tatgtgaata   6240
tgtatgtgtg ttgttctgct tctgtgattg acttctgacg gacacttccc aactcttttt   6300
atgagtctag cataaatttg gtaccaagac ctgataatgc tattacaaga agggaaaatt   6360
ataggccaat atttctaatg aacatggatg taaaaatcct aaacaaaatg ttatcaaata   6420
gaatccagtt atgaaaaagg taaaatttca tgaccaggtg aggtttattt caggaatgta   6480
aaattgaact ttcagaaaaa aattggtaaa attcaccact gtaaatgaat acaggagaca   6540
aaaacacgat catctcaaat atagaaaagc acaatgattg gctgtgctga atgctactgg   6600
ttgagtaaga tgagaactga gaatttatct ttgatttggc tatgtgatag tcattgctga   6660
ccttaatgaa gcagtttcaa tgacactggt agagattcaa ccttgatagg agagaattta   6720
ataagaatgg aaagagaaca aatggaaaca gtgaatataa atagtatgtc accgatttac   6780
actgaagaat gcagaaaaat tagattgtag atggaagaga gttggctatt gctatttaaa   6840
gatggaagat attgtagcat gataagaagt ggctatgctg aatttgtggg actcaagtaa   6900
caaaaggatt tacatgctgt aaacagtatg gaataaaata gacattcatc ctccttccca   6960
actcttaagt atgtgtggtg gtaatgggat cagtgaagtg gagaacgcta taagggtatt   7020
tgttattcag aaggtatagt acaaagattg gagagagaag agagaagaaa cacagtgctg   7080
tttagagatg aaagtgtggg aggatagata tctagagggg ctcatatctg gatggagagc   7140
aagggtaaga gagaacaagg tgtggtaatt tggctagcaa gggaattagt cctgacactc   7200
ccttagaagg tgtgtgtgtg tgtgtgtgtg tgtgtgtgtg tgtgtgtgga gttgatgtag   7260
```

-continued

```
ttggcaggga agggtagctc ctggtaggcg tttaggccac tcagaattca gcaataaaat   7320
taggaggtta tccttctgag acagtttgaa tttggttggt aagttgacct ccagtttttt   7380
tttctttctt tgagaagagt caacttgagt ttttttgttt gtttgttttt aatttgaagg   7440
ctcagaagag agatccaagg cttccagcat gtgggcttgt agagagtact tagagacgcg   7500
agatatgggg gccagctgag agtggtgaag atggttaagc tcttgttttg ctccaagaat   7560
tggagtgggt aaggtatctt ctcaccatgc tcaatgcagt tggtttgtga gatagtgggg   7620
tgggagacac agggagagtt tatgatgctc cactgtaatt agtccagtaa ctgtgagacc   7680
agttgagtag gaacgtggat atcctcaagc tttgttccac tgttacagct ggtaaacatg   7740
gatgaattga tttaaatatt tattttgcaa caatgtggat ttgaattatg gatatagttt   7800
cctcttttttg gttaattata tgcacatttg aattcatctc tgtctatgag tactagtgga   7860
ctagctgctt ccctggatct cgttactgga tggtatgttg ctcttagtgt catccaaaca   7920
gaattatttt aaaagtgaaa tgaagaaacc agttgtagtg aattacacat caccaatttt   7980
tagagctgta gactaatatc ttgaaaattg ccttaacatc tttttgccac aaatcaagat   8040
ataagtaaca ttaagagtta tgtaaggcca ggcgtggtgg ctcacacctg taatcccagc   8100
actttgggag gctgaagagg atggatcatc tgaggtcagg agttaaagac caacctggcc   8160
aatatggtga aaccccgtct ctactaaaag taaaaaaaac aaaattagcc ggctgtggtg   8220
gcatgtgcct gtagtcccag ctactcggga ggctgaggca caagaatctc ttgaatgcgg   8280
acagtggagg ttgcagtgag ctgagaatgc accactgcac tctagcctgg gcgacagagc   8340
aagattccat ctcaattaaa aaaaaaaaaa gttatgtgaa catgcttgaa atgatgttca   8400
tggctaaatt tttcagttac cttgtaaaga tgattcttgg atattgtttt gattctgagt   8460
acttttggag tcatctgata gtatgcttcg agaataacaa tctgatgata gctttcaaca   8520
ttgggttacc aacaaagctt gttattttgt atacattgat tcataatttc aggtttcttc   8580
accattatgg taagtagtgt attgagtctt cattctaaca catgttagga atttatgttt   8640
gtactcatgg atgtctttaa ccctcagaca tttctactta tattgagaac tctagactga   8700
aaacattttg aaatgtagtg gttttactat gtaggaggaa catgtgattc atttgttctg   8760
cttcattttc ttctgtttgt gatagagatt ggatcagatg aaagtgtctt gataatgata   8820
tacatgccat tcttttcatt ctatgtattt gtagtccttt tttgccatca taactttgtt   8880
tatgatattc cctgctctta aaataccctc atcttgtccc tccacctatc tatatctaaa   8940
atatccttca agaccttcct tttgcagctt tctctgagta ctacagccaa atcctcttgt   9000
ctgaactcca acatgtgtaa tacattatca tcctgtttaa atataattat ttcttatatt   9060
tattaattta tcaaggccct aaatatctgc ataagcttgc cttcatggtt tcactttttc   9120
attgttctct atattcatgc catgtaactt tggcatgcct tcccactgtg ggtggggtaa   9180
cctgcccact gtttgactct ggtttcaggc atgtgatttg ctttaactaa tgagatatta   9240
tcagatatca tgcaagcaga ggcttgaaat ggtcttgcac attgggaatt ccctcttgag   9300
cctctgccac caccatgaaa acattcccat gctagcctgc tggagagagc cacatggagg   9360
agagccatgc taccctaact gccatagctg aggctatcct cgatcagcac acatccattc   9420
aagcaccaga cactggagaa agtccacttg aggtcagtag agctgcctag cagatgccca   9480
actgacccaa aaagcataag acataaacat ttattgttgt ataccctctg aagttttgca   9540
tgtgttacac catattacta tagtaataga taattgatac aaatgtccta catggcctgg   9600
```

-continued

```
accatgcatt ccttgctaaa tttatttctt gctactctgt ccctctttcg tcactctcta   9660
gtgatattgg ccttctgttt ttatgatatg ccaagatcat ttctgacgca agactttttc   9720
cctgctattc tctttgtcag gagcatcttt ctcctgttat ttatctgagc atttatcact   9780
cattattgtg atgctcagct caaatatcat ggtttctgag agtgcttcct tgaccctatg   9840
agctaaagga gccccccttcc cactcattct ttccctattc ctttcactcc tttattttct   9900
tcactgtgct tctgtctaaa attatcttac ttgtttacat gcttattgtc catttcctct   9960
aatgccagtg agggagatgg tatcaagaac agagtatcaa gaacagagtc tggcacatag  10020
tagcctttca ataaacatgt aataaatgta tgaattattt tttcattaag agaacagatg  10080
gtagaaacta tgataggttc tagaatatga tagagtattt acttattacc taggtctgct  10140
gtgacaaatt accacaaact tgatggctta aggcaacaaa agcccaaaat caatgcgtgg  10200
acaggactgt gtttcctcca gagactctag gggagagccc ttccttgcct cttccagctt  10260
ctggtgactg ttggcattca ctgccttgtg gtagcatcct ctgctctgtc ttcaatgacc  10320
ttctcctctt tgtgtctgtt cctaatattc ctctgcctct ctcttataag gattcatgtg  10380
atggcattta gggcccacca ggattatctc ctcatctcaa gattcttagt cacatctgcc  10440
aagactcttt taggggtaac attcaaaatg aataaagaaa actacaggac aatatgcctg  10500
atgaacacag atgcaaacct cctcaacgta atactagcaa accaaataca gcagcacata  10560
aaaaattgct tcaccatgat caagtaagtt tcatttctga gatgcaggtt ggctcaacat  10620
atgaaaatca ataaatatga ttcaccacat atgcagaatt aagaagaaaa accatatgat  10680
catctcagta gacacaggaa aagctttcag taaaatccaa catcccttca tgataaaaac  10740
cctcaaaaaa ctaggcattg aagatacata cctcaaaaaa taagcgccat ctctgacaaa  10800
cctacagaca acatcatact gaatggacaa taactggaat cattcccctt gagattggaa  10860
taagacaagg atgcccactc tcaccactcc tgttcaaaat agtactggaa gtccttgcca  10920
gagcaatcag gcaagagaaa gaaataaaag gcatgcgaat aggagaaaaa gtcgaactat  10980
cttcactgat gatataactc gatacttagg aaactaaaga ctctgccaaa aggctcctga  11040
aactcataag cgcttcagta aagtatgagg atacaaaatt aacatacaga agtttgtagc  11100
atttctatac accaataaca ttcaagctga aagctaaatc aagaatgcaa ttccatttac  11160
aatacacatg gacacacaca cacgcctagg atacaaataa ccaaagaggt aaaagatctc  11220
cccaaggaga actacaaaac actgctgaaa gaaatcccag atggaaacaa acaaatagaa  11280
aactattcta cgctcacaga ttggaagaat caatatcatt aaaatagtca tactgtccaa  11340
agcgatctac aagtccaatg ctattcctat caagctatca atatcatttt tcacaaaact  11400
ggaaaagact attctaaaat ttatatggaa caacaacaac agaaagccca aatagccaaa  11460
gcaatcctaa acaaaaaaac aaagctggaa gcatcaaatt acctgacttc aaactatact  11520
ataaggctac agtaaacaaa acagcatggc actggtgcaa aaacagaaac acatagacca  11580
gtggaacaga acagagaacc cagaaataaa gctgcacacc tacagccacc tgaccttcat  11640
caaagttgac aaaaatagtc aatggggaaa tgactcccta ttctataaat ggttctggga  11700
tagctggcta gtcacattgc aaaagaatga aaccagacct ctatatttca ccatatacaa  11760
aaattaaccc aagagggatt aaagtgtaag accacaaatt ataagaattc tagaagaaaa  11820
cctaggaaac atctttctgg agattggtca taggagagaa cgtattacta agtcctcaaa  11880
agcaattgca acaaaaccaa aaattgataa gtgggacctg cataaactaa agagcttctg  11940
cacagcaaaa taaactatca acagaataaa aagacaacct acagaatgag agaaaatatt  12000
```

-continued

```
cacaaactat gcatccaaca aaggtctaac atctagaata tataagaaac aaacagttga  12060
acaagcaaaa aacaaatagc cccattaaaa aatggagaaa atacatgaag agacacttct  12120
caaaagaaga catacaagca gccaacaaac atttaaaaat gttcagcatc actagagaaa  12180
tgcaaatcaa aaccacaatg agatgccttc ttataccagt taaaatgggt attattaaaa  12240
agtcaaaaat caacagatgc cggcaaggct gtagagaaaa gggaatgctt atacaccgtt  12300
ggtgggaatg taaattagtt tagcccctgt ggaaagcagt ttgcagattt ctcaaagaac  12360
ttgaaacaga actaccattt gacctagcaa tcctattact ggtatgcatc caaaagaaag  12420
taagttgctc tactaaaaag acatatgtac tcatatgttc atcacaatgc tattcataat  12480
agtaaagaca tggagtcatc taggtgccca tcaaaagcag attagaaaaa gagaatgggg  12540
tattatacac catggaatac tatgcaccca tagaaaaaaa attatgtcct ttttagcaac  12600
atggaaacag ctggaagcca ttatcctaag caaattaaca caggaacaaa acaaaatacc  12660
acatgttctc acttataagt gggagtaaaa caggtacttg tggacataaa ggtgctaaca  12720
gtagactcgg gactactagg ggagggagca aggaaggcag ggggtagggg ctgaaaaatt  12780
gttgggtact atgctcagta cttgggtgac tcaagtaatc tgcacatgta caccctgaat  12840
ctaaaaagtt gaaattataa aaataataaa atattttttt aaaagatagc attcacagct  12900
tccagggatt cagtgtgaat acttttgggg gccatttttt ggcctgccag aagtataaac  12960
actatcaact ctagtatata agaggcaaaa cagtattatc tgcacatgac catgctgttt  13020
aagctctgtg cctacttgct ctcctgcaaa gcacagatat caatagtacc tatttccaaa  13080
gattgttgtg aggattgata tgtaagtacc cagtagtttc tatgacataa gtattcaata  13140
aatatcatta cactgttaaa caatgcctac tgaacatttc ctatgtgcca agcttcgtcc  13200
caagtacatg tcatgcctta gccaatttag tcctcacaac aatcctatga gtagagactg  13260
tctcttgctg aaggtcatat acctagtaag cggtggtgag attgaaaccc agacactctg  13320
ctccagaagt ctgtgctctt aaccgctcca gatgtggcct ttctgaatga tgctactgtt  13380
gttttaaaat aattgctcta ggctcggtgt ggtggctcac acctgtaatc ccaagacttt  13440
gggaggctga ggcaggagaa ttgcttgagc ccaggagttt gagaccagct tcagcaacat  13500
ggtgagaccc tatctctacc aaaaaaaaaa aaaaagaaaa aagccagata tggtggcaca  13560
tgcctgtggt cccagctact taggaagctg aggcagaagg atcgcttgag ctcaggaggt  13620
caagactgcg gtaagacatg attgtgtcac tgcactccag cctgtgcaac agagcaagac  13680
cctgtctcaa ttagtaataa tagtaattgc ttcagggcca ggtgcagggg ctcatgttta  13740
tagtcccagc actttgggag gctgaggctg gaggatcact tcagtccagg agttcaagga  13800
cagcctgggc aataaagtga ggccccatct ttacaaaaaa ttgaaaaaaa aaaaaaaaaa  13860
ggcaggcctc ttggtgtgca cctgtggtcc cagctacttg ggaggctgat ctgggaggat  13920
cacttgagcc caggaggttg aggctgtagt gagccatgat tacactaatg cattccagcc  13980
ttggcagcag atcaagaccc tgtctcaaaa aaataaataa aaataaaata attgctgtga  14040
aatttctatt aacgtttttg ggaaaaccag aggcttctgt gtgacatgtg aatcacagag  14100
gagaaatcat gaatctttat agccttgtgt taacatgact tccttttgtt gatagagtgg  14160
tttattagtc tcaagacctt tgaaatggca catgaattgc ttggacagat tatggagaca  14220
tccacccttc tttagagatt taagtaagta gaaccagtta gtgtgcctct tctgtttctc  14280
accttgctca atgcagaatg aacttggtgt atatccacca gaagcacctg cttatctact  14340
```

-continued

```
gtttgctgtc gttgcaggta tctgttgaga ttagctgtaa cgagttgtat gtaattttat  14400
aactaactga attaagaaaa gcctttgtaa gattcagtat ctgcttcagg tcattgaaat  14460
gtaaaattag aaagtaagct gagggcaggg gattttttc tgttttattc catttattcc  14520
ctcaccacct ttgccatcca ccaccaacag tttcttttaa atttagcatc cagagtagac  14580
ctttgacaac gcaaatcaga tcacttcatt tgttcattaa aaaccttcaa caggtttcac  14640
attattctta ggattatatt taacatcctt atacagtaat ctccaagcct ctccttgatc  14700
tggtaccctc tttccatctc taatctcttc tttaacactc ctatacttac ttactcagcc  14760
ccaggcacat tggcatattt gctgttgcct gaacatgcaa attccttgaa cttgctgttt  14820
ccttgcctga aactctcttt cctcagatat ctgcctggcc ttcctcttaa cctccaagtc  14880
ttgtctcaaa tatcattttt tcagtgaggc cttgcttggc cagccctttc cctcactata  14940
tcctgctccc caacaattga tttttactta tccatataac ttttatcccc ctgtgtgcta  15000
tatattttac ttatttcttg gttcattggc tgtctccacc aaaatgtaag tgccatgagg  15060
acaggaattt tattaatatc agtttgttca tttctatacc tttagtgctt taaacagtat  15120
ttagcacaca gtaagcattc aataaatatg tattggactg ggcacagtgg ctcatgcctg  15180
taatcccagc actttgagag gccgaggcag gtggatcacc tgaggtcagg agttcaagac  15240
cagtctggcc agcagggtga aaccccattt ctactaaaga gaccaaaatc agccagtcat  15300
ggtggcatgt gcctgtagtc ccagctactc ggtaggctga ggcaggaaga tcgctagaat  15360
ccaggaggca gaggttgcag tgagtcgaga tcaggccatt gcactccagc ctgggtgaca  15420
gagcaagact ctgtcttcaa aaaaaaaaaa aaaaagtatt gaataattga atgaatgttc  15480
tgcaatgtaa cagtccagtt agctatatag cactgcttgg gatgcagtgt ggcctgcttg  15540
tctaacacta ttatggagat atttctatgg atttatttgt attattaatg attgagttta  15600
taatcctatc ttttaatgtt gtgtacttca aatgctatta gttttctaga tagccaaaga  15660
tggctaaact ctcttctgcc cttctttaac tacaatttag agaagtggaa tttccatgta  15720
agcaacctat tgagcatctt tactgaatat cttttatttg tgtatatttt gggggtagtg  15780
gggaaaaggg acattttaat ggcaaaacct aagttagggc cccattctct acttgaaact  15840
ctagacattt ttaactgaat ttttaataaa aaattactga ggctttgtag aaaaagatga  15900
gaatggggta gcatagagta gttgcgctag ccacatttca agtgctccag tgctgcatgt  15960
ggctagtagc taccatattg aacagtgtag atatagaaca ttttcatcat tacagaaagt  16020
tctattatac agcactgctc caaacagtag gaactctgaa cattgagcta gataataaga  16080
tataatcatt ttatgttttg tatccacagt ggggaaatgt aaggaattgt gtcttgtaat  16140
tctcttatac tgtaccttta tttgctcaac agatgtttgt tttgcctcta ataatatata  16200
ccaggcactc tactaggcac tgggaattca ggggtagaca caatagcctc aggcctttct  16260
gtatggagct tgtattctca tggaagagca gtcattaagt agataatcat acaaataact  16320
atagtctcta tagtgctggt tgtatagtag atgtttaaat gactgttgat taattgacta  16380
atgtgtacag tcccatcatc ttcttagata ctgacaaatc ataggaacaa aaagctagct  16440
agtaatttat agttaaggtc tgcaagtaac attaaaattt cagtgcagtc aataaattta  16500
gttctgttca gactgttttt gttatttttc ttatttttga catagagcaa agattatgtc  16560
agttgccctg tggtttaaag ccacagttat tctagaagca cagttgccat cattgagtag  16620
tagctgatcc aaaagaattc cagccaaggt cttgccaatg atggaaagaa atgatgtgtc  16680
ctggaagttg ccaaaaatta tgtttttctt gttgaagaca atctttgtat ctttaagccc  16740
```

-continued

```
ttcatatgtt gtgacatgag cacatatgaa tgttccctaa aaggcaacaa ttatgctgtc  16800
aaattcattc aagcagtagt tatccctgta taatttgaag ttatacagat gcctaataag  16860
tgttttgatg ctgttgctac tgatgttgct gatgacatta catagaaagt tgcagaagat  16920
aaaccatgaa gattgacact ttaccattat tattttgatt ttgtttctct cttcacatca  16980
tcaagtcttg cttatgctgt taagccctag cagttcttta atatggaagg gggtatgaca  17040
tataatttcc acctctgaga attattttct ttttgttgat ttttgcaact tcatccagac  17100
ttctctaaaa tggtgtatct gtgtgctttg tattgttgga cactgacact gttgatgtaa  17160
taatcagggg cttattgtac cagttaataa ttagccaaac tcaggaggct gaggtgggag  17220
gatcacttga gcccaggaga tcaaggctgc agtgagtcaa gatcagatca ctgcactcca  17280
gcctgggcag cagcaagacc ctgcctcaaa aacaataata acaataatta taataattag  17340
cttagtaata gaaattcaaa gtatgggtgt ttaaataaat cagaattcag tttttctatg  17400
caaagagaag tgtggaaata aatttttaa cttcccaaat ttttaaacac aagatttttt  17460
aaaaacttga tcatctgata aaatagccta tacattttta gggaaataat tctgcatagg  17520
gtcttacctc cagatagcaa aacatttttt taaagctata gtaattaaaa tatggtacat  17580
atggaaccag gaataggtag ataaatgaat tgagtggaaa gctcagaaat atacccaact  17640
gtttgttata atttattata agctaaaaat tacactcaaa tcaatgagga aaagttattt  17700
tgtacaatga ctagtttaac ataatggtct aatcgcttgg gaaaaagtaa agttagaact  17760
ctataagtcc ttatcagaaa atgcagtcca aacataatta caatcatatg ccacttaata  17820
gggacatgct ctgagaaatg ctttgttagg tgattttgtt ctgaggactt tatagattgt  17880
acttacccag atctagataa tatagcctac tacccaccta gactatatgg tatagactat  17940
ttcacctagg ctataaacct gtacagcatg ttactgtact gaatactgta ggcaattgca  18000
acatgatggt attgtgattg tgtatctagc catatctaaa catagacaag gtacagtaaa  18060
aatacagttt atatatatat aaacagaata atgtatatat aaacaaaata tatatatgta  18120
tatatattta aaatggtatg cctgtatagg acacttccca tgaatggagc ttgcaggact  18180
ggacgttgct ctcagtgtca ttgagtgagt ggtgagtaaa tatgaaggcc taggacatta  18240
tactactgta gacttaagaa gtctacattt aggttatact aaatttattt taaaaaattt  18300
tctttcttca ataataaatt aaccctagct tacttttttt attttatgaa ttaaattttt  18360
taacatttta ttttttgta ataacagctt aaaacacaaa cacatagttc agctatacaa  18420
aaaatatttt ctttataacc ttattctgta agctttttc tatttttaaa ttttttatgt  18480
ttttacttat aattttttgt tcaaaaacta tgacacaaac gtacacatta gcctaggcct  18540
acacagggtc aggatcatta atatcactgg cttctacctc cacatcttgt ctcactgcag  18600
gatcgtcagg ggcaacaata ctcgtggagc tgtcatttcc tataatatca atgccttctg  18660
taatacctct tgatggacct gcctgagact atttacagtt aactttttttt tggaggtaga  18720
aggagtatac tctaaaataa tgattaaaag tatagtaaac acatacatca gtaagataat  18780
catttattat gatcaaatat gtagtgtaca taatcatatg cactgtactt ttatatgact  18840
gggactgcag tggatttgtt tataccagca tcaccacaaa catgtgagtc atgcattgca  18900
cgatgacatc actaggcaat aggaattttc cagcttcatt ataatcttat gggaccacct  18960
ccatatctgc agtttgtcat tgactgaaat gtcattatgc aacacatgac tatatatttg  19020
tacacggaaa aaagctttta atatattatt taaataatta tttactatat tatttaaaga  19080
```

-continued aaaatacaaa accattgtaa gatacattta aaaaacatca agcatatatt tctttctggt 19140
cgtgtatatg tttgtgtgtc tcaaagacta tacaatcatt cctacctatc acaggacatt 19200
ggttccagga caccaaacca aaatccaggg atgctcatgt cccttatata aaatggtgta 19260
atatttgcat ataacctatg cacattctct gagatacttt aaatcaattc tagatgactt 19320
acaacatcta atacaatata aatgctatgt caatagttgt tatatgtaat ttttaaaatg 19380
tttattatta ttgtgttttt taaattgttt tgttttagag tattttccat tcacagttgg 19440
ttgaatctgt ggatgcagac acacagggag aaccaagtat atggtaaaat atcagtagtg 19500
ttatttctgg gtagtgggat tataggtagt taaaatacat gtatttactt ttctttgtgc 19560
ctatctgtat tctgagtttt ctaaattaag ccttgttata aaaaaagaac taaaaataag 19620
tgatctctat tattgattat atcacaatgc atataggaaa tatgctttga tgcaggaata 19680
gttgttaaaa gttgatttat aactcatttt gttttcttat ttaattattt ttaagagatg 19740
gggtctcact gtgttgccca ggctagagtt gcctattcac aggcatgatc ccactaccga 19800
tcagaacggg agtttcgatc tgcttcattt ccaacctgag tggttcactc ctccttaggc 19860
aacctggtgg tctcccactc ctgggaggtc accatgttga tgcctaactt agtgtgggca 19920
ccccatttgt atatagcaca ttacagccca gaactcccag gctcaagcga tcctcctgcc 19980
tcggtcttcc tagtagatga aactacagtt gtgtgccaat gtacctggct tacataactt 20040
attttatccc cggctatcca gtactgactc ccggtgattc cacagctcca gattggcact 20100
tcttccccct gtaccaatgc gtaatttgat cagttttctt gattttcagt attcctgttg 20160
tgtgtgacta gcagtttccc ttttgccatg actttaaaac tccccacacc tggccgggca 20220
cggtggctca cgcctgtaat cccagcactt tgggaggcgg aggcgggcag atcacgaggt 20280
caggagattg agaccatcct ggctaacacg gtgaaacccc gtctctacca aaaatacaaa 20340
aaattagccg ggcgtggtgg cggcgcccgt agtcccagct actcgggagg ctgaggcagg 20400
agaatggcgt gaacccggga ggcggagctt gcagtgagcc gagatcgcgc cactgcactc 20460
cagcctgggc ggcagagtga cactccgtct caaaaaaaaa aaaacaaaaa caaacaaaaa 20520
aaaaactccc cacacgtgat gatcaccctg tggtcagttt tgtttgaata tgttccaacc 20580
tacagagtag ttgtgggtag ttttgactgt tcacgataat atttacaaag aattgaataa 20640 atattttttta tttccaaata ttggtggtgg tcgtggtgat taagaatctg aatcggatga 20700
accagccttg cctttagaga aatgtccaag ttacgtttgg tttatggggg ctctatattg 20760
ggagaagtga agaggcctag gacccaggat ttccaagata aggttgttca gcagggctca 20820
tagagaacat catttagaat ttggcttgtt cccaaatgat tccctttata attcttaaca 20880
gagaggctct gactgtatca gtatggtgtt tctttattaa gcaaaagctc atgccaagtg 20940
acttcaggtg catttgactt catatttagt cacagtgtga atttctgtat gattaactta 21000
cccatcaccg tgatgaagaa tgagatggtg gtagtgatgc tgtgattata ttacctcttt 21060
catccttgat ttttggtgat tagtcttcct tgaaactttc tcttgacatg gaccatcaat 21120
atggaaatct gaagcttcca ttgatggagg tggtctctga actagcatcc atccaagcca 21180
ggaatagact gcaataaact tattgagaat aacacaatcc ttaattgtat gtgtaatcca 21240
tggctttcac tgtctttacc acaccaaatg gcattgccaa gtcttatttt tcctccttcc 21300
tctgcttctc acacaacctc ttttcttcat gcaattccat tttccattcc atttccattc 21360
aatgaatctt ccaagcctaa aggtttaaat ctggtcatcc ccctctcttc catgcagttt 21420
catttctaag atggcattga ggatattgcc atggttgttt catacttagt tgttattgtt 21480

-continued atgataggta atatataatt ctgaactaaa attgctggct attttttgtc attgtgacaa 21540
caggttttag aaacatagca ctccaatttt gctactgaat gttttgatta aatgggaggg 21600
actagaagac tacaatttaa gagcaggctt cagcaataat ttttaaaaat agattcagag 21660
tcgatcatct tactatattt ctatctaggc ttatctccct tcatgcagtt agttacaaca 21720
cttggagggc tgtttccaag actggcacta aagaggtcac tttttccact ctctctccca 21780
gaaaatatca ggaagtgcag taaggttcat gaaaatttaa gcttgaagtt tagaaaactc 21840
aaaacaaccc aaaccctcaa acattcagtt tggtttgaat cttggacaaa ggttttctat 21900
gcagctagtg gagttatttc agtttaacgg ctgtagtaac ttcatttcag ggctagggga 21960
aattatgaaa ccataacttg gatcttattt taacaaaacc aagaaataaa aacactgggg 22020
aatctgcatg ggaaagggga cctacctaac cccaattgct gctattttac tgtggcagct 22080
cctcttacta taggaattat gaaaccattc tttccaattc cttcagagag agctgacttt 22140
tgaaaccgat tgagtggcct gcatccaatt aataaccctc ctgatgtgcg caacagggaa 22200
gatctttcat aggtgattaa atccaataga gttaaggtct gtcatcgtga tttccctcct 22260
ggtcaacttt catttcaaaa gtcatcccag gagaaccact gtagttcttt acctagttga 22320
cttctgaaac aaaattttcc acttcaaaga gagcccaata atttagaccc tatcctcctt 22380
ggatacaatt tatttttttcc aagaataaga atttaattta atgactattt attgagtggc 22440
ttcattatat ctggcatagg ataatatatt ccaggcagag gtatacaaca tagggggaaa 22500
aatgtcctca aagatctttt ggaccagttc aataatcaac aatgaaacat cttagaacaa 22560
aaacaaattc aaaaaggatt tattttgaaa taatctagaa aacctcagtt gatttttaaa 22620
catacccaat agagtatgtc acctcattta cagttgatca cttatcaaat actgcagagc 22680
aaaatgaggt cgagcctcag gctctgcaga tgtggagcac agcctaaagg ggcaaagcat 22740
cagcagcctg ctgaatttct gaagcacaca atctcagagg atttccggac tatttggggc 22800
ttcagagcat ccagaaatac tgaaaattta ataaagttcg tgttttctta tttaggtaga 22860
gacagatttg ccagataata gaagtgactt aactaacaag gttccagtta ataagtgcca 22920
taaatattcc cccaaagtat ctatattctt atcaaactag cttgttctct taattgagga 22980
tatacgtagt gattttagtt ggattatatt aagcattcac cacccttttta agtgattatt 23040
tctgctatta tatggaatca tgttactatg aaatttgaat taactcacat gaaatctgaa 23100
tcacagccag tgaaatgtgg ttaatggtat ttgttgtaac ttgaaatttt cctttttttt 23160
tttgcatttc ttttaaaata ttgttttaat attatgcttt gatgatgtca gtatctaatt 23220
tctttccttc tttatgtact ttagaactac agggagcaaa tctgtttctt agaatataaa 23280
tccatctagt aaacttttca aaatttggag atctcctaga actattttct gaactaataa 23340
tgatgcaata atgattacag ttaatagtgg aactgtagga atatcatatt ctttaataac 23400
ttgaaatttt aaaatttgat tctgaatatt tatcaaaact attattgggc aaccaataca 23460
tactgtgtaa agttctgtac ttagggattg aaccagtggt tgaggaaatg aaacaaatct 23520
gaatgttaaa tgcctattaa gtggcaggga cagtcaattc caaacaagga agtaatcatt 23580
tccagatggg gatggtctga gtcctcatgg aggaggtgaa attagtgttc tcctttgaaa 23640
ggtatatgca tttagagact agtgagcacg tgtttcagag gtgagaaatt gatgcatcag 23700
aggctggaaa atgcatgctg tgtgtgtgaa ggacaatgag aagacctctt tgctgggctt 23760
aaacacagag ttgatgtagg agagtagtgg gtattagagc ttaaaaggta ggataaagcc 23820

-continued ggattttgga aggctgtggg ctttttgtca tagatgcaag gagctgtttt aagtttttga 23880
gatgaggatt gaaatggtga agtagtgttt taggaagata acgcaggtag taacagggta 23940
agtgggaaag aaaatggttg aagatacgac aattgattag aaaatttgca cttgcctaag 24000
aaaagatgat aaaaaatcta gtgtgtagta gtggctacag tgctggaagg agaaacatta 24060
ggaagagaac aaggaatcaa tataattttg agattgctag acatgggaag tgagggacaa 24120
cttaaaaatg acaccttttg gcttaatgta tgattttgaa cctgcgtatc agggataatg 24180
attatcataa atgagaaatc tggaaaatag gtcaggttgg ggttaagggt agaaaatagg 24240
ctttgtttta agtgaattgc tcttgagata gtggcatgtc ttctaataag caggtggaaa 24300
tgcaggactc aattttatga gagagatcag gactagtaac aaaaaatggt gaccatttat 24360
atataagtaa caaccaaagt tggagaggta aatatcacct gaaggcttag aaatgctaaa 24420
aatggaaaag caaatatctg agctgtgaga tgtaggacac acgagattta ggtgatgaaa 24480
ggtggaaaaa agacagtaaa agagacagaa aacaaagcaa ttgaaaggta aagaaaagaa 24540
ccagaatatg atagagtcat agaagtcaaa caagttatga gttttcaaaa taatagtagt 24600
gattggcagt atctcatact ttagacaggc tatgcagaat ggggaatgga aaacaccatt 24660
gattatgtca actaggagtc tttgaagcca attaagtata attttcatag agtaggaaga 24720
gcagagccaa attgtgtgag aaataaggag gcagtcgtgg taagcaggta tattcaaccc 24780
tttgggaaga aaggagaaaa aagaacagtg gcaagatgag taccaggccc tctccttttc 24840
tccctcccca ggcagattca atctctttca tgtagaatca ccatttgtat gtcaatacct 24900
tctggaatta tatcacaaat atagaacatc gtccctaaca ccctagctcc catatatcaa 24960
cagctcttac tttggtatca atagatgcca cttcaacttc aacatccgaa actaaattta 25020
taatttcccc gtgctcctac taaaaaacaa aacaaaatac aaataagcat aaataaacaa 25080
caaccaggtc ttcttttagt gttttccatt tcagtaagta acatgacact ctccccactt 25140
gctcacgcta gaaagctcgg ggtcattttt gataccccccc tttgctcttc atttctgtca 25200
tctaattcat caccaaatct tgtaaacaca cttctctcca catccactgc cccactagtt 25260
gaagactcgg tcatctgaac aaactcagta atatttcacg tgtctcctct gcatctcctc 25320
ttgctcctca cagaagccag tgtaatcctt taaatccaca aacctgatta ctattaccct 25380
cctatttaat accttctagt ggcctctttt ttccttcaag ccaagtgatg ttatgaaaac 25440
aactatttta gaatgaagca actaactctg tatggaggaa ttagaaaaac cttcattaag 25500
atattggcat atggactggc cttcagtgtc ttcaggtgga gaattctatt agtgtgaagt 25560
atgggatgag agtgacagaa gatcattccg gcttgaggaa cgtcatgtgc caaggtagga 25620
agtaggtgtt cagaaaagcg tgacaagttc agagggtgat gtcaagggat ggggagtagc 25680
tgtagaagcc agtttttgaa agccctttga tgttggattt tatggaggtt ttaaagcaag 25740
ggataatata aagaaccaag ctttttgtgg caaaggggaa agttgactgc aatgtttgag 25800
agtcttagag aagagagagc agtttagtgc ctgttgtagg gacccaagaa aggtgataga 25860
ggccaagaca aaggctgtgg ggctggggag aagattccag gcatatttag agtaggacct 25920
acagaagtaa tgcaacattt gaggctagat gtccttgaat aatgttattg tgagtgggtt 25980
tatgtgcaaa gcctatgatc tgaccctaaa ttgacatgtt attctgtggt ctcatactct 26040
gtagaatgta ttatttttgc cacatgtaaa atgtactaga gataaattac aattagtttg 26100
tttcctagtc aaagctacac taaaattaca acccagtaaa aatattttta agaatccaaa 26160
tatctggatt tttcacagtt ctgtctctga taagttttag aaacttggtc aagtcatata 26220

-continued

```
ctcagccgga ggcttaaatt tctcatttgc aaaaggaagg agttgactag actcactgaa  26280
tgacctctaa ggttccttca agttccttgg aaccagtgtc aacctctagg gtatttttct  26340
gctttagttg attgacttga ttctaactag caggaagcag acggcttcag agtttcttga  26400
aaacatagtt atctccttga agaactgtgg tctagggagt gttctgagta gcattcgtag  26460
acccaccttg tcttataaaa tgcattacat ttataatcct tctagaggat ctttccaatc  26520
tcccgtagct gggtaccaag caaaaatcat tccagttaat aagagccatt tgttggtaat  26580
agttctatta tatttggtgt ggcatatttt cttttctccc caaggcttct cttaactagg  26640
agaaacttaa aagtacattc attgtcaagt cttcctaggc ttttgatttc aagaacttgt  26700
gtagaattat gtgttttttt ccttcaagta caatttgcag aagggtagag acatatataa  26760
tttaattgaa caaatttaaa cttccactgt gtatgaagca ttgtggagaa aaagcaggat  26820
gggtaaagga atgtgccaag agggataagg cgcaatttct gtcttcaagt aagtatatta  26880
tttaacagga gagcctacaa tgttaataca tacttcaagt aggtatatga aaatggtagt  26940
acagtagaag agagtgctac atgtaggatg agtatgatta ctccagcctt gggcttgcaa  27000
attggaataa ctgtcttctg gtaagcgcta ttcctaaatt ctgtctgagc tggtgaatat  27060
tggtatgaat aacccaggta taggtctaaa ataattgatc aacttgtctt tggcaagtgt  27120
atataaagtt ttaagcaatc tcttaaccac ttcagattac agcgtattgc tcatgtgaga  27180
gataaaaatg accaactgct tgaaaatggt tgattggtta taaatagaca cagtctaaat  27240
ttttggcaag agcatgataa aagcttttat gaagttatga aattgtggca acatattgtc  27300
aactgtggca cttgaagtca agtcattaga gaatcacatg aacagattta gtatactact  27360
aagctgacag acatactggc ataaacagtt attaagctgc agactaaact gaagatcaat  27420
tttttaaaaa tgatgctttg cagcatgttg tatgggtatt acatttttta tgtacatcat  27480
attcaactcc tggatgagtg ttatcttaag gttttctggg ttgaatttaa cataaagata  27540
acaggattcc atttctaaag atggggcatt tgtctcattc aatgtgagtg ctaaaatatt  27600
cttgttctat aattcattct tctgagagat aactatgatt tctggtagtg taaaggtgtt  27660
cttccctgtt ttgtctttgt accctgagaa taaacaatca taggtaaaat aaacttaaaa  27720
taaattgtag gtgaaataaa cttgcaggtt taaaaagcat aagaaagcta gtaagccagg  27780
aaactggtat gtatatatat tttataaacc tggtattata ttttatgtct tcatctaatt  27840
atgaaagtga ttaaaaagtt taatatagtg aaaaatgtgt ctaaattgtg acaaaagttc  27900
tgatcccaga tttatgtctg tatttgttct cacgctgcta ataaagacat acccaagact  27960
gggtaattta taaaggaaag aggttcaatg gactcacagt tccacatggc tggggaggcc  28020
tcacaatcat ggcagaagac aaaggaggag caaagtcaca tcttaggtag cggtggacaa  28080
gagagcttgt gtagggaaac tcccatttat aaaaccatca gacctcgtga gacttattca  28140
ccatcatgag gacagcacca tcatgagaag agcatcatta aaacccgccc ccaagtttta  28200
attacctccc accaggtccc tcccatgaca catgggaatt atgggagctc caattcaaga  28260
taagatttgg gtggggacat agccaagcca tatcagtgtc actaggcctt taagttggag  28320
cagtcctata agagggcatg gaaaagtcta agtcacctta aggtatgttt ccaccagctc  28380
taagcctcta ttctccatca gtatgttaag gcatactgtt taaagaaatt tttgttaaaa  28440
tgaagtctgt tgtctggcag gagtaagatc ttaatattag ctgacaatta agcacttaat  28500
ttgtgcctaa cattatgcta aggactgtac attggctctc ttaatgctta ttaaatatag  28560
```

-continued

```
tatggctata taatatatat aatatataat acttatgaaa ttggtactat tgtatttaat  28620
catttttaag acacttttca cattttagca ctctaaaatt gggatgtttt acaatcagtg  28680
actttttttg ttgttgttat tgttttgaga caaagtcttc ctctgtcgcc cagactccag  28740
gctggagtgc agtggcacta tcttggctca ctgaaggctc cgcctcccgg gatcacgtca  28800
ttctcctgcc ttagcctccc gagtagctgg gactacaggc gcccatcacc acgcccggct  28860
aatttttttg tatttttggt agagatgggg tttcaccgtg ttagccagga tggtctggat  28920
ctcccgacct cgtgatctgc ccgcctcggc ctcccaaagt gctgggatta caggcgtgag  28980
ccaccgcgcc cggcctacaa tcagtgacat cttacaaaca taatttagag tattcttgtt  29040
ctgtaagtgg cacataaaat catggtgaga gtgacaataa gaaagcatca tagattagat  29100
gaaatatgat attagccacc atcccccttt acccaatctg acctaaaagg aaccgaaaca  29160
tgaagaagtt aagtaatctg ttcaatatca cagaactggt aaatgcttga gccaggattc  29220
cacacaattg tttaactcaa cccaggaaca atgcttccac acagcatacc atgctgcctg  29280
ctggtaatct accagcactt cttaagcttt ggcgaaattg gtgtatctga gtagccatct  29340
tcagagagct gcacactgga gttgcagtgg cacagtggag ttgggaggag agagaatttg  29400
caaggtccag aatggactgc tgagtgaaga ggcatggtgg aagacccttg gcagtcgggg  29460
taatcatgag tgaaatagac cctgaaagga cagaaaagtt acaggaatgt agggaagcca  29520
taaaggtgga ggccacccat tttactattt tatccaggtc cagacctgcg tgtgcaaata  29580
catctatatg ggacacagaa agaaaattct tatgtatcag ggagagttat ttatctatag  29640
ctatatatta tctattttta tatatttatc catatacgta tatctaaatc catatatttt  29700
gagagacaga aaaaaaaaga aaaaagaaag ttgtgctttt tttttttttt ttttatgatg  29760
gaggcttact ctgttgtcaa gctggagagc agtggcatga tctctgctta ctgcagcctc  29820
cgcctcccag gttcaagcga ttctcctgcc tcagcctccc gagtagctgg gactacaggt  29880
acacgccacc actctcagct aattttcgta tttttactag agatagggtt tcaccatgtt  29940
gggcaggatg gtctcaatct cttgacctcg tgatctaccc gcctcagcct cccaaagttt  30000
gtgctttttt aaagggaata ttacattatg aataaatatt ttcttatcct acaattagaa  30060
tttaagattt gatgtgttct gcatgtttct tttttatttg ctttcccccc catagtgcca  30120
tagcacaatt tagtgtaaat attaggaagg gcaagcattt attgaataca taaataataa  30180
gaactctctc tttacctcaa ataccataca gaatcttgga agcttatttg agtttaacaa  30240
aaagatgctt taagtggggg tggggaacct cctaaagagt tgtatcagtt actgaaataa  30300
cacagactag tgtaatttct attcctgctt gtcaagaaac aaggtaggca aattaaagtc  30360
atcaggatct agcactgctg ctctgcctcc aacagaaaag atgagccaat gaaaagacaa  30420
gccagtgaaa atacactgtt actccctgtc agccccagtg gccatatgca caaacactat  30480
gcagaccaac acgtacacac acacacacac acacacacac acacatataa atttatgtat  30540
tttcttttgc ctatgtgtct agtcagctta aatgggtcga ctcgtgtttt ggctcctata  30600
accaaaccag actctttggc tcagctctac ctgcaaactt tctggcctgc ttcagtatag  30660
tgaagtggtt taagtttctg agaacaaata attaggctct aggagaaggc caggattata  30720
caaaacccat tcgtttttgc ttctgtgggt tctgtgtctc cgtaaaaaag gaaaacaaag  30780
ttaggtaaga acagtgttca gctatgtgag cttcatgata tttctcctat tatgttatca  30840
gaacacttat ttaattttg ttgttctgaa cctgagatac ttagggatta gtattttaag  30900
ttacatctcc ttttaaccaa caatataaat cttagactca gaattagtgt tggcatggac  30960
```

cggaatctgc ccttatcttt gttccctcac cttatctttg ttacttatct tcactctttg 31020
gacttaaaag gtaatgaagt ttcaaactag gtttaggagc atcttcagct acagaaggcg 31080
agatataagg tatttattta tttatttatt taaacttact ccactatctt tctatggtac 31140
tttctccata tcataaaaac tttggagacc tgtattattg ggaagattgc tcagctacaa 31200
cagagactaa gtgaggcact gacttcatca agtgattttt ggtgatcaag cagcaataaa 31260
tgtgcccaat ataaaccttc tcttcctcca gttcacaggc acaggattta aatcaatttt 31320
aagtggtttt aaaatgtagc agagatttca ctttttaggt atttttttctt tatcagagat 31380 ataacttcca agagattttt ctttattact ccatttaggt gtttttccaa attatgaatc 31440
atctactata cttatttatt aattgatact ttagtgagtt agagtgaact gcttgcgtct 31500
tcatttaccc agaggtgacc actagtatta tttttataga agttacagat atttaatttc 31560
ctaagaaaac cacaaccttg tctgttaagc ttggagtgag gtagacagag gagagggcag 31620
gaagcacttt tctcacattc aagctcaaca tcatgtccag aggaaatagg acagaaacct 31680
tctttcccag tcggggggct atttcctaag ggaaagcagg gaagtgagtg ttcctttcct 31740
aagggaaagc agggaaggga gtgttcccct cgatggcttt attttctgtt tttaatctag 31800
ttcgtcagat ggaattttat gattcaggaa ttatcagtgt cacctatgag ttattaatag 31860
aatagcaagt tattttgacc agtgaggtgg aggaaaagga aatgataata agagtaactg 31920
ctcactttat gggacaagga gatgaggtca gaggagagta aaaataatcc atgtgaaaga 31980
ttatgtaaaa gttagctaga taggaattat tctactcctt tccccaaata acttttgtag 32040
ggtaatccta attccttaac ttaaaaataa ggacaaaatt atgatagaaa actagtttaa 32100
gccttagaga accagagaag tgtgctttat ctttcatttc catatttatc ttcacccttt 32160
gctttttcaa gctgtggaca aaaactccac cacctttaga ggttctggct tatcctaata 32220
atttgaatct ttccttattt tggtttctaa gctatcaatt cattttcagc ttaacctatt 32280
ctggagcttg gtactgagac tgcagagaag ggaggtaaga aaacctcaac atttctaaag 32340
tttggaagtg aacattggac atattccttt atggttcaag tgcaatgtta taactcttca 32400
atggtgattt agtaacttgt cacatctgtg attttcatgt gtttattctg ctttttttatt 32460 tggagtgcca gagagttttg cttgggtcct tcaacaattg tcttggtctg atacctggca 32520
acacaacata ataatcaatc tgggtttgta cttttcattg gaatgctgaa aatgtacagt 32580
ttggcaaaga ttggaagggc agttctatgg aactacacca actgaggtca ttggccacat 32640
gaagatggcc agatcttcca ccagaaacag acaaatgatg agttttgagg tccaatgaag 32700
tggtcactct cataattatg gcaaatttat gaactctgaa aacagttcaa ttgcatggcc 32760
ttcttggatt tttgtacagc ttgaatgaca gacttgtaga ctctgaagct gatggtgaca 32820
gagaagagag ccatggtgaa ataagaagcc acagtgatga tgctgaaatc tccagggaaa 32880
gtagcatgat ccatgtgggg tgaagacaaa ctcagatttc ttcacttttt gtcaggaaac 32940
cagatggtgt attatacaga aagctgaaga acaggctccc aggcagcccc tttatcacac 33000
ctccttctcc tgttgctggg catggagtgt ttgtccctca aggacaaaga ggaattagat 33060
ggaattgagt ggcctccaat agctttgcca tgggcttttt cagcaaggac aataggaaaa 33120
gaaacaataa aataattacg ccatgggttc tcccaagtcc cttcactctt tccctccatg 33180
cttagacgcc aactactagt aatgtcttga tagctgacct tctagatttt attattttac 33240
ataccatttt gaacctttct tgcttaatat ttcatttaaa aatctcttcg gccattgtat 33300

```
ttttcctcat caaaaatatt ctccaaatgt tttatttcca attgtctctc taccccttgct  33360
ccaatcccat tccacacagg tagctaccag taatattttg acttcaatta ttttatatgc  33420
taactggaat tatagactgt gataactgga agagaccttg gagatcatct ttccatcttt  33480
ccctaccttc tttcactgtc ctaccactgc aggcttccag aagatatata gacaggctaa  33540
atgccccacc ctaaatccca cctcagctag gaattgacat gggactagaa cccaggtctt  33600
ttcattgcta gttaagggac ctcaccaacc tcatcccaca attttatatt tttagtttgc  33660
tggatgtcct aaagaagtag tttctgtaag acggatttga gtggtttatg gccagattga  33720
atttacaagg tgaccatccg tttttgaagg aaaaacaaac acacttctaa ccaaatagaa  33780
atgactgtag ttcatctatt ctgtccctcc tttggcctcc atgactggtc ccacaggacc  33840
agcgttctgc tttcctggag cagctttgtt gtactgagat tgtccttaga tccatctatc  33900
acatggtaac gttggccttc ttttctcttt ttttggtcac ttgctttggg cataggcaca  33960
gctctccatg cttttgcttc aaatgtttct agaaagatgg aacttaaacc agctggctat  34020
tggagttgct gatcttctgg gtatcttcta aatattccac ataaaaccag gatttctcc  34080
tgatagagac attgtgtttt tttattcatg tgccctcaac tgagatttat aatttgatca  34140
gtaaattctt acttacctta aactctaggc tggccttttt ctttatattt atatatctat  34200
atctatatct atctatatat atatttatag attttttctt tatattttta agcagacccc  34260
tccctagact ttcactctaa gttcaatttg aacacttctc acaccttctt ttatagacat  34320
aaaatgcaca ctttcacaaa ataacactaa taaaaacctt cagatctcat tctacctcca  34380
ccccctaacc attctcagaa cttctcactt acctggccca cctagaagtc ctaagatcac  34440
tcttttccac actggcccag atctttggtc tttgttcagg gtccataatg tcttttgagt  34500
tatattaagc atgcttactt taactatagt cagttctctg acacagacag aattcatagt  34560
gagttttgga taaggtcttt tgttttgttt tgttttttttg tcaaggatcc aaattgaccc  34620
aacttgaatt tttaaagaag aacatgtcag gggtggatgc caaagaggcc cactctgcaa  34680
atatattttg caattaacag agttcaagtg agctcttctg agtttggtgg tggctgttgt  34740
tgcttgggga tctctttctt tcacataagt ctctgtctat tgtttccctt tgtgtgtgct  34800
tgtgtgtgtg ctgtgggaca tgataaacaa gtatcatttt gtttcatgta attacagaat  34860
catgctttta tgtttacctt tcatatccac tttaaggata gaatctgttt tacaattggg  34920
actgcttcta tgaccaattc tgtagtgttg ccttcagttc aggcacatgc ctctgaaacc  34980
ttaatcgcaa acagatgctg ttctgaatca agagtttccc tctttggcta ctcagcctga  35040
gcaatgagct gcctgacttg gatcctacag gcttcttgaa aaactccaca ggctgcctta  35100
ctagcacact ggtaacatgc agaagattga tattttccag gcccaagcaa gactttgaaa  35160
tagtacctag cagttgcaga gagctattta ttttcccctc ctcccagaag tgttttcaca  35220
tacatgatct cattttatcc ttcaaatagt ccttggagtt aagtaggaaa agcagtattt  35280
tcccctagga acctgaggtc cagagatgtt aagtaactcg ctcaaggtca cacaattagc  35340
cttgacttgt agtctgttat tctttccacc aaaatgacac tagcatttac tttgtcttgt  35400
ttcaaagttg ttcaaagtct tttaggtgct ggttggatcc aagctgtcat tcttatagct  35460
cagatttaaa taaaatttgt aacatctttt agtgtttcat gtgttttttt ttttccccta  35520
ggccttaaga tgtgtctaaa gtggtaattt tgtggggcct taaaaattat gtgggagaga  35580
gaacctttat aaataaaagt tgaaggaaaa aaattatttg gggagcttgt tcagtagatc  35640
atggttcaat agagcaaaga tgcagtcgta aatttggcat tctataacaa aaaccaccca  35700
```

tgtgattctg aattaggagg tctgtgtaat cactgttctc agagctaaag taagcaaggc 35760
atgtaagacg tctgaggctc actttcctta tttaaaaaac aaaggcaaga ctagaatcaa 35820
ttagtaaatt gtctccagaa attaacatag attctaatct cctgtaaact taacagctcg 35880
catcagcatt cttatgatgg aagaaacagt atttgtctga aaaaatacct tggagttaga 35940
aagtccccca caagggactg ggttttctgg agagggaggg aggaagaata gaggagaatt 36000
tattgaaaga catgaagttg ggaactctgt aggttaagga ccaacagaga aatccctagg 36060
agtggatggc cagaaaggac tctggagaaa gagggatgat tggtatagag tttttaaatg 36120
tttgctctgt gatcttcata tagtcagtaa aatctatatt ttgtgtgact ggtaactttc 36180
ctataggaat tcatgaagag gccgagcttt gctttcagaa tgacataatg cagaactgag 36240
cagaagagat actgagaata taagtcttgg gaatttgcag aagtcttggg gacagctttg 36300
gatttctgca aactagaact gaaggcttaa atcaacttca cttaactatc catgggatca 36360
atgtgatcca ggtgatgtct ggggtaatat atgacaataa gcatgaagat ctagaaaata 36420
ttatttaaaa aatactctta tggctttaga acaggggtct ctggtacccc acagaggtac 36480
cggtctgtgg tctcttaaga accaggatgc acagcagaag gtgagctata agcaagtgag 36540
tgaagcttca tctctgctcc ccatcactca tagtacagcc tgagatctgc ctcctgtcag 36600
atcagtggca gcattagatt ctcatagagg tgtaaatcct agtgtgaact gtgcatgcaa 36660
gggatctagg ttgtgtgctc cttctgataa tctaatgcct gatgatctgt cactgtctct 36720
agtcaccctc agttaagacc atctagttgc aggaaaacaa gctcagggct cctactgatt 36780
ctacattatg gtgagttgta taattatttc attatatatt acaatgtagt aataataaag 36840
tgcacaataa atgcaatgca tttgagtcat cctaaaactg tcttcctccc actggaccat 36900
ggaaaaattg tcctccatga aaccagtccc tggtgcccaa atggttggaa actgctgctt 36960
tagaaaaact aggataagat tagatatctc ataataaagg tgcacatcaa gaaagtgaat 37020
gtgaacaaag atgtttgcaa acagagtaca tgaagatcaa gaaccttgag atgcagttcc 37080
agctttggcc agtttgcaga atgattttaa ctcagtttta atgtgtttgt tccctttccc 37140
atgtaattta taatggtagt tcacatggac tgttgatgct tgtactctag cagccagaac 37200
cagaaaactg ggaattttct acatctggaa atatttacct cgggatcttg agaaagagtt 37260
cttggtctga agaagcagag gatggggagg agcaaggcag agaacaacag aaccaaagtg 37320
ttaatttcca gtttagtaaa gaacggacat tttacatgaa tgcaaggaac agaaatgtcc 37380
tctttacaga gaaataggca tccagatatg ttgtcttaac gatactggga tactagacta 37440
gtatactaga gagtcgcaaa tttagaggac aacaagattc tactggaatg cttatgtcag 37500
atggtttcaa tcctttcagt aaaaaaaggg aattagcatt atctgctgaa aagtaagggt 37560
tgggattgta gaagtttgtg gccttcaaaa gaggtctgaa ctagttttgg aagaatgaag 37620
ctagggaggc agtgataaat taatgacagg acctgcccat gagtggctag ggccaaagag 37680
ttcctgtact gtcttatata aactgctaaa ataaaaactc cttctacctt cttactgtca 37740
atgaaattca attccctttg agaatactgc ttacatggtt tcttattctc accaccctcc 37800
ctgcccagcc ccactccacc acagtgatgg aaccaggaga gaaaagcaga gaaaatacca 37860
atattcctct ggtgttctct ttcaattatt cttgcaatta gcaaatattt gttgagtagc 37920
tactagtcta ggtgttctgg tctaggtgct ggaagaagct tattttaact cttttgataa 37980
gaatacctct tttgaagcct atgctgtata aaaataccac ctcttctttt tgccatcttt 38040

-continued

```
taccaaattg cacatttgtt gaaggtattg atgcttgtct ttcaagtctg gattatgggt  38100
atgagttgag tggagcattc tttgagctgt ccctctgctc ttcagatgat tgagaccata  38160
ccctaaatct cttttcatta agccattgca tacaactgaa aagatttatt ggatatcaca  38220
atcttgctct gggacacttt aacctattca gcaaatttaa ctatgagtgt aatggccata  38280
cccttgtttt gatctttgcc tcaaggttga gtcttgatca gcgtttgttg ctcagttgtt  38340
tattttacct tatgggattg aaaagcagtt gctttctcta accctgttaa gtccccaaat  38400
tcctggactt tttccctttt attactgatt gcatattggt cgatcctttt ctaagtacat  38460
ttcttccttc taataccttg ctatattcgt tttctggagc tgatgttaca aagtcacaga  38520
aactgggtgg cctaaacact agaaatttat tgtctcccat ttctggaaac tagaagtctg  38580
agattaaggc atcagcagag tgggtttctt ctgagggcta tgagggataa tctatctgtt  38640
taagcctctt ttctagcttt tggtggttta ctgacaatct ttgctgtctc ttgaccggtg  38700
gatgaatctc cctatttctg ccttcaactt cacatggcac tctccctgta tgcatgcctc  38760
tgggtccaaa tttccccttt gtataatgat accgattata ttaggacttc ctttaaataa  38820
ttatccgtat gtccaattct ggtgtactgg ggattaagga tgacagtata tcttttttga  38880
ggagctagga ggacacagtt taatccgtga tacttaccaa atacagccaa cagcaactac  38940
gacatgctac tgacattctg ttttctaacc tttctttcct agggttacaa gttagttaag  39000
tatatgattt gccttccaag ttacctcaag caaaagtttt aacaaatgtt accagtttta  39060
gcccgttcta aattttataa ccaccaaaat acaggctcct aagccaatgc cacgtattct  39120
ttcacattcc aatttgtggt tctggagaca ccaaaaaatt aacataatat tcacaatagt  39180
tgccgatgga ggctggaaaa catttgcaat attagactac taatattact cttaaattta  39240
taaatagtcc atttgtactc ttgctatctc cctgcaaatg ttagaggagg tgtttctgac  39300
tccagatact tttttgcctg caccagttat tttagtttct ttctttcttg ctttctttct  39360
ctttttttgt ttttgtagtt ttgtacctgt actgtacttg taggatcatt ttgaagagag  39420
aggaagtatt acaattagtc ctatgttcaa agaggtaaaa gcaactagaa aagagaagtg  39480
gcagcacaga aaagcagtag aaatatagaa ccaattttct gagcatacag agaaagaaca  39540
aatgacttgt ttaaaagggt cctttttttaa aattatactt taagttctgg gatgtatgtg  39600
cagaatgtgc aagtttgtta catatgtata cacgtgccat ggtggtttgc tgcatccatc  39660
aacccatcat ctacattagg tattcctcct aatgctatcc ctcccctagc cccccacccc  39720
ctgacaggtc ctggtgtgta atgttcccct tcctgtgtcc atgtgttctc attgttcaat  39780
tcccacttat gagtgaaaac atacagtgtt tggttttctg ttcctgtgtt agtttgctga  39840
ggatgatggt ttccagcttc acccatgtcc ctggaaagga catgaactca tccattttta  39900
tggctgcata gtattccatg gtgtatatgt gccacatttt ctttatccag tctatcactg  39960
atgggcattt gggttggttc caagtctttg ctattgtgaa cagtgctgca ataaacatac  40020
gtgtgcctct atctccttca gttctgctct gatcttagtt atttcttgcc ttctgctagc  40080
ttttgaattt gtttgctctt gcttctctgg ttcttttaat tgtgatgtta gggtgttgat  40140
tttggatctt tcctgctttc ttttgtgggc atttagtgct ataattttac acactgcttt  40200
aaatgtgtcc cagagattct ggtgttgtat ctttgttctc actggtttca aagaacatct  40260
ttatttctgc cttcatttca ttatttaccc agtagttatt catgagcagg ttgttcagtt  40320
tccatgtagt tgtgtggttt tgagtgagct tcttaatcct gagttctaat ttgattgtac  40380
tgtggtctga gagacagttt gttgtgattt ctcttctttt acatttgctg aggagtgctt  40440
```

-continued

```
tacttccaac tatgtggtca gtttttggaa taagtgcgat gtggtgctaa gaagaatgta  40500
tattctgttg atttggggtg gagagttctg tagatatcta ttaagtctgc ttagtgcaga  40560
gctgagttca agtcctggat atccttgtta aacttctgtc tcattgatct gtctaatatt  40620
gacagtgggg tgttaatgtc tcccattatt attatttggg agtcgtaagt ctctttgtag  40680
gtctctaagg acgtgcttta tgaatctggg tgctcctgta ttgggtgtat atatatttag  40740
gatagttagc tcttcatgtt gaattgatcc ctttactgtt atgtaatggc cttctttgtc  40800
tcttttgatc tttgttggtt taaactctgt tttatcagag actaggattg caacccctgc  40860
tttttttgc tttccatttg cttgttagat cttcctccat ccgtttattt tgagtttagc  40920
aagactaata aagaaaaaaa agagagaaga atcaaataga cgcaataaaa aaatgataaa  40980
ggggatatca ccaccaatcc cacagaaata caacctacca tcagagaata ctataaacat  41040
ctctatgcaa ataaactaga aattctagaa gaaatggata aattcctgga cacatacacc  41100
atccgaagac taaatcagga agaagttgaa tctctgaata gaccaataac gggctctgaa  41160
attgaggcaa taattatccc accaaccaaa aaaactccag gaccagatgg attcacagcc  41220
gaattctacc agaggtacag agaggagctg gtaccatacc ttctgaaacc attccaatca  41280
atagaaaaag agagaatcct ccctaactca ttttatgagg ccagtatcat cctgacaaaa  41340
gcctggcaga gacacaacaa caaaaaagag aattttagac caatatccct gatgaacatc  41400
gttgtgaaaa tcctcataaa atactggcaa actgaatcca gcagcatatc aaaaagctta  41460
tccaccaaga tcaagttggc ttcatccctg ggatgcaaag ctggttcatc atacacaaat  41520
cagtaaacac aatccatcac ataaacagaa ccagtgacaa aagctacatg attatctcaa  41580
tagatgcaga aaaggccttc gacaaaattc aacagccctt catgctaaaa actctcaata  41640
aactaggtat tgatggaatg tatctcaaaa taataagagc tatttatgac aaacccacag  41700
tcaatatcat actgaatggg caaaaactgg aagcattccc tttgaaaact ggcacaagac  41760
agggatgacc tctctcacca ctcctattca acatagtgtt ggaagttctg gccagggcca  41820
tcaggcaaga gaaagaaata aagggtattc aattaggaaa agaggaagtc aaattgtccc  41880
tgtttgcaga tgacatgact gtatatttag aaaaccccat cgtctcagcc cacaatctcc  41940
ttaagctgat aagcaatttc agcaaagtct caggatacaa aatcaatgtg caaaaatcac  42000
aagcattctt atacaccaat aacagacaaa tagagaggca aatcatgagt gaactcccat  42060
tcacaattgc tacaaagaga ataaaatacc tagcaatcta acttacaagg gatgtgaagg  42120
accttttcaa ggagaactac aaaccactgc tcaatgaaat aaaagaggat acaaagaaat  42180
ggaagaaaat tccatgctct tgggtaggaa gaatcaatat catgaaaatg gccatactgc  42240
ccaaggtaat ttacagattc aatgccatcc ccatcaagct accaatggct ttcttcacag  42300
aagtggaaaa aaatacttta aagttcatat ggaaccaaaa aagagcccgc attgccaaga  42360
caatcctaag caaaaagaac aaagctggag gcatcatgct acctgacttc aaactatact  42420
acaaggctac ggtaaccaaa acagcatggc actggtacca aaacagatat atagaccaat  42480
gaaacagaac agaggcctca gaaataacac cacacatcta caacaatctg atctttgaca  42540
aacctgacaa aaacaagaaa tggggaaagg atttcctatt taataaatgg tggtgggaaa  42600
actggctagc catatgtaga aagctgaaac tggatccctt ccttacacct tatactaaaa  42660
ttaattcaag atggattaaa gacttaaatg ttagacctaa aaccataaaa accctagaaa  42720
aaagcctagg caatatcatt caggacatag gcatgggcaa ggacttcatg actgaaacac  42780
```

-continued

```
caaaagcaat ggcaacaaaa gccaaaatgg gatctaatta aactaaagag cttctgcaca  42840
gcaaaagtac tgccatcaga gtgaacaggc aatgtacaga atgggagaaa atttttgcaa  42900
tctacccatc tgacaaaggg ctattatcca gaatctacaa agaacttaaa caaatttaca  42960
agaaaaaatc aaataacccc atcaaaaagt gggcaaagga tatgaacagc cacttttcaa  43020
aagaagactt ttatgcagcc aacaaacaca tgaaaaagtg ctcctcatca ctggtcatca  43080
gagaaatgca aatcaaaacc acagtgagat accatctcac accagttaga atggcaatca  43140
ttaaaaagac aggaaacaac agatgctgga gaggatgtgg agaaatagga acacttttac  43200
attgtttgtg ggaacataaa ctagttcaac cattgtggaa gacagtgtgg caattcctca  43260
aggatctaaa actagaaata ccatttgacc cagcgatccc attactgtat atatactcaa  43320
aggattataa tcatgctact atacagacac atgcacacct atgtttattg tgggactata  43380
cacaatagca aagatttgga tccaacccac atgtccatca atgatagact ggattaagaa  43440
aatgtggcat atatacacca tggaatacta tgcagccata aaaaaggatg agttcatgtc  43500
ctttgtaggg acatggatga agctggaaac catcattctg agtaaactgt cacaaggaca  43560
gaaaaccaaa caccgcatgt tctcactgat aggtgggaat tgaacaatga gaacacttgg  43620
acatagggca gggtacatga cacactgggg cctgtcatgg ggtggaggga tggtggaggg  43680
atagcattag gagaagtacg taatgtaaat gacgagttaa tgggtgcagc aaaccaagat  43740
ggcacatgta tacatatgca acaaacctac actttgtgca catgtaccct agaacttaaa  43800
gtataataat aaaaaataaa aattacaaaa acttaaaaaa agaaaataaa aataagaaac  43860
catatgtttg catgtgtcat tatagtagac tgatttatat ttcagttact ttctaatgca  43920
ttgtgtccca gtagattagt tcacatttgc ctcttttttt cctctattta ttctgggccc  43980
cataatctat tacttgagct tgtccttctt catcaccctt aatactctca ctttctgttt  44040
ctctgctctg cttggcctga aaaatgtcag cagcaaacta tatctgatca ttgtcatcct  44100
cctctgacat gcaacactat taaggattta tgaaggaaat acatagtaag ctcctacacc  44160
tttatgatgt ttagttcaac tgtgttctca acactgctag ggagtcttgc aagagttacc  44220
tcactctctc tcttttctct ttatggatat gctgtataag cataagacac ctcttaaaga  44280
ataaccttgt ttttgttatt tattccacta tgggaaacct gatctagtca gtaatttttc  44340
agtggttact tttagcttct gtaacattct tactacctgc atccatttgt tccattttcc  44400
tttctgtttc aatatccctc ctcttgttca attcagtcct ttgccaaggt gttctatcct  44460
accttctcca cctctttagg agccttactc cagcaaatgc ctcctcttat ccttcatttt  44520
aaactctgac tcttgattgg ctctttcacc tgagcatact cattgctcag tttgtctcta  44580
tctaaaaaat catttttaga ctttatacct ttattttctt tgtaaatgtc tttatatata  44640
ttttcttata acctcccgtc cctccttctt tcttcccctc tcccattgaa aatcaacagg  44700
atagtatttg gagacttttg tttccctggg attgacacat ctcacagcta agaatgaaag  44760
ccatgaaata tctaatattc taagttcgga gaaccactag gtcacctcct ggacagtaaa  44820
atttcaatgt atgagcaaca aacaatcatg ctaggatgta aaatgattaa aatgtcactt  44880
tctgagtatt agacaattca tatggttttt aacaaacagt ggctttatat ccattgtaat  44940
gcctctttta gcatcaacat tcagaaattc acattccatt tttttggaca cttcatgaga  45000
ttttgaaact actctttatt ctgagattct gttaattgta tttagaatgg accttgatag  45060
ttttcctgct cataattttg gtaaaactgt attgcatttt gaggaagtta atatcaaatg  45120
ttcctatata aactttgact agaaaatgat gtatggagat attcacacat ctataaagtt  45180
```

-continued tggttattta aatccaagag atgttttgtc atgaatatct taactacaga gacatggagc 45240
tgcttggata gaacaaactc tgtgctttaa tggttgtata gtattctttt catatgtata 45300
tctgtaattt tacttctgtt tagccatttt cttcttttta ttatgtatac atttttttatt 45360 tctgtagctt ttggggtaca agattttatt tcatggatga attgtatagc ggtgaagtct 45420
gagattttag tgcacctgtc acccaagtag tgtacattgt atccaatatg tagctttcta 45480
tcccttactc ttggcccctt ctgagtttct aaagtccatt ataccacttg gtatgccatt 45540
acatacccat agcttagatc ctacttataa gtgaaaacat atggtatttt gttttccaat 45600
cctgagtcac tttacttaga ataatggccc taagttccat ccaagttgct gcaaaaaaac 45660
cccattattt cattcttttt taatggctga gtagtattcc atggtgtata catactgtat 45720
tttcttaatc cacacatcag ttcgtggaca cagattggtt ccatatcttt gcaattgtga 45780
atgaattgtg ttgtgataaa caggcatgtg cacatctctt tttgagataa tgacttattt 45840
tcctttcggt agatactcag tagtgggatt gctggattga atggtagatc tacttttagt 45900
tgtttaagaa atcttcatac tgttttccat ggagcttgta ctagcttaca ttcccaacag 45960
cagtttaaac gttccctttt caccacattt atgccaacat ttgttgtttt ttgacttttt 46020
aataatggtc actctggctg ggttagatgg tatctcatta tggttttaat ttgcatttct 46080
ctaatcatta gtgatgttaa gcatttttca tttctttatt ggtcatttgt atatcttctt 46140
ttgagaagtg tctattcatg tcatttttcc actttttgat gggattattt gtttttttct 46200
tgctgatttg cttgaattcc ttgtagattc tggatattag tccttggtca gatgcatagc 46260
ttgcaaatat tttctcccat tatgtgggtt gtctatttac tctgatgatt atttctttcg 46320
ctatgcagaa cattttagtt caattaggtc ccatttttat ttatttattt atttgctttt 46380
ttgttcattt acttttgggg tcttagtcat aaattctttg tcgaggccaa tgtccagaag 46440
agtttttccc taggctttct tctagaattt ttaaggtttc atgtcttaga ttatgtcttt 46500
aatcttgatt tgattattgt atgtggtgag agatagggat ccagtttcat ccttctacat 46560
gtggctatcc agtttcccag cacaatttac tgaatagtgt gttctttctc caatttatgt 46620
ttttgcacac tttgtccaag attagttgct tgaaagtatt tggctttatt tgtgagttct 46680
ttacactggt cccatggttt gtatctctcc ttttatatca gtaccatgct gttttggtta 46740
ctatagcctt gtagtataat ttgaagttgg gtaatgtgat gcctcctaat ttgttctttt 46800
tgtttaggat tgctttggct atctgggctc ttttatggtt ccatatgaat tctaggattg 46860
tttcttctaa ttctgtgaaa aatgatgttg gtattttgat aggaattgca ttgaaaatgt 46920
agactgcttt gggcagtttg gtcattttca tgatattgat tcttctaatc catgggcatg 46980
gggtgtagtt ccattcattt gtgtcatcta tgatttattt cagcagtgtt ttctagttct 47040
ccttgtagag gtctttcacc tccaaggtta agtatattcc tatgtgtttt atttatttat 47100
ttttgcagcg attgtaaaag ggattgagtt cttgatttga ttttcagctt ggtcataaga 47160
agcaacagta tgcttccagt cgcctctgct cctttatgtt attattgtca cacattttag 47220
ttctacatat gttagaaatt ccacactaca ttattattat ttttgcttta catagacaac 47280
aatcttttaa ataaatgttt aaaaaaagaa aaagttatgt atttatatat atctttacca 47340
tttatggtgc tcttattctt tgacattgat acaattttca tctggtatta ttttttttctg 47400 tctgaaaaac tttaatattc tttaatacta atcttctgtg atgaatctct caacatttat 47460
atgtctaagt gaaatatgtt aattttttaat tgtttttgaa ggatattttt actatatata 47520

-continued

```
aaattttaga ttgacaattt ttttttcttt tagcaattta aagatgttat ttgattgtct  47580
tctagcttgc atagtttaca atgagaagtc ttcaggtact cttgtttttt gtttctctgt  47640
tcattatgtg tctttttccc ctctttggtt gttttaagat tttcttttta tcatcagttt  47700
ttggtaattt atttatgata tgctcagttt gctcctggat ttgacattgc ttgcttctag  47760
acctcagaca gtttcttttc ttgctatgtg tgtgagccac cacacctgac cgagtgtctt  47820
tattttattg tcttccttca ataattgttg ggctttgttt cagcaggtgg ttaattcact  47880
tggagatctg gttgacattt ttgaggacca ttttaaaaac agatatagtg catctagaat  47940
agtaactctg gatcactagc atttctattg tttcttttcc tgttggtttc agttgtttct  48000
atttcctttt acactttata atttttaatt gaatgataaa catcacatat gagaaaatcg  48060
tagagataat ttgaccgtct tatagacacc cctttttgct aaattttcag actctagacc  48120
ctgtgacact aacgaatcag caaatgtatt cagagaaaaa gagggacaga attttgtgtt  48180
ttatctcagt tcacttcctg gtttttgaag agctttatct ttcatgtcct gactgccttg  48240
atagttttga atgctttcaa acagatgttt taattttatc gaacttttct agcttttctt  48300
atagggaggt ttgattcaat acaagctttt ccatggaaat agaaattttt tatattaatt  48360
ttgaacctag gcattttatt aaattatctt atctataatt actttttgtg tgttttccaa  48420
ctgtacaaat tatttgcaaa tgcttctcat tttagaattt tgcatttctt atttcaccag  48480
actagtccaa ttgaataggt tagtactttc agaaaaattt tagataatag ttgtaaacag  48540
gaaaaactat attacattta tgtcacaagg ttgttgtgat gactaaatta aaacatgtaa  48600
agtacctaga aaagaatgac ggtaatgata gtgatgatga tgatggtgat gatgatgatg  48660
gatatccttg tgttgtttct gactgtaaca ggggtgttcc tacggtttcc ccactaagaa  48720
ttatgttaaa catacaagga tacatttacc tattcttttt ttaattaaga attttcatct  48780
caaatcaata ttgaatttta tcaaatgtct ttgtaggaca tatggagaag accatatgat  48840
ttttcatttt gattcattaa tatggtgaat tatatttatt ttctcatatt gaatcagaac  48900
tgtcttggta ggagccccat ttaatcattt tgtggtattc tgtaaatatg ctgctagatt  48960
ttaattttaa taatttattt aaactgtttt gtattactac tcatatgtga aattgatcta  49020
tagtttttct ttttgggctg ctcatttcag gttttggttc tattatgttt ttataacaaa  49080
tatttgataa gttgttcttt ttcaatgctt tgacactttt aattagcact catgtcactg  49140
gtttgtaaaa gcttgggaga atttagttaa ttaaacccac tgggcctggt acttttcttt  49200
ctctttctct ctctcttttt tttttttttt tgtagggtga tcttaatttt ttttttttta  49260
ttacatagtc tatctctttt gggtcagttt tggcagtctg ttttcccaga aaacaatcta  49320
tgtctttcaa gatcccaagt ttatttacat agaattgact cagttgattt tctgtgtaga  49380
catgatgtgc aaaatgttga aaacttagtt ggcatgggca ttaataactc atagcagatg  49440
ctacaaccaa ccacaatata tatcaaacac aaatatctga tatggtcata atagtgccta  49500
ttggctaagt attagccatt gtatctgtat ttattctctg tattattttc ccattctcac  49560
ttcttatttt atgattttat tctgtccttt ttttgattag gtaagctaat aatttatcta  49620
tttcattatt ttaaacagta tgctcttggc tttatttgtt attttatctt ttttcttgtt  49680
ttctaatgaa tgaattgttt gtgccttatt taactcattt tattttcatc aggtttactt  49740
catttctctc tttatgtctt gtgtgatttt attttgtttt atgaatatat gttttatgaa  49800
tttatatcag attgatatat atacatatac aggtcatttt atcccattaa tgtaagacag  49860
ataaattttt gtcatcatat tttatatata tcgtgatttc agtttatatt ggttctttgt  49920
```

-continued

```
ttaataatct ttttatataa tttgtttttt attgcttttg tgtgtatgca tgtatgtatt  49980
cacaggcaca tctatgcatg cacatgcttc cttgtaattc aaagatttat tttaaattct  50040
gttagtggtc atcttaaaac cttgcaattt aatatgcttt agcatttatt ccagccagtg  50100
tctgttgatt caccattaga gcaatgacat ttggtagtac tcttctactt tagtggttct  50160
cagcactggt ccacattagt atcatctggg agcttttaaa aaataccagt gcctctaaga  50220
ttaagagata attattttca aaaagtcccc catatgactt taaagagcag ctatagttga  50280
gagccactgt tttaccctct ctcccctcca ccaacaattt taatcaatta tatattattt  50340
aaaaattttt ttctagtctt tatgtttttg aaagatgatt ggccgtatgt aggagaaaat  50400
acgcatactt gcacatcttc tgtcttctct ctttctcacc ttcatctaat attatcattc  50460
attcttataa tttgtaacct atgcattctg ttttgctgcc atctttatcc gtgattaaat  50520
agattccata gtcactgtga gtaatttttc tccattcatt ttttgattga ctgaagttta  50580
ttgtctagta ggttcttcag aagtgttcat ggaagtcaca tctatctgtt tcctttatat  50640
ttaaatgaca gtttggctgg atatagaaat catggatcac atattatttt cctgggttct  50700
ttgtatcata tttctgtctt ccagcatcaa atattgttgt gaactataag gtcagtctaa  50760
tttttcttct ttgtattaag tatgggaaag aaactaatac tgtaacaaag tacaaaaata  50820
cagtgagtta actaagattc aaccttgtat cactctcatg tatcagtctg gctggtctaa  50880
gttatcagag caactgctgc gcaaggtcac ccagagagcc atttcttcca tgttgttgct  50940
ccactatccc tttttgggca ttttgtcacc ctcaaaatca aaagtgggat gttggcaaat  51000
ctaccttcca gcttgcaaaa gaggaaaaga ggcaaaatac agagaaagca gattttcttt  51060
aaattgcaaa tgactttaca tacttttgta catattcaat attcagaact tgctcatggc  51120
caccgtagct aactgaaaaa aaaagctaga aaatgcagta tctagctggg tggccttaga  51180
gttagaaata gaaaatttag gaagaacaaa tatgagtcca cttcaaactt gtaggttact  51240
taataatctt agcctgaatg cccaaagttt ttgttgttgt tgttttgaca tttgaagacc  51300
tatactatca ctaggaaatg tttcagcatt gataaaattg catgaggttt tctgcttttt  51360
taattttggt aaggatttc ggtttaagct ataggttctt caaaattatg tgttaaattt  51420
tattttatgt tttatttatt gtgtgttccc cccaccaccc tattttttttt tttttggtc  51480
tgttttccat gtctattatt ttgcttgctt tcctcaatcc tgctcttttg tgccttagta  51540
tgaattcagt gatggctctt tgtgctgctt aatgtagcct tgatttcttg gatggcttta  51600
tttatttatt tttctattta tttttcaagt ctgccagctc atgtttcatc tcctccagct  51660
gtctgctttg agctttttga ttcattaggt gcctagtatt cacggccata tttatttggt  51720
catgattttt atctgggcag tgacaatatt gttctggtgt gtattcatca cctgccactt  51780
gtttttccca catttttctt ccttttcctg aaagtaactt tgtatagatc cttggctggt  51840
tctttttgtg ttatttcttt tgtgaatgag gttaattcct ccagttattt tcaagaggtt  51900
ccttcagggg agagaataga gtagtgttcc aggcaagcag taactcctcc acagtaaagc  51960
tccttatgac tcaggggtgt gtgtgtgtgt atgtacacta ttttaacctt cgtttttctc  52020
tagttcaaag aaatcagcaa ttgctggatt actcataatt cagatccatt tccttcaccc  52080
ttcctcaagg atacactgct tctcagaaat gtgtgtgttt ccttgttcag cctcaccttc  52140
cctgcctgtt ctctgggctc agagaaggtc cagataagct ccctctaaag accaggcatc  52200
ctgttctcat tgttctagac aaggtttgtg gttttgcctc tcatattgtg tcacatactt  52260
```

-continued

```
tgaactgtac tctacctggt ttagttgaga cttttttttt tttcgagacg gagtctcgcc  52320
ctgtcaccca ggctggagtg cagtggcggg atctcggctc tctgcaagct ccgcctgccg  52380
ggtccacgcc attctcctgc ctcagcctcc caggtagctg ggactacagg cacccaccac  52440
catgcccagc taattttttt gtagttttag tagagacagg atttcaccgt tgttagccag  52500
gatggtctcg atctcctgac tcgtgatctg cccaccttgg cctcccagtt agctgagatt  52560
ctcagccaca gatgtctata ggtatttccc tgcactcctg tttgaacttc cctgttggca  52620
gctcttactc aaatattgta gttcgaggtt acagatgtgt tataacttta tcaaaaatta  52680
ttattttttt ctttttagt tttcatcatt ggtttgagtt gattttgtaa agaaaactat  52740
gtggagccat ctttagtttg gcatttccta atcagctacc atgagtattt atttagagaa  52800
atccattatt attttgttag gattcatttt tctaagtggt aaatttacaa aatttcaaga  52860
attccaatct gcatttcaaa aagattatac aaatctatac tcttctactc atatatcaga  52920
gttactattt tcctacacac ttactaatat atagagagaa ctttgcctat ttgatattct  52980
aacaaggtgt acctcttaag ttgtactttt aattattagg ggacaaataa ttatatcttc  53040
ttcttttttt tttttttttt ttttagtatt tattgatcat tcttgggtgt ttctcggaga  53100
gggggatttg gcagggtcat aggacaatag tggagggaag gtcggcagat aaacacgtga  53160
acaagggtct ctggttttcc taggcagagg accctgcggc cttccgcagt gtttgtgttc  53220
ctgggtactt gagattaggg agtggtgatg actcttaagg agcatgctgc cttcaagcat  53280
ctgtttaaca aagcacatct tgcaccgccc ttaatccatt taaccctgag ttgacacagc  53340
acatgtttca gagagcacgg ggttgggggt aaagttatag attaacagca tcccaaggca  53400
gaagaatttt tcttagtaca gaacaaaatg gagtctccta tgtctacttc tttctacaca  53460
gacacagtaa caatctgatc tctctttctt ttccccacat ttcccccttt tctattcgac  53520
aaaaccgcca tcgtcatcat ggcccgttct cagtgagctg ttgggtacac ctcccagacg  53580
gggtggcggc cgggcagagg ggcccctcac ctaccagatg gggaggccgg gcagaggcgc  53640
cccccacctc cctcttggac ggggtggctg gccgggctat atcttctttt gggaattttc  53700
cattattatc ctttagtgaa tattgtttcc ttttgatgcc tttgtcaact tcatatagat  53760
ttatatgagc tttttcttaa agatatgttg catatatttt tctgttagta atttgcaagt  53820
ttattttaat gtaatctttt accaaatgaa aatatatttt tatagcaagt ttaatatttt  53880
cccttgtggt ttctacttta ggactcattt tctttaccac agcaaaatta tatatccacg  53940
tatatattcc tttagtgttt caatgttgtt ttattttttg tacctaaatc tttaataagt  54000
ctggaatttg ttttgaatat agtataaagt actaatctag cttatttttc ccaaaattgt  54060
tagttatgta tttcattacc atttatagag taatgtcttc ttccccactt atttaagatg  54120
ccactactaa cacattaatc ttaggtttat acagaaacag ttctaaactt taaattttat  54180
ttcattgttt gcttgttttt atggcagcac tgcaacattt taaccattat tttatatatt  54240
aatgcatttt attttctagc agggcaaatc tctaccatta ctagaatttt caaaatctct  54300
tacttagttt catgtattat tcttccagat gaactgtgga atcatttgtt gagtttccag  54360
aaataaatcc tcgaacccac tgggattgta ctgagtttat ttatttattt gggaagaatt  54420
aacatcttga caatattaag tcttcttagc tggtaacatg atatagttct ccatttagac  54480
aagttttctt ttatgttctt caacaacaat attgtggttt tcttcacaga ggttctgcac  54540
atttctcatg agtttaactc ttaggtgata tatattgttt tgctattatg aatgcaattt  54600
attttccaat ccattattgc caaatataag aaaagattga gctttattta ttttgtaatt  54660
```

-continued

```
actactctac aaatatttct tacaaatcct agttgctttt caggttattc ttttgagttt  54720
tatatctaga tagtaatgcc attttcaaac ttagtttttc ctcgtgtcca atattcatac  54780
tttttaactt gctttcttat tcaattgcac tggccaactt tcccagaaca atgttaatta  54840
acaatagagt tagcaggcat actttactta ttcttgatta tagtagaata aattgattgt  54900
tttactgtcg ttttgatgtt taatgtaaaa gtacattgtg atggttttgc agtgcttgtg  54960
tagaccacac gaagttggat ctaaaaaaat tttaattttt tttgcttagg attgtcttgg  55020
ctatatgggc tctgttttgg ttctatatga aatttaaagt agttttttct aattctgtga  55080
agaaaatcaa tggtagcttg gtggggatag cattgaatct ataaattact ttgggcagta  55140
tggccatttt cacgatattg attcttccta ttcatgagca tggaatgttt ttccatttgt  55200
ttgtgtcctc tcttatttca ttgagcagtg ttttgtagtt ctccttgaag agatccttca  55260
tatcccttgt aagttgtatt actaggtgtt ttattctctt tgtagcaatt gtgaatggga  55320
gttcactcat gatttggctc tctctttgcc tattattggt gtataggaat gcttgtgatt  55380
tttgcacatt gattttgtat cctgagactt tgctgaagtt gctcatcagc ttaaggagat  55440
ttggggctaa gacgatgggg ttttataaat atacagtcat gtcatctgca aacagagaca  55500
atttgacttc ctctctttct atttaaatac cctttatttc tttctcttgc ctgattgccc  55560
tggccagaac ttccgatact atgttgaata ggagtggtga gagagggcat ccttgtcttg  55620
tgccagtttt caaagggaat gcttccagtt tttgtccatt cagtatgata ttggctgtgg  55680
gtttgtcatg aacagctttt attattttga aatacattcc atcaatgaga tacattctag  55740
tttattgaga gtttttagca tgaaggggtg ttgaatttta ttgaaggcct tttctgtatc  55800
tattgagata atcatgtggt ttttgtcatt ggttctgttt atgtgatgga ttatgtttgt  55860
ttatttgcgt atgttgaatc agccttgcgt cccatggatg aagccaactt gattacagtg  55920
gataagcttt ttgatgtgct gctggattca gtttgccagt attttattga ggattttcgc  55980
attgatgttc atcagggata ttggcctgaa attttctttt tttgttgcgt ttctgccagg  56040
ttttgctatc aggatgatgt tggcctcgta aaatgagtta gagaggagtc cctcttcttc  56100
tattgtttgg aatagtttca gaaggaatgg tacaagctcc tctttgtacc tctggtagaa  56160
tttggctgtg aatctgtctg gtcctgggct tttttctggt tggtaggcta ttaattactg  56220
cctcagtttc agaacttgtt attggtctat tcagggattc gacttcttcc tggtttagtc  56280
ttgggagagt gtatgtgtcc aggaatttat ccatttcttc tagatattct agtttatttg  56340
catagagatg tttatagtat tctctaatgg tagtttgtat ttccgtggaa taagtggtga  56400
tatccccttt atcatttttt attgtgtcta tttgattctt ctctctttct tctttattag  56460
tctggctagc agtctatcta ttttgttaat cttttcaaaa aaccagctcc tggattcatg  56520
gatttttga agggtttttt gtgcctccat ctccttcagt tctgctatga tattagttat  56580
ttcctatctt gtgatagctt ttgaatttgt ttgctcttgc ttctctagtt cttttaattg  56640
tgagcttagg gtgtcaattt tagatctttt ctgctttctc ctgtgggcac ttagtgctat  56700
aaatttccct ctaaacactg ctttagctgt gttccagaga tcctggtaca ttgtgtcttt  56760
gttctcattg gtttcaaata gcttatttat ttctgcctta attttgttat ttacccagta  56820
ttcattccgg agcaggttgt tcagtttcca tgcagttgtg caggttcgaa tgagtttctt  56880
ggtcctgagt tctaatatga ttgcaccgtg ctctgagaga ctgcttttca tgatttccat  56940
tcttttgcat ttgctgagga gtgttttact tccaattatg tggtcagttt tagaataagt  57000
```

-continued gtgatgtggt gctgagaaga atgtatattc tgttgatttg gggtggagag ttctgtagat 57060
gtctattagg ttctctaggt ccagagttga gttcaagtcc tgaatatcct tgttaatttt 57120
ctgtctcatt gatctctcta atattgacag tggggtgtta aagtctccca ctattattgt 57180
gtgggagtct aagctggagg cgtcatgcta cctgacttca aactatacta caaggctaca 57240
gtaaccaaaa cagcctggta ctagtaccaa aacagatata tagaaaaatg gaacagaaca 57300
gaggcctcag aaataatgcc acacatctac aaccatctga tctttgacaa acatgacaaa 57360
aagaagcaat gggtaaagga atccctattt agtaaatggt gttgggaaaa ctggctagcc 57420
ctatgcagaa aactgaaact ggacccctc cttacacctt atataaaaat taattcaaga 57480
tggattaaat acttaaacat aaaacctaaa accgtaaaac cctagaagaa aacctaagca 57540
ataccattca ggacatagac ataggcaaag acttcatgac taaaacacca aaagcagtgg 57600
caataaaagc taaaactgac aaatggatct aattaaacta aagagcttct tctgcacatc 57660
aaaagaaact atcagagtga acgggcaacc tacagaatgg gagaaaattt ttcaatctat 57720
ccatctgaca aagggtaata tccaaaatct acaaggaact taaacaaatt tataagaaaa 57780
aaaatcaacc ccatcaaaaa ttgggcaaag gatatgaaca gacacttctc aaaagaagac 57840
atttaggcaa cccacaaact tgtgaaaaaa agctcatcat cactggtcat tagagaaatg 57900
caaatcaaaa ccacaatgct gtaccatctc acgccagtta gaatggcaat cattaaaaag 57960
tcaggaaaca acagatgctg gagaggatat ggagaagtag gaatgctttt acactggtgg 58020
tgggagggtt aattagttca accattacgg aagacagtgt ggcaattcct caaggatcta 58080
gaaccagaaa taccatttga cccagcaatc ctattactgg gtatataccc aaaggattat 58140
aaatcattct actataaaga cacatgcaca cgtatgttta ttgcagcact gttcacaata 58200
gcaaagactt ggaaccaacc caaatgccca tcaatgatag actggataaa gaaaatgtgg 58260
cacatataca cgatggaata ctatgcagcc ataaaaaaga tgagttcatg ttctttgcat 58320
ggacatggat gaaggtggaa accatcattc ttggcaaact aacacaggaa cagaaaacca 58380
aacacatgtt ctcactcata agtgggagct gaacaatgag aacacatgga cacagggagg 58440
ggaacaccac acactggggc ctgtcaggtg gtggggggca aggggaggaa taggattagg 58500
agaaatacct aatgtagatg atgggttgat gggtgcagca aaccaccatg gcacgtgtat 58560
acctatgtaa caaacttgca cgttctgcac atgtatccca gaacttaatg tataatacac 58620
acacacacac acacacgcac acacacgcac aaataaattc atacaattaa gtgtttttta 58680
aaaagtattt taatttaaat tcccatctaa tcattttttt aaattggtgt gtcaattatt 58740
tgcctttaaa gtaactattg gtttggttgc atttagatct acctttatat tattactatt 58800
attattattt tacttatcct ctctggtttt gtcttctatt ctttttacct gctgtccttt 58860
tctgatagtc tatttttgat ttctctattc acttgtgttc tatatctctg tatttttttag 58920
cacttgctct agagattata cacataacta agttatcttt ccaattaaaa tgcagagcaa 58980
aatttggagc cacatgatgt tttggaccaa agaatgaaat taatctgatt atgtcttaac 59040
aagataactt tgttgttctt ttgagaatag attttacagg tacaaaggct aaagttagga 59100
gatgaatgca aatatacagg agtgtctttc tattactctt tactgagagt ttttgtaaaa 59160
tcaggaaaca gtgttaattt tataaactgc tttctctgct tctattgagg taattagtga 59220
ggtggccatt ttattctgtt aatgtggtga attatgttga tttaattttg aatgctaaat 59280
caacgttgca tttctgagat aaaccccact tgctcatgag gtactattct ttgtatatat 59340
tttctgattt gatatgctaa ttttttgtga agatattttg agacaataag catgagagat 59400
gtgggtctgt aattttccat gttttgcaag gttcttatct agttttagta ttacggtgtg 59460
cttgtctcat acaatgaatt ccctcctctt ctatgttctg aaagatctca cattagacta 59520
ggattaattt ttctttcaaa gtttaaaaga attccccatt gaagccatct gggcctggaa 59580
tttattttat gtaaagaatt ttaattacaa attcaatata tcttttacag atacagtagt 59640
cctcccttac ccatggtttc actttctgca gtttcagtgg aacatgaaca tggtcaacgg 59700
tgatcagaaa atgttaaatg gaaaatttca ggtataaaca attcgtaagt ttcaaatcac 59760
acaccatttt gagtatcata atgagatctg ttgccatcct gctgtgtccc accaggatgt 59820
gaaacagccc tttgtccagc tgtcagtact atatatgaca cctacccatt agccacttac 59880
tatccctctc ttatcagatt gactgtgatg gtgtcacatt gcttgtgttc aaataaccct 59940
tattttactt aataataacc ccaaagcatg agcatagtga tgctggcaat taggatatac 60000
caaagagaag tcaaatatat gtcaaagaga agttgttaat ctcttactgt ggataattta 60060
taaagtaaac ttaatcatag gtatgcatgt atatgaaaaa ccatagtatg tgtagggttt 60120
gatattgtct atggtttcag gcattccctg agggtgttgc aatgtatgcc cagtggatta 60180
aaggggacta ccttagagga gtattctgtt tttttttttt cttaactatc ttcctgtgtc 60240
agttttgtaa tttacgtgtt tcaaggaatt tgcccatttc ttctgacttg tcaaattaat 60300
tggcatttag ctgttaataa tattccctta ttattattta actatttgca tcatctatag 60360
tgatgtgcct tccttcattc cagatgctct ctttcttttt cttttttttc ccttttatt 60420
ttttggtcag tcttggtaag atattaccag gtttattaaa ctttgcaaaa aactagcttt 60480
tcgttttatt aatttttctc ttgtttgtgt tctatttcat tgatttccat tattttattt 60540
tttagttgcc tacattttca tcctttaggt ttaattttgt agagttttga gggaatttaa 60600
gagttttcaa cctttctcct tttttctgaa gtaagctagt aaagctacaa attaccttct 60660
acgtgcttct ttagatgcct ttcataatgt ttattatgtt ttgttctcat tttcatttat 60720
ttcaaggtat tttaaaatgt ctttcatgat ttcttctttg attttggatc ctttagtact 60780
gtgttgctta attttcagat atttggggta tttttttcaa gatatatttt tgttattgat 60840
ttttaactta gttcctttat taatttctaa tttagtatgg tattaatcct tttaaattta 60900
tgcccaatat atgacctatg ttgattaatg taccatgaat acttgaagga ttatgtattc 60960
tgtagttgtt tggttatagt gttctataaa tgtcaatcag atagtattgg ttgataatga 61020
ttgtttcagt tatctattgc tatgtaacaa atgtccccca aatagtagat taaaacaaca 61080
gcatttattt ggctcaaaat tctgctattt tggcaagtct tggtggtaac agtttagtta 61140
tgttacattc agcatcagct ggagtatctc aaaggcagac tccactcagt gtcagctagt 61200
ttgtgctgaa ttaaaggcta taagctggga atctctctct gttttaaaat gatctcttta 61260
tatggcctct gcaatggctt tggggaagcg actggcttag agctcctaag tttcatgtca 61320
cgagagagac agagccaagt agaaactgta tcaacttttt gacctagtct tggaagtcat 61380
gcagccctac ttctgctgtg ttccatttgt tttggtggtc acagagtact gtccattttg 61440
acaaagagag gggatataga cttcacctct taatgagggt atgactaggt ctggaagagt 61500
ttgtgggaca gtaaatcttg ctgagaacat ttttggaaag tacaattggt cataatattg 61560
atcaaatctt tttctaatct tttttaccct tccaataatg gactgagatc tttttctaat 61620
cataccaact tttagaaaat tgatttctgg gagtagtgtt aaaatatcat actggatgta 61680
ggaacttgta catttatttc tttagttttg ccagtttctg catcatttat cttggcttgc 61740

-continued tattgattgc atacacattt tagattatgt ctttctgttt gttatacata tgttacaaat 61800
acaatgaaac acttttatat ttgctttagc caatttttaa ataaattgag aaatgagagt 61860
catttatatt taccctttt tttcccagta tacttcattc ctcgtagata caagtttctg 61920
catggtatcc ttttcctttt cttttttttt tttttcttct tttttgaga tggagtcttg 61980 ctctgtcacc aggctggagt gcagtggtgt gatctcagct cactgtgacc tccacctcct 62040
gggttcaagc gattctcctt cctcagcctc ctgagtagct gggactacag gcatgcacca 62100
ctatgcccag ctaatttttg tatttgtagt agagacagag tttcaccatg ttggccagga 62160
tggtcttgat atcttgacct catgatcggc ccacctccac ctcccgaagt gctggaatga 62220
caggcatgag ccaccgtgcc cagccagtat cctttttctt aagcctaagg ttcaggtctt 62280
gcccctattt atgaattctc tcagattaaa aaaatctaaa tatatttgtt ttgccttcaa 62340
tatcaaaact ttttttctga atatagaatt cttgttgatt atgttttcag tactttaaat 62400
atgtcacatt ttattgtcat ctggcttgta ctgtttctga tgagaagaca gcaatcattc 62460
ctgttgctca cctgtatgta atatgtcttt taccccttct gtgccctttt aacattttct 62520
ctcactcctt gtctttcagc agttttattg tagtgtgtcc atgtgtggtt ttatttgtgt 62580
ttatctgatt agttaaactt cttggaaaat atgagactat agtgtttttt aaatttcccc 62640
ctctgatatc tttttcctct ccctctagaa ctctaattac atatttgtta gattatataa 62700
tattgttcca caggccactg aggctgtgtt cacttttcta atctaaattt cttctttcta 62760
tgctttagat tgggtagttc ttttgtctaa tctccaaagc taatctttct ctggcaatgt 62820
atactctagt attaaggcta ttaggtgaaa ttttcatttc agataagttt tttagttcta 62880
gaattttcat tcctttctcc acccaagttt tattctcttt tcagtgtctg tatctgttta 62940
cttactacaa tcatctttgt ctttaatact tgaacatgtt taaagtcctt gtcggttaat 63000
tccaacatta gtgccatctc tgggcttcca ctgacttttt cctcctgttt ttggctcttg 63060
ttttcctgct tcttcatatg tctagtaatt tttattgtat gctggacatt tatgatgcta 63120
tgttgttaca aatttgatag agtatgccaa gagcatgtat tccattaagc aaggttgagt 63180
tttgttgtgg atggcaggaa atatattcag tcatctttat cctacttgat tttaagcttt 63240
ctctgggtgg gtctggaata gcccttaatc tagtgataga gtaactcttc acttaagaaa 63300
taccctttct gggatccaaa ctaaatgtcc aaggtattcc caaatctctt cattctggct 63360
tatcaaaaat tgaacatctt cggcattgta agagctgtga agtttgcatt aatctcacag 63420
tcttttagta gttgttccct aaccgatctc ttggagtctt gctctgtgca tgcatagctt 63480
aatattcatg cagatactaa agtggatctc tatacaaaca aatgggacta taattctatg 63540
cagctctctc ttctctgtta acttgcctca cacatttcac tttgctttct ctattaggca 63600
agatatctgc tctctatttg tgatctactt ctctgtgcta ctattcataa ggtgcccaca 63660
ggcaaaaaac cagggagaac atgaagttta ccttatggat ttttttcttc tctcaagaat 63720
tgcacctgta ctgttttctt ccagtgtctg aaggccattt atttatttat ttttgttgaa 63780
ttttagagtt gtttgttgta ggaggataaa tattatatga attatttcat catggcataa 63840
actatatatc tagacatgtt aaatctgaga tgtctattag ataaacagat agtgaggtgt 63900
gatagactgt tgaatacatg aatttggagt tcaagggtga ggtccatgct ggagtcatac 63960
atttgagatt caccagcata tataattcat ataaagtttt gaagtgaatg agatcttcta 64020
gggatttggt atagattgag agaagagata agggctgagc ccctgggcag ctttaaaata 64080
tcaggaagat caggaaaaat tagcaaactc agaaacagca agtagatagg agcaaaacta 64140
gtagagtgta atgacctaga gaagaatata ttttagggaa aaggtaatat tcaactgtgt 64200
aaaatagtgc taattggtcg agtgagataa gaatgtggac tcaccattgg atttgtcaaa 64260
cactggggtc aaaatggtct tgacacaagc agttccagta gagtgctggg aatgaaggcc 64320
tgattggaat ggattcaaaa taaacgtggg gatggggagg attgaagaca gagagtatga 64380
agaacttgtt caaagagttt tgctgtaaaa ttaagaatgt gaagattatg tgaaaaataa 64440
tttaaatata aatagcaagc attgtaatac agtaatcact tgttcttgaa tgtttgccag 64500
aactttactg ggaaaccact ggacctgagc tactttggat agaggattaa ttccaggaat 64560
atgctggtaa atgttcaaca actaggtctc tgaaaagaaa aaaccttgtt ttgtagccgt 64620
tgccaatttc tgtgatgtaa atattcccat catggtagat ttcaagctat aaatgtgatg 64680
tcgctgaaaa cagagttggg aagacatgca tgcaatccac tctcaagagt ttagtatatc 64740
actgagtaat ttctggtcat cttttctaat ttactgtatg attattggta tgtttagatt 64800
ttttttgaga tagggtcttg ctttattgcc tagactggag tgcagtggca tgatcacagc 64860
tcactgcagc cttgacatcc tgggctcaag caatcctccc acctcagcct cccgagtagc 64920
tgggactaca ggcatgcacc ccactgtcag ctattttttt aaaaaaattt ttgtagagac 64980
aggtgttcct atgttaccca ggctggtctc gaactcctgg gcccaaacaa tcctcttacc 65040
ttagccttcc aaagtgttgg gattgcaggt aggagccacc gcatctggcc tagattttta 65100
ttttacttat ttttgatttg gctttaagaa tttataattt tctggaaaaa tcattcattt 65160
aagttgtctt atgttgttac tgacagtaga agaaatataa tgaagaatgt gagtgattta 65220
ggaatcacat aaagttttgt ttataccctt catttgtgtg aaaataatta tagtacatta 65280
aaaaagaaat tcttgttgaa agcataaata tggtctactt ttatcactct ttttatagaa 65340
gggaactata tgatatacaa gaagtataaa tatggaactc cttttaatat acaagaagtt 65400
tgaatatgga acttatataa gatggacaaa taaggttgaa taggacctgt tatattaaaa 65460
aggctggccg ggcttggtgg ctcatgcctg taatcccagc actttgggag gcctaggcag 65520
gcagatcacc tgaggtcagg agttcagacc aacctggcca acacggtgaa accctgtctt 65580
tactaaaaat acaaaaatta gctgggcatg gtggcatgcc cttgtacaga agaaagactt 65640
aattgaaatc tttgaaaatc ctaaaccagc ataacaagac tgaatactaa catgttgtat 65700
cttgataatg cacatatttt tcactttata cttgctttaa ggatcttgta taattctact 65760
ccaggtgtgg atgctgaaac tgatgggcat gcaatgaaag ctggtatgca gaaaaaattc 65820
agaggtggtt ttactatctt ggtattcagt tacatggttt tattcccagt cttaatctaa 65880
gatcaaggac aaggttttgt aggcgattgt gtgaaataga agtatgtaga tgaaaatatt 65940
tgaaattaaa gtataaggga ggacaacaat cttaagtgca ttttggaaat atttcaaaag 66000
catcttaaag cagtatagtt aacttgtgag actattttaa taaaattggt tcatttttga 66060
ccaaatcttc gagtccagga gtttaagtca atataatctt ttccttagct accattagag 66120
agaaaggaga acctaataac ttggtggcga cattaccaca atagtacttt gtgtcagcag 66180
agttagctaa aatatagctt gcttctccat tgacttcacc tgaaaatgag cctcgggcct 66240
ttcatatggg aactgtagtg gctagaggag caatttagta gctaattgca aaattatatt 66300
gagaaattct tcatgcatgt taaatttttt ttaaagatta ctaaaacctt taataaaatt 66360
gtaatagctt ttacttttga aagataaaat ttcaacttaa tcttgtagct cagaagttta 66420
ttctatgata gtgacatttg attttggctg gatgttgatt ctaatacttt gccctttgtc 66480

-continued

```
atacagctaa agtacatatt cagtaatgga tatgaagtaa tatgtagttc aataatagaa  66540
tgtgtttttt tcacagtttt gaagacatac aatttgtctt ccaggtgttg ctactgagaa  66600
attcaatacc actgggatcc ctcatcttat gcataagaac tattacctct ggataaattt  66660
aggaacttct gtgtgtctct gtcagcataa aatttcataa ctatttgctt tggtgtgggt  66720
ccggttatat tcattttttt tagagactca gtaatttctt cccactgtga actagtgctc  66780
tttagctttg agaatttctt ttgtattttt tctttgataa tcttttcacc attttttttt  66840
tctgttcttt attctgtaaa ctattatttg gtcatctcct ggagctcctg agctgatcct  66900
ctaattttc tcttctttt ctcctgtttt tcagcttttt gtctttttaa aaaatgattt  66960
aattatctgt tgctgctaaa cagattaaat gactcttcat cttttagttt acttcctagg  67020
gacttcttca agtttatctt ctaacccttc cactgagttt tcatttatcc taccatactt  67080
ttaatcccta agaactttgt ttttatattt tgtttttgct catggatgta gtatcttatg  67140
gaagatatta attatatttc tgagatttta ttctgctttt agaatggatt cctttcctcc  67200
aagtttctcc ttctgcctct tggtttgctt ctgttttttt ctctttaatg ttagagtctt  67260
tccttacatg tctgctgctc ttggtagtcc cagcacactt tagagctaag aggttttgtg  67320
tttgtgtgta ggttttaaat ggtgtgcttc atgtttggtt atagaaatgg gccatttctt  67380
tgggagactt cctacctttg gaagtctccc aaagaaatac acacacacac acacacacac  67440
acacacacac acacacacac acacacaatc ttcagtggtt taattttccc agagcaatat  67500
tcgttcagtc ccctgcctga gagttaaaat ctttgctacc agtattctgg gaatcaagtt  67560
ggaaatggag gctcccaaat atcaccattc acgatatact ttccaacatt ttcccagttt  67620
ttttttttt cttttagtag cacaccttat ctcaattctc tataagcctg gtgctactaa  67680
gtctggttca gtatgcaaga gaagaaagcc ttcaaccttc ttccaaggtg ggggaagagt  67740
attcacccag atgtggagtg aactggagag ctaggaatcc tattgtttct tattcagact  67800
tgccatcagt tcacccattt tcagcttcac cttcatagtc actttctggg atacctgagg  67860
tttccaattc ctcaggccct cttggagttt gcagtccaaa tcagcttagt tctgctcttc  67920
cttcatggcc agtttgtttt cacctttctc tggtttgcta gggagtttta cttgtccatc  67980
tgctttcttg tttctaaatt tgaatttctt tatctcttct gctattctct ttttacctgt  68040
gggtttatat cttaaaatcc tttagtgcca ttttggtgag gtttcaggag gaatgagtca  68100
agattaagtt ctatctttta tgttttacta taagtcaact agtttaaatt ttattcttat  68160
gtaggcatac tttttgtttc tctctctctg gatgatttca gagccacttt aaccttaaac  68220
atatgtcttt ttcagcacag aaaatatttc taccaatgta tcattgagta tagtgtatgt  68280
tgtgttttct tcaagcctct ttctttaaga gctagctctg ggaatacctt ccctgtgaac  68340
caaatctaac ctcccctggc agagccaaac tctccattct gtatctccat agcactttgt  68400
atgtgtgcta ccaaagtgag tactctccag ttttaccttg gtatctgtgg gggattggtt  68460
ccaggaaacc tctcaaatac ccaaatccat agatacccaa gtaccttgca taaaatggtg  68520
cagtgtttgc atataaccta tgtacatcct cctgtacact ttaaatcatc tctagattac  68580
ttgtaatagc taatcctatg caaatgctat atgaatcgtt gttatacagt attacttaga  68640
gaataatgac aggaaagaag tccatatata ttcaatacag atgtaaccat ccacttaaaa  68700
atatatttgt atttatattt tttctgacca acggattctt gccacatcaa ctatccactt  68760
ttcccccagc tgtggttggt tgaatccatg gatgcggaac ccacaaatat ggaaggctga  68820
ctatagctag ttacaattaa tttgatttat taaagactca ccactttcaa tgatggatca  68880
```

```
ataattatag ataggagata ctggaaagca gcatggatct gggtccccca tgtgagaggt  68940
gggagatgtg gtggctaagt gactatggag tacagagttc ctcaatagtt ggttacccac  69000
gttacactga gcatctatag caagaagact ataagcacat gcaattttag caacagatta  69060
gctactacta taattttgaa atagagataa atgtaaatgt tatttttag atatacattg   69120
caactatagg gtggtatgaa aatatttgtg atttctgttg gtgactaagt catagatgct  69180
gctaatatta tggtggttta ttaactttat ttagaattaa gaaaaatgtc aagttagagt  69240
ttggtaaaaa atgtatcttt tcctccctcc catgaccatg aatctctcaa attttactct  69300
gggaccccag gttaagcaca ttagccttag attctttatt ttagtttcac ttatgatctt  69360
ctgccatatt agtcatggag tcttagacag taatattgga gacaatctca attccaacat  69420
taccatagta ctttagttta attgttattg aatctagaaa aaggtgtttt tgataaagat  69480
gttaaattct agatggtgaa atctgagaag agtggactat gccagaagcc atggagtctg  69540
gttgttttca cgtcctaaaa ggtgactagc tccatgaaca aactccccct gtttttcctc  69600
aggacttgag aaagattgag ccatctttct ttctacgttg aacctttccc tgggtcatcc  69660
acagggaagt atatgaatca gagacacatg ctgtgatgtc tggccctcag aggtatggtt  69720
agcccagcag aactatcctg caaggcatac tctgaatata tggttttaat caaagcaact  69780
tgcctagatt tatttattta tttgtctctg ttaatggaga tagtgtgtgg gggaaaaatc  69840
tatatctgct gtaggcttag atccagtcag aaagctatag tgagtgctaa tcttataatc  69900
tgtgttttcc atacatataa atttaaagta tggatatttg agctatatac agtagcaacc  69960
aacttaatgg taagtagctt tatgatgtta tatctaatgt ttcttccaaa tattatggct  70020
tcaaggccat tcttataatt taagactgta aaattgaacc catttttcaa aagttgaacg  70080
catggtacct tattatgcat actgttgtct gaggtttgga aagataatga agactctcat  70140
ttcgtgtggg attctcaact gagaacaagg aatagaactt aacatttgag tttgaaagtc  70200
cttgggttct gcttttgtta tgcaataagt cccaatgata agcacaaaat aggcactaga  70260
aaaagcctac ttttaatagg catccatttt aaatggggat aaaaatttta cggtatatag  70320
ttaataaaag gtttcattac ggcattagca aataaagcaa aaatcattaa aacaagttta  70380
ttttatttct ctttataaaa tttagcttgt aactatgcat tgatttaaaa caaggaataa  70440
atcagatgtt gactttggca tacattttct gacaaatggt atgacagtag aatatgacat  70500
tcttctcttt atgtttttga tttttcttga tgtgatcatg tagagtcagt ttttgaaaaa  70560
aatttcattg gcttcataga ttttcctgag ggcctcattt catattttta tattcaaatt  70620
atccttttttg aggtgtctat cttgtctttt tcatattgca agacttaaat ttcactcttc  70680
agtctgtgtg ctttgtgttg ttaaatgtta taaagattga ctttccgtga gggtagatgt  70740
cagtgtatta catgagggat attgagagga aaataatttc acaggtattt agttcatcag  70800
tgaacatttt caggttgtaa caattgcttc catatacatt ctcctaactg ggagggttgg  70860
ggaggaattc atctcccaat aattattcat gaaattatta ttatctcctc tttatttatg  70920
aaaacatgag aagaaatatg aagttgtagt agcattaaaa cataggcata ttgagccggg  70980
cgcagtggct cacgcctgta atcccaacag tttggaaggc taaggcgggt ggatcacctg  71040
gggtcaggag ttccagacca gcctggccaa catagtgaaa ccccatctct actaaaaata  71100
caaaaaatta gccaggcact gtggctggtg cctgtaatcc cagctacttg ggaggctgag  71160
gcaggagaat tgcttgcacc tgggaggtag aggttgcagt gagccgagat catgccattg  71220
```

-continued

```
cactctagcc tgggcaacaa gaataaaact ccatctcaaa aaaaaaaaaa aattaaaaaa  71280
ttaaaaaata attaaaaaaa ggcatgtttg acaaaattct agaggagttt ctaatagtga  71340
aatatggaaa gggccctgag gaggaatgtg gggttgagct ggtaagtggt atgacatttc  71400
tacccattct tactatgcca tctaccttgg acacaggaag ctttcactga gtaggagtaa  71460
gagacaagag tctcttctgc gttctgcagt ctgtcttcta catctgttct ctgaaaccac  71520
ccagagcatt agcctttatc ttcaactcta acacctctct ctcaaatagt tctttgtaag  71580
cccatatggg gatgaaaatt tgctataata cactacagca ggggcaatga acaaccagtg  71640
atgttttaga atagagatgt aaaaacttaa cataatgatt atacaaaatg gtgctgctat  71700
tatgactaaa aacaatagtg gctaacattt atggagccca tactacctag taggcactca  71760
cttatgaact catcaagtct ttatgacaat gctatgagaa aggtactgtt attatttcca  71820
tcttattaat gaggaaactg atacatagaa acattcagca acttgcccga gatcacatag  71880
ccaataaatg gaaggtcaga atttgggaac ctaagtatct aactctaaga tcctaccact  71940
ttaaatgtct tctattgtat ttgaggcaga tcaatattta atactgaaca ctaacttatg  72000
ttcttatttg tttagaatct ctgctttcaa gaggagagtt ggccctgaga tccatttcaa  72060
aggtaaatga tataatgtgg tagaaaaaag caggtgttca aaaagtctaa gctttagctg  72120
aagttagaag attgagaata tagataaaat gtttctgaga aacattgaga aataatatgg  72180
cttttactta ctttaccaga aaagaaaaag attccctggg gctgagagga atgaggttat  72240
atagaggaga attaatgaaa atggggagtc taggaggtcc cagagagagg gtccttgtct  72300
cttgcctcca ggctgacaga caaggcatgg tgccagactt tagagaagct tgggtatggg  72360
tgggtgatat gacttgggca tcctgcccct ggatgataat gccgtgtcag cctcaaagaa  72420
agtcatattc tattattatt attattatta ttattattat tgagatggag tctcgttctg  72480
acacccaggc aggatttcag tggtgcgatc tcaactcact gcaacttccg cctcccaggt  72540
tcaagcaatt ctgcctcagc ctcctgaata gctgggacta caggcacgtg ccaccacacc  72600
cagctaattt tgtattttta gaggagatgg ggtttcacaa tgttggccag gcttgtctcg  72660
gactcctgac ccacaagtga tctgccagcc tcgacctccc aaaagagagt catattcttt  72720
agtgtgacat gaaaacagga gcaaaaagaa tcctgttcca ctcttagtgt ggtgctgaag  72780
aagcagagga aatggagatc ctgaaatgcc cattcggaca ggaataagaa caacttcttg  72840
ctaagctgtg tgggctgatg atggaagacc aattgggatt gtagatttct cagtgtatgt  72900
ctgtgtagag aagtgattcc aacactacat ctgctctatt ccctcctccc tgccaatatc  72960
tcaatacttt gtcagctccc tggaacttag acacaactgc acacaagaga aaggtagctg  73020
agattcagat ttataaaatt ctattgctct cttgacatag tttacttacc cagatgtgca  73080
ctctgagatc tatggctact atgtttagtc tcaagttttt caggctgttc tttaatcttc  73140
ctagaaaatt atgttgtaca caaattgtga agttgatcaa gcatctgcat gtatttacaa  73200
attctccccc acccaatttt agttaatttt caaagtaggt aatatatgca cttggtacaa  73260
aaaaaattca aaaggcggtc gggcgcggca gctcacgcct gtaatcccag cactttggga  73320
ggccgaggcg ggcggatcac gaggtcagga gatcgagccc atcctggcta acacggggaa  73380
accccatctc tactaaaaac acaaaaaatt agccgggcgt ggtggtgagc gctggtagtc  73440
ccagctactc gggaggctga ggcaggagaa tggtgtgaat ccaggaggcg gagcttgccg  73500
tgagccaaga acgagccact gtactccacc ctgggtgaca gagcgagact ccgtctcaaa  73560
aaaaaaaaaa aaaaaaaaat tcaaaaggcg tcaacaaata gacaatgaaa ataaatgttg  73620
```

cccctcagtc ctaacacagc tatcagttat ttgtgtttcc tgagatatta tgtatacata 73680
ttatcatata tatatacagt ctaaaaacag acctgcaatg atagcatatt ttacactctg 73740
ctctgtatct tgccttttcc ttgtaacaag atgtcttgga tactattcta tagttgtatt 73800
tagcattcca ttctagggat gcaccatgat ttatttaagc aatctctatt gatgggaatt 73860
tagattattt ccagtttttt tgctattaca agttgtgcta tagtgaattg tttttagctc 73920
cctctttgtg catttgtttg aatatatgtg aatgataact ttaaaagtag aatacaggga 73980
tgatacttac atgtattgaa aatattaaca ggtattgccc agtgactctc catagggact 74040
gtaccaagtg aaattctcac ctgaaagtat gagtgcccat ttcctcatat tattaaactc 74100
ttaaaatttg ttctcatctg ataaatgaaa atcagcatct tcttgttttt cctttcgttt 74160
taaaaaatga atttgtattt ttgtctgtac tccttttttt tcttatctgt ctatgacctt 74220
tgcccatttt tctatattga ttttcctgag cttacacatt ttatgaaatt agccttttat 74280
aatttgtatt gcagatgctt tcttccaatt tattggctgt gctttgactt tgcttgcttg 74340
tttctttagg tacttagact ttttatttat atatagttga attcatccat cttttaaaaa 74400
atggttttag tcaaaccatt ctcactcaag agattattgt cttatacctc atgctttctt 74460
tagtatcttt tcctaatttt atttttatgt tgaaatcttt ctcaatggag aatttgttta 74520
aagggaaaag cagactatta attgctacat ccatgatgtt ccatttataa cttttacttt 74580
aattttttga tgaatcatgg gcaatggaat aagattccat tttttacctt caaaataata 74640
tgtttgaatc acttatttaa tttacttgca aaaataagtt ctgcaagaaa agagtcttca 74700
ttagattttt ttcccactcc aagaaaagcc atatagtctg gttgagttaa ttgtaacaag 74760
attagggtgg gaagaaggtc agagagtgtg tttagctatt gtaaactttg tgagcaaatg 74820
caaactatgg cgaatacagt ttacagtttt atggaaacaa agacaattct ctagggccaa 74880
tgttctaaaa aatgtagttt cctataacaa aaatttatat tctcaacatt acaagtcaac 74940
aattcttgaa attattaaaa caaacctttg aatattataa gaaaactgtc ttattctgta 75000
aacttaggca gaaattcaat gttaagataa catgatacag aataagtata gatttaattt 75060
aaattttatg gtaactggta tataaatatt ctctgaactt cttcaatatt tagctaaaac 75120
aaagggcaat atctagtcca atgctttgtg ttttaaaagc acttgtgtca acaactcaaa 75180
gtttctcatt aaataacatt gaaacatatt gctatcatta taactattat tttaaccaaa 75240
gcttagtcaa agaccttggc cacagaatga tacactttaa cagataatga acctaagcta 75300
tatgacattg caaaacatgg cactttgaat ttaaatttaa caaatttgat gaaaactctc 75360
attattgata gagtactttc tgttgccaca cttactaatt ttgattactg ccaaactttt 75420
taaaaattaa ttttaattac gcaacaaaac atggatacgt tcacatttga aaaagacaag 75480
agaagataaa cctaaagatc cctttgtttc tactctcttg cctgattttc tcttcaccaa 75540
aacctcaacc tcagactgaa gtttggggct tatacttcca gagattgttt cacttcttca 75600
ctcaacacta tatttttcat atctatttgt attgagacat ttagatcttg ttcatttgtt 75660
ttaactgttg cacagaattt tattaaatac atatacacat aatcacattc ctctgttgat 75720
ggacatgtag tttgcttttg gtttttcatt attataaata acaatgctta taactgtcta 75780
ccagtgcaga ctttttccta aagaaagagt cctggaattg aaattattgg tttataggat 75840
atgagcattt tgagttttaa tagatactgt caaactattc ttcaaaatgg ctgtacttat 75900
ttattcttcc atcagcagta tataataatg gtgatttctc tacatctttt caacacttaa 75960

-continued

```
ttttgtcaaa cttctaaaat tagtgctaat ttggtgaatg tgaacaagta tctcattatt  76020
taatttgcat tttcttgatt actactgagt tgattatctc ttcatatgta tactggccac  76080
tcaagtttct ttccctgtga attatccttt gcccagtttt cttttgggct gcttttcaat  76140
ttcttgtagg cctgtacgag ttctttattt tgtcccaaat attaatcctt tttatattat  76200
ttgtgttaca gttattttat ccaagcctag tgattatttt taaactctat ttcttgtgtc  76260
ttaagtagag caggatattg catagtggtt aagagtatgg gctttaaaag caaatgactt  76320
gggtttgaat ccccactctg aaactatttg tgtgatcttt ggtaagttac ctaacctctc  76380
ttattctcaa gtttctcacc tgtaaactta agattataat agaaatcacc tcacagggtt  76440
gatgtgaatg ttaaatggct taaataatga atagtctctg gcatataata agtactcaat  76500
aattattatt actatatagt caaatttaac aataatttgt ttataataat tgttaaataa  76560
ttgttagata aaaagccttg tttgagaatg cttttcctaa tgtgaagttt aaaaatgttt  76620
tatattttgt attagtaatt ttattgattt tatgtttatt ttaaaaattt gtctagatat  76680
tttccatgtg gcataggtag gaatgttaat tttaattttt ttcatctgta tatgaagcta  76740
attataccag ttccatttac gtaaaggcct attatttcct gattgattta aagtgtaact  76800
tctataatat attaaattcc cataagatca ctttcatatt atcttctttt ttagtgattt  76860
gtctattatt gtgtcattgt tacattttta aaatttaatt attgaagatt tataatattc  76920
cctgaatttt ttttgcatgc ttctaaattt cagttgtgct tttaatattt gatggtcact  76980
taagttggat acaaaatcat tgactcattt ttttcttggc cttgagtaag aaatatatct  77040
ctccattgtc ttccatatct aaaagagtta tgcctaaatg ataactttcc ttcttgtatg  77100
taatttactt ttttggctta aataacaaga aaatattttt taaggtacaa tagttttatt  77160
acattttggt ggtaatcatt ctgggaaaat tttcctatgt acatggtatt ccctttaata  77220
tgtaaagtat tttgttattt taacaaagtt ttctttaatg acatatttaa aattttgttt  77280
tctggcactg atttgctttt ttcctttgag aatcttatac atacatgctg tgtatatata  77340
tccttttgtt ttttcatttc tacttgattt ttttctaaaat ttctgctttc cattctctat  77400
tgtctaagtg tcatctgtat actgctgtgt ttcttctagt atagtcctct cttctgcaat  77460
ttacgaagtg tgttttgatg acaaactcca aatttatagt tgtatgttaa atctttatta  77520
tactctcatt tttaatattt atatttttag gtatagaatt ctattttagc agttagtacc  77580
attgacacaa agatattcct ttgtcttcta gttttcattg ttgttattga gaagtcagct  77640
gtcttttcta actgttgttt ctctcaaggt aattatttta aaatataggt tttattataa  77700
ttcaggtata ttgaggccat cagatcagga gactactgcc attaaaaaga tagtttgttc  77760
ttcacagctc tcaacaggag gggacatgca tgctatgtaa tatcacatgg agaaacacca  77820
ggttggtcag gaagcagaaa gaatggaaac aaaacatggt caaaaggcat tattgtggct  77880
tctgtataaa ggaatgtgta ttagtcaagg ttcttcagag aaacagaatg aataatgtga  77940
taggtagaga gattgatagc tagatagatt tatcataaga aattggctct ggtaattata  78000
gagactgaga agtttcaaga tctgaagtca agaagctgga gatccaggag agctgatttc  78060
agtccagtag ttccagtcca agtctgaaag cctatgagaa gatctgatgg tgtaagttcc  78120
agttcaaaag ttgtcagact gggaagccaa gaagagccaa tttttcattt caagggtaag  78180
agaaagaaaa gaccaatgtc ccagttcaag aattcaggca ggaggagttt cctcttactc  78240
agccttttca ttctaatcag gtcttccact atttggatga ggcccaccca cattagagaa  78300
ggcagtctgc tttactcagc ctacctattt aaatgttaat ctcatccaga aacactttcc  78360
```

tatacacatc cagagtaatg tctggccaaa tgtctgggca ccctgtagcc cagtcaagtt 78420
gacatgtaaa atgaactata aaagaatagg tgaggcaggg cgaatggttt caggattggc 78480
tagtttgaat aatttcagca ggctctgggc tgtaggagat gtcttgagtt gtctgatatt 78540
tgatcctggg ttgattgagg cagttgaata ttggcctaaa gagtaagagc cacatagagg 78600
agatagggga ttgtgccctg gattggttag attgcatgtg aaagttgtga gttgtttgct 78660
atctttagga attatgtaac cctggcaggg gcagtccttt cctggtcagt gaggcctcag 78720
atgccagaac atcaagaata aagaaaataa agtataatta atacagtaat ctattcttct 78780
ctctggttgc ttttaagact ttgtctttat ttttctatac ttttgactct gaaatatcta 78840
atttgggtac attttaattt atctggcttg tgattcttcc agcttttcga atatgtgggt 78900
tggtatcttc catcatttgt agaaaactac cagtcattta tctcttcaaa tattgtgtta 78960
cacatctctt cccttcttct ccaagcaaag caatctttgc atgtctttgt cttctattgt 79020
ctcttgtttt tcatattttc tgtattggtc tttctttcta tgctacagtg agttttttaa 79080
tggcctattt tctagctcag caattttatc ttttgttttg ttcagtatgt tgctaaacac 79140
atccaattca gtttttaaaa ttagatattg tatttttatt tcttaaggct cttatttgtt 79200
ctttttcgta tcttgtaggt catatttcta cttccctttg ggtattttca atcttgactt 79260
atttcttcaa acattacaag cctattcact ttataatctg tgtctgacta ttccaatatc 79320
tgacatcttt gtgactctct tttcactggc cgttcatgtt tctggtctcc cttatggtat 79380
cattttttcct tgtgggcttg gttatttttg actatgtacc accacgtttc cttaaaaatt 79440
atttatgggg attccctagg ccttaaagtt cctcctctag ttagaatttg tatttactcc 79500
tgttggatcc ctaggcgcat aaccatccca gaattacttt aaactaaatt tacagcttga 79560
ggattcctgg accactccac taatgtgaga cagggctgaa aatccatgca agagttcact 79620
tgtggttacc agttttaagg gacaactttt taaagattcg atttccccct tctctgctca 79680
gcatgaaatc tcacccttag aaagttccct acatgtggat tgtgattagg aaagtgcatt 79740
tacttagttc agagttttag tttaatgtgc ttgtctccta tttggattct catggatctg 79800
gaccttgact tatatacccc atgccccttg aggccctcta aacttcagct caattttatc 79860
taggtcagaa aatttcctca ggggaaaaag aaagcagctt aatgaggtgt tcatttttct 79920
gaatatttgc tctcttctag agtttggctt ggtatctcat cctcacaatc tttcgaaatt 79980
ttttattctt tttttttttt cttttttttt ttgagacagg gtctcactct gtcaccctag 80040
ctggggtgca gtggtgggat cttggctcac tgcaatcttt tcctcccagg ttcaagtgat 80100
ccttccacct caccctcctg aatggctgtg agtacaggca ctcaccacca cttctggctt 80160
tatttttatt tttggtaaca acggggtttc accatgttgc ccaggctggt ctcaaattcc 80220
tgagctcaag caatctgccc accttggcct cccaaaatgc tgggattaca ggtgagccat 80280
cgctcctagc cttctttgat tcttttaaga aaatgagttt agcaattaga attgttatga 80340
atagactaat tcgttactgg aaatgctgtt actggaattg gaagttgtag gaaatctttt 80400
acatttacct gaatgcttat agaattgctt cagtttcctt gaaatttaaa aatagcacca 80460
ggatatttta aggtgatgac tttttaaaat taattttgcc tagttcataa gaagcctttt 80520
tgatttactg atttcatgag ttttcccaca gataaataag atagttattt tattatatct 80580
ttatcacctg tgttccattt cttctgatca tttctttaga aacaaagtct ttttatatct 80640
atcattttcc tcctttggat tcatttactt catattgttg gataatttct caagcatttc 80700

-continued

```
taaccttaca agtgattttt tttgtctaca gtggtgttgc tattttaatt tctacttgta  80760
gtaatgtaga agatatttat atgacattat ttccttcatt atagctttaa aatttttcta  80820
gttctctttt gtctcagtat ttcattgttt ttgattcagg tttctttctg tacttccaga  80880
atccataatt tttgtaattt tattgaatat taattcatga tatagtattt tatgaaaata  80940
attgtattta ttttcataaa tacactcata tctttccttg ttttcagaat tgttatcaag  81000
caaatgggtt cactacctga tgtacacaga aaccaataac tatagcacta gcttttgaga  81060
aaagaaagac tttattgcaa aatgagtcaa caaggagtca ggagtgagct caaatctgtt  81120
tcctcaatct ggggtctgga gcaagtgtat gggcttggag agcaagagaa aagatttagg  81180
aatgtagatt tgtagaatct gattgcaggg gttcaaattt gaccagttat ggtaaggtat  81240
attgaagtga attttagctc tagatcttct gggtcaacag accccttgct tcagaaagag  81300
ttctggtatt atggttccag tcatgttcca gtcttgttgg ctttgaggag agaaatcatt  81360
tgttttgggt attgttagag gtcaaagctt ttcctgttgt gcatgcctgg gcttcatgac  81420
ttgcagtttt tggctctgtt actacaaggt aactcaacat tttgttatta acaacatggg  81480
cccagtttgg gctggtccca gagttacagg atctttatat tggtccattg tgattttatt  81540
tatttttcaa atttttttata atcactttta aagtcttaga taataaataa aatttaaatg  81600
atagattcca ctgaaaataa ttagccaaaa cataaagcag gtaaattgca ccattcaaac  81660
acataattct ttttaaacct aaaaataagg aagaaatact taaatcttag ttctttattt  81720
gtacatagaa ctttttaaca ctatatataa atgtgagaaa tcattttggc caaaaaagaa  81780
gtcagaagtc aaaattcata aaacaaacct taggaatgtg gaggttaaga tattttctgc  81840
cctaccaatt aattattatt tattaaaaga agtagagaga tctgtataca tgaacaaaat  81900
tgagacaaca tgcaggtata tctgttgaca ccacttaaaa aaacccacat ttattttgaa  81960
aggacttgtg aacatccagt caatagaaaa atacattcag aaaacactta ctgaacattt  82020
atgatgtgtc agacactgtg ttagaaactt gggaggcaaa gcttctacgt ctaagaagct  82080
cagagtcaag ttgggggcag gtaagcacaa actttaaata tttacagtat tctctctctc  82140
tctctttctc tctctctctt tctcctcccc aacctgtttt atctaaacat gagttataca  82200
tgatatgtac aagcttatac attcagttat gtgtccctta acagggatat gttcagagaa  82260
atgcatcatt aggccatttc atcattgcgt gaacatcaca gagtgtacca tatgtacata  82320
aacccagatg gtgtagtgtg gtgtggtgta cataaaccta ctccacactt aggctatatg  82380
gtatagccta ttgctcctag gctacatacc tgtgcagcat gttactgtac tgaatacttt  82440
aggtgtctgt aacacaatgg tatttgggta tctacacata tctaaacata gaagaagtgc  82500
agtaaaaata tggtataaaa gattcaaaaa tggtgcacct gtatagggta cttacaataa  82560
atggaacttg caggactcaa agtttctctg ggtgagtcag taagtgagta gtgagtgaat  82620
gtgaaggcct gggacattac tgtacactac tgtagacatt ataaacactg tgcacttagg  82680
ctacactaaa tttattaaaa atacttttct ttattcagta agttaaccat agcttactat  82740
taaattttta ctttacaagc tttaaaattt tttaactttt tgattctttt gtaataacat  82800
ttagcataaa acataacata tacacattgt acagctatac aaaaatattt tctttcttta  82860
tatctttatt tcataagctt ttttctattt ttaatttttt actttttaaa gtttttggta  82920
aaaactatgg tacaaacaca cacattagtt taggccttgt attagtcagg ttctgtagag  82980
ggacagaact aataggagag agatatataa agggaatttt attaagtatt aactcacatg  83040
atcacaaggt tctacaatag gtcacaaggt ttcacaatac gccgtctgca ggctgaggag  83100
```

-continued

```
caagaagagc cagtctgagt cccaaaactg aagaacttgg gagtccaatg ttcaagggca  83160
ggaagcatcc agcacgggag agagatacag gctgggaggc taggccagtc tagtcttttc  83220
acgttattct gcctgcttta tattcagtgg tagctgatta gatggtgtcc acccagatta  83280
tgagtgggtt tgccttcccc agcccactga cttaaatgtt aatctccttt gacaacaccc  83340
tcacagacac actcaggatc aatactttgc atccttcaac ccaatcaagt tgacactcag  83400
tattaaccat cacagaccta tacaagataa ggatcatcaa tattgctgtc ttccacctcc  83460
acatcttgtc ccgttggaag gccttcaggg gtattagcag ctctgttata atcttatggg  83520
accactaatg tatatgcagt ttgtcattga ccaaaatgtc attatgtggc acatgactgt  83580
acttatatat atcacttatt tgtgtatacc atatgtcttt gaatgtatat atggaagttg  83640
gtcatgaagg taacgtttgt gtgaaatatt tgccctttta gtttcctgtg gaacctggaa  83700
ggatcaggat tcctgaaaat ttaaaccaga actcagatat tccagtaatt gctcatcaag  83760
tgcccactag tagctaagca tctgctacac aacagcatac aaagtctgga aggtaatgaa  83820
aatagtgcaa atgggttccc catttctttt ccaagaaaaa cctcctaatg ggttgctgat  83880
gagctaatca ggtcaagtgt tctctgagtt gccctctttc tacagtcagc aagcataaca  83940
ttttgttaac ctattgacac agaggaaatt tgttttccat ctgacctttt acagtaacta  84000
ctcaaaatta ctttctcttc agctaacaaa gctaatgaat aaattattca agtttgacac  84060
tcatagaaaa taacatttta catttttcat ttttattcct gattattttg ctttcttttt  84120
cagccattac ttctttccct atgaagagtt ttaatcttta cggaaatttt gcagtgttgg  84180
tttagagagt catactcgga ctctctggaa ctaatcacat tcacaaaata agtttcttat  84240
tttgcaaata taacatttat atatgttgaa atggtcacat gataattttg taaatgcaga  84300
taaattccat taagaattta taaccatttg tataagaata aaattttaac tttgggctac  84360
atgtaaacaa aaggtttcct aaggaaatag ttattagaac aaaaatattt gggacatttt  84420
aaacctgaga ataaactctt ctccaagatg gaaaagtgaa ttataggtct ttgttattat  84480
tctttatgaa atcttaattc taagcatctc tactcactaa cattttgtta aatttattcc  84540
tttaataaaa atttcttcaa aattatctta atgtccagcc ttttatctgt ctcaaactgt  84600
cctttcacta aacaggtcca aattggatgt ttacttgcag tgaatatgtt tttaatggtt  84660
tgttatattc agaggatcat aacttcaaag atggtcatca attaattcac aaaggtaagc  84720
ttttcttcac tctttgtggt taggccaatt taaataatac atgttagaga atgagcatct  84780
acatatttcc tctgcagact gactattcta acattcacta tgctaagagt attgttattt  84840
gagcatcact aaatgcattc accttcccaa ttttcagaga caaagtcaaa ctcactcata  84900
tttatcatga atgtgcatac aattctatta atttaacatt ttccatcaat gtaataaaat  84960
agcaatatta ttttatactt gttagaaaga ttctaccaag agtatttttg atcatcatca  85020
gcaagtggtc actgtttctt ttggaagatg ctcctggtca ctaaaaactg tatcacttta  85080
accacaacct cgttaaactg ggttcagaga ctcacaaatt atatcaacag tagcatttct  85140
ttcagttgaa tttgcaaagt aggcttttat tctctatgtg ttccaatatc taccttgaac  85200
agtcttagaa ctagttaaag catttattaa gtactcttgt aatgaaggaa gtaatgatta  85260
attgataact acttttgtta tgcttataaa acattttccc taaactttac cttaattttg  85320
ggggattgtg agggaagtct cctttacttt aattacttat cgacccaggt atcagacagt  85380
cataatatct ttttttttta agcaggtaaa actagacttt gtatgggaat tcttaagaaa  85440
```

-continued

```
tgtcagagag ctggtcctgt tgaaaagttt agcagttata gaaaaatatt tcaaaacata  85500
aatgtagcag tttaaacatg atttggtgtc cagaataact tgttggtctt atttttcatt  85560
ttcaacataa atatcaactg ccactgtata attgaatcac aaacatattt gaattcagga  85620
atttttatac tgaaatattt ctctgtgagc aaatcccacc tcaccaaaca gaaagatttt  85680
gttactgttt gtgtgttcta aaatcgagaa agccttatat tatataattc tctgttgggt  85740
attttatgta tctgtatact tttttattcc acttcccctg tcatttttgt attcctcaaa  85800
atatctagga cagcattttt gcatgctcgt gtacatttaa gaatatagca tagtggttaa  85860
aaacttggct tctgcaacca gactgcttag gttcaaatct tggctccata accttcagtg  85920
ctatgacctt tgtaattcac tcaaacctcc tatgccttgg atttctcatc tataaaccag  85980
aaggtggatt aactgtcggt ggattaaatg agtcagcaca tgtagaacac ttcaagtagt  86040
agctggtaca tatcaggctc ttagtaaaca ttagctatta ttatttttaa caagtattaa  86100
gcacctgtta cactgaaact gtgctgtggg tgctggggat gccacgatga acaagtactc  86160
atctttactt ctatcataaa atgtaaagtt tggtgaaata ttcaggcaaa cacatgggtc  86220
attgtaatac agtatgataa ctgctatcat agggtagtgt agggtgccac aattgcctaa  86280
tggaggaccc cttaccagac taagggtatc aggaaagttt ttctggtcta agcagtgtct  86340
aagctgagat ctgaagaatg gtgatatagc ttgtaccctc caaatctcat gttgaaattt  86400
gatccccagt gttgaaagtg gggtccagtg ggaggtgttt gggttatgga ggtggatccc  86460
tcatgaatgg ctttgtcatt cttgtgagac tgagtgagtt cacactctta ttcccgtgag  86520
atctggttgt taaaaagagt gccaccttcc tcccaccccg tctcttcctt ctgctcttgc  86580
tgtgtgatgc ctcctcccct tgccttctgc catgagtgga agcttcctga tgtccttccc  86640
agacatagct gctcttgcca tgcttcttgt acagcctgca gaaccatgaa ccaaataaac  86700
ctcttttatt tataaattac ctagtctcag gtgttccttt atagcaatgc aaacagatta  86760
gacagatggg taggggcttg ccatgtgata gtgaatggtg tggaggaatg cagtttcaag  86820
aagacagggt agccagagga tccatgatac aggggaaaga gagtatgaca catttaagga  86880
cttaacaagg ctcagttaaa tgcactatat agttcatgac aggggatggt gcacaaacct  86940
ctctattctg agaagaatag gcaatcactg aaggtgtaga agagaagggt gtcatgttca  87000
tattttagtt ttcagatctc tccaactcca gtgtaggtaa tatactaaag tgagtttaaa  87060
agttgatata ggaagatcag ttaaaatgcc agtgcaccat ccaagagaaa gatgttggag  87120
gcttggaact agagtggtag gggtgaatag aaaaagaact tgagaaatct aagagacgtt  87180
tatgggaaaa gagtcagaag gacttggtaa taatacagtg ctagatatgg agtgagagtg  87240
agaaagaaga cctaaagatg gattcccagg tttctagatt gagcatgtga ttgatgccat  87300
ctactgagac aggaaacatt gtctgtaatg aatggacagt ggttgtggct agtcagtata  87360
tatccttggt aattatgtct caattgtcaa ctaggagcaa ctcctgctca atctcaattc  87420
atgtgctctt agatggagtt gattccacct ccagctccaa gggtggagca catgaaccag  87480
attggaccaa ttagtgcatc acattctccc agccacatgt cagggttggt cacagcaact  87540
aagctgacac agttagagtg agtctgatag ctttggtggg acttgttgaa aaaggcatgg  87600
gagtgtgaat tgttggagct gaagcagtta tcttgaaccc actagaggaa tgtctgcgag  87660
aaaggagcca acgcagtgga aagcagagct gagagagaga agaaaattct gagaatgccc  87720
tttaagtact gaatctagct atgcctatgt catcctctcc cttgcgcttt ttcttttctt  87780
tttttaaatt taatttaatt ttaagttcca atatacatgt gcaggacgtg caggtttgtt  87840
```

-continued

```
acacaggtaa atgtgcgcca tgatgatttg ctgcacctac caagccatca cctaggtatt  87900
aagccccgca tgcattagct gtttatcctg atactctccc tctcccgatc ccccaccccg  87960
acaggcccca gtgtgtgttg ttcccctccc tgtgtccatg tgttctcatt gttctgctct  88020
cacttataag tgagaacacg cggtgtttgg ttttctgttc ctgtgttagt ttgctgagga  88080
taattgcatg tctaattttt taagaaacta ccacattctt tcccaaagta gtggaaccat  88140
ttagctctcc cactggtagt ctgtgagagt tccagtttca gaagaaatgg taccaactcc  88200
tctttgtacc tctggtagaa ttcagctgta aatccgtctg gctctgggta tttttttggt  88260
tagtaggcta tttattattg cctcagtttc agaacttgtt attggtctat tcagggattc  88320
aacttcttcc tggttcagtc ttgggagggt gtttgtgtcc aggaatttat caatttcttc  88380
tagattttct agtttatttg catataggtg tttatagtat tcgctgatgg ttgttcgtat  88440
ttctgtgggg tcagtggtgg tatccctctt atcatttttt attgtgtctg tttaattctt  88500
ctatcttttc ttctttatta gtctagctag cagtctatct tattaatttt tttcaaaaaa  88560
accagctctt ggatccattg aattttttga agggttttc atgtttctct ccccttctgt  88620
accaccctga tcttggttat ttattttatt ctgctagctt tggggtttgt ttgctcttgg  88680
ttctctagtt cttttgcttg tgatgttagt gtcaatttga gatctttgta gtttttttaa  88740
tgtgggcatt tagtgctcta aatttccctc ttaatactcc tttagctgaa tcccagagat  88800
tctggtacag tgtctctttg ttctcattgg tttcaaataa cttcttgatt tctgccttaa  88860
tttcattatt tacccaggag tcattcagga acaagttgtt caatttccat gtagttgggt  88920
ggttttcagt gagtttctta atcttgagat ctaatttgat tctgctgtag tctgagagac  88980
tgtttattat tatgtcagtt cttttgcatt tgttgaggag tgttttactt ccagttatgt  89040
gatcagtttt agagtaagtg ccatgtggca ctaagaagaa tgtatatttg ttgtttttgg  89100
gtggagattt ctgtagatat ctatcagttc catttgatcc agagctgagt tcaagtcctc  89160
aatatccttg gtaattttct gtctcaataa tctgtctaat attaacagtg gggtattaaa  89220
gtctcccact attattgtgt gggagtctaa gtctctctgt aggtctctaa gaacttgtgt  89280
tatgaatctg ggtgctcctg tattgggtgc atatatattt aggatagtta actcttcttg  89340
ttgaatcgaa ccctttacca ttatgtaatg ctctctttgt cctttttgat attttttggt  89400
ttaaagtctg ttttgtcaga aactaggatt gcaacccctg ctttttctg ctttccattt  89460
gcttggtaaa ttttcctcca tctctttatt ttgagcctat gtgtgtcttt gcacatgaga  89520
tgggtctttt caatacagca cactgatggg tcttgactct ttatccagct tgctattctg  89580
tgtattttaa ttggggaatt taatccattt acatttaagg ctaatattgt tatgtataaa  89640
tttgatcctg ccatcattat gctagctgat tattttgtag gcttgttgat atagttgctt  89700
cacagtgtca ttggcctttg tacttcagtg tatttttgca gtggcaggta ccattttttc  89760
ctttccacat ttagtgcttc ctttaggagc tcttacaagg ccagcctggt ggtgacagac  89820
tccatcagca tttgcctgtc tgaaagagat tttatttctc cttcacttat gaagcttagt  89880
ttgcccagat ttgaaattct gggtaggaaa ttacttcctt taagaatgtt gaatattgcc  89940
ccctatctcc tctggcttat agggtttctg ctgagagggc cactgttagt ctgatggggt  90000
tctctttgta ggtgacctga cctttctctc ttgctgccct taacattttt tccttcattt  90060
tgaccttgga gattctgatg attatgtgtt ttggggttga tcttctcatg gagtatctta  90120
ctggagttct ctggatttcc tgaatttgaa tgttgacctg tcttgctagg ttggggaagt  90180
```

-continued

```
tctcctggat gagatcctga agtatgtttt ccaacttggt tccattctcc ctgtctcttt  90240
catgtacccc aatcagttgt aggtttggtc ttcttacata accccatagt tctcggaggt  90300
tttgtttgtt ccttttcatt ctttttctc caaacttgtc cgcctgtctt atttcagcaa  90360
aattgtcttc aagctttgaa attctttcct ccacttggtc catttggcta ttgatacttg  90420
tggttgcatt gtgaagttct tgtgttgtgt tcttcagctt catcaggtca tttatgttcc  90480
tctctagact ggttattctg gataacagct cctgtaatgt tttatcatgg ttctcagctt  90540
cttgcattgg gttagaacac actgctttgg atcagaaaag ttcattatta cccacctttt  90600
tttttattat tatactttaa gttttagggt acatgtgcac aacatgcagt tttgttacat  90660
atgtatacat gtgccatgtt ggtgtgctgc acccattaac tcgtcattta atattaggta  90720
tatctcctaa tgctatccct ccccgcttcc ccaaccccac aacaggccct ggtgtgcgat  90780
gttcccctta ctgtgtccat gtgttctgat tgttcagttc ccacctatga gtgagaacat  90840
gtggtgttta gtttttggc cttgcgatag tttgctgaga atgacggttt ccagcttcat  90900
ccatgtccct acaaaggaca tgaactcatc atttttatgg ctgcatagta ttccatggtg  90960
tatatgtgcc acattttctt aatccagtct atcattgttg gacatttggg ttggttccaa  91020
gtctttgcta ttgtgaatag tgtcgcaata gacatatgtg tgcgtgtgtc tttatagcag  91080
tatgatttat aatcctttgg gtatataccc agtaatggga tggctgggtc aaatggtatt  91140
tctagttcta gatccctgag gaatcgccac actgatttcc acaatggttg aactagttta  91200
cagtcccacc aacagtgtaa aagtgttcct atttctccac atcctctcca gcacctttttg  91260
tttcctgact ttttaatgat tgccattcta actggtgtga gatggtatct catcgtggtt  91320
ttgatttgca tttctctgat ggccagtgat gatgagcatt ttctcttgtg tcttttggct  91380
gcataaatgt cttcttttga gtattaccca ccgtttgaag ccttttctg tcaattcatc  91440
catctcagcc tccgcccagt tctgtgtcct tgctggagag gtgttccaat catttggagg  91500
agaagaggca ctctggcttt tttgagtttt cagcatattt tttcattgat tctcatcttt  91560
gtgagtttat ccagcttgat ctttgaggct gctgaccttt gggtggggtt ttggtgggga  91620
ctgttttgtt aatgctgttg ttgttgttgc tttctgtttt tcttttgaga gccaggcccc  91680
tcttttgtag ggctgctgca atttgctggg gatcctctcc agaccctatt tacctgggtc  91740
cctcccacac ctggaggtat caccagtgga agctgcagaa cagcaaagat ggctgcctgc  91800
tccttcctct aggagatcag tcccagaggg gcaccaacat gatgccattg ggaacacact  91860
cctgtataag gtgtctggag acccccgttg gggggtctca cccagtcagg aggcatgggt  91920
tcagggaccc acttaataaa gcactctggc tgccccttgg cagagggggt gcgctgtgct  91980
gggggaatc ccagtcaccg gactgcccag attcctcaga gccggcgggg gaaagactaa  92040
gttggctgat ctgtggagac catggtttcc ccttccctca gggactctga catggtttgg  92100
ctgtgtcttc acccaaatct tatcttgaat tcccatgtgt tgtgggatga acccagtggg  92160
aggtaattga atcatggggg gcaagtcttt ccccgtgctg tgaataagtc tttctcatga  92220
tagtgaataa gtctcatgag atctgatggt tttaaaaatg ggagtttctc tgaacaagct  92280
ctctttcttt gccttctgcc atccatgtaa aatgtgactt gctcctcctt gccttctgcc  92340
atgactgtga ggcctcccca ggcatgtgga aatgtaagtc ccttaaactt ttgtttgtaa  92400
attgctcagt cttgggtgtg tctttatcag cagtatgaga acagactaat acagtaaatt  92460
gggaccagta gagtggggca ctactgaaaa gatacctgaa actgtggaag cgactttgga  92520
actatataac aggcagaggt tggaacagtt tggagggttc agaagaacac aagacaatgt  92580
```

-continued

```
gggaaagttt ggaactcctt agagatatgt tgaatggctt tgacaaaaat gctgataatg  92640
atatggacaa tgagatctag gctgaggtgg tctcagatgg agataaggaa cttgttggga  92700
ctggagcaaa gtgactcttg ttatgtttta gcaaagagac tggcggcatt ttgtccctgc  92760
cctagagatt tgtggaactt tgaactgaga gagatgattt ggggtatctg gtggaagaaa  92820
tttataagca gcaaagcatt caagaggtga cttgggtgtg ttaaagtcat tcagtttaat  92880
aagggaagca gaacataaca gttcagaaaa tttgcagcct gacaatgtga ttgaaaagaa  92940
aatcccattt cctaagaaga aattcaagct ggctgcagaa atttgcataa gtaacgagga  93000
gccaagtgtt aatccccaag actgtgggga aaatacctcc agggcatgtc agaggtcttc  93060
acagcagccc cttgcatcat aggcccagag gcctaggagg aacaagtgat ttcatgggcc  93120
gggccaaggg ttccaatgct gcgtgcagcc tagagactgg ttgccctgtg ttccagatgc  93180
tccagccatg gctgaaaggg gccaatgtag agtttgggcc atagctttag agggtgcaag  93240
ccccaagcct tggcagcttc tatgtagtgt tgagcctgtg agtgcacaga tgtcaagaat  93300
tagggtttgg gaacctctgc ctagatttca gaagttgtat gaaaatgcct ggatgcccag  93360
gcagaagttt gctgcagggg tggggtcctc atggagaacc tctgctaggg cagtgtggaa  93420
ggaaaacgta tggattggag cccccataca gagtccctgc tgagacactg cctagtggag  93480
ctgtgagaag agggccacaa tcctccagac cccagaatgg cagatccact gacagcttgc  93540
accatgtgcc tggaaaagct gcagaccctc aatgccagcc cgtgaacgca gctgggaggg  93600
aggctgtacc cttcaaaacc acaggggtga agccacccaa gaccatagga acccacctct  93660
tgcatcagcg tgacctggat gtgagacatg gagtcaaagg agatcatttt ggagctttac  93720
aatttgactg ctccactggg ttttggactt gcatggggct tgtagcccct ttgttctggc  93780
caatttctcc tatttggaat ggccatatta acccaatgcc tgtacccccca ttgtatctag  93840
gaagtaacta acttgttttt gattttacag gctcataggt ggaaggcatt tgccttgtct  93900
cagatgagac tttggactgt ggacttttaa gttaatgctg aaatgagtta agactttgag  93960
ggactgttgg gaaggcatga ttgtttttga aatgggagga catgtgattt gggagggtcc  94020
aggggcagaa tgatatggtt tggttgtgta cccacccaca tatcatcttg aattcccgta  94080
tgatctggga gggacccagt gggaggtaat tgaatcatgg agatgagtct ttccccatgc  94140
tgttctcatg acagtgaata cgtctcatga gatctgatgg ttttaaaaat gggaatttcc  94200
ctgaacaagc tctctttctt tgcctgttgc catccatgtt aagacgtgag ttggtcctcc  94260
ttgccttctg ccatgattct gaagcctccc cagccatgtg gaactgtaag tccattaaac  94320
ctctttcttt tgtaaattgc ccagtcttgg gtatgtcttt atcagcagca tgagaacaga  94380
ctaatacagg ctccattcca gggagattag agttctgtct gtaaaccgct ggctggagtt  94440
gctaaaattc ctttagggag gccctgccca gtgaggaggg atgggtcagg gtccagccta  94500
aagaggcagt ctggccacaa tctgccacag ccactgtgct gtgctgtgct gtggggaatt  94560
ttccctaggt tcgaacctcc cagtcttcct gagtccagca ggggaaacag gcagactaga  94620
gctgcagtga tggctgccgc ctctcttgcc tggagctcca ttgtcttagt catcttaggc  94680
agcagacaat tgcagtgatg gtgtccaccc ttcccctcag gagttcagta gtcttaggca  94740
gtctctagca gagtggctgc tgagaatctt tacagctctc tgcttgggac ccaagagcct  94800
ggtggcatgg gctcacgagg gggtctcttg atcagtgggt tgaacggatc tgtggaaaaa  94860
gcatagtttc ctgggcaggt tagcacactc agtcaccgct tcccttggct gggggtggga  94920
```

-continued gctctccttg ccctgggtgg ctcccaggtg gcccatcgta ccaccctgct ttttcttgct 94980
ctctttgggt cacaccaatc acctagtcag tcccagtgag agaacctgga tacgtcagtt 95040
gtcagtgcag gattcactcg ctgttttcat tcttctcagt gggagcctct gaccacagct 95100
gtttctagtc agtcatcttg gccccacccc ctgcaccttt tcttttatgt gcactaataa 95160
gttgtttttt ggcttaagcc agataggttt ttaaatatat acactttcaa aaatatataa 95220
gacaccacat atgaaggaac tagttgtgga ggtagaggtt gaattcagcc ttggctatgt 95280
tgagcttgag gtgtttgtga gacatcttta tagaaaagag atatccggta ggaaattaga 95340
tatgtggata gaaagttaac aataccttat acagtctttg gtaaaaattt ttagagagtc 95400
cttttgtaat gcatgcagaa aagatcttca caaaatgctg acctctcctg tagaaccacc 95460
tagacccaaa ggatttgaag gaagcaattc tttattttca gtttttttcaa ggattattag 95520 tctattcaga gtttctactc ctagatgcaa catttacaat gaatgtccat ttcatttcca 95580
atttaccttc tagttgtgat gaactgtgta atggcccctc aaagatatct aattcctgga 95640
acctgtgaat gttaatttgt ttgttaaaag ggacttttca aggtgcgatt aaggtaagga 95700
ttttgagatg gggtgattat ccttggttat ccaggcaagc ccagtgtaat cacaagggtt 95760
ctcataagag agaaggtgat gtgctgaccg aagcagagat tggagtgatg cattttgcag 95820
atggagaaat gggccaaaag caaagagtac tggtggcctc tagaaactgg aaaagacaag 95880
ggaacaaatt ctgtcctaag gcttccagga agaacgtggc cctgccagca cctttatttt 95940
ataccagtga aactgatcca gactcctctc ctccaaaact gtaagaaatt aattttgtgg 96000
tgttttaata caccaagatc tctgaaactt ttttacagca gccccactga ggctgttagg 96060
gtgagcccta gtccaatctg actagtatcc tttcagggaa ctaacacccc actgtaatat 96120
gatatttata tatttctttc tatgtatata tctcaaattt aacagctttc ttgagtataa 96180
ttcacatacc ataaaattta tccaagtata aaattcaatt attttttatt atatacagag 96240
gtatgcataa ccatatctgc agtcaatttt agaacctttc aatcaccaca aaaagataac 96300
ccatgtactt tagctatctt ctgcctgtcc accagtttcc atatccctaa gcagctacta 96360
atctactttc tgtctctata gattttccag ttttagacaa ttcatataga tggaatcata 96420
tataacacga ggcccttgtg atcagcttat ttcacttagt gtaatgtttt caaagttcat 96480
ccacattgta gcatttatca gtactttatt cctgtttttg gttttgagac agagtctggc 96540
tctgtttccc aggctagagt gcagtggcac gatttcagct cactgcagcc tccacctcct 96600
gggctcaagc catcctccta cctcagcctc ctgagtaact gggactatag gcgtgcacca 96660
ctccatccag ctaattgttt ttgtagaaat ggggtttccc catgttgccc aggatgatct 96720
gcaactcctt ggccttccga agtgctgaga ttatttcctt ttatagatga atattatccc 96780
actatataga cacaacacat ttttatgtat ccattaatta gctgatggaa aagtttttat 96840
gtagacatat gatttcattc ctcttgggta tatatcgata agtagaacta ctgggtcata 96900
tggtaaccct aagtttaact gtttgaagaa ctttcagatt gttttccaaa ggctacatca 96960
ttttgcatcc ctaccagcag tatatgagca ttccgattcc tccatatctt ctccaacatt 97020
gttattatat gactttttga ttctaggcat cctactgggt ataaagtgat atctcattaa 97080
ggttttgata tgcattccca ttataatggt tatgacctga attatcttcc ccaaacttcc 97140
tgggttcata tgttgaatcc cttatctcct gtatttcaga atgtgactgt gtttggagat 97200
agggcctttt aaataggtaa ttaagttaaa atgaggctgt tagggtgagc cctagcccaa 97260
tctgactgat atccttataa gaagagaaga ttaggacaaa tagagagaca ccagggatct 97320

```
atgtgcacaa aagaaagacc atgtgaagac agagcaagaa gacaaacata tgcaagccaa  97380
agagaagggc ctcagaagaa agaaaacctg ctgacacctt gatcttgttc ttctagattc  97440
cagaactgtg aaaaaatttt tttctgccac ctgctctatg gtattttgtt atggcagccc  97500
caggaaactc atgactaatg atgtcaagca tttttttctt gtgtttattg gccatttgta  97560
tattttctgt ggataaatgt tttctgagat tgctcatttt aaaattgtct tcttattgtt  97620
gaattgttga gttgtaagag ttcttatata ttctgcatac tatgccctta gcagacatat  97680
gatttgcaaa tatttcctct aattctgtgg gttttctttt accttgttga tagttccttt  97740
gatgcacaaa agtttttaat tttaattaaa gccaacttat ctaatttttc atttcttgct  97800
catgcttttg gtgtcatatc catttcaaaa tccaaggcat gaagatattt cctttatatt  97860
ttcttctgag agttttatag ttttagctgt tacgtgtata ttcttaatcc atcttggatt  97920
aattattacc tatggtgtga ggtaagggcc catttttttt tttttttttg gcatgtggct  97980
atgtagttgt tttagcaatg atttgttgaa agagctattc tttcactatt gaattgtctt  98040
gacacctttg taaaaaataa gttgactaaa gacacatggt tttattctgg actcccagtt  98100
ctttttattt attttatttt atccacaggg tgtatatgtg cttgtttgtt acatcggtat  98160
attgtgtact ggtggggact gggcttctag tttacccatt acccaaatgg tgaacactgt  98220
acctgataga tagtttttta tcccttgctc ccctccacaa cctcctctca tttggagtct  98280
ctagtgtcta ttatttccat ctttaggtcc atgtgtatcc attgtttagc tccctattgt  98340
aagtgagaac atgtggtatt tgattttctg tttctgagtt agttcactta gtataatggc  98400
ctccagctcc atccatgttg ctgcaaagga cataatttca ttctttatgg ctacgtagta  98460
tcccatcgtg tatgtatgcc acattttctt tatctggtca actgttgatg gacacttagg  98520
ttgcttccat gacttggcta ttgtgaataa tgctgcaatg aacatacaaa tacggatgcc  98580
tttttgatat gattgtttcc ttttctttgg gtggatagcc agtagtggga ttgctgggtc  98640
cagtggtagt tctattttta gttatttgag aaatctccat actgttttcc atggaggttg  98700
aactagttca aattctcacc aataatgtac aaatgttccc ttttctccac atccatgcca  98760
tttattgttt tttcaccttt taatagtagc cattctgact ggtataagat gatattctga  98820
ttttaatttg caattctctg atgattgctg atgttaagca ctttttcatg tgtttgttgg  98880
ctgcttgtat tttttctttt gagaaatgtc tattcatatt cttctcccaa gttttaatgg  98940
ggttgttatt ttcttgttga gttatttata ttccttatag attctggata ttagtccttt  99000
gtcagaggca taatttgcaa atattttctc tcatttggtg ggtggtctgt ttactctgtt  99060
gattatttct tttgcttttt agtttaatta agtccaattt gtctattttc attcctgtta  99120
catttgcctt tgggatcttc atcataaaat tatttgccta tgccaatgtc cagaatagtt  99180
ttttctatgt tttcttctag gatttttata gtttcaggtc ttacatttaa atctttaatc  99240
catcttgggt taattgttgt atatggtgag agatagaggt ccagtttcat tcttctgcat  99300
atggctagcc aattttccca gcactattta ttgaataggg tgtcctttca ccattgttta  99360
tctttgttga ctttgtcaaa aatcagttga ttgttagttt gtggctttat atccaggttt  99420
tctattccgt tccattgata tttgtgccat ttttgtacta gtatcatgct gttttagtca  99480
atgtagcctt gtattataat ttgaagtcag gcaatgtgat gcctccagat ttgttcattt  99540
tgcttaggat ttctttggct attcaggctc ttttttgatt ccatgtgaac tttagaattt  99600
ttttctaatt ctgtggaata tgacattggt aatttgatag gagttgaatg tgtagattaa  99660
```

-continued

```
tttaagcagt atggtaattt taacaatact gattcttcca atccatgagt gtgggatgtt  99720
tccccatttg tgttatctat gatttatttc aacagtattt tgtagttttc cttgtagaga  99780
tctttcacct tcttgattaa attaattgct aggtattttg tgtgtgtgtg tgtggctatt  99840
gccaatgaga ttgagttctt gatttggcgc tcagcttaaa tgttattggt gtatagaaat  99900
gctgtcgatt tatgtatgtt tattttgtat attgaaattt gtttatcaag tctaggggtt  99960
tttggaggag tctttagggt tttctaggta tatggtcatg tgatcagtgg gcagagataa 100020
tttgacttcc tcttttccaa tttggatgct ttttttcttt tacctgattg ctctgagtag 100080
tgctcctagt actatgtgca ataggaatgc tgagattgga tatgcttgtc ttgttccagt 100140
tcttaaaggt aatgcaatca acttttttcc atttagtata atgttgactg tgggtttgtt 100200
gtaggtgggt cttatatttt taggtacttt tttattttta tttttatttt ttttagagga 100260
ataaaatagt ggctactcca taggcagagc agccaggtat ggtcttttga tgcctagttt 100320
gttgagggtt tttattatga agggactttg gattttattg aatgcctttt ttcatgtatt 100380
gagataatca tatggttttt ctttttagtt ttgtatgtgt gatgaatcac ccttttcaat 100440
ttgcagatgt taaaccgtac ttgcatccca gaaataaaac ccacttgatc ataattaatt 100500
atttttctga tgtgctgttg gattcagttt gctggttttt tcttgagaat ttttgcctct 100560
atactcatca gagatattag tctgtagttt gcttttctgt gtgcgtgtac tggcctgatt 100620
ttggtgtcat gatgatactg gtttcattga atgagtcaca gaggaatccc tcctccttga 100680
gtttttggaa tattttcagt aagattggta gcagctcttc tctgtgtatc tggtgaaatt 100740
tggctatgaa tctctccggt cctgggcttt tatttgttga aagatttttt tattactcac 100800
tcaatttcat tacttattat tggtctgttc aggatctcta tttattcctg gttcaatctt 100860
ggagggttgt aggtttccag gaatttatca atttcctcta ggttttctag tttgtgtgca 100920
tagaggtgtt tatagtagtc tctgaggatc ttttgtattt ctgtggcatc atttttaatg 100980
tccctttttct catttctgat tataattatt tgaatctctc tttcttggtt aatctagcta 101040
gcaatctatc aattttgttt atccttttaa aaaactaact ttttgtcgca ttgattcatt 101100
atgtctttaa aaataatctc aatctcattt agttctgctt tgatctttgt tatttctttt 101160
ctgctactag ttttgggttt ggattattat tatttttcta gttccttgag gttcaatgtt 101220
aggttgttaa tttgagattt ttctatcttt ttttataagg gcatttaatg ctacagaatt 101280
tcctcttagc actgcttttg ctgtatacta gagattttag tatgttgtgt ctctattttt 101340
atttgtttca agaagtcttt caatttctgc cttaatttat tatttaccca aaggtcattt 101400
gggagcaagt agttttgctt tcatgtactt gtgtagtttt gagagttcct cttggtattg 101460
atttataatt ttattctact gtgatctgag aagatacttg ttattatttt gattttctga 101520
gtttattgat acttgcttta tgggcaaata tatagtcaat tttggaatat attccatgtg 101580
gaggtgagaa gaatgtatat tctgttagat aaaatgttct gtgaatctct attagattca 101640
tttggtctac atcccagttg aagtccagag tttctttgtt gattttctgc cttgatgatc 101700
tgtctagtga tgtcagtggg gtgctgaagt cccccactct tattatattg ctatcaatat 101760
gttttcttag gtctagtagt atttatttta tgaatctggg tgctccagtg ttgggtgcag 101820
atatatttag gatagttaaa tcttcctgtt gtattgactt ctttatcatt ttataatgac 101880
ctttttgcc cccttttttt tttaactgtt gttggtttaa agtctgtttt atttgattga 101940
ggatgactac tctctcttgc ttttgttttc catttgcgtg atatatcttt ttcaacccat 102000
ttactttgat tctatagctg tctttagcca gtatgtatgt ctcttgtagg cagtacatgt 102060
```

ttgggttttc ctttttata cagtttgcca ctctgtatct tttaagtgga gcatttaggc 102120
cacatacatt caaggttaat attgatatgt gaggttttgt ttctatcatg ttgttgttag 102180
ctgattgcct tgggatttca attgtgtaat tgctttataa ggtctgtgag ctttttactt 102240
atgtgatctt ttatgatggt gaatgttgtt gtttaatttc catgtttaga actcctttga 102300
ggttgggcag tggctcatgc ctgtcattcc agcactttgg gaagctaagt gggaggattg 102360
cttgaggcca agagttttag accagcctgg tcaacatagt gagacaccat ctctactaaa 102420
acaacaacaa caaaaacaaa actccttcga gcatttcttg gaggaccagt ctagtgttga 102480
tgaattccct atttctcctt gatttatgaa gcttaatctg acaggatata aaattattgg 102540
gtggcatttt tttttcttta aagatgctaa aaatagaccc ccaatctctt ctggattgta 102600
agttttctgc tgagaagaca gctactagtc cgatatgatt atatatatat aaatgcaatt 102660
agacacttct ctcttgccat tcaggattat tttgtttaca ttgactttgg atagtcttgg 102720
tgaagttctt gcaatgtatt atccagaaat tctctgagct tcttgtatct ggatgtcaaa 102780
atctctccta aaaccaggga agttttcttg aagtatttct gcaaataggt tttcacact 102840 ttttgctttt tcttcttctc cctctggaat acctataact tacaggtttg tacactttta 102900
tatttcacaa aggctttgtt cattaaaaaa aattttttaa atattatgtc tgactgagtt 102960
aatttgaaag acctgtcttc cagctctgaa attctttctt ccacttggcc tattgttaac 103020
actttcaatg tattttgtaa ctccttgact gaatctttta tttctagaag ttttgtgtgt 103080
gtgtattttt ttaaatgaca tttatctctt ctttcatgtc ctaaattgct tttctatttg 103140
tatgggtttt ctgctttttc ttggatctca ctgagcttct ttaaaatcag tattttgaat 103200
tatttatctg atatttcaaa gacttcattt tggttaggat ttgttctgag gagttagtat 103260 tccccttttgg gggtgttgtt acattctgtt ttttccatac tttcagagtt gtttccctgg 103320
ttgtttctta tctggataag ctgtctctcc ttcttatttt ttaattttgc ttccctttgg 103380
acaggattat tttgcccccct tgaggaggtg tctgtactgt atgatgtggt gtagtgtcct 103440
ttgggtttgg ttctgggtat tttcagtggc aaagagtctg tataaattct ttggtaatag 103500
cctttgtatg gtgactttct caaatgctgg ttgttgtagt gatgtgctaa gcatgtgagc 103560
agcctcactc actgcctcct gtgggctcag ggtgatggaa gtctcaggaa gcttatttca 103620
ttctccagta ctctgcactt gagtcagcag atttcctgtt gtgttgcacc attcaacttc 103680
caggccagta ggtggtgctt atgtctgttt ttatctccta cacccttgtg gttcttatgc 103740
ttagtgttct acccatgagt gaaaattggg tattgaagta cccaattatt gatgaattgt 103800
ctatttctct cttcatttaa atcaatttat gcttcatatg tattggtgct ctgttgttag 103860
gtgcatatat atttttgatt gatgtatctt tctggttaat tgacctttta aaaaacatct 103920
tcttttatct atagtaatat cttttgtttt aaggtatatt ttgtcaggta attgtataac 103980
cattccaact ttcttgtggt tgctgtttgc atgatatttc tctttcatct ttttacttta 104040
agtctatttg tattttgaat ctaaagtgtg tttcccatag atagcatgta ttgactcttg 104100 tttttgatc tagtctgaga atctctgcct tttgactgga ttatttagtc cattcacctt 104160
taatgctatt attgatatag ttggaattat gtttgccatt tttgtttttt atatatctca 104220
tgtttctctt gttcctctgt ttctgcttta ctgctttctt ttgcatgaag tgaatatttt 104280
ataatgtagc attttaattt tttaaattat tttttcacta tatttttgag ttattagtgg 104340
ttactctagg gtttttctat atacactgtg acttataata atcagtttga gatttatact 104400

-continued aaattaattc tagtgagata cagaaatgtt acttctatat acctttgttc ccttcccccc 104460
atttttgtga tactattctt attcatatta catctattac atctaatatc tgaatattac 104520
aaacccaaca atgcattgtt gtaatgataa atttacacgc ttttatgttt tttaaggata 104580
ttgaggagag caaatacaga cacacacaaa cacacacaca catttatagc ttttgttgtg 104640
ttagcctttt aatttatcat ttctggttct cttcatttgt tcctgtgcat acaagttgcc 104700
atctgaagtc atttccttaa tccaatacag ctttgccccc acccacctct tttgttctat 104760
tattgaccaa tattacattt ttatgttata ggctcaacat cacattatat acttctttat 104820
acaattactt ttaaaatctt ttagaagaag aaaggaaaag aaatgccttg acttttacaa 104880
ttagataatt acctttcctg gttctttttg ctttttttcat atatatattc caattactct 104940
cagggttcac ttgtttgtag catgaatttc ttttagtact tcttataagg taggtctgct 105000
agcaacacat tccctctgtt tttattagga catgtcatta ttttacctta ttttggtgga 105060
tatagaattc ttggttaata attgcttttt ttggttcatt ctgaatatgt tgtccttctg 105120
gcctcaatta attctgctga gacatcagct gttaatcttc ctggagtttc agtctaagtg 105180
atgagtcatt tttatcttga tgtagtcaaa attttcttat tgtctttagc tttagctttt 105240
tcacttttag gtgtcttttg atgtgacatt gtaatcatac tttttaaatc atggcccatt 105300
ttatttgaaa atattatttg aaattattta taatctctac tttgaaaact ttttctgttc 105360
aatctgacat ctgatgtctg ttaaatctga catctggtaa gtcttccagg cagtttctgt 105420
tgtctacaat tttttttcag tgtattgctt attctttcct gcttctttat atgtctcata 105480
attttttgtt gaaaaatttt aggtagtata ttgtaataat actgggtact ggtcttctgg 105540
ggcttgttgt tatttgctta tttacttgtt tgttgattga ctagattatt ttggtgtaat 105600
ttatttcttc ctctgaagca taaagtctat aaagttgttt ctcaggggat gcagtttgat 105660
atgctcacag tcagctggca acacagtgga tttgggagag ctctcttttg tctttttctc 105720
tggtcatacc caggtattat gctccactac ttacttgctg gctgatggct ctgttgcttt 105780
caacaatgcc ctggaatata gattgtttta caaactgacc caaaaatttg ggctcttctt 105840
aaaaaattgt tcctgaggtc agtttttgag atttgttttg accctaagag ggttcctccc 105900
agatgtcttg ctttctattt ctctatagca aatcatccag cttacaactt aggctatatc 105960
tctaacaaat ctatcaattt tttcccaatt gcttttcaca aactttcact gtttttgaga 106020
gtgactttag gcttgaaatt gtccatggtt tgttggaaat gaagtcaatt tctttgggga 106080
gagattttaa gtattctgtt atacagcgtg cttctctacg tttgggcaaa atctctgagc 106140
cacagctctg gtcctggaac agggacaatg acagacttcc ctctaaatga tatacccact 106200
ttaagtgcta gtaacttttg gtgtgtgtgt gaagtggtcc cagttcaact cggcttgact 106260
ctgctagtat ggcactgata tggtttggct gtgtccccac ccaaatctca ccttgaattg 106320
taataatccc cacctgtcaa ggacagagcc acgtggagat tgaatcatgg gggcagttta 106380
ccccattctg ttcttgtggt agtgaataca tctcatgaaa tctgatggct ttataaatgg 106440
gagttcccct gcacaagctc tctcttagct gctgccatgt aagatgtgac cttgctcctc 106500
attcactttc cttcatgatt gtgaggcagc cttgtgggac tgtgagtccg ttaaacctct 106560
ttgctttaca aattacccag tcttgagtat gtctttatta gcagtgtgga acagattaat 106620
acaggcatct gttaaagcag actaaatatg gcctgagaag gactctgtat ttctatattt 106680
gagtccttgt agatgaactg taacctagct taatagccag acaaaattga aaacctaact 106740
taatagtatg caccgtaaca atagttgagt gttggccatt ccagtggtca tacttcaacc 106800
actcatagac tgctgagtgt tcaaacaagg caaacgcaga gctgtgacca acctcactgt 106860
ttctgtactt cacttttgat tcccatacat cactttaact ttttgtctat aaatttgttc 106920
tgaccacaag gcacccctgg agtctctgtg tatctgctgt gattctgggg atgcccaatt 106980
cgtgaatcgt tcattgctca attaaactcc tttaaattta actcagctga agtttttctt 107040
ttatcagata atgtcagaag caggatccaa agtggagctt ctagtgaccc ccaggagtgc 107100
tgagtaaaca cgcaaggtac ctgcaggacc cacttgtgtc cattgatctc tcagagcagc 107160
tgggcatcgt gggtaagttc cctcttggat tttggagctc cacggatttg tgttttgagc 107220
tctctgagtt tctttgggca aatttctgat ccaaactggg tttggagttg tgacagaaac 107280
tggactgggt ccaggaacag atttgatccg ggaattaact ggcttggatc cagttagagg 107340
cctcttacat ctgactgggt cagaaaggaa ctggtagtaa gcagtaatat ttcaggggtt 107400
atagagtttg gcttttgaaa attcacaagg atttttgtgc tctacccttt tgttcatttt 107460
tcttgcctgc atcggtagga aaaaaaatca ttggataagt taatcaagag agcctgagag 107520
taaagccaat attttaggta aaaatggaat ccttaatttc tggaaaactg agttccttct 107580
ggcttatact ttaggcctgg gaggcagtga agtcttacag aaatggcaaa atcttactaa 107640
aggtaactta cagtggaacg ttccgaatga acaacaatgc actgaagtac atttacaaat 107700
gagggctctt ggtaaagtcc cttttggcta agaacagggt tggcactacg ggatgtcaac 107760
tgctgttttc tttggaataa tctgccttgc actctttgct gacaactatg ggtgacagaa 107820
ttaggatcgt gggacacgga gagctttttc ctcccccaaa agggaaaact tgaaagctga 107880
tgggactgct ggaaaaaaaa tccttttaca acagcagctg cagccgcctg aacttctcag 107940
tatcactgca atgggttggt ttttctctgg tcttcctgag cattttgcct tccccaccct 108000
gccataggca aaccttttct ctctctcctt tctgtttttc atcttttctg ttactcaggg 108060
caaccatcat gcccagagac catgtgttga aactcctagt cagaggttgg attaaagatg 108120
atggggccca gctgagggca aatttaagcc ttgtcagttt gatattgggt gctaagcaga 108180
gtggctaatg tctgtttatc acatgtgttt tactctggcc agaatgaaaa aagataattt 108240
tcctttatga tgcagcttgt cccccaatgg gatggtgtgg caagctgggt taccggggcc 108300
acttagggaa aggaaacaca gaaacctggc atgcaggcca aagggtaaga atttcttacc 108360
agtcagattt ctggcttctc cctctctgtg cagacagttg attaaatggt aaaaattgct 108420
gtttaagcca ggcacggtgg ctcacacctg taatcctagc actttgggag gttgaggtgg 108480
gcggatcact tgaggtcagg agttcaagac cagcctggcc aacatggcaa aaccccatct 108540
ttactaaaaa tacaaaaaat tagctgggtg tggtggcagg tgcctgtaat cccacctact 108600
cgggaggctg aggcaggaga atcacttgaa cccaggaggc ggaggttgca gtgagccaag 108660
atcacgccat tgcactccag cctgggcaac aagagtgaaa ttccatctca aaaaaaaaaa 108720
aaaagaaaga aaaagaaaaa agtcactgtt tatctcttct gtaaagtttt gattaatgca 108780
aaaaagaatt ccgaggctag tcttaaactg atatatttgt gctatgaatt tgtttttctg 108840
tgtcaagggg tgccttaaga taaaacatgg gcttaggacc ccataagctc gctgctcaag 108900
atggcccagc aggctggtca ataacaaact ttcctgcagg tccctgaaac aaacaaatga 108960
aaaactggat ggggtctcca tcttgtttca tgtccttggg agcttgacct tgtaaccacg 109020
tggcagtact ttctcttggt ctccaccttc cagggaacac gaattttagg ttttatgtca 109080
tagttagctc taaaaattat cttaagtagt taaaagcctc tacaagctca aaattaacta 109140

-continued ctctagactc cttctgggaa gaacagtgga actttccctg tggtatagct tggtacataa 109200
ggttttggcc tttcacacta gaagtccagg ttcaattccc tgcttagaaa gcaagccttt 109260
tctggtttaa tatctacata accttgtcta gtctcttctc caccatggac tatcctaagt 109320
tttcctttcg ctgagcacct gggaggttac ctttggtaaa gttcaaaacc agaaatattg 109380
gccaaactgg gtaataagaa attttaaaag gatattatta aagggtgcta tggttaaaag 109440
tcagcttaat taaaagcaga tattcaagct ctaagagcct ggattccttg ggaaaaacag 109500
gaggcaccag aaacccattt cctggccctg ttcttcctag ggctccaccc taaagccaat 109560
aaccaattaa gaaacttaaa aactggcaaa tgaaaaatct tataactact gtagtaatct 109620
tcttatgtct gtctatttgt gtaattatat atgtgttgtg tgtaatgttt atataaaaga 109680
gctccaatta attggcttaa acaaaaacaa gtgcttaaat aaaatatttt gaaagcaaaa 109740
taaaaactgt aaggcctttt agttcatgta actttagtaa ttactgggaa ataaaaacag 109800
ctttaaagat tattgataaa ataaacacat tttgtctaaa ttatgccggt cagatattag 109860
gtttgctaaa tgctttaagg tcataaactg ctttgacttt tgaaaattgt tcaatttatt 109920
ttgaagacat taaattctaa ataaggcctg gggatatatg gaattatcca tgtcccctag 109980
ctatgcaaag aaggttataa agagatttta cataagaaag gatgtttttt ggtaaattat 110040
tgtcctaaag taaaatgact ggttgtttaa aaagagggat gtttagggca ggtcagaaag 110100
tctaaacatg tcatacatgg tatgtgtaag tcgtgacaat ttatgaaaag aaattaatgc 110160
cagaaatgct ttacaattta tttttttatt attattattt tttattatac tttaagtttt 110220
agggtacatg tgcacattgt gcaggttagt tacatatgta tacatgtgcc atgctggtgt 110280
gctgcaccca ctaactcatc atctagcatt aggtatatct cccaatgcta tccctcccta 110340
ctcccccgac cccataacag tcctcagagt gtgatattcc ccttcctgtg tccatgtgat 110400
ctcattgttc aattcccacc tatgagtgag aatatgcggt gtttggtttt ttgttcttgg 110460
cgatagttta ctgagaatga tgatttccaa tttcatccat gtccctacaa aggacatgaa 110520
ctcatccttt tttatggctg catagtattc catggtgtat atgtgccaca ttttcttaat 110580
ccagtctatc attgttggac atttgggttg gttccaagtc tttcctattg tgaataatgc 110640
cgcaataaac atacgtgtgc atgtgtcttt atagcagcat gatttatagt cctttgggta 110700
tatacccagt aatgggatgg ctgggtcaaa tggtatttct agttctagat ccctgaggaa 110760
tcgccacact gacttccaca atggttgaac tagtttacag tcccaccaac agtgtaaaag 110820
tgttcctatt tctccacatc ctctccagca cctgttgttt cctgactttt taatgattgc 110880
cattctaact ggtgtgagat ggtatctcat cgtggttttg atttgcattt ctctgatggc 110940
cagtgatgat gagcattttt tcatgtgttt tttggctgca taaatgtctt cttttgagaa 111000
gtgtctgttc atgtccttcg cccacttttt gatggggttg tttgtttttt tcttgtaaat 111060
ttgtttgagt tcattgtaga ttctggatat tagccctttg tcagatgagt aggttgcaaa 111120
aattttctcc cattctgtag gttgcctatt cactctgatg gtagtttctt ttgctgtgca 111180
gaagctcttt attttaattg gatcccattt gtcaattttg tcttttgttg ccattgcttt 111240
tggtatttta gacatgaagt ccttgcccgt gcctatgccc tgaatggtaa tgcctaggtt 111300
ttcttctagg gtttttatgg ttttaggtct agcatttaag tctttaatcc atcttgaatt 111360
gatttttgta taaggtgtaa ggaagggatc cagtttcagc tttctacata tggctagcca 111420
gttttcccag caccatttat taaataggga atcctttccc cattgcttgt ttttctgagg 111480
tttgtcaaag atcagatagt tgtagatatg cggcgttatt tctgagggct ctgttctgtt 111540

-continued ccattgatct atatctctgt tttggtacca gtaccatgct gttttggtta ctgtagcctt 111600
gtagtatagt ttgaagtcag gtagtgtgat gcctccagct ttgttctttt ggcttaggat 111660
tgacttggca atgtgggctt ttttttggtt ccatatgaac tttaaagtag tttttttccaa 111720 ttctgtgaag aaagtcattg gtagcttgat ggggatggca ttgaatctgt aaattaccta 111780
gggcagtatg gccattttca ccatattgat tcttcctacc catgagcatg gaatgttctt 111840
ccatttgttt gtatcctcag tggtttgtag ttctccttga agaggtcctt cacatccctt 111900
gtaagttggg ttcctaggta ttttattctc tttgaagcaa ttgtgaatgg gagttaactc 111960
atgatttggc tctctgtttg tctgttgttg gtgtataaga atgcttgtga tttttgtaca 112020
ttgattttgt atcctgagac tttgctgaaa ttgcttatca gcttaaggag attttgggct 112080
gagacagtgg ggtttctag atatacaatc atgtcgtctg ccaacaggga caatttgact 112140
tcctcttttc ttaattgaat accctttatt tccttctcct gcctaattgc cctggccaga 112200
acttccaaca ctatgttgaa taggagtggt gagagagggc atccctgtct tgtgccagtt 112260
ttcaaaggga atgcttccag tttttgccca ttcagtatga tattggctgt gggtttgtca 112320
tagatagctc ttattatttt gaaataggtc ccatcaatac ctaatttatt gagagttttt 112380
agcatgaagc gttgttgaat tttgtcaatg gctttttctg catctattga gataatcatg 112440
tggtttttgt ctttggctct gtttatatgc tggattacat ttattgattt gcgtatattg 112500
aactagcctt gcatcccagg gatgaagccc acttgatcat ggtggataag ctttttgatg 112560
tgctgctgga ttcgttttgc cagtatttta ttgaggattt ttgcatcaat gttcatcgag 112620
gatattggtc taaaattctc ttttttggtt gtgtctctgc ccagctttgg tatcagaatg 112680
atgctggccc cataaaatga gttagggagg actccctctt tttctattga ttggaatagt 112740
ttcagaagga atggtaccag ctcctccttg tacctctagt agaattcagc tgtgaatcca 112800
tctggtcttg gactcttttt ggttggtaag ctattgatta ttgccacaat ttcagctcct 112860
gttattggtc tattcagaga ttcaacttct tcctggttta gtcttgggag agtgtatgtg 112920
tcgaggaatt tatccatttc ttctagattt tctagtttat ttgcgtagag gtgtttgtag 112980
tattctctga tggtaatttg tatttctgtg ggatcggtgg tgatatcccc tttatcattt 113040
tttattgcgt ctatttgatt cttctctctt tttttcttta ttagtcttgc tagcggtcta 113100
tcaattttct tgatcctttc aaaaaaccag ctcctggatt cattaatttt tttgaagggt 113160
tttttgtgtc tctatttcct tcagttctgc tctgatttta gttatttctt gccttctgct 113220
agcttttgaa tatgtttgct cttgcttttc tagttctttt aattgtgatg ttagggtgtc 113280
aattttggat ctttcctgct ttctcttgtg ggcatttagt gctataaatt tccctctaca 113340
cactgctttg aatgcgtccc agagattctg gtatgttgtg tctttgttct cgttggcctc 113400
aaagaacatc tttatttctg ccttcatttc gttatgtacc cagtagtcat tcaggagcag 113460
gttgttcagt ttccatgtag ttgagcggtt ttgagtgaga ttcttaatcc tgagttctag 113520
tttgattgca ctgtggtctg agagatagtt tgttataatc tctgttcttt tacatttgct 113580
ggggagagct ttacttccaa ctgtgtggtc aattttggaa taggtgtggt gtggtgctga 113640
aaaaaatgta tattctgttg atttggggtg gagagttctg tagatgtcta ttaggtccgc 113700
ttggtgcaga gccgagttca attcctgggt atccttgttg actttctgtc gttgatctgt 113760
ctaatgttga cagtggggtg ttaaagtctc ccattattaa tgtgtggagt ctaagtctct 113820
ttgtaggtca ctcaggactt gctttatgaa tctgggtgct cctgtattgg gtgcatatat 113880
atttaggata gttagctctt cttgttgaat tgatcccttt accattatgt aatggccttc 113940
tttgtctctt ttgatctttg ttggtttaaa gtctgtttta tcagagacta ggattgcaac 114000
ccctgccttt ttttgttttc catttgcttg gtagatcttc ctccatcctt ttattttgag 114060
cctatgtgtg tctctgcacg tgagatgggt ttcctgaata tagcacactg atgggtcttg 114120
actctttatc caatttgcct gtctgtgtct tttaattgga gcatttagtc catttacatt 114180
taaagttaat attgttatgt gtgaatttga tcctgtcatt atgatgttag ctggttattt 114240
tgctcgttag ttgatgcagt ttcttcctag tctcgatggt ctttacattt tggcattatt 114300
ttgcagcggg tggtaccagt tgttcctttc catgtttagt gcttccttca ggagctcttt 114360
tagggcaggc ctggtggtga caaaatctct cagcatttgc ttgtctgtaa agtattttat 114420
ttctccttcg cttatgaagc ttattttggc tggatatgaa attctgggtt gaaaattctt 114480
ttctttaaga atgttgaata ttggcccccca ctctcttctg gcttgtaggg tttctgccga 114540
gatatccact gttagtctga tgggcttccc tttgagggta accagacctt tctctctggc 114600
cgcccttaac attttttcct tcatttcaac tttggtgaat ctgacaatta tgtgtcttgg 114660
agttgctctt cttgaggagt atctttgtgg cgttctctgt atttcctgaa tctgaacgtt 114720
ggcctgcctt gctagattgg ggaagttctc ttggataata tcctgcagag tgttttccaa 114780
cttggttcca ttctccccat cactttcagg tacaccaatc agacgtagat ttggtctttt 114840
cacatagtcc catatttctt ggaggctttg ctcttttctt ttcttttttc tctaaacttc 114900
ccttattgct tcatttcatt catttcatct tccattactg ataccctttc ttccagttga 114960
ttgcatcagc tcctgaggct tctgcattct tcacgtagtt ctcgagcctt ggttttcagc 115020
tccatcagct cctttaagca cttctctgta ttggttattc tagttataca ttcttctaaa 115080
tttttttcaa agttttcaac ttctttgcct ttggtttgaa tgtcctcccg tagctcagag 115140
taatttgatc gtctgaagac ttcttctctc agctcgtcaa agtcattctc catccagctt 115200
tgttctgttg ctggtgagga actgcgtttc tttggaggag gagaggcgct ctgcttttta 115260
gagtttccag tttttctttt ctgttttttc cccatctttg tggttttatc tacttttggt 115320
ctttgatgat ggtgatgtac agatggattt ttggtgtgga tgtcctttct gtttgttagt 115380
tttccttcta acagacagga ccctcagctg caggtctgtt ggaataccct gccctgtgag 115440
gtgtcagtgt gcccctgctg gggggtgcct cccagttagg ctgcttgggg gtcaggggtc 115500
agggacccac ttgaggaggc agtctgcccg ttctcagatc tccagctgcg tgctgggaga 115560
accactgctc tcttcaaagc tgtcagacag ggacatttaa gtctgcagag gttactgctg 115620
tctttttgtt tgtctgtgcc ctgcccccag aggtggagcc tacagaggca ggcaggcctc 115680
cttgagctgt ggtgggctcc acccagttgg agcttcctaa gcaagcctgg gcaatggcgg 115740
gcgcccctcc cccagcctcg ctgccgcctt gcagtttgat ctcagactgc tgtgctatca 115800
atcagtgaga ctccgtgggc gtaggaccct ccaagccagg tgccggatat aatctcgtgg 115860
tgcgccgttt tttaagcccg tcggaaaagc gcagtattcg ggtggaagtg gcccgatttt 115920
ccaggtgcgt ccgtcacccc tttctttgac tcggaaaggg aactccctga ccccttgcgc 115980
ttcccaagtg aggcaatgcg tcaccctgct tcggctcgcg cacggtgcgt gcacccactg 116040
acctgcgacc actgtctggc actccctagt gagatgaacc ctgtacctca gatggaaatg 116100
cagaaatcac ccgtcttctg cgtcgctcat gctgggagct gtagactgga gctgttccta 116160
ttcggccatc ttggctcttc ccccgtttta caatttaaag gtgattaggc ttcctaaatg 116220
cttcataaaa tgccactatg actcttaact gtacagcttg cctactctac agctgggtaa 116280
ggcctgggac acatggagtt agacactgga aaggctcaga tcttatctgc atttctgttt 116340
gggtcgtagg ctccacacct agtacataat taaaatccct taccaaggtt ttcaccaaaa 116400
gtaaaagatg ctaagagtta acattttaat atgtaattga gactactgaa aaaataagtt 116460
tacatacaag gtttgtaaag ggaataaaat gtgtttttgt gagagattat aagaaagtat 116520
gggaatgtaa atttttgtct aggttagagg gttaaagatt tattttgaat taaaaagcta 116580
aaggttagaa caagttgtga atggtttata aaaattaatt acaagagatt ctatgtgtga 116640
atgtattggc taaagttaaa atggcattat tcattttttt tctataaatt ggacattgga 116700
atagaagaac aacagagttt tcttagaaca ttgttctgct ctgagaaaaa aagttgtaaa 116760
gggttataaa aggtttatga aaatcttacc ttatggtcaa actaattaaa acaatagatt 116820
tataaaatgt cattaaaaac tagctttaac ataaaaaata cactaatggg aacataaaat 116880
ttgtttttct cttttaaaaa ggatttttat gtaatattaa aagataaaag gttttagttt 116940 acctttttaag taagctacaa aagggaaaag tggagggaag gaaagaaagg agacagagtc 117000
aattgtccta atgctatctt cattgggtct tgcttggaaa gctgagtctc ctctttatca 117060
gaatgttttg tccttttaaa aatttttgag ttatcatttt ggctaaatga atgacttatg 117120
gtaacctaag attctatttg gtaatatcca atgttttaaa catttggtat ttaacaaacc 117180
tttcaaaatc aagctctaga ttatcatgct aaatcagcca atactaaaat tgtttaaata 117240
tacaatttaa atgaactccc tggtctaagt caaattacct atgataaccc attagttatc 117300
agtgctatgc atctaaattg gagaaacaac tggtattcaa gaggacatga gtctgatgtt 117360
aagcatggac tcatgaagaa ccaggacagc ctcctagtcc ttcccgagtc cttaaagctc 117420
ttgttactaa aggttctgca ttccatgact catcacggaa aagataaaat aatccaaata 117480
gaatatactg atgtggtgac ttatagatag tggaaatatt ttaaaaccaa tgtttggttt 117540
catattcctg ggaaggcaat caaagcttca ggtacatttg gctacctaat gtgtcattta 117600
aacatttata aagagatttc attcaattgt cattttcact gcatgttttc tggttgtata 117660
aaagctttcc catgcaagag ggctgatgta acagtagatt attgtgctac catgtatttt 117720
caccaggtaa agaccttcac aatcgggaac ccgtagattg gatcttctga aaacatcaga 117780
gaaagactat ctttgccatc cacactacag taaaactttg gagccttgaa ccttggattt 117840
ataatctcac aactgagaag ggtccctcca tactcctgga actgtacacc cattggaact 117900
cttaaggtaa aactaaccag gaaagtttct ccccagaaaa agatggcatc cttgatgtga 117960
acagcttttc ccaagatcac aggtcaaaac ttctactatc atgagactct tacctttgaa 118020
tatttttacc ttgtttatgc ctctatgagc aacagaaatg aaaagtgggt ctataatgtg 118080
cacttatagg gtataatttt atttgtgaag gattttgcgg gaagccagcc ttatacataa 118140
ataaacttat actttaatag ataaaagatg aaggcccaag gtgggtgaga aactttagtg 118200
gtacatatgt tgactcataa tcagtcaaaa ctcctcttaa cccacatcat ggattaaaga 118260
gaacattgcc aggaggcctt cactcttcta gaaggacata atttgttagg tcctttttcc 118320
atggtttaga atacaagagg caataattag aaatgtctcc ctcttaatag gcatgggttc 118380
aaataaggca aacgtggagc tgtagccaat ctcgctgttt gtgtacctca cttctgattc 118440
ctgtgtgtca ctttaacatt tttgtctata catttttttct gaccaggaga cacccctgga 118500
gtctgtgaat ctgctgtgat tctgggggct gcccgaatca tgaatcattc attgctcaat 118560
taaactcctt taagtttaat ttggctgaag tttttctttt atcacaccct tgccccatga 118620

-continued gccagggaaa gggcaactga ggccgcagta ttttcagtgg caccaaggta caccctgtat 118680
tccacgagta gggtctggag agaagggagt ccccgcctct caaccagatt tcagaaacta 118740
tagtagatct tctatcctca aggaaatgca tcttatttct ggtatcagaa tcaaggagaa 118800
gcaggcaaga ctgttctata agatgagtta gcatcctgga gggtttttag actcaggaat 118860
ggggatctct agggaaccga tagtaaaggt tcctactaat ctgggcaaat agagcttagt 118920
gttgcattac agctgttttc taagatggtc aatattgttc tactctcttc ctccattcag 118980
tacctttttt aaaacaatta ctcagaggtc attgcttata tcccaaacta cttattagga 119040
caatatcagt tataaaaggt tgctggattc tctttgattt gtgccagctt cccatcactt 119100
gctgctagga acctcatatc ataagctggg agactggttg atatgcatag ctccttacct 119160
attttatagt gttttccagt cttttatttc atgtgaattc tgattgccta acaagaaatt 119220
ttcttatcct actaaatttc tcactaagag gaaatgtcaa gcctctaaag ctcttcccag 119280
ctatctgtac tcacagttaa attgaactgc agagactggt atgagtagct gattgaggag 119340
gtaatgaaat atcccaggct gcttttggca gcaactctga atcaaccaag gccagccaag 119400
gcaaacttta aacgcaaaaa cccggactaa atggatgaat ttattctaat gtatttttgt 119460
ccacatgcct ctgcaaattg tttacaggtt ttctgccttt tgactagtag aatttttat 119520 tgcattcaga tagatcattg atgaacactg ctagtttcct gggctattga aaatttgcct 119580
ttcttattgg gttttcatga atgtttctct ggtagagaaa ggaggttaaa aaaatgagag 119640
attgctaact ttctaccatc ataaagtctg gatttggata ctgttttatg gcaaagacag 119700
taatgttccc ccaaatttcc tagaattctt gcagttgggt tgagtcatgt ggttagttgt 119760
ggtcaatggg ctcgaaatga catatattgc ctctgatatg aatcttagaa gagtccacac 119820
aaacgtctcc atctatcttt tacttttctc tattgaccaa gaaggccata tggtagagcc 119880
ttcatcatcc tgaataattg gggaagagat ctttttgacc cgacaattga taagagccct 119940
ggcaagtagt gtgagccgca gtaaactatt tttggtacaa gccagtgagg tttttagggg 120000
tggtttgtta ttgcagttgc ctatcctgac taatgtattt ttctacatac ctaaaccatc 120060
aggtttcatc aaaacattgg tggaaaataa gaatatttct agatgatttg ttggcttttc 120120
attcaagttg aatatgtacc tatctattgg ttgaaaaaat taatagggat tgtagacatg 120180
ttattcttag taggacagga caggataatg gtttttgaac attctccctg ctgtatatta 120240
gctttgcttt taaataaata cagtagtgag gtgtgtttat cagtgtttat tctcccacta 120300
ttggataaca ggggctcctt gatctaaaat gataggtaag tgatcccctc tactgtccta 120360
aggtcattac ttattgacac ctccctatta tgcctagtca atgtgtgata aaagattgca 120420
tggaaatgac aggcatgaac caggatcttt tctcctctgt cctccttttc atttgccttt 120480
tgatgtttct gctgctattt ggcacctcca ctagaagatt agaaggggaa aagagaggaa 120540
attaagctct tttcctgcag actagcagtt ctgattttta aagggtacct cggggtattg 120600
tttcatctac ttatgagttt caggagtgtg tgtttgtgtg cgtggtggtg ggggagaaga 120660
gaaagagaga aagacacaga gagagagaca gatataatta aacatggagt ttgagtttcc 120720
atgttatctg attctaggaa tttagtgttg cctccatatt tatcaagaat tatagtcctt 120780
taccgtaatt tactataatg tattatgttt ctgtgtgtgt gtgtgtgtgt gtgagagaga 120840
gagagagaga gagagagaga agagagagaa gagagaaaca gagagcgaga cagagatgga 120900
gagagagaga gagaattaaa cggattttca gagtttccac attatctgat tctaggaatt 120960
tagtgttgct tctatattta ccaagaatta tagtccttta attattatgg aggataacta 121020
aaaatatcct gcataataat taaaagttcc ttattttcaa gtggcataat gactttctgt 121080
gctaagatca cttgaaaatg ttaattaaag aaatctattt gctcaaaaaa actaaatgtg 121140
catactttac acctgtggta aataatataa aattataatt tgcctttgag cttaatcaaa 121200
atcagcttta aatttattag gcacctgact tttttatttt taattaaaga ccattttgtt 121260
cagtatgtag tttaaatcat ggaagcgtag ttacttctca agcaattcct ttaagacttg 121320
gggcttctgt gtttgaaggg atccaggggt tacagtgtgg gcagtacccc tataccaatt 121380
taaggttttt cttactcagt aagatgtttt ctaagatgaa agagatgggt atattctatg 121440
taacagagat aaatgtaaaa ttttattcac cctatgggaa aaatttggat agattcctct 121500
tggcagtgaa aggtataaaa tgaacttaaa ggatgactct ccataacata atattgagtg 121560
aaacaagaat aaacacatta tgactccatt tataaaatat ttttaaggta aaattaagca 121620
atttattgtt taaggacaca tgtttggtaa aaccataatg aaaaacacat ggaaatgaac 121680
acaaaatacc atctaatgct tactttgggg aacgggaaga gagcctcaaa cagagagatg 121740
tatgtggagg tttctaccac tttagtgtta tatttctaaa gttgagttgt gaatacacag 121800
atgttgattt ctattctagt tcttcacact gtacatatgt tttctgtact cttttggaac 121860
tatactgtat tttatgtata gttcaataag tgatagttca atatgaattg ttgatgtgat 121920
atgactcact caaaagagtt agtgtctctt gtacataata ttgttaagaa acttggagtt 121980
aaggaaattg aaggtattgt catatccagc cttgatcaga ccatgcttta gtactttgtt 122040
cagttatatg cagcccactt taagagtgat gcagacaaac tagattatgt ttaggggaca 122100
gtgatgaggc tcgtaatgat tcttgaaact atatatgata tatgattctt catatatttg 122160
aagggaagac atgagaatga gagcttagat ttatactaca tactcaaaag aatagaatca 122220
aaattaatag atgatgcaac aagaaaatat tttattgtaa caaaaataga ttttatcata 122280
acagaatcaa gaacttacta ataactacat ttgttcaatg agtcgtcttg atacatagtg 122340
agtttcttac tggtggagat gttctagcac aggttgaatg atctcttggt gggttattat 122400
caggagatat gcctaaaagt cattctgggt cccgaaattc ttcgaagatt tccagaaatc 122460
tctagtcaac ctgaaatttc tattcaagat ctcttagtta agtggcagcg gagtgagtaa 122520
aatcacagag tctaggacca gattcctggg ttgaatcctg gcgtttttca attactacct 122580
gtataacctt gagaaaatta cttctctgtg tttccttttt gcaatccata aaatgggtct 122640
atcagcctca cagagtggtt gtaagactta gaagaatgcc agatagtaag tgccactaaa 122700
tgtttatttt tttaagaaat aatttttttc taaagatcag tcattcaatt tactttgaat 122760
caattacatt tttgcttttg ttttaaataa aaaaacttta tttctctctc ttcctatgag 122820
caaatatatt taattatcct ctgacataca agggtattgg agtttttttt ttttttaatt 122880
ttgtgggccc taaattctaa caattccagt aagtatagaa ttttaaacta aaaaatctct 122940
taacctgact taagtggctt tagaatagct ttgttgcatt atcacagaac cacagaaccc 123000
aaaaagccaa gaagaacctg aaagaatgat ttagtttctc ttactcttgg aattaggtac 123060
cttgtctgca aagtctcctt gcccttgagg gattgctgca aagcctgtct cattgttcaa 123120
tctttgcatg gctccttcaa tcgttgctaa tacgaggtgg attgtctgtt aaaagttaat 123180
gatggtgagc cagggagtag tgtactgttt tcggtttatt tgcaacagtg gaaagggcaa 123240
acctattcat ctcaatgaaa atgtaactgt ttacattgga agcttaaatt ttaggacaca 123300
ccatgtcctg cttttgaaaa gacaatttgt agggtaagag atgttacagt gatattatgg 123360

-continued aggccacaag aagtatattt tctggtcatt ggtagaaaac aatgattaaa atcaggcttc 123420
ttttgtagga gatactggtc atgttttcta aaatgttgac tgtgagagaa gaaaacaaga 123480
attattaaat ctagatctct gatgggaagt aagaacagaa atgaggacag gtgaaaggaa 123540
ggctagacat ggtttacaca ggtacatttc ctgctgatga ttggtagtgg ttgggagggg 123600
acagaaggca gggagatgtg aattgatgag gcacggagta tacctgggaa tggtgagact 123660
tgaacctcaa gttataacct aagattcaca taaatcttga aaaccatact cttgttttct 123720
tccaaacatg gagccatacc tattctaact tcttatgagt gatttgagca ttatgacacc 123780
tctacaggag atagagaaaa ggcagagcaa gagattgtca gcttggaatg cctctaggtg 123840
atgctggaga tagcatcaat ctgcttatca gggctttctg ggtgtggtgt aacccagaat 123900
agcagtcagg ataggctagg tactgctgct gtgacaaagt attttccaat cttgatggct 123960
tacaacccca gaggtttatt ttttcttata ctacatgctt cccctgtttc tctctccttc 124020
acaattctct agaatagggg tgtccaatct tttggcttcc ctaagccaca ctggaagaag 124080
aagaattgtc ttgggccaca cataaagtac acgaacacta gcaatagctg atgagcttta 124140
aaaaaaattg caaaaaactc tcataatgtt ttaagaaagt ttacaaattt gtgttgggcc 124200
tcattcaaag ctgtcctggg ctacatgtgg ctggtaggcc atggactgga caagcttgcc 124260
atagaggcta gacaagtaag ctttttgtgt tttcctgtct tgttggcact tcctctttgt 124320
cataatcctc tccttgccat aggggtaatt ctctggggct ataatagtta aagaacaaca 124380
aaaaagaaca ttggtttaat attttcaaaa tgttaacccc tttaaatatt tgatgaagtg 124440
gagatgttat aagaataaat gtgaaagcta ttagaaaaat tctggttaat tggatatata 124500
tagagaaata taggctgact gctaaatata tgcagccttt ctagcctcat tggtggatgg 124560
taatgccatt tggtgagatg agaattggtt gggaggtgag ggaaggtttc gagggagaaa 124620
tctgtctaga cttttattaa tcttttgcta gcttaaaaag tataattata ggtgattttt 124680
ttcttcccta ttttttaccc ctaaattttt cgtaaaagag gctttgatag tgaaataacc 124740
taatactgaa gaacatatgt aggttacatt ctgaggtctg tgtctgggat atcccaggct 124800
gggttgggcc tgatctgaga ctgaggaatg ttgctgaagg aggctgggat gagcttcctg 124860
tggtttctta gatggtcctt gctgggtgga cagggtaggg catatggctc aggttgccaa 124920
gatggtgcta aatgccttaa tttggttcag aatggtttga tggatgcttt tgattttttt 124980
ttttaatgct tctcagcttg aaaacatttc cagtttttgt ccttttcatg ggaatttatt 125040
gaacataagt aagttggatg tttttcttgt taactagaag acttaatcat gtaacatgac 125100
aaaggaaaga aagaaaaagg atttatgatt ctaaagaatg ggcaattccc ttgaaggagt 125160
gggtcattca gtgaagctgt ttgtttggcc tgggttttct ttaagtttat ttttctcact 125220
cagttgagat tttgactgtt tctgactacc ttcctcaact ctatcactct ttctatggct 125280
tgtggttgga aaacagggcc atccaagtag cttgttgggt cccaggcgaa tgccctttga 125340
ctctcaacac ctttttagaa aggtacattc tctttcaagg aaaaatgaag ccatgtaagg 125400
gaagcttatg tacaaaatag gataatccag ttaactcagg ttatggtgat ttgtcctttt 125460
tgtgtgtttg tttcagctgt tgctattgaa aactcttata gaagaattta gttatttctt 125520
aattttattt agttaataat tttagtaaat agatttactt tttctatggc aaatgagaac 125580
ctagcaatac tacagaatca taggacatat acatgtacaa gacacttatt gatcttccca 125640
caacatctaa catttctaca tgttttgaaa tgtttcttca gtagacgtgt tctgaaatgt 125700
tttgaaatgt ttcttctaaa aactgttcac tcctttctcc ctaaatgtgt attatatgtt 125760
ggtattatac tgggtgctca gaattatctt taagaatgat ggggtgtgcc gggcatgtgg 125820
ctcatgcctg taatcccagt actttgggag gctgaggtgg gtggatcacc tgagcccagg 125880
agttccagac caccttgagt aacatggaaa ccctgtctct actaaaaaca caaaaactag 125940
ccaggtgcct gtagtcccag ctactgggga gacaggcatg agaatcacta gaacccagga 126000
agcagaggtt gcagtgagcc gcgattgtgc cattgcacgc ctgggtgaca gagtgagatt 126060
ctgtctcaaa ataaaaataa aacaaaataa ataatgatga ggcccaattg gtttctcaag 126120
aagtgcactt ggtttctcaa gttgcccact tggccctccc gcaagttgta ctttacttta 126180
cttttccttc ctttccttac tgttctaaag cttttaaata aactttcact cctgctctga 126240
aaaaaaaaag aatgatggga aacacagggg ctgctaaaat caagatcaag tactgtacct 126300
ggtcttgggc tgcttataag ctagttggaa agaaaagaca cacacttgga aagatagcta 126360
aaatatgaca aatagctaaa atatgacaag tgtcatgtga gcaaaacata gaaaaaaagg 126420
ccatggaagt tcagcaaggg tatattctct gtgcacagaa caatctgata agccttctca 126480
gaagaaatgg aattggagct gggatctgag gtttagatta gcagagacgg cagtgggaag 126540
gacatttcag ggaggaaaga agcaaaggca cagaaatgaa aaagtagaat acatgtttgg 126600
gtggggcagg atgatgaaag caatgagaag attaatttgt ttggagcaga aaccctccca 126660
tccccatcac caatcctatt aactcaaagg ttcatttagt taaaatacag taaagcttca 126720
gtcccttact tgccctttg agtcccagtt tccttatttg taaaacgagg ttaatcatac 126780
ctaccagcca tagattaaat tattaaatga ttaaatggat taaatgagat aggatactaa 126840
aaggaaggtg ttgagcaggg ttcctcacac tttatcatcc ctcttcactc aattcattgc 126900
attcaattta attccagtgc tgtctgtcat actatcaaga catctcctat gctactcccc 126960
cttgaggata atttaaattt gactgttatt gcatttctct aaactagttt ctattcacct 127020
tctggtttag gagaattttc ttggcataag ccatctgtat atgcaaagga gaccaatgtc 127080
acatttgagg gctttaaata attcctcact aaccagttca gggtggctag agtataacaa 127140
gctaaaaggg agtagttggc aataagaaag gtgtctcagt ttgttttctc ttgctataac 127200
agaatacttg aaactggcta atttataaag aaaaggaatt tatttcctac agttatggga 127260
gatgagaggt ccagagttca gcagctgcat ctggtaagag cctttttttt ttttttaag 127320 ttttgattct tttttttttg tttttttgtt tttttatttt attttatttt attattatta 127380
tactttaagt tttagggtac atgtgcacaa tatgcaggtt agttacatat gtatacatgt 127440
gccatgctgg tgtgctgcac ccattaactc gtcatttagc attaggtata tcttctaatg 127500
ctatccctcc ccccttcccc ctaccccaca acagtcccca gagtgtgatg ttccccttcc 127560
tgtgtccatg tgttctcatt gttcaattcc cacctatgag tgagaacatg cggtgtttgg 127620
ttttttgtcc ttgtgatagt ttactgagaa tgatgatttc caatttcatc catgtcccta 127680
caaaggatat gaactcatca tttttatgg ctgcatagta ttccgtggtg tatatatgcc 127740
acattttctt gctaatgggg atgctgcaga gtcctgaggc agtgcagagc atcacgtggc 127800
aagggggctg agtgcgctaa catgctagct taggtttttc ttccttttcc tatatagcca 127860
cagttccctt ccaatgataa ctcactattt cattaatctg tgaatagact aagtcattca 127920
tgagggcaga gccctcatga cccaatcacc tcttaaatgc ttcacttctc aatactgcct 127980
gatatggttt tggctgtgtc cgcacctaaa tctcatactg aattgtagct cccataatcc 128040
ctgcatgtca tggaaaaaac cccatgggag gtaattgaat catggcagcg gttacctcca 128100

-continued tatcatgttc ttatgatatt gagtgagttc ttatgagatc tgatgagatc tcatgagatc 128160
tgatggtttt agaaggggct ttcccccact tctctctgca catctcctgc tgccatgtga 128220
agaaggacgt gtttgcttcc ccttccacca tgattgtaag tttcttgagg cctcccccgc 128280
cctgtggaac tgtgagtcaa ttaaacctcc ttcctttata aattacccag tctcagatat 128340
gtccttatag aggtgggaga agggactaat acagtaaatt ggtaccacag agagtggggc 128400
gctgctgtaa aggtacctga aaatgtggaa gtaactttgg aactgggtaa caggcagagg 128460
ttgaaaccat ttggagggct cagaagacag gaaaatgtgg gaaagtttgg aaactcttag 128520
agacttggag ggctaagaag gcaggaagaa gtgggaaagt ttggaacttc ctagagactt 128580
gtcgaatggc tttgactaaa atgctgatag tgatatgggc aataaagtcc aggctgaggt 128640
ggtctcagat ggagatgagg aacttgttgg aaactggagt aaatgtcact cttgctatgc 128700
aaagagactg gcggcatttt gcccctgccc tagagatctg tgaaacttta aacttgagag 128760
agatgattta gggaatctga cagaagcaat ttctaagtgg caaggtgttc aagaggaagc 128820
agagcataaa agtttggaaa atttgcagcc tgattatgtg acagaaaaga aaaacccatt 128880
ttcttgggag aaattcaagc cggctgctga aatttgcata tgtgatgagg agccgaatgt 128940
taatcactga ggcaatgtgg cagctgtttt cagggcatgt cagaaacatg tcaaagttct 129000
caggtatcct ataatcccca tgggtcatgg gaaggactta gtgggaggta attgaatcat 129060
gggggcggtt acctccatgc tgttctgatg atagtgagtg agttctcatg agagttgatg 129120
attttataag ggctttcccc ctccttttct ctgcacttgt ctctcttgcc accatgtgaa 129180
ggaggacgtg tttggttccc cttccaccat gattgtaagt tttctgaggc ctccccaacc 129240
atgctgaact gtgagtcaat taaacatctt tcctttatca attaccgagt cttgggtatg 129300
tccttattag cagcatgaga atggactaat tctctgccac atttgggata aaatttcaac 129360
acaaattttg gtttgctatt caaaccatag caaaaggata ctttccttct tgtagtttta 129420
tcaacatctt ccaggacata aatttaatgg taaacaacag gtaaaataaa tgacattgct 129480
caaaggaatg caattaaaac ctaactgcta ttgcatttaa tccatagagg aatgtgaccc 129540
aggtctgggg agagggagca ctgcattatg tttcattctc atgccatgtg agaatgttta 129600
caccagcttg agttgttgtg atggggtcgt ccatatcatt tggttcttgt ccttgtgact 129660
cactgcttct gctgtagagt tagcttcctg cagtggaaaa gggaggagtt attttccaga 129720
ccatatggag tagaaaacaa cagattgaca taggttttgt ggaagctaaa ggcacatgaa 129780
ctgaagcctc ccagagtgta accttgcaaa actctttaaa atagcatttt catagaggtg 129840
tttagtattt aggatctatc ttaaaacctt aagattccaa agttagctta cagaaaatag 129900
gcaagagagg ataaattgta ttaggtatgg aatttcactg cctctgcttg tgtttccagg 129960
ttggagaagc tggagaaaag aatgcttccc tttgatttac ctgggctggg gagtatgaca 130020
atgtccatgt gtgtgtatag gagattcttg tacttaaact ctgtaaatgt gtgtttctgt 130080
ggtcctatgc tgggtggagg gttcaactaa ggtattgtta aggaatatgg atgagccaaa 130140
aagactggaa agtttcaaat gcatgtgtgt ttccaactaa tattggagaa aactttttg 130200 gcatcgaaca ctggcaattt atagacttgt tgattgatag tggatttacc tttagagtgt 130260
acctggatta tagaggaatc tagcttccct gtctaactca tttatcataa gcttactgaa 130320
taactgctat ggactatgca tgtgttagat gctggggtag aaagataaat aggacacagt 130380
cccacaggaa ttatagtcta gtggagagag gtgtatataa acagtcacag aacaatgtga 130440
taagtattat gatgaaggaa tatgtaataa ctgctagcaa agagaaggaa acatttaaac 130500
ctgcttggga gtggagggaa aagtcagaga aagctctata aaaaagctaa ctatataata 130560
tgtttggtag gatgagttac ttggcaaatg ggctggagtt acacacccag ttggggaata 130620
tgttgcctcc aaaatccaaa gagccccatt aggcgttgtg cttttctttt cttttctttt 130680 ttttttttt tttttttaa ctgtaggaag caccagatgc aatagcttat tccttgcctt 130740
ttaattcttt taattcctgc aagataaata atccaagcca aaatgaagca gaaatatcat 130800
tagactgtca ccagttaagg ctccagatta attgtctgag aggtagagaa gagaaacagg 130860
aaagcagaaa tagactttaa tttaaaacac aagcaagtaa gagtggatca gtcaaggggt 130920
tctggcaaga aacacagaag aaacacagca tattctgaag agtagaactg atttgtgaag 130980
agactatgtc agagccatga taagaaaacc aacaaaggat agtgaggcac ccagggacta 131040
gcaacatcag ggagctatta gtactcttgg ggctgcaggg gccagggaag gaaatggtgt 131100
taatgagccc agtgaaagct ggcgtcatgg aggaggggaa atagtttatc atgaaaacag 131160
aactatggct cctcactcac aatcacttcc agacatgaac cactttacag actcagaata 131220
ccctgaatga agggaaggct ggatcccctt gaggaaggac ccctgtacgt ggacaaatat 131280
ttacactgtt aatattcctc ccagaattcc acaaagagct ttatgccttt ttaatggtac 131340
tgtgcattgg gaaaaaaaac aaaacaaata atttgaactt tcagagatta ctggacactg 131400
gctctgaact gacagtaatt ccaggagact caacacatca ctgtggtcta ccagtcagag 131460
taggggctta tagaggtcag gtgattagtg aagctttggc tccagtttat ctcacagtgg 131520
gcccgatggg tacctgaaca catcctgtga ttatttctcc agttctagaa tgcataattg 131580
caatagatac attcagcagc tgttggaatc ccctcattgg ttcccttacc tgcacagtaa 131640
ggactactgt agtgggaaag acctagtggg agcagccact agaactgcct ctacagagga 131700
aaatagcaaa ccaaaaggaa tgctgcattt ttggaggaat tgcagagatt agtgctgcca 131760
tcaaggactt gaaagatgca ggggtgatga ttactactcc ccactcaact ctcttatttg 131820
gcctgtgcat agaacagatg gatcttggag aatagcagtt aagtaagctt aaccaggagg 131880
tgactccaat tgctgcattt cattgcttga gcaaactaac acatcccttg gtacctggta 131940
tgcagctatt gatctggcaa atgcttttcc ttcatacctg tcaataaaaa ccatcagaag 132000
cagtttgcct tcagctggaa aggccagtaa tataccttca ctattctacc tcagaagtag 132060
atcaactctc cagccttaca ccataattta gttcacatgg atcttgatca tctttctctt 132120
caaaaggata ttatactggt ttgtcatatt agtgacatta tgctgtttgg aagtagtgag 132180
caagaagtag caactactct agacttaagt catttgcatt tcagaaggtg ggaaataaat 132240
gagacaaaaa atggaaagac tttctatctc agtaaaatgc ctaagggtga caacccccctc 132300 accccccacc actgccaaaa aaataagaac aatgcttaat ggacctcttt ggattttgga 132360
gtcaacatat tcctcatttg ggtatgttac tccagaccat ttgctaagta acctgaaaag 132420
ctgctaattt taagtggaac ctagaacagg ggaaggctct acaacaggtc caggctgctg 132480
tgcaagctgc tttggctctt gcatcatatc atccaacaga cccaatggtg cttaaaatgt 132540
tagtggcagg tagggaagct atttggagcc tctgccaggc tcctataagt aaatttaggc 132600
atagtccttt aggattttgg aataaagctc tgccatcctc tgcacataac tattttttt 132660 ttttttaagg aacagctgat ggcctactac aaggccttaa tagagactga ctgcttaatc 132720
atgggctaca aagttacggt gcaacctgag ctgcccatca tggtgttttg actcaccaag 132780
ccataagttt gggcatatac cacttcaaat ggaagtggta tatatgtgat aggacctaag 132840

-continued aaagccccaa aggcacaagt aagttacaca aagaagtggt ctaaatgcca atggtttcaa 132900
ctcctgttac actgccttct ctccctcagt ctgcacttat ggcctcatga ggagctccct 132960
atcatcttag tacattttct gttgctatac cggaatcaag cagactgggt aatttataaa 133020
gagtagaagc ttatttggct tacagcctta gaggctggaa ggttcaaaag catggtggca 133080
gcttccagtg agggcttttc atactgcatt ataacatgat ggagaagtgg aaggagaagt 133140
gggtgtgtgt gaaatgatca aaacatgagg agtggcctca gtttataata cccccagccc 133200
aatcttgtgg taatgaatca agttccatga cagtgagaac tcattcccca gagaattaac 133260
tgagtccttc aagagtgaca ttaatcccat ttaaggaccc aatgatgtct tcttcttctt 133320
tcttctttct tcttcttctt ctttcttctt tcttcttctt tctgagacag ggtctcactc 133380
tatcacccag gctggagtgc agtggtgtga tcttggctca ctgtgacctc aacttcttgg 133440
gctcaaacaa ttctcccacc tcagcctcct gagtagctgg aactacaggc gtgcaccacc 133500
atgcctggct aatttttttat ttcttgtaga gatggggttt tgccacatag cccaggctga 133560
tctcaaactc ctgcactcaa gcaatctttc ctccttgacc tcccaaagtg ctgggattat 133620
aggcatgagg cactgcaccc agccacaatg actttttaaa gtccctacct cccaacactg 133680
ttgcaccaag aaccaaattt ctaacacatt aattctgagg gtacactcaa actatagcac 133740
ctatgatcaa ttgataggag aaaagattac tcagacctag tttatagata gttctgtatg 133800
atatacagga atcaatgggt gaaaagtgag agttgcacca ttcacaatta cattccattc 133860
acattcacaa tttgctaatg acccactagc aaaacttttt tttccttgtt cctatgaccc 133920
tgttctctgc tggcctagaa gtcttagttc caaatggaga aatggttcca ccaagagaca 133980
caacaatgat tccattgaac tgcaagataa gagtgccacc tggacacttt gaacatgcct 134040
ctgaatcagc agaaaaagaa gggagttatt gtgtagactg agtgaagtag attgccttcc 134100
ccagtatggt tgggcttcgt gcaatccatt gaaggcctgc atagaacaaa aagaagaaaa 134160
aaatagaagt cactctttgc ttgactgtct tccagctggg acattgattg ttccctggct 134220
ttgccctaga acttgtgcta gaacttacat ctttggatct acaggttctc agatctttga 134280
actcagactg aaacttatac cattggctct cctggtcctt acccactgga ctcagagaag 134340
aagtatctca ctggctttct tggtcctcct gctagatgac tgtagatcct gaaaatttct 134400
agcttccata accatgtgag tcaatttctt ctaataaata tatatctata tttacatctt 134460
catctatatc tttatcttct attctgtttc tctggataat tcataccaat acatattttg 134520
gtactgaaaa gtgtttgtag ttctgtcata acaaatacct aaacatgtgg aagtggctct 134580
ggaattgggt aatgaataga ggctggaagt attttgaggt gcatgctaga aatatggatg 134640
ttaagagcaa ttctgatgag ctctcagatg aaatgagaaa catatttttg gaaactggaa 134700
gaaaggcgat ctttgttata atatggaaaa gaatttggct gaattatgtt tgggttctag 134760
tgtttgtgga aggtagatct tgcaaatgat gatattggat atttagttga ggatatgtct 134820
aagcaaatgt ttaagaagtg gcttgcttcc acctgactgc ttatactaaa acctgataag 134880
agacagttga agaagggatt gttaaaggat aagttgaaga aggaattgtt aagcaaaaag 134940
gaacctgaat ttgaagattt ggaacagttt cagcctacgt atattgcaaa aaaatgaaaa 135000
agtattcaga agagaacacc aagggtgtgc ctggactgtc attcaatgaa gagcttatgg 135060
gactatataa gcagcaacat tgccagttta aactgaagga gatgcagaaa ggactaaagg 135120
aaggaaggtt attagactca tcaggatttg tgggggaaaa gatgaaagag tcttttggct 135180
gtgaacatgt gctatccttc aataagagga aaaatgaccc taaaggtaat tcagaaatta 135240

-continued acagagccac catcttgttt tcaataagtc agatgccctc tttcttgaag ctgtgaggcc 135300
aggaccactt tgttgtgctg aaggatcagg acaccttgaa gaacgctggg gacagggtgc 135360
ctggaagggc catgaataca ggatctctgc cccatgggt tttgaagata ggaccccagt 135420
gggtctggaa gatagagaat caagtcaaag agaatgattc ttgagcctta agatctgatg 135480
gaatgtatct tactaggttt tagatttgtt tgggactaat catccttttc tttcctattt 135540
ttctctcttg taatagaaag gtctttccta tggctggctc gccattttag aagtacatga 135600
cttgtttggt ttcacagatt cagagctgaa tctgaagagg aattttgctt caggatgaat 135660
tgtaccttga gtctcactca tacttgattc aaatgatatt tcgataagac tatggacttt 135720
agactttaga gttgatgctg gcataaattc agacttttga ggctgttggg atgaaataaa 135780
tgtactttgc atacaataag aacataaatt ttggggggcc aggggtggaa tattatggac 135840
tgaatgtttc tgtcatcact gaatgtcatg tgttaaaacc ctaactacca atgtaatgtg 135900
gtttgaagat ggggcatttg cacagtaatt atagctaggt gaagtcatga ggatgggaat 135960
cctcatgatg ggattgttgt acttctaagg ggaagatcct ctctctctct ctcggctccc 136020
cactccccaa ctctacccta ggtgagagca cagagagaaa gtggccatct aaaagctgga 136080
aagataaccc tcaccagaac tcaaacatgc tggcacctga tctcacactt acaacctcca 136140
caaacgtgat aaaaaaaaat tctgtaattt aagacctgta gcctatggct ggcattttgt 136200
tatagcagcc caagcacact aaaacagtca attaagttta taatattatt cagatcttct 136260
atcactcatc aactaatttt ttgtgtctac ttgtcctgtt aattagtaat agaggtgtgt 136320
ccgaagtctc caactgtaat tgtatatttg tctatttctc ctttcagttc tatagatttt 136380
gctttatttt ggagttttat tgggtgcata tacatgtagc aatattatgt ctttttaatg 136440
aattgaccct tttataatta cataatgttg atgttaatat accttattct gaatactact 136500
ttagctaata ttaatataag cactgcagct tcccttaatt aatagtataa tttttccatc 136560
cttttacttt ttcctttgtc tttataagta gatttattgt agacaacata taattgcatt 136620
ttacttgttt gtccaacctg acaatgttag gctttaattg gagtgctaat tccagatgta 136680
tttaatgtaa gtattgatat gtttgggttt aaatatacca tcttgctaaa tgttttctac 136740
ttgtcccatt ggttccttgt ttttcctttc ctcttttagt gcctactttt gaactaaata 136800
tttttcatta ttatatttat tttcaaaatt ggcttattag tggtttctct aggatttaaa 136860
catctttaac ttatcacagt ttacttccaa atgtatcact ttacatagag tgtagtagct 136920
ttaccacata tacttctatt tcctttcttc caaccttagt gctattgttg ttacagtttt 136980
tacttctgtg tgtattatca accccataat atattgttac tattatagtt ttagacaatt 137040
atattttaaa ggaattcaaa atttaaaaca tcttttatac ttaaccatat ttttaccatt 137100
tctatgctct tcattctttc acacagatgt aattttctat ctggtatcat atttcttgtg 137160
cctaaagaac tttcaatagg ttagttgcag gtctgctggc aatgaattcc ctaagctttt 137220
gttggtctga gaaagttttt attttatctt tattctgaaa gctatttttg ctggatatat 137280
cattatcagt ttattgttgt gcttgtttta ttactttgaa gatgttacat catctgctga 137340
actgcatagt ttctaaaaag aagtctggtg tgattcttat cttcctccct atgtaatgtt 137400 tccttttttcc tcttctacat caagattttt ctctttaaac ttgaatttca gcagtttgac 137460
tacaattttc atagctgtgt ttttaaaatt tttgtttata ttgcttagag ttttctgaga 137520
ttctttggtc tggttttttt tttttgcttt ttgtttctgt ttttgccttc aatttacttc 137580
agacaattct tgatcattac ctcttcaaat atttctttgg ttcttgctgt cttcttattc 137640
tggagataca agtccatgta tattagactg tttggtttta ttccctaatt tttggatgat 137700
ctgttctttt ttcccatgca tttaattatt taattttcag tagttcctgt catcaagttc 137760
atcaattatt tcctcattgt gtctagtcta cagataaagt tgtcaaagga ataataataa 137820
taaaaaaact ctagaatttc cattggtatt ggtttcctat tgctgctgta acaaattacc 137880
acaatgctac tagcttaaaa ctacacaact ttattatact aaagttctgg aattcagaag 137940
tctgaaatgg gtctcagact tgtctaaaat caaggtgtca gtaaggctgc attcctttag 138000
gagactctac aggaggatct atttccttac cttttccatc ttctagagac caactgaatt 138060
ccttatctca ggacctcttt ctccatcttt aaagccatgt tctctttctc catctttctc 138120
catctttaaa gccaaactgc aaatcatctc caaattactc tgtctctcct ggttccctct 138180
ttcacagtcc ttgtgattac attgagccta tcaggataat cctggataat attctcatat 138240
catgatcctt aacttagtaa catttgtaaa gtccctttg ccatgtaagg taatatagtc 138300
acaggttcag agaagtagga catggacatc tttggtaata atggggtgtc ccattattgt 138360
gctgatgaca ccatctgatt ctcaggattt ccacctttag taggtagaat ggtggcctct 138420
caaaagatat atctatgtcc aaatccctgg aacctgtgaa tgttatctta cttggaaaac 138480
gggtatttgc agatgaatga agttcaggtt cttgagagta gatcatcctg gattacttgt 138540
gtgattccta aattcaatga taagtgtgtt tgtaatatac agaagaagtt aagacacaga 138600
cagacagagg agatggcaat gtgaagatag aggctgagat tggagtgctg tggccacaag 138660
tcaagaaagc caaggaatgc tgactgcccc cagaagctgc aaaaagcaag gattttccct 138720
ttgcacctcc aggagtgtgg ctctgctgac accttgattt cagacttgag gcttctagaa 138780
ctgagagaat aattttctct tattttaagc cacccagttt gtggtaattt gttatggtac 138840
ccctaggaaa agaatacatc tttctgttga aatctttatc tctttaagta tgtattatag 138900
tttttccatt agatccttta acgtattaat tataattatt ttaaagttcc tgtctgttag 138960
tttcaacatc tggaccaaat tctgagtttg tttaatctct tgacaatggg ttgttatgtt 139020
cttgcttttt gtgtatatgg caattttgtt tacataccag ataatgtgta caaagtaaca 139080
ctagaaactg agctaaataa tatttatgcc cagcagtagg catgcttctt cttctgttag 139140
atcatgagtc tttgggcagt tgaggctctc tgatatgtac atgagctgag tttaagtttg 139200
ctgttgtcgt gttgatatat tgttatattc agtgaaccct aggcttcaaa ttcctcctgc 139260
ggtagacaag tgctacctta tccttagtgt gaggtctgaa gtgctagagg aatttctaa 139320 atgtttcttc actctcagct ttcagcaatc catgtatgac tttgccactg gggggattta 139380
tctccatgtt cttgtattta ccctagccta gagacttcag ttgtttgtta ttctgtgcaa 139440
gactcatgct ggagttggaa gctttcactt ctcctgttcc agccttagtt tcaggcaggt 139500
cctgtgctcc tgagcctgat gtcagttgtt ttgaataccc ccatgtctct cccatgacaa 139560
gcctttgcct ccttttcagt ccatgtttta gagtgcaggt aggtttcctg tacttccctc 139620
cccgctgaac aggtgaactc tgcctccgcc cccagcaata gcagtcctct tctttgtatt 139680
agtgcaggat cctgcgcatg agaaagtttt ctaccacttt cccagtagca gcctaccttt 139740
gcctggaaat agggacatga cagggtttca tgtccctccc tcagtggcag attcatttta 139800
cttcatataa aagcattgtc atgtctggga tgtgaacatg ttctttctat catctcaaca 139860
gcgacagatt ttacttccta tctgagaaca ttctgggctg tgggaagtag cagctgctca 139920
ccatactgta ctcatgcaga gcccattgag agatgaaatt ccatagacac tcctgtggcc 139980
gggcacggtg gctcacgcct gtaatcccag cactttggga ggccgaggag ggcggatcac 140040
gaggtcagga gatcgagacc atcctggcta acttggtgaa accccgtctc tactaaaaat 140100
acaaaaaaac aaattagctg ggcgtggtgg cgggcgcctg tagtcccagc tactcaggag 140160
gctgaggcag gagaatggcg tgaacccggg aggtggagct tgcagtgagc cgagatggcg 140220
ccactgcact ccagcctggg caacagagca agactccgtc tcaaaaaaaa aaaaaaaaaa 140280
aaaaaaaaaa gaaattccct agacactcct gctcttctct caaacctcag cagaccctgt 140340
acacctgtgc caccaagagg cgccttctcc agcttcctac ctgccctcaa tcgttcttgt 140400
gaatattcag atgagaccca tcaagaaccc catgagtggg tgcagacttg cctgtgcctg 140460
tggcacctga agattctaca ctttcacact agtccacatt tgtcctttaa gaatgtgcta 140520
aatttcatct attttcatct tactgactcc aataactgcc tcccttccct cctattctcc 140580
ctaaaaggtg aaacatttga gtgtcctatg ttacctatga ggagcctttc acccttagga 140640
atttagttca actgatcaac ctcagcgcac tgatgaactt gaaaactatt ttgtagattt 140700
tcagcttttt tttttttttt ttcctgaggc agtgtaaatt atttaagagt ttagattacc 140760
aacttttcct gttttggtga tagtgacatt cttttgcagt ttctgtatcc taagtgaaat 140820
tagaactata ttcattgatt taacagatat tcaaatcaac aaatgcatac ccagaggacc 140880
aagtgatgtc tgaaacttaa catatatata atggaacttt tggtttgccc caaccattgc 140940
ctgttccacc ctaagcctat ctctgtaagt tgtaccactg tccacctagt tggttaagcc 141000
agaaactcaa gtgttttcct gattttctct tcttcacctc atacatccaa tacaacagta 141060
accactataa ttattgattc tatttccgaa ataaatataa aacccattta ctttttttcca 141120 ttattgctgt cactagtgtg gtccaagctg tcatcatctg ttgtctggac ttctttgtca 141180
accagaggat ctcacagctt ttacttttgt cctcgtagac tacatcatcc acccagcagt 141240
caaagttaaa acataaatct tatcacattc taaaaatata agtaaatttt gagcatgtca 141300
aatccctgct caaaatcatt cagtgtttcc ccattacctt tctaaaggca actcaatctc 141360
aactcctcac catgacctgc aaggccgtga atgatccagc cctgcctatt tccacaacaa 141420
cttcatttgg ggccactttc ttcctcactc acttattcat ctgttgagaa aagagaggca 141480
cttttaactt atacatgtct gaagaatcag agcagctgtg aacataccc agaactctga 141540 aatttcaaaa gtataaaatg ttaatccaaa aagaattcta aacttcaaat aatcttcttt 141600
ttgcttattt tttatggcat atgtgcatta ttatttcatc actttcaaaa ctgacacagt 141660
ttccatagtt aacttcgagt tatttttgtg aactgactat tgaacgaaag ctctccattt 141720
actaacaaca gtgtagtctt ctgaatcttt tagctcttat tgaaaaaaac attcctttgt 141780
tatagagtgc aatgtggttt gttttggagg gagtaaagga ggcaggatgt ctgtctttgc 141840
ttggtttcct ggccagtgca tctcatttga aaatagtttg tttcaagtag ttaagtctat 141900
tcctgggaag cctctatttt tatatatttt tttaattttt agacaaggtc ttgctctgtt 141960
acccgggctg gagtgtggtg gcacaatcat agctcatagc agtctcaaac tcttgggctc 142020
aaatgatcct cccatctcag cctcccaagt agcttggact acaggtgtgt accaccatgc 142080
ctaattgctt tttttcaaaa ttttttagta gagatgaggt cttgctgtgt tttctcaggc 142140
tggtctcaaa ctcctgggct caagtgatcc tctaacctca gcctcctgaa atgctagatt 142200
acagacatga gccactgtga gccttttatt tgtttaagtt ttattttttc ctttcttccc 142260
ttctcccttc ctttctttct tttgttttta gacaagtaat ttgacattag gaggtcttga 142320

-continued aggtgatggt ttcctctggc agtagtgcct tttctgtcac tgaaggtgtt cagttggtca 142380
gaatgcatgg ccaatggaat cattctttca ttaaagaaca aacatttgtt aaacgcctcc 142440
ctttgccaaa gcattgggac actcactagg agttcaaaga taaaaaagca cgctttttaa 142500
caagtgtacg tttcagtgtc agacatacag ttttaataca actgctcatt gttctaatgg 142560
gaaataagag attcagccat taaactactg tgtggtgtag aagacctttt aaaatagact 142620
gatttctgag agtctgtgat ttcacttata aggcttatga gggattctta gcaaggaaaa 142680
atgagaatcg tttctggtta tactaattat gaactttgtg agccttgagc aagtctctaa 142740
actttctgaa gctcagtttg ttttcttata ttttaaaaga gaatattttg aagagagata 142800
aatggaataa tacaaataaa gttccagcac ctattaagtg ggggtaaggt ggagcagtgt 142860
ttactgaaaa tgaaaattag attaaaggac agacacttca gggccatttt tttttcctcc 142920
tccatatgtg tgagtgtgga tggggtaggg agaggagggt gttttataat aaagaagtaa 142980
acggaaagaa aaaatgtgaa gatatagttc actgggggaa acactgtaaa tatagactag 143040
tgacaggcaa tgaactgcag gacctgagct ggttctgagg cagtgagcct cagctagaac 143100
atcccatata catcgcagga ggatgatgac gtttaatgtg tcaaagtgta cgtaactgat 143160
gacagttttg tgatcaggct ttgtttgcaa tcatagagaa tccagaaaag ttaattttaa 143220
tactcttgat tttgacagat aaattctttt taaaatgtaa aattattatt tctcattaaa 143280
gaaagaagaa taggacattc ctagcctttt tttttttttt ttttttttga gacgagttct 143340
cacctgtcac tcaggctgga gggcagtggt gcgatcatgg ctcactgcag cctcaacttt 143400
caggctcaag cgatcctccc acctcagcct cctgcattgc tcggactaca ggcacatgct 143460
atcatgccca tctaaatgtt gtattttttg tagagatggg gtctcggtct gttgcctgtg 143520
ctggtcttga actcctgggc tcaagcaatc ctactaactt ggtctcccaa agtgctagga 143580
ttacaaatgt gagccactat gcccagcccc tgatctatta acattttaga aactagttct 143640
ttgtgaggct ctttcataat aaattatcag tatgttacag cattatacaa attgcaagtg 143700
ctttcacatg gataatctca tttttatcac cccctttttac acatgagaaa attgaagctc 143760
agaaatgact agtctgaggt cacacaggta agatatgcca aagttgaaac ttgaactctg 143820
gtgtttctta tcatgctgca cataaaatta tggactgtgc ctcaggttag gagaaatcag 143880
aattttcaat gaaaatacaa ttaaaattgg attagtatgt cattctatct ttgatcagtc 143940
ttaaccttaa ttggctaatc atataaaagc tcttacactg tgatctaatt cagtcctgct 144000
ggacaaatgc tattctattg tattcaatat gatgtcactg aaaacttcat ggaatatatt 144060
gagctggaaa gattagacaa acaactcctc acttacggtg cacacacgca cacacacaca 144120
cacatcccca cacacttaca catccctact catttaaata tagaactgta tacaataatt 144180
aatataatca attaatattt acatattacg ttattagtaa gttacttttg aatactccag 144240
tataaataat gtaaacaaat taactttaat caatacttta gggccagtta gttacagtaa 144300
tgtaataaaa aatgtttaac aaccagctct ggggaggagt agagtcctga tttgtagcat 144360
ttgctgattt ctgtccatca atactctcac catggctggt ttcaggctcc cagtgtgagg 144420
tcacctaatg caggaataca gatgctgcta tttaaatctg caccagaggg ttcattgatg 144480
agggtaaggg atgttgagca taattttggg ggataagtaa atggtgtcca atgtatgtct 144540
ggctgaaaaa agattacaca ggcatctttg tccttgaagg aacagtattg aaggacccat 144600
caagcccaga agccttacat cttcagagta tcccctgggt ctagaacttt ggttctacac 144660
ctccctattt aatcaaggct ctattacctg atccaattac aggctttgct gattcttctg 144720

-continued ttagattatt attgtaaagc ttgttggagt gcctaaaaga tagatatcag ggactgactt 144780
cctcaagcca ggggaatagt ttctatgact attttgaagc ttgcttgcta atagatattt 144840
ctatgtagca gaatattgtc taagatttcc tttattacac ttgccaccta atggtgaggt 144900
gaaggaagaa gtcatagctt ccatttctct tttatcgtat taccaaatat tgaggtgata 144960
aatatttacc aaaaaatctg acagttgtat agggccaact tggtttatta tatcaatttg 145020
caatatcggt aagtacctac taagtttggg gcactataac atgataaaat ccttgtctac 145080
agagagcttt taggtggatt taaaaatgca gtgttaccat ttctatttat aaagtgtgaa 145140
aacaaagtgg atgccagatc acacacaagc cagcagagaa tgtctcccag tcttgtttac 145200
agtactggga ttgtggtcaa ggtgaataca cacagtcctt tactctctta tcagagagtg 145260
aaggtttaaa gagaaaccaa caaaagtgtc caggtacttt tttttttct tcagacaggg 145320 tctcagctag gctggagtat agtggcacga tcacagctga ctgcagcctt gatctcctgg 145380
gctcaagcaa tcctcccacc tcaggctcct gagtagctgg gactacagac gtgccaccac 145440
acctggctat tgttttaatt tttttgtaga gaccaggtct cactatgctg cccagtctgg 145500
tcttgtactc ctgggctcaa gtgatcttcc caccttggcc tcctaaagtt cttggattac 145560
agacctcaaa caccatgtcc agcctccagg tactttttaa ctgtagtgat tatgtggcat 145620
tttgatgtaa tggctctaaa atattgcccc tgaattcttg gaaacttctt ccttgtagag 145680
gttgggtgtg gtctatgtcc ttttccttaa agctgggttt ttgactactt gaccaatagt 145740
acatggcaga agtgttgctg tggcagtttc ttaagataca ggtctggaaa ctggcacttg 145800
atctggtaag gtccgaacta tataccaaga aactggctat ttccacttcc tatctctggg 145860
atatttgctg ttagaaccta gtctctattc tgtgaggaag cctaggccac ctcatggaga 145920
ggaaccaata ggcagcatca acttaccatt catgaaagta agccatcttg gaggtgggtc 145980
atccaacccc agttaggcca catggagcag agataagctg tcctgctgag acctgccaaa 146040
atggcaaatt cttaaataat tattgctgtt taagtcatga aattttgggg tagcttaata 146100
tacagcaata gaaacctgga cacctagtaa tctgtttgtg agaagagact atcagatgct 146160
tctcagtact atttttcctg ttagttggtg actcattcct ttgtagacag tctatagatt 146220
tcttttgtgt ttactccctc ttggggactt cccacttgtg cctgcctcct gtttagcagg 146280
aatctgtagc agacaaatcc caagctgaag cagggattag gggtgagctt ctgtgagcag 146340
tggaagtttg cacaacctaa caaagaggta atttctgcag gggtgctttt ggcaagagag 146400
atgcccatat gttggattgc ataattcttt tttcttccca gttgggggtc atcaggtcat 146460
ctgactgcta attcttcagg tatggacttt tcttccagct ctgtgaatct gttctaaagg 146520
gtagagtctg agatgagaat ctagagacac aaattgttgc tgtgtcacca actgtgtgag 146580
ctcaatcaag ccaattgaca ttactaggaa cataatggga ttaagatact tagaagccct 146640
acacattgaa catgttatga tattatgacc ccagatgtaa tgtaagcaaa tacaacaaaa 146700
ttctgatttt caccaaggtg actacttgat gcatttttttg aattaccaaa tgttaaattt 146760
gttaattttt gttattttag tgttcctaat tagtctacct agtgaataac cattgtctag 146820
gcctcaattg cttcatccat aaaatagata agtagatggt ttgatctgtt cgatttcttt 146880
tgtatctaaa ttttgattct gcaatcactt ttattccctt tcctttgttt ggtatgtttt 146940
tttttctctt tgctatagct ttattgaggt ataattgaca agcaataaac tgaaaaatct 147000
aaagtgtaca atttgagaat ttttgacata cttttacacc gatgagcatt acctaatcaa 147060

-continued aacagtaaac atctccatca tctccacaaa tttctttgtg ttcttccctt tccctttctt 147120
taccccagct tctaggcaac tattgagctg ctgtgtatca ctatagatta gtttgcactt 147180
tacagaattt tagataaatg gaattctaga gtatgtattc ttttttgtct gacttctttc 147240
actcagcata attgatttga gatacagaca tgttgttgca tgtaccagta gttcattttt 147300
ttaagttgct gagcagcatt ccattgtatg gatatgccac aatctgtttt tccatttacc 147360
tgctgatgga catttgggtt gtttccagtt tggggctatt agggataaag ctgctgtgaa 147420
cattcacata taaatactta catagacaca tgattttatt tttcttgggt aaataaatac 147480
ctatgagtgg aatggttgga tcatatggta attacatgtt taatttttaa agaaatggcc 147540
acacttttca aaagtcgtgg aacaatttta ctttcccact ggtagtctgt gagagttcta 147600
gtttctccat attctcacca acattttgta tggtcagttt ttaaagttta gccattctaa 147660
taagcatgta gtggtatctc attgtgtctt aaatgtacat tcttgtggta actaatagtg 147720
ttaaaaatct tttcatctgc ttattggctg atatggtttg gctctgtatc cccacccaaa 147780
tctcatcttg aattgtaatc tctgtgtatt gggggagggg cctggcatga ggtgactgaa 147840
tcatggcagt agacttcccc cttgctgttc ttgtggtagt gagttctcgt gagatttgat 147900
ggtttaaaag tgtgtggcag ttcctccaca ctcactctct cctgcttcac catgggaaga 147960
aggtatgcct tgcttcccct tcagcttgtg ccatgatttt aagtttcctg aggcctccca 148020
gtcatgcttc ctattaagcc catggaactg tgagtcaatt aaacttatgt tcttaataaa 148080
ttacccagtg tccggtagtt ctttatagca gtgtgaaaat gaactaatac atttgccatc 148140
tgtatatctt ctttggtgaa gtgtctgtca caatattttt tctagttctt aaaaattatt 148200
actgattttt gagagtttaa aaaatatatt gtgcataaaa gttgttagat acataatttg 148260
caaatatttt cttgcagtct gacttatatt ttaattctat taatatttgg tatgttctta 148320
aagaggaaaa aatcttaaca tgtgaaatat tttacatact cttaagttca aagagcagca 148380
taggtggatc tgggaagaaa aagacattag caaaccattc aatggtttgg cattgaatgc 148440
ctttgtgtaa gattttcttt agttagcttt tattaagtga cttttgtgta taaagtattg 148500
cagtataagt aaacattgta gtaagtaatg ttttagcttg aattctgggc tttatgcatg 148560
tttttcagaa cagccaccaa tttagactca tggtttctct cagtattatg cctggtctac 148620
aaagagtcta agctaaaaca cccatgtgtg atatctatat ctcccacatc atcatacacc 148680
aatctatttc tatttctata tatgtatgta taacttgcaa aaaatccaac ttatattcat 148740
attcaactta catctttggt caaatataac catcaggcaa actgttgtga cctcacaggt 148800
ataataaact aaatgataat ataaaatatg tatcacaaag cttgtgcact ttacttcaca 148860
gtagaaacat ggatctgcct tcaggtactt atgtagacaa ttatttataa agcaagatag 148920
attataacca gtgaggccac actgacagca tgtggaaaaa cagttcacaa cagtgggaag 148980
agagacagag aaaatacaga ccccaaaact agaatgcaaa gaagtctgga tatattttgt 149040
atttgtatag aaagcctttt aagtatgaat ttcccagagg acatggagtc atgagatttg 149100
taataattta tctcagaaat gcttggaata aattataagt tcttaaaggg aataaggttt 149160
tgaagaatgt atagttaact ccttgataat ataatttata ttatgatatg atcagaagct 149220
ataaaaagta taaaacttgc caaagaaggg agtgagactg ctgaatgaag ttaaagtaga 149280
gggtttatct tgaaaattct tctgctttaa atattctgaa tatgaaatag aaggatatgg 149340
ttaattgtca gtgggagaga aaggaacagg tattgaatgg acctctgtat tgtaagagta 149400
aaagagaaat tcccaaccaa ccaattatta aacctcctaa tattaagaat ttatatctag 149460
catttgaaaa atttgatcta gaaatttaag aacaggtaga atttccttca tcatccctgt 149520
tatttcctct cttagtgctt ataagtacaa actccagaac agtctagttt gagtttgagt 149580
ttcaacatca tcagtgggtt ggcttccaca aacccaagtt ttctaaccta cagaatggaa 149640
ctaaaatccc cacctgaaga ggtggtggtg aggattatag gagatgcagg taaagggctt 149700
agtatagtac ctggcccagg gttttaaaca cttagtaaat ataaaatatt acaattattg 149760
tttattctag ggagaaattt gaaggacaag cagcactgaa aaattcaagc aaaaacatta 149820
gcagtcaata tcccataatt tgaaattaag gattaaaatt aggtattatt ttcatctgtt 149880
tttgtttctc ttattttaat aaaaaagctg tggaagcccc cagaaataac tgccagcttt 149940
tggagggtgt ctctggatgt tttgtgtgtt ccatctgggc tgcagccatt attctaccta 150000
cttgacagac gatgaggtca tggaggccaa gtgttcttca cgacgacacc caggtcaaag 150060
gcagagttaa agtacatccc aggtcacata actcattctc tgttcaagaa tctttcctaa 150120
tccctggtgc catttgggaa ctgtttcaaa ggcattccaa cctcagaatc atgccagtgc 150180
actggttatc aattattttg ttgatccttt agcaaatcct caaactgatt tttctgccct 150240
cctgagacac aaatcacaaa gctgacctta agtgctttgg catccccctc cagtcccgag 150300
gcacacaaaa aagcagtgca gggttggtga tttattgttt tcccacgcag gtcacgctca 150360
agcccagaca gatagagaag atttgtcttt aacgagagaa atgcaccatt acttggtcat 150420
aaattcaact taatggtaat tttagtaggg cagcttgccc agggtttgta gaaacacaaa 150480
tcaaaaatcc caaattccat gcatatcctc ctagaaactc ttttggcaac tcccttccat 150540
ttgcttttta aggaaatcaa tttccttagt tatggtccct agttgcttag ggtggttttg 150600
cacagagtct agaatcactg tggcagcaga gaggggagtg ggtggcatgc tgcttgaact 150660
atttttgcca agcattcggc cttgacttca gttgtcaagg aggcacaagt gagctgacac 150720
acagattcgg tagacagtcc caaaaaagta gtatgtggtg aaaatgttca gatgactctg 150780
tctaaggaaa aattttttttc aaatcctcct gtccttgact gattccaaac tgacaaattc 150840
tggtcattat gaatctcagg tcacataaca agctctgaat ccttacagag ttggtttagt 150900
ccaagctggc atagaaatat ctatggagta tattcaggca caaggctacc agacacccct 150960
ccagactctt agaagtagac tcaaacatac catcttgtat gcatgccata tcctgtgctc 151020
cctatgatca tagcaactag aagaccttat tgtccttaat tacttatgcg tgttccctta 151080
tagcacactg tgtgctccca ggtgtatggc aatgccatac ctgaatttgt ttctccagtt 151140
tttaacccag tgcctgacat gtgacagatg cacagttagc attggttgaa tgaacagaag 151200
tatgaatgaa taacgttcat gcctttccag taaggtctga cttttaagtt ggggaacctg 151260
ggaaatggcc attccttctt cttctttttt tttttcagga tgatatacat ggccaggtga 151320
agacagtaga gagaaaacag aactgaaagt aagtgtctcc cataagtagg gtaatttgta 151380
ctttatttac ttacaccaaa atttacagaa tgccaataca gtcaaaatat agtgtcaggt 151440
actgaagaat atttaactag gaatcaaaga actcaagatc tcttactctt tagatctaag 151500
atccaatgta taatgctacc ctaaattact ttattcttaa tagcatcact ctatccagag 151560
aaaatacacg acattctagc ttctctgatt tggttttgca gatgggtcta cctataacct 151620
tcccctcagg ggtagagagg agtttagctg gcagtttatt tctgtttcta ctcacacgcc 151680
tagcatatga gaaggctggg attagagcca aaggagaagc ctggaacacc caggtgatgg 151740
catgtttgga tccttataat tctctatgaa agagtgaaga gactcaaagg ctatggctct 151800
ccagcttgag tgggcatcag aatcacctgg aaggcttcct aagacacatt atttctgggc 151860
ccccaccccc agagttcctg agtcagtagg tttaagttca gattccagaa gttgcattcc 151920
taggaagtcc ccaagcaatg caaatgctac tggtttagga ccagctgaac taaggtaagc 151980
cctgacactt tccaccaaat caaattctct cattccctca tataatgcca caagatgatt 152040
ccatttgtat ggttttgtcc aggtagcctt ggactcaaat aaaagaatca gttggaatta 152100
cttatttcat agctgttttc cactgatctg gggcaaattt tttgtgccag ataccttcct 152160
ttgtggttta acctgtattt atgggctgcc tctcttgtca ttagttggaa ataaaaacaa 152220
tgatagtatc aatgaaagca acctgcaaaa gtattgttaa catagagatg catacacata 152280
aactgtttat tcatgccatt gggcttgtgt ggataactgt gtaaaataat gaatttaaca 152340
ttagcctttg gatttttct cctttccttc atctgctctg actaggagaa taattgtagc 152400
ttcagtctaa atggagaaat attagccagg tctttctgtc ttctagatag gtcctgtagt 152460
ccagccaagc tatctggatt tctgattaga cagaaatcca tttttataaa gagaaaaaaa 152520
tgtattttct caagaattat ttttagttat tttctctctt gtgatgaaag gcttatctaa 152580
atagcccaag cttcattcaa gattcttccc cactctttgt tgtcacccag ccttccctga 152640
cctcactcac cctcagacag ccagggattt aaaaatacgt tggaagattt taatggtctc 152700
tgcagagtag aattacattc ttctgtgtaa catttggaca ccaagcagag agatagcaca 152760
gtctgtctag ctcttttgta attatttcat ggtattgttt taattgtggc atggcttaat 152820
cactggctgt gcacagatta tgccacatac ttaaaataat tacagggatt tggtaagata 152880
atgctgtgaa ttcatttaat gcttcttttc caatagactc cacactctta aaaggagaga 152940
gaagcaaaga aggacagtca atcaatgcca gcattggtca ttttctgcac cttgtgagga 153000
ctgaccagga tgatatatgc acattttttt atttcagtca tcttccacct gcccaaggag 153060
gcattttatc tagtactcaa agatcctgaa actagtgtga caccctgtta agatcccttt 153120
accagctaac acttaatata ggttcacaac tagtaaccta gccaggcctg tgtgaacaca 153180
ttagttttaa atccaatggt ttgtctatgt aactgtatta gggttctcta aagggacaga 153240
actaatagga taggttaata tatgaaagtt tattaagagt ttattaagga gtattgactc 153300
acatgatcat aaggtgaagt cccacaatag gctgtctgca agctgaggag ccaggaagca 153360
attccaagtc ccaaaacttt aaaagtaggg aagctgatag tgcagccttc agcctgtggc 153420
caaaggcctc agagcccctg gcaaatcagt gatgtaagtc caagagtcca aaagctgaag 153480
aacttgggag tccgatgttt gagggcagga agcatccagc acaggggaaa gatggaggcc 153540
agaagattct gccagtttag tccttccaca ttcctctgcc tgcttttatc ctagccatgt 153600
tggcagccga ttagatggtg cccacccaga ttgagagtgg gtctgccttt cttagtccac 153660
taactcaaat gttaatctct tttggcagca ccctcactga cacacccaga aacaatactt 153720
cacatttttc aatccaatca agttgacact caacattaac tatcacagta actgatgact 153780
gctatctcca ttagcagttc tttagcttca gaagagtgta atctggttat aaatctttgt 153840
tagaattact tcgttggtta attttatgtg tcaacttgac tggcctaagc aacgcccaga 153900
tagctggtag aacatttgtc ctgggtgtgc ctgtgagagt atttctggaa gacactacca 153960
tttgaatcat cagactgaga aaagaagata cactcttgcc aatgtgggtg agcatcgtcc 154020
aatccattga gagccaaata gaaaaaaaaa ggtggggcaa ggtgaattta atctcttttc 154080
ttgagctggg acgtccaact cctcctgccc ttgggtctta gagttcttat ttcttgggct 154140
tttggacttc aagacttaaa acaatgcccc cactcaccac aaggttctca gttttatggc 154200
cttggacttg gagttatacc atcatttcct ctgatctcag gccttcatgc ttggattgac 154260
ttctgccact ggatttcctg ggtctcccac ttgtagatgg catatcatgg gacttcttag 154320
cctctgtaat ttcatgagcc aatgcctgca ataaatatcc tcttatatct atctatctgt 154380
ctatctatct atctatctat ctatctatct atccatccat ccatcttctg ttggtgctat 154440
ttctctggag aactctggct aatacaacta tcatgcaatt tgtatggttt attgaatact 154500
gatttaatca ttcattcaac agatatttat cttgtgcctg ctatgtgcca agtgtgttct 154560
aaactctagc agtgaacaag ctaagcaaaa ttcctacttc gtggcactcg tgtttgagat 154620
gtaggggaga cagacagtaa accaacaaca aaataacaat ttcagatatg gttagtcata 154680
tgagtaacat aaagcagggt tggggaatag agagtggcta gagtgtggag attttagata 154740
gaagatagca tttgaacaga gtcctggtga tgagaaggaa tcagacttgt gaaggtttgg 154800
gggaagggaa ttttaggcag aaggaaggca aagtgtaagg ggctgaatcc atggtaagct 154860
tagtggttct gcgaacagtg aacagtgcag aggggctgga gcagagcaag taagcagtag 154920
agttgttgga agaggaggag gctgaggcca tgtcaaaggg ttctgccccc atggcaataa 154980
ggttagattt ttatgtaatg ggatgtctta gagggtttag attgcctggt tgatattttt 155040
gaaagatcag tctggttgat gagataagat ttataggcaa gaatgaaagt agaaagggcc 155100
atttaggaag ctattgtact ggcccagtta tcctcggctt ggattaggat gggagtggta 155160
gagaggttag aaatattttg gagctagaac tcacaagatt ttctaataga tagtgtctgg 155220
ggattaaagg aatgaataga atcaaaactg attcctagat ttctggctta agcaactggg 155280
gaatggtgga accattaact gagagggaga aaactagggc atgcaaaatt ttgtttagat 155340
ttgttgagtt tgagataagt attatacatc caagtgggag tttagtagac agttgaaaat 155400
ataaatctag ggttcagggg ataggtcaga ggtggagata tatgtgtagg attccttact 155460
gtatacatgt aatagttatt acctaagcta catcttggct gagtgatgag atgaggtgat 155520
gcaaacaaag tatacatcat tgtcctgccc tactggagta tatacttgta aaatcttatc 155580
tttttaaaat gatgtactta atgaataata gaaggaaaca tagagtaggt tttgaataca 155640
atatgttttt gttcatttgt tgtttaatag caaataatcc aaaatttaaa tatttaaata 155700
agaattatct ttcaaggtag cctcttggga gggctagcca atcagcccaa caatttctta 155760
gagctttctt ggagtgattg ggattccctt ttagatttgg tcatgccaca agaaagttag 155820
tctacctttt cataaaacta tatctcattt tttgttaaaa aataggactt gcttgaaagt 155880
tcacctgttg ttggacttgt gacaacaaga aaaataaaaa aaaaatacgt caccgaggaa 155940
tatgacttgg tacccatatt agtccattct cctgctgcta taaggatata catgagactg 156000
ggtgattcat aaaggacaga tgcttaattg actcacaatt gcagggctag ggaggcctca 156060
ggaaacttac aatcatggca gaaggggaag caaacatgtc cttcttcaca tggcagcagg 156120
aaagagaaga atgagagcca agcaaagggg gaagctcctt ataaaaccat taaatctcat 156180
actcgtaaga actcactcac tgtcatgaga atagcacagg ggaaacctcc cccatgattc 156240
agttacctcc cactggatcc ctcccatggc atgtgggaat tacgggaact acaattcaat 156300
gcccttccaa cagtccccca aagtcttacc tcattccagc attaactcaa aagtccaagt 156360
ccaaaggctc atctgagaca aggcaagtcc cttctaccta tgaggctgca aaatcaaaag 156420
caagttagtt atttcctaga tacaatgggg ctacagatgt tggcaaatac cccctttcca 156480
aatgggagaa attggccaag acaaaggggc cactgtctcc atacaagtct gaaatccaat 156540

-continued agggcagtca ttaaatctta aagctccaaa atgatttcct ttgactccat gtctcacatc 156600
gaggttacgc tgatgcaaga gatggactcc catggccttg aagagctctg cccctatggc 156660
ttttcacggt acagccccct tcctggctgc tttcatgggt tggcattgag tgcctttggc 156720
ttttccaggt gcacagtgca agctgtcagt ggatctacca ttctagggtc tggagaacag 156780
tgaccctctt ttcacagctc cactaggcag tgccccagtg gggactgtgt gtgggggctc 156840
caaccctaca tttcccttct acactgccct agcagaggtt ctccatgagg gctccacccc 156900
tgtagcaaac ttctgcctgg acattcaggc atttccatac accctctgaa atgtaggcgt 156960
aggttcccaa acctcagttc ttatctcctg cacatacaca gggccaagac catgtagaag 157020
ctgctagggc ttgggcttgc atcctctgaa gcaatgactc aagctgtgca ttggcccctc 157080
ttagacatga ctggagccga agcagtggga atgcaggcca ccatgtcctg aacaggaggg 157140
ccctgggcct gatccactaa agcatttttc cctcctaggc ctccaggtct gtgatggaag 157200
gggctgccat gaaggtctct gacatgtcct ggagatattt ttcccattgt cttagtggtt 157260
aacattctgc tacttgttat ttaggcaaat ctctgcagca ggcttgaatt tctccccaga 157320
aaatggggtt ttcttttctg tagcatcgtc agcctgcaaa tttttcagac ttttatgctc 157380
tgcttcctct tgaatgcttt gccacttaga aatttttttcc acctgatacc ctaagccatt 157440
gctttcaagt tcaaagttcc acatatctct aaggcagtct ctttgctaaa gcatagcaag 157500
agtcaccttt gttccagcac ccaagaagtt tctcatctct atctgagaca atctcatcct 157560
ggacttcatt gtccttatca ctgtcagcat tttggtcaaa gccatttaac aagtctctag 157620
gaagttccaa actttcccac atctttctgt cttctgagcc ctttaagtct ccaggaagtt 157680
ccaaactttc ccacattttc ctgtcctttt ctgacccttc tcaatgattc caatttcttc 157740
ctgttaccca gttccaaaat cacttccaca ttttgggata tctttacagc agtgccacac 157800
tctctgtggt accaatttac tatattagtc tgtaataagg acatacccag gactcgataa 157860
tttataatga agaggttgaa ttgactcaca gttccatagg ggtggggagg cctcaggaaa 157920
cttataatca tggcagaagg ggaagcaaac acgtccttca catggcagca ggaaggagaa 157980
gaatgagagt gacaaaaagg gggaagctcc ttataaaact atcagatctc ataagaactt 158040
aatcactatc atcagaatat catgggagaa actgccccca taattcaata cctcccactg 158100
gattcctccc atgacatgtg gagattatga gaactataat tcaagatgag ttttgggtgg 158160
ggatacagcc aaaccatgtc agtaccactg atgattttaa atggactttg tcgcttgcct 158220
tggtggttca tagaagagtg tctggatatg ttttgagcaa taaagaaatg attggaaaaa 158280
gtacacaatc tcccatgtga taactttgaa ggaaacactg tttatttgct tttagagctt 158340
tagttttatt cattcactta tccagtcatg aaaaaaatat ttattatctg acatgtgcct 158400
ggtggtattc taggcagtga aaaggcagtt acaagtagtg aaaagaaaaa aacaatacta 158460
attattaagt cttcatcttt ggcctaaaat gttagtatct cttagcctta aaaaatccag 158520
tgttttgcaa atggctcaat caatcaatca atcaatttat tgaacaaaca aaaacattca 158580
aatgaaggaa taaaatttaa ctttaccttt gccttcacta tctgtcttcc tctttgtatt 158640
atatccccag aaacctcatt cccacccctc tgcttttgaa gtctaaagta atctgttcct 158700
gtatgctgta acatctcctt caaacatgaa acactctttt atttttcttt ctccccccatt 158760
ttgctgctgg gatatgtcaa caaatctctg ggctaggacg gtaatatact aattaattca 158820
tagtcaggta taaatgattt gacgctgatt tactaagccc taaactttta ttttaacaac 158880
aggacaggac ttaaatatat ctctattgat ggaaatgata gcatttgcaa gtagtaaaat 158940

-continued gatatatttc ttggctgaga gccttctcca tgtctctgaa atcacagcct atacaatcta 159000
cttaaattgc caattataat tcctaggaac aaaaaccttt cagtttctcc ctgatgctac 159060
tatttctttt tctttttaag agatactttg cagcgctctc atgtcatgta atatattagc 159120
aagtaatcct catagttgtg ctagaggaat gggccaaatt ttgccttggc ctttgtttag 159180
ctggatggta cctccacact gtactggggc tctccatcac catagctcct tcagtcttgt 159240
gcaacatatt attacaatca gcttcacttg ttcccagttc tttcagcatc tgtagtggca 159300
gctggcgcat ctcccacttc atcaggaagt gcattcaagg gtatccggct agaaagttcc 159360
cccagcaagc atttcttcat attgcaaaat gaagaagcaa ggtttcactt gtaggtattc 159420
atatctgggg tcaagtaagg tagaataaag ttagggggat cttccatcat caaagtgtct 159480
tcatcatggg tgaggccagt aaaaaatatc ctcttttttt tctagtagac tggtattcct 159540
ttgatcctgg ttttaatcag aaaaggaatg aacagaatta tgcgattggc actgcccttg 159600
tttgttttct aaattctcaa agggaattgc tctcatacca tgggtttccc ccaagatcta 159660
caattctggt taccaaggtt cacttttgtg tggggtttcc tgcattttgc ctttggacac 159720
ccaagtctat ctttcctgca attaacagga aaattccatt gtgccaattg tggttttgct 159780
ttttcttctt gagaaaacaa cctttattgc ccttcacctg cctttgcgtc cagtattctg 159840
tacaaatgtg tcatcgcatg acaaagaggg tggcaatgag gaccagcatg tgtcaaaagt 159900
gtttgaaaac tgttctagtt aattagaaag agccatgctc tagaaagttc aactcacgtg 159960
aaaattactg gctcggagaa ctaacttatc ttcaccattt tctctctggg gaagagcttt 160020
gggacaaccc cctccaaggt cattcatttt tgtctttgta atttcatagt atgccatgtg 160080
tctggtaatc agtattagag ccagaagtgt tgctagactt caacaatctt tggcagttat 160140
tgagatagat gtgtctcttg gagaaagatt aattggagtc tgaaatgttt aaggaagcta 160200
acaattattg agtgcttgtt ctgtgccagg caatatgcta ggaatttctg catatgctat 160260
ctcatgtcac agaatctcaa tttttctgct tatgagttgg aatatgggat tttatttaag 160320
tcttcctttt agcaattttg tctgaagtgt tgcctatgta attttacact tgaaggaaag 160380
tgtattcagt ggttaaaaag agccacagag gtagcaaata atttggaatt cggcttgttc 160440
attaagtaca caaataaatc caaagtacac aaacaaattc acattacaga gttagagctt 160500
gtattaggcc attcttacat tgctataaag aaataatgag acagggtaat ttacaaaaaa 160560
ataagtttga ttggctcaca gttctgcagg ctgtacagga actgcaggct gcatagtggc 160620
atctgcttct caggaggctt caagaagctt ccaatcatgg cacatggtga aagcaggaac 160680
aagagaaaga gaggagaggt gttacacact tttaaatgac ccagatatca tgagaactca 160740
cccactatcg tgaggacaat accaagggga tgttactaaa ccattcataa gaaatccacc 160800
cctatgagcc aatcacctcc cagcaagccc tacctccaat actggggatt acatttgaat 160860
ataaggtttg ggtggggaca acatccaaac tcttattagg gctagtcaac accactagag 160920
tcaagtgagc tcacaggaca attttgtgaa tttggtacta aagcagtcat tagaactatt 160980
tatcaatatt tccagacttt ctcttcctgc agtgttctca agccatataa tgtattagca 161040
agtgatcctc atattagacc acaattcccc aaatccttga aattaggtgt ggccatgtaa 161100
cttgctttgg ccaatgaaat gtgagcagaa ttgatgtacg tctcttcagg tagaagcctt 161160
taggttcagc ggaggagaca tcttcccttc ctccagccat ggtgaccaac aacattccag 161220
aggatgcagg tctgcaagcc tgagtcctga gtgatgacaa tgtgaagaca aactcactac 161280
caacccaaag taccatgagc gagaaataaa taaacctctg ttataagtca tagagatttg 161340
gggattgttt gttaatgtag cacaaactag attgtgctaa ctcatacagg aaccatccag 161400
ccagaaagcc aaaaagtcct tcctaaatgt atttgctttc attaccggag aggtttaacc 161460
agaggtttga attgaccaaa ttcttgtgat gattatacag tttggtagtt aagaggtctc 161520
tgcagtcagg ctgtcaccat aggtacatca gccctgctgc tttctacctg tgaaaacttg 161580
aatgtgttac ttgatccatc tgggtctcaa tttcctcatc tgaaaaatag gtataatagt 161640
aatactgacc tcctagagct attgtaaggt gaaataagat aatgtacaga aagcacatgt 161700
cagtttgtaa gttttctgtg attaatgtta gctgtcattc cattatccag taccagcact 161760
cactttatac aagtctatct ttttgcagtt taatggtttg gataactgat ctttcaagtc 161820
cctcccagct ctgaaactat gagtccatga aatatcttgc tttttggtac ctaaatttcc 161880
ttagagtagc tttaaattgt agtttgagtt ttgtggcgca tgtgggaact gatgttagca 161940
gagtttctct ggcttaagaa atccatctac aaaaaatcag ttttctctgc ctcaattatc 162000
tctcgcttgt cctactacat cattccttga agtttttcca gaattttttg actttgtagt 162060
tgcttgcttc tttttcattc tgaaatacat tttttccttt tggcttttga cactgaacaa 162120
cataaatttt ccttttaatg gacttgccta tgtgtatggt aaataaaagc aggaatatgt 162180
gaggaacaat ttcccaatag attatggagg tttttggtgg cgttttaagg ttttatgaca 162240
ctgaagagag gaaaggagaa aaacttgttc ttagaaacat atcaacttta acattacacc 162300
gaaacatttc atacacacat atttgcagga atattctgat ttgctgtgta tgttttccag 162360
tgttctctct aggaaagaat gcactaagat ctgaaaaaag tagttatgat tggttaaaaa 162420
tgttttgtta aaatagaaaa aagtgtagcc ttaagtattt tgctggcata gtaggaacca 162480
ataactattg ctttgaaatg cagctgtgca ttgtgaagct gtgaacaaga cttttcaagg 162540
aaaatagcat tgtctaggat ggaggaagag gccaggacct atagttgtgt cagatgtgag 162600
caggtagtgc caaagttatt tgtagaaaag atcatgatgg ttgagttcct gggacaataa 162660
cctgagagat cagggaacac gaaaaggtag agtcaggaaa atcaagcttg gggaatgggg 162720
atggggtatg aaagggagaa aaactgaggc aggaagaggg atgagatcaa agaggataca 162780
gaataaatgc agagctacag ataaagccct caggaccaaa agtcagagat cccagttgtt 162840
taatccagag acaggaaaaa ggacatcctc taaaaagacc taggttatgg gctgaaggga 162900
gaagatagat aacaggaaag aaccaggttt ctcttgggac ccagagagca agaccagccc 162960
taacttcccc ccttcctttc tctgttctaa cacttctcat aaaacaatag tttaacttga 163020
tgctagaatg tggagatgaa acaaactctc tgaaaagaga gagaacctca gagtccccaa 163080
gccaggagac tgacagagaa gccctgacag aaagactagc ataatgatgg gaattgcagt 163140
gacaggccat ggccggaagg gattgtctca tgctttacaa gtattgtttt atagaataag 163200
tgagtgtgtg caataggaag cattgaactt gagctgggct taccagtagc atggccttcc 163260
actccacttc tggaaagcta acaccctaaa attccctccc aggtgggaaa gtgccttgcc 163320
tagagttcct gcccaacaaa taatgtatga gagagaccac tccagaggaa ggtagtcaga 163380
tgtgagctgg ggtagggaga aggggcagga gaggtatatt gtgctggaaa gcaagtggga 163440
agaagagcaa tttcctcttt tccctcttcc aaccctcaga taaggtgaat catagggaac 163500
actgattggt aaatccatca acctaagtag gttcctttca ccatgtaatg gcattgtgta 163560
atttgctgca atatttccat tgtctaggct atactagagg gtcactgata atccaaagca 163620
aataaaagaa gagtttggga aataattgat gttagacaag gctccagaat cctatgacaa 163680
tgcaatgtct tgaatgcctg cctatttttc ccttgtaatc tttatgaatc ccaatggaat 163740
cagatctaat tcagccttag gatactttaa tttgtccaat ttgggttatt agaccctaag 163800
aattccttga cttacctcct ttctccattc tttggaggga gggattccta aatgttttct 163860
agaaggatag tcttggatgc tgttacctca aacttgggtc cgctacttgt cttggttttg 163920
ttttgtgctg caataacaga atagcacaga ctagatccct tataatgaat agaaatttat 163980
ttggcttaca tttctggagg ctgagaagtc caagactgag aggccacacc tggtgagggc 164040
cttcttgctg tgttataaaa tggcaggaag catcacacag gtgggagaga gagagagaaa 164100
gagagaggaa gaagaaggaa gaaggaagaa gaagcagaaa cagaagaaga aaagaagaag 164160
cagaagaaga agaagaagag gaggaggagg aggacggagc agaagaaaac gacgaaggaa 164220
ggaaggagaa gaaggagaag aaaggagagg agagggctaa ttttttaaa taaaaaatta 164280
gcaacctcta atataacctc tattctcatg aatggattaa tgctgccatc gcagtagcat 164340
taatccattc atgagagtag agccctcaag acctaattac ctcttaaaag tctcatctct 164400
taacactgtt gcattgggaa ttaagtttct aacatataaa cttctgggga cccattcaaa 164460
ctgtattacc actcattagc tgtatgtcct taggaaattg ccttaatcac ctaaatttca 164520
gtttcttcat ctgtaaatgg ggtaccacct ccttcttata gagaagttgt ataaactcat 164580
gacccagtag atttgagaag tactaaggtt acatatggca cccttctctc aggatgctga 164640
gtgcctagta tgtcttcttt gcccaaataa tcctagggga tctttcccca gaagaaagca 164700
agccaatttt gtgtgaaggt ctcaaggact tggctccaga gacaaagttt ctcctaaata 164760
accaaactag tatgtgcaat gaattgtcca ttgtttcttt catctcccag cttcaaatgt 164820
tttcttgaaa gtctggctgc ctgacagctt aagctgctag cctcttcatt agtccaacag 164880
aggactgggt atgagaattg gtgaaaatgg gcatgaccag tacacatgtt ttaggtgaat 164940
atgatggtta atactgagtg tcaacttgat tggattgaag gatgcagagt tttgttccta 165000
ggtgtgtctg tgagggtgct gccaaaggag attaacattt gatcagtgga ctgggaaagg 165060
cagacccacc cttaatctga gtgggcacaa tctaatcagc tgccagtctg gccagaataa 165120
aaagcaggca gaagaacgtg aaaagattag aatggcttag cctcccagcc tacatctttc 165180
tcccatgctg gatgctgcct gccttcgaac tttggtctca aagttcttca gctttgggac 165240
ttggactggc ttccttgctc ctcaacttgc acatggcctg ttgtgggacc ttgtgattgt 165300
gtaagttaat actacttaat aaactcccct ctgtatatat gtctatccta ttacttctgt 165360
ccctctagag aacgctgact aatatagcaa gttatacctt gctgaggtca acttaaagga 165420
aagaagtctc accaaaggct agggatgata taaaatagga gacattcact gagtgtagat 165480
tcttaggacc cacaagtaca aaaagatgac acagttaggt tcttccatga ccttcaatct 165540
catcacccct gaacctagtg tggtcatggt ggcatcagtg ttcattgctg ctttagtcac 165600
aggttatgaa ataatcacta gatatcacac atgtgtgact ccgcaatgat gacttgtgtt 165660
ccagccatga gacctgagac agagtacgtc cagcctgacc atggcaaccc caggcttgca 165720
gtattcgtgc tgaagcctgc tctgaatcag atagttgagt tcaatagtgt ttatgggcaa 165780
catagagaga ctcctgtgcc ttctgctgga ccctttggag agctaatgcc atctctgttg 165840
cagggagcta tgtttcccag gttccattac caactggttt tcaggtaggt ttggctaatg 165900
agaggcactg cagagcagat gaaccagagc atttctcctc ctttttgctt taaatgaggc 165960
ttccagcagt ggctactttt gtttgtttat gaaattttag ctcttattgg ttaaccccat 166020

-continued

```
tctttgtgtt tccagctcct atggagtgat ccctgccatg gttttaactc tcaccaaatg 166080
gctttagttt ctggttctgg taatgctgta ttctctcttt gtccttccag ctctagaggt 166140
ggtgaccact tttggctgtt tagctctttc atcatttatg taaccaattc cctgtattaa 166200
attctttctg cttaaaatgc ctcagttggt ttctgttttt ctgactagac tttcactgtt 166260
acatgtttct cagtcattgc tacttcatct tcattttgga ttgaagtctc ccatgcaagt 166320
tttgcagtct cccaagccac aaactgggaa accaggtaat gattccttca gtccttaggt 166380
ttctctgaac ataccctagg tttctttcac tgaactcttt gggcttttga ccctatgaag 166440
gagacagggt gctttttatt tccaagtgac ctaccttata tcaacaccag tcaagattcc 166500
tgagattgtt ctcccatcca atggttaatt tcttttagaa tagaaaagct gctcttagtt 166560
tatcactcat tttctccttt cctttgtttt atgttataaa ctctatgtta tctctctaga 166620
ctttactgtt ggagaaaaaa gccttccagt aatacaaata aacacaaaca caaagacaaa 166680
acagggatgg atgcagaact tcaaggatca catagatcta ttgaagtgat gagtggcagc 166740
aacagcatta cttcaaattt caagggacag caatggctgc agggcaatta gcaattccca 166800
gtcatgggag tgtggatcat cacacccact tagtagtggt aacagtggtg tctttatcaa 166860
ctagggtttt gtagcatgat tttgaacatg atcccttaat gtatagcatc gaagcctgat 166920
ttgctgactt tcctagagat tttttgagct actcaatata attttttggt agatcattac 166980
aaatttgttt ctgtaattaa aaatagttac aaaattgaaa ttctgaacaa tgttttctga 167040
ttacaaaacc atacattccg acgtgtccag gtgtacttta atctgatgtg ccctcataat 167100
gaatctacaa tatttgagtt ccatgtaaca ttgtggttcc ccacaattat taggtgatta 167160
atgtaatcta ccctttgaag ggctttgtcc tcagctttgt caatggtgct cagtggactt 167220
gttagtcaag tggccatggt ggcagaaagt gacatcctag cttaactatg tgagcttccc 167280
ttcaccaagg gtttcttgac atcatcaatt tgccagctct ggtgacaaac actgacactg 167340
ccatctgata ccattccaag gatactggtc agtcacatgg tggctggtga gccatattta 167400
actccttctt ttggggagga ggaagcacta taccgtaact aaaataagca ctatttggat 167460
ttggatttac tttcctttcc tcccccacct tgcttctgcc aaagctatga tttgtagata 167520
atctagattc cttgttcact atcacagtat cccacccaat gttgcttctc accaagaaac 167580
tttttggga gaggaagcca acaggctgac acacatgaaa attcatgttc ttataaactc 167640
tctgtcctgg aagcaactgg ctttacaaaa cagtggaatg actgaggtaa gactcagtta 167700
tgatgccaac ttgaagttga aatcttgaaa ggttggggta ccattttgga ggtgagacgt 167760
gttttcctgt gtttgataca tgatgaaggc tcttgctgaa aagataaatc cagggaccaa 167820
ggtaaggaaa tgggaatgcc atttctcatg atcacattaa tattacacct gtgactctgg 167880
acaataaatg tataggattt tagtagttgg aggagaaatg ctttaaccac aggaagcaac 167940
agatactgcc atcctgctat ttcaggctcc ttttactact tggcagggaa aatatgggtc 168000
atagtattgg ctggggtgac tgatcctgtt agcaaagatt tctgatacat attttgatac 168060
acagtgggat cagagaggaa tataaatgaa tctaaaggaa ccttttagga ttcccctgtc 168120
tggtggtaag ttaagggaag atatagcaat tctatatagg caggaaccac tgaaaactca 168180
gatccctcag gagtcaagtt ttgggtcact tcacaataga aacagtggcc atttgaagag 168240
aaaataaaag gaacgtagat gagtagttga gggtggaaat aataaatttt cactatggtc 168300
tttttaccag ggaagccatg ctttgagaga agacatgaaa agagcaggac atatttttat 168360
ttaaccagtt ctgttactga gcacataaaa tcataaagca aaccctccaa agattttctt 168420
```

ctgcaaccag aataaaatcc aaacttattt gaatttattg aggcttacaa aatactatgt 168480
aaattggcac ttgcctacct ctctcactct atctcattcc acttatccaa ttgcctgcca 168540
tgtttaagcc tatgggtaaa gctcatttca gcctcaagga tttgctctag ctgttccctc 168600
cacctggaat gtttccccca acatatccag atggcttaat ccctcacttc atttggctct 168660
ctgctcaaat gctcttgtta gtgaaacctt cccttcgcac cctatataaa cagcactacc 168720
ccatgttctc tctcttcccc ttatccatga tttagtttcc atgttagaac tggtaactgt 168780
attacatatt agacatgtat gtgtttctta tctgtccctc tccagtggga tataatctcc 168840
acgaagagag agactttttg ttggttgttg aatcctcaga gcctagaact gtagagttgc 168900
tcaagtattt gttgaataca tgatttaatt aatttatgac agaggaaaga tttgttaaca 168960
gattctagaa agccttggaa atcagactga gatgtttgga accttaacat tttgaataaa 169020
ttagtaagga gtaaaataga agctatttta gagagttttt gaaattgctc agggaccttt 169080
gctgtcttcc aagttctttg gtcattcaga attgtgccaa tgacttccgc tgttctgggg 169140
atgcttttat gttgatccct attcttcaat aagtgccccc aaccctccct gctggttacc 169200
cttgtttcct tttccagcta gcaacagacc tctctccctc tttcccattt tttgtttaac 169260
attttcttct ctaagtggta tattttgatt attcagcagc tgcttcatgc agatggtggg 169320
aaggggcctt gtatatttgt tattgcccag tatcctgatg aatatgccat ttgcttctgt 169380
gtatcagctt ttgaaggcta ttctaaagct tctgcttcgt actttcatta tcagaatgta 169440
caggctgctg ctcagatggc tggttctagt gaaatagata tagtatggag ttagctcttt 169500
actatccagc agggcagttg aggtggcctt ctttttccac ttgttctgtc caaatcattc 169560
tgcttcaaat cattgctgct tcaaggtttg tctggaaact cctgcttttt tttcaggcct 169620
tgctggtctt ctccttgagc tcctttcaca tgtatagctt atatctcaca tctaagccct 169680
taattatatg ctgttacaca ttattccttc agggcttcag acactcttct gccttcatgt 169740
agttataagt tcacacattc ccatcatcaa cacatttctt catcagtaat catcagtatt 169800
agagagcttg acatgcccca ctccattcta tttgaaaacc tctgcctatt atttcatttg 169860
tctgaattat cttcctcaat tagattgtaa attcttgcat ccttgattgt atctcatgtt 169920
tctatagtat tcttctagtt atggtttgat gcctagaata gtactgggca cataatggat 169980 gctttttct acaagaatta attgatattt tttattgagt cctaattgat tttttttcac 170040
tgaaatatag tcaccatgtg tatatatatt tgatgttttt acctccattc caaactttca 170100
ggacagctgt gctagttcta atctgttctt agattgatcc tatgactatg caatgtgact 170160
acaaggaaaa tccagttttg gttctgtaag aattaactcc attcctaaga tagcaaagac 170220
caggcctacc ttccctgcca ccactcaggc ctcttccagc ctgaccccca acatccaaga 170280
aagcaggagt gcagctgaag acagggtaca accatgtgag caatcaattg attgataatt 170340
aatgaatcaa tcaatcatgc ctatatcata aaaccccaat aaaaactctg gacactgagc 170400
tgagttcccc aagatggtaa tactctgtat tgttaaacat caatgctgga aagataattt 170460
gtactgagga caatagaagc ttctcatttg gaatcctaaa ctctattctg tgtgtctttt 170520
cttttcgctg gtcctaatcc ttttctgtaa taaatcgtag ctgtgagtat aatagttttc 170580
agtgagttct atgaatcttt ctaaataatt atcaaatctg aggtagttta gggacttccc 170640
caaactcgca gttagtgtca aaacttaggg cagtctggga gattgttccc actttggcta 170700
actccaggta atgaaacacc tacaaccccc ccgcctttcc tgggtaatga caacttatcc 170760

-continued agttgactgg aatgacaact ttacactgtt gtagcttgag agagacagga ctggattttc 170820
tttgtgttct agtttatttt ctcacccact ccgttagtgc tggcttcatt tctcagcttc 170880
cagaccctct ctgcataata tgcctcatct tgtactcatc cctgcctcag ctccaggctt 170940
catggaggta ggatagatag gaagacctgc aatgcagctg gtgcagctca ctattaaggc 171000
tctctaaaag tcagaagtgg cctcctggga accaggaatg acccttggcc actgtcccac 171060
aaacttacaa cttccctcac ttccaatcac acctgggact tagtaccacc aggacagatc 171120
attaggtgcc tgaggatgct gggtttcctc tgcattaaga accttttctg cctcttccca 171180
gtacttcctg atgttggctt agccccatgt attagtccat tctcatgctg ttaataaaga 171240
catacccagg actgggtaat ttataaagga aaaatgttta attgactcac agttcagcat 171300
gtctgggaag gtcttaggaa atgtacaatc atagtggaag gagaagcaaa cacatccttt 171360
ttcacatggt ggtaacaaga agaagtgccc aacaaaaagg gggaaaatcc ccttataaaa 171420
ttatcagatc tcatgagaac tcactcacta tcacgagaac agcttggggg taactgcccc 171480
tatgattcaa ttacctccta ctgggtccct cctatgacac atggggatta tgggaactca 171540
attcaagatg aggacattca agatgaggat atgggaactc aattcaagat ggggacacaa 171600
ccaaacccta ttattccacc ctggccccta ccaaatctca tggcttcaca tttcaaaaca 171660
caatcatgcc cttccaacag tcccccaaag tcttacctca ttccagcatt aactcaaaag 171720
tccaagtcca aagtctcatc tgagacaagg caagttcctt ccacctgtga gcccgtaaaa 171780
tcaaaaacaa gttagttact tctcagatac agtgggggta caggcattgg ctaaatacac 171840
ccattccaaa tgggagaaat tggccagaaa aaaggggcta caggccccat gcaagtctga 171900
aatccaatag ggcagtcatt aaatcttaaa gttccaaaac gatatccttt gactccatgt 171960
ctcacatcca gggcatgctg ttgcacaggt gggctcccac agccttgggc agctctgcct 172020
ctgtggcttt gcagggtata gcccccctcc ctgctgcctt cacagctggc attgagtgtc 172080
tgttgctttt ctaggtgcat ggtgcaagct gttggtggat ctacaatttt ggggtctgga 172140
ggatggtggc tgtcttttca cagctccact aggcagtgcc ccattgggga ctctgtgttg 172200
gggctctgac ctcacatttc ccttctgcct gccctagcag aggttctccc tgagggctct 172260
gcccctgcag caaacttctg cctggacatg caggtatttc catacatcct cagaaatcta 172320
ggcagagatt tccaaacctc aattcttgac ttctgtgcac ctgcaggctc aacaccatat 172380
ggaagctgcc aaggcttgga gcttgcactt tatgaagcca tgatccaagc tgtaccttgg 172440 tccctttag ccatggctgg agctgaagct gctgtgacac aggacaccat gtcccaaggc 172500
tgcacagagg agggggccc tgagcctggc ccatgaaact atttttccct cctaggcttc 172560
caggcctgtg aagggagggg cctttgcaaa ggtcttggac ataccctgga gacattttcc 172620
ccgttatctt ggtgattaac gttctgcacc ttgttactta ggcaaatttc tccagcaggc 172680
ttgaatttct ccccagaaaa tgggtttttc ttttctatcg tattgtcagc ctgcaaattt 172740
tccaaacttt tatgctgtgc tttctctcga atgttttgcc acttagaaat ttcttctgcc 172800
agatacccta agccctctct ttcaagttca aagtttcaca gatgtctagg gcagtggcaa 172860
aatgctgcca gtctctttgc taaagcataa gaacagttac ctttgctgta gttcccaaga 172920
attttctcat ctccatctga gatcaccctg gactttgttg tccatatcac tatcagcatt 172980
ttggtcaaag ccattcaaca agcctccagg aagtttcaga ctttcccaca tcttcctgtt 173040
ttcttagccc tccaagtttc taggaagttc caaactttcc tacatttttt ctgtcttttt 173100
ctgagccttc cgaatagttt caatctttgc ctgttaccca gttctaaaat cacttccaca 173160
tttttgggta tctttacagc agcactccac tctctgtggt accaatttac tgtattagtt 173220
tgttctcatg ctgctaataa agacataccc agaactgggt aatttataaa ggaaagaggt 173280
ttaattgact cccaattcaa catggctgag gaggcctcaa gaaatttata atcatggtgg 173340
aagggaaagc aaacacatcc ttcttcacat ggtggtggca aggagaagtt cccagcaaaa 173400
agggggaaaa gcccctaata aaaccatcag atcttgtgag aactcactta ctatcatgag 173460
aacagcatga gggtaactgc tcccatgatt caattacctc ctaccatagt ccctcccacg 173520
acatgtgggg attatgggag ctacaattca agatgagatt tgggtgggga ccatggagtc 173580
cccacccaag tgggatcatg ggatgatatg gtttggctgt gtccccaccc agatctcatc 173640
ttgaattgta gctctcataa actccatgtg ttatgggagg gacccagtgg gaggtaattg 173700
aatcatgggg acgggtcttt cccatactgt tcttgtaata atgaataagt ctcatgagat 173760
ctggtggttt tataaagggg aattcccctg cacacactct ctcttgcctg ccaccacata 173820
aggtgtgact tagctcctca ttcatcttca gccatgattt gaggcctccc tagccatgtg 173880
gaaaggtaaa tcaattaact ttccatgata aattacccca tctcgtgtat gtctttatta 173940
gcagcatgag aacagactaa tacacaccat gttttacaaa ctggactgat gataagaatc 174000
acctggggct gttgttaaat gttcagattc gcagcatgtc taatggagat tttgattgta 174060
ggtctgggtt ttggctcagg agtctgtttt attttaattt aaatattaag tgccccagtt 174120
attcttataa tcatctacta catccctgtg ccttaagttt tgcttcatgt ccattttgaa 174180
ctttaaatta ccatcttaca tatttcccct gtccttgctg gtgttagaaa acaaacctga 174240
atctgttctg catacctcct gtgttggagg agtcatgccc tagtcctcat cctggggcgg 174300
gcagttctct taccctgcct cattatgacc aaccctcctt tctggcacta ggctctttcc 174360
tgtgccccat tccagtgtct gcagtcttgc cacttgtaga tggacatctg atatggtgat 174420
caactccaca aacaacttca tttaattcaa taaacattta ctgacttgag ttatgtccca 174480
ggcactgtgc taggtgctgg caagatgaaa aaaggaaaga acagtttaaa gggtgtgaca 174540
gacacataaa gaaacagcca taatattgtg tgataaatgc tttagcagaa gcatgtacaa 174600
agtgctatgg aaactcagac gagagtgtga ttaattcctc ctgggaaggg tcaggaaaag 174660
tcacagagaa gagtttacat ttggaaggta atcaaaagtt ctctcagagg tcagggagag 174720
gggagggcct tccaagcaga gagcaaagcc gaaacaaatc caaggagagt gagagtgctt 174780
gatttactcc ggcaacttgg actgagtcac ccagtgggcc aagagcagtg tttttccaa 174840
gtgtagtcct catgccatct tcatccataa ttccttgggt agcctattag aaatacacat 174900
ttcaagatct taacctcata cttactgatt tgtaatcttg gggtgcagcc tgacaacgtt 174960
tattcataac taaccccctc agtgattctt taaactgaaa ataaagcagt tgttctctac 175020
tttggtacat tataatcatc agggagcttt agaaaatact gaggcctgat cttatcctcc 175080
aaggttccca tttaagaggt ttgggatata gcctgggcat ctccattttt aaagctcccc 175140
cagtgatttt aatgcatgga accactgcac ccaatttgag gaccacagaa cgagagcatc 175200
agattcaaga aggcaaagca ggcacttgga gacctgctac aaattataat ggagatgtaa 175260
aaagttcatg cagagttttc catgccatgt tggggagttt ggtttcaatt ttgtagatgg 175320
tgaagagaca atgcaagagg tggctcctac gggctcatat ttctgtttag gcctcaataa 175380
atggtggtgt tagaaaacaa gattgaatct ggtttgtaca cccatggtgt tgagggaagg 175440
gatgctttac taccactcca tgaagtgggc tcaactatgc cctcagagta actgttcgtc 175500

-continued tttcagataa aggctctgaa tactcctgtt gctttcttaa gagacacagt gggcacctat 175560
cctgtactca ctgttgaaaa atcctcaact gtatcccacg taaattctga gccgtgcaaa 175620
gcttcatgaa gggaagacct aagggagatt ggtggtgggc attatatatt cacatggtct 175680
ccattaggcc cagcagttac aggtattgac ttcaaccttg aagttcagga atagaagaaa 175740
atgtgttgtg tggattattg tgcctacaag gcacagagaa gttttgggat agattgcaat 175800
ggcatagaag aaggagaggt gagaggtgag tggggaaagt atagttataa gccaatcacc 175860
actccacagt gaggtgttgg gacttttgtg gaccaccttg attaagatag aaccagatat 175920
gttgtgggta cagttgtgaa ggaaaatgaa gggaggtcag aagtctaatg ctggagccac 175980
ctgaagaccc tgactagcag ctagtcatgc agacctcaat gaagtctctc cctctcattg 176040
tctcttcaat tttctcccct ttccctcttc tatcttctca gtcttttccc ctcttcttta 176100
accctctgca tcctcactgc ccatagtgct cccagaaaca acaataaagc ctaccagact 176160
ccaacatttc ttaatgggcc catgagttac agcctttgtt gaaacttatt gctaagaaga 176220
atgttggtga ttctttggta caacctcttc aatttgtgaa tggagaaatg gaggtccaga 176280
aaggagacat gattgtccag gggaaaaaaa aaaggtcata gagctagtta gcggtagaat 176340
tcaaacagat ccatgtcttc tgactttctc tattagcctg catctactgt gctatgctcc 176400
ggtcacaatg gggaattctc atactttgca tgctttgagg ggtaaattgt acactcttca 176460
cgtttggttc ctacaaccac tttgtaagaa ggctatagcc attagttcat catgtgtgct 176520
aagttcaaag agaaggaatg tgctttgctt aagaatgcga gtttcaccag aaaggaagta 176580
gaaatttata aaataggaaa gttcaggttt acataatttt aggccatatg agtagaattt 176640
ttatatagta gattctaaaa ttactgtttt ccattatcat gatgtagagt cccagaacca 176700
ttaccctagg acaaggaaag actttgtctg atggttgtgt gtttgagtgc aggaaaagac 176760
aggatgtggt tacataactt tggtgttttg accttggtct tgcttcattt tgaaggcttc 176820
taaccttgtt tgctggtgcc ctcatgagta tgtggaagat gagatcgttg cttctctcac 176880
acaacagtgc aatgagaaca ttatctgtga cattatggag tctgggaatc cagtgtagca 176940
tctgagtcag tcctagccca atagcaggca ctcatgggtt attttttgag ttgagttgag 177000
atgaggcctg caggtctgca gcaaattact attgatgcca tcttgagcaa gtcgttttct 177060
ttctccaaac tcactcttct ctcttacaaa ataacagaca agaacaagac aacttctgac 177120
attccttccc actcagagat tggcatccct tttttaaaaa atcccagaaa tttggactta 177180
ggagaccctt tgaaggtcaa ttagcccaac ccacagcttg ttcaaggcag agccagatta 177240
ttcaaagaag tagagatttg gcaacttcat ggcttgtata atagtggaaa tcagccaaaa 177300
agaataattg aggttaaaaa gttatttgag ggccagaatt actctctttg gtcaatatcc 177360
atcacattaa tgaggaatag tgaaatctct attttgcttt ggttttctcc tttgctctct 177420
actgatatat aacatatata catcagtaaa atgcacaagt cttaagtgta cagtgtgagg 177480
aatttttaca tatgtatcca cccatgtaac tatctcacaa atcaagatac agaacatttt 177540
gacaactgga gaaagcttcc tcatgccttc actaccctct ctcaagggat agatctaatt 177600
tctatcactg taggtttgtt ttgtctagtt ttgaacttta tatgaatgga accacagcgt 177660
atataaccca ttgtgtctga cttttcactc aaccttgtgt ctaagattca tccatattgt 177720
tgcatatgtc aggagtcttt ttgttgttgt tgcaatgtgt gaattgtaag actaccacaa 177780
cttaagaatt catcagtgca gattattagc tacagacgag gagaaaaagt tagaagattt 177840
gtctcctaat cttattatta agtagctaca tgaacctctc tctgggccca ttttcctcaa 177900
ctgtgagtga agaggtcagg ctaaagaatc actagcaatt tttctaattc taaaggccaa 177960
agaatgtatg tgaatcacag accaaacaag catctggaag atatgaaaaa aatcacatat 178020
ctgacaaaga actcatccta gaatatgtaa gtgactccta caaatcaata agcaaagaag 178080
aaaagtcaat taaaaatggg aaacatgcgt gtgtgcatgt gtgtgtggta tttgctgcta 178140
ttgttgttat agtaaagaaa aaaattgttc agtgggaaac cttagggtca tcatgatgac 178200
catgtaataa atattttcaa atatgcagaa atgttgggcc atccacatga tgcagaagct 178260
gatttttgaa aaaggatccc tttgtattat tttctgtaag ggaggcacca tgtttaattt 178320
tagtgaatgc atgaaatgca tgcaaaaggg cttcataaac tgtaaagctc tctgcaaatg 178380
aaaagcatta ttattattcc agatacaata taagtgcagc tgacatcaac caccatttat 178440
cccagttgca ggtgtaacaa ccaacaaggg tattgtcctt tgttcctttg ccacagctgt 178500
gagagagcat ctgaatccaa tacataaata acagctgtga ttttaattga gacttttgag 178560
tggataagca aggtgtacac tgaacgcata gcaacagata ggttttcatt tgggcagcca 178620
cattattatt tcctcagact ttgaaaaggg aaagttttaa cagccctctt ggaagtgacc 178680
cttgtttttc cccccacctg ttcgcagtta ctgtcacaga atgcgtcatc actctcccac 178740
gcgcacagtg ggaaaacaag tttgccatcc agagcaaagg gagtttttat gctgtgtcag 178800
ggatacaaga gtctgtgtat ggttcattgt ccatttccca attaggctcc ctccctaggc 178860
gttggagctt cctgcccaga gagcctgcct ggactcctta tcatttcagc agaaataagt 178920
cacatgagaa gccactgcaa atcagatttt tgccagaatg cttgtggtct ctgccttgcc 178980
ctttttttcc cccaagattt tgcaactctg ttcttgtctt aggagggtga gaaattatcc 179040
catcaatgta atcaacccag attggtcaac caaagggaat ttgcttgttg aatcacattt 179100
gctgctagta tgttcttgga caagggtatc tccatgactc tgtcccttga ctggggtgtc 179160
taactattgg gtattctctt tcttgtactg tgcatagata tgtttcagac tttgtatttg 179220
ccccttaaag ctgcccttgt gatagattta gcagctctgt agtaatacac actgaaaact 179280
aatctaaaca ctatatagtt gtagagtgga aagagtttca aagcccagca aatctgaatt 179340
ggaatcaaaa tttatcacta tacctgggtg ataggcctca gctgccttat ctgtaaaatg 179400
gggataaaaa tacctcccta gctctgaaga tcattgtaag gtcaagagag gcaatgcatg 179460
tacacttccc agagagggtc tggcccatag taattgcctc ataattagtg agtgagatga 179520
ttgttccata aactgtacag ctggggaaga tcccccaatg cagacacatg gctagcccaa 179580
gtttaacagc aacttaatgg cagatgtagg agaaaagtta agatccagag cttctttcta 179640
ctacatctaa gaattgtttc ctcaggtttg gggaggagac agcaaagcta aacacttcaa 179700
ggtaaattat gatgctttga tgatttctta agctgagtgg tctatagttc actggcatag 179760
aaggaaggtt tttgttttag aaatatcatc tctgcttatg tttacagcat atctttcctg 179820
ttcagccaga ggcatcccata ttgctttgag gagagttagc attgttagat taggacagca 179880
agaagaaaga aactaataaa atagattctt gcaccccaca atagaaacat ggattcgaat 179940
gctaaagtgt tgacttgcaa gagccaggtt cttaatgaga gaggaagaag cttgagaatc 180000
caaagagaag gtctttaagg aagcaagttg tccatgacat aaagttaggt tacaaagaga 180060
acaggggaag aacgaggtca ccccaccccc tctctgggct agtgggtagt tgatagtgac 180120
ctgattggag gagggagaaa agtggtgggc tgagggttgg gatgaagatg ctagagggga 180180
ccatggggag gagagcctgc aagtataagt ggacagtgta ccttgctttg ccatttaggg 180240

-continued

```
gagggccatg ttagctgtct ctctcagcct ttgctgttga gaaccttctg taaacatatg 180300
cttacatacc aacccataga ttttcagcag aagtgatacc ccacaatgtc cccagatttt 180360
gctaaggtcc atatgagtta tctatttgga tatccttttt cagtgaccac ggtcactaat 180420
aaataccgtg aaacataggc atgatttcca gaagatgctt ggagatgtgg agcataggcc 180480
ctcagcattt gtactggatg cagcaaccat cctcatgccc taggtttaat tttaggagtt 180540
aatacagcat ggcaattaag aatgtggtct ctggcatcag actgactgcc ttagatcctg 180600
gttctctcct cttattagct gggaaatttt gaggaagttt ataaaaccct tagattctta 180660
gcttccttgt ctcctcaatc acagtatcat aatttctgca acatagtttg cagtgactaa 180720
ataaattaat acacaggaag gacttagtta gaacaatgcc tgctacatag tatagtttaa 180780
taattgcctg ttgtagttgt tcttactgcc tgtgcccagc caaatttgtg tgtgtgtgtg 180840
tgtgtgtgtg tgtgtgtatg atacagagct aacaatctga cagctttttt ttttttttgc 180900
aataacaaaa agagaagtta tttatttact atttcacctt tctggggttg ttaatttgat 180960
tttctactca ttcatttgta tatgctttta agaaatattt atggagcccc ttctatgtgc 181020
ctatcaggca ctgggctgac tgctggggat aaaatggcat gtaagatagg catatccctg 181080
ccctcatgta gtttacaact acaactagtc tattccaata actgttttcc ctttatctga 181140
ttttggggcc tgggccaatc tcctgagcac atttcctagt gctggcaatt ggggtcctgc 181200
agcaggccat aaaatgcatg gtatatgggt ttaataatgt caggggaaat tttcagttaa 181260
tcccttggac tgtgggtaca cccaggattc aaaggccaga ccaaaacggc acgaagagaa 181320
acagagaact ggtaattatc tggtgaattt gggtcatgtg gaaagccaaa ctaaattact 181380
ttcgccaagg aaaaaatgat tttttttttt ctcttcaaat gaattcgttt tggtgagatt 181440
ttcctagggt cttcccttcc ttgctttgca ttattcaacc aggtatttcc tagaaaccag 181500
cacagcgtgg gtaaaatata aagacaagga cttcgaggga aatgaaaact gcttgtccat 181560
ggggtatttg gggagccctg gtcttattcc cgatatataa catataagga aaattgtact 181620
aagttgacag tgctaccata aatccagtca gctcgtgggt gctctaattt tgaactaaat 181680
ctaacagctt ctgtttattt gtgaaacaga tgttttaagt taaacgtttc ttatgtcttt 181740
ttgttcagaa ttatatcata ttataatttt gcatttctaa ggcaaaagca aatgaaggga 181800
acatgcttaa tttttaggat atgagtaatt tattatactt ttaatagagg atttcaatgt 181860
attccccatc caggaaatgg taatggaaat tgcctacttc aacatgtaat ctataagatc 181920
ttgttaaata gtgtaatgag aatttgtcac tttgtcacct agctgacctt ttacaaccct 181980
gaaactcaaa gtgaagtgac acctccctca attcagatga aatgcctgca tattttactg 182040
tgttttcacc aagaaatccc ttcagccaaa atttcagcta gtccaagtca atttttaagc 182100
aaagtgcata accagaaatt ggcacaaaca tttgtgtatc atcctttcca tattcaaaag 182160
ctgtctgaga ctcatttgat taagcataaa aataactctg tgaatgtcat tagaaaggca 182220
gcgaacattc tatgtctggt cccttgaatt tgtattctgg ggatgcatta ttaagtcact 182280
gctaagtcgt ttctcttgta agaacctgat catgctctct agagtctgaa aaaattattt 182340
tcattttgag tttagaaggc ttagtttttc tatttccgtt caacagaaag gaaacagctg 182400
gtaagttagg gaaggccagt gtatttggct actgtaatct ccactgcctt ccctggttaa 182460
cagaatatct ttattccaac cagggctccc tccctgccaa atctccttat taaactaaat 182520
tgtgattaga aaagaataaa tgacatttta tttcatatgt ggctcctttc aaacttccat 182580
actcctcttt aagttttcct cttacaaaac ttttccttgg ccttgggcat ttctcctcct 182640
```

-continued tggcagacct tcaacattgc aaagttcctg acaagtcttg tagactacta ctgaatgaag 182700
cacctcctca ttcgttcctg tgggatcaac tgttatccat gcacttattc attccataaa 182760
cattaattct tacacacaaa atggctatgt gtattctaga ctcaagtggt cgtctctgag 182820
gatcatgtat tggttcaaaa atgggatgct ctttctcttt ctcagatttg tttttctgtt 182880
aggtgcagtt gctttttttcc aaagtcaagg aagtccaaaa tgcaggttgc atattggtgg 182940
aatgggttcc aaatgtggac agatgttgac agaagaagtg tcagttgggg agtttattac 183000
aaatggatat ttagggtccc agtttctaga agttctgagc cagttgggtg gggctcagag 183060
ttttcttatg tgcagctata tgttgtccca ctgatgtgta gggctagagt gatagcagtg 183120
gatgtggaga aagaggatgg attgaaaaac gacctaggag gcagagtgtg cagggcttga 183180
tggccacaga taggagtgag gccacaggta ggagtgagaa cagaggagtt gaagataacc 183240
tgtgtataca tatttgttct tagttcatct gcaaaaacaa aaagaatact acttatttca 183300
gcaatggaaa attacccagg attgtttcaa caaggcaaca ctaaaaatat tccccaaaca 183360
attctttggt atcaaaaaat aaataccaga tggagtatac actttttgat tgactgcaag 183420
gaatttattg aaggttgaaa gaaagtaaaa cttaatgttg catttagcaa agactttgac 183480
ttttctcctt tgtacattca acctggggcc atagtgaaag tcatattggg gataaaatgt 183540
cactatatat ttgtaattca gaacttcaaa aggaccttct ctgttgatgt agttttctac 183600
taaagttgtc ttgcctgcca caatgagcat tttttttttt ttttttttct gagacagggt 183660
cccactccat tggccaggtg cagtggtgtc ataatggctc actgcagcct tgacttctag 183720
ggctcaatag atcctcctac ctcaacctcc caagaagctt ggagcacagg tatgtgctgc 183780
cacatcaggc taatttttttg taattttttt ttttaagaga cagagtttca ccatgttgcc 183840
tgggctggtc tcaaactcct gggctcaagc gatccaccca cctctacctc tcaaagtctg 183900
gaattccagg catgagccat catgcctgcc ccacaatgaa cattttatac cttttacgct 183960
cacttcaaac tttcaccctc cagcccactt cttcaccatt atcctcactt tgagtgatgg 184020
acttgaactc tacctcatgg agaagataga cattatcaca taggcacacc ctactttttc 184080
tgctaagtct ataaacctac ttgcagctgc actttttttt tcttcttctc gccgcaccat 184140
tgtcatcaag gaagtaacat ttctcctgca agattttgga ttttatgcct tctcatcttc 184200
tcaaggactt cattcttcaa gtttctcttt ttctctcttt tttaccttta gcctctaact 184260
ttatactgga tcattttttt aaatttccat aggtttttttg gggaacaagt ggcatttggt 184320
tacatgagta agttctttgg tggtgatttg tgagattttg gtgcacccat cacctgagca 184380
gtacacactg aacccaattt gtagtctttt atccctcacc cccttcccac cctttccccc 184440
tgagtcccca aagtccattg tgtcattctt atgcctttcc atcctcatag cttagctccc 184500
acttatgagt gagaacatac aatgtttggt tttccattcc tgaattattt cacttagaat 184560
aatagtctcc aatcctatcc aggttgttgt gaatgctatt aatgcattcc ttatttatgg 184620
ctgagtagca ttctatcatt tacatttaca tatatacaca catatatata atacatataa 184680
tacacacaca catatatata tctcacagtt tctttatcta ctcgattgat gagcatttgg 184740
gttggttcca catgtttgca attgcaaatt gtgctgctat aaacatacat gtgccagtat 184800
ctttttgta caatgacttc tttccctctg gatagttacc cagtagtggg attgctggat 184860
caaatggtaa gttctacttt tcattcttca aataatctcc acagtgtttt ccatagtggt 184920
tgtactagtt tacattccca caagcagttt agaagtgttc ccttttcact gcatccaaga 184980

-continued caacatctat tattttttga tattttgatt atggttattc ttgaaggagt aaggtggtaa 185040
cacattgtgg ttttgatttg catttccctg atcattagtg atattgagca ttttttcatg 185100
tttgttggcc atttctataa cttttttcga agatttatag attgtgattt tctcctactc 185160
tgtgggttgt ctgtttactc tactgactgt tccttttgcc atgtgaaagc tctttagttt 185220
aattaagtcc aagctattta tctttgtttt tattgcattt gcttttgggt tcttggtcat 185280
taaatccttg cctaagccaa tgtctagagg ggtttttctg atgttatctt ctaaaatttt 185340
tatagtttca ggtcttacat ttaagtcttt gatccatctt gagttgattt ttgtataagg 185400
tgagagatga ggatccagtt tcattctcct acctgtggct tgccaattat ctcaacacca 185460
tttgttgaat aggatgtctt ttccccactt tatgtttttg tttgctttgt ctaagatcag 185520
ttcgctgtaa gtatttgagt ttattctggg ttctctattc tattccatcg gtctaggtgc 185580
ctatttttat accagtacca tgctgttttg gtgactacag ccttatagta tagtttgaaa 185640
tcaggtaatt tgatgcctcc agatttgttc tttttgctta gtcttgcatt ggctatgtgg 185700
gctctttttg tttccatatg aattttagga tttttttttg tagttctgtg aagaatgatg 185760
gtggtatttt gatgggaatt gcattgaatt tgcagattcc tcttggcagt atggtcattt 185820
tcacaatatt gatgctaccc atccatgaac atgggatttg ttcagtttgt ttgtgtcttc 185880
tatgatttct ttcagcagtg ttttatagtt ttccttgtag agatctttta cctccttggt 185940
taggtatatt cttaagtatt ttattttatt tttgcagcta ttgtagaagg ggctgagttc 186000
ttgatttgat tctcagcttg gtcactgttg gtgtgtagaa gagctactga tttgtgcata 186060
ttaatttcac atccagaagc tttgctgaat tcttttatca gttctgggag ctttctggca 186120
gagtctttag ggtttctag gtaaacaatc atatcatcag caaacagcaa cagtttgact 186180
tcctctttac caatttggat gcctttattt ctttatcttg tctgattgct ctagctagga 186240
cttccagtac tatgttgaag aagagtggtg agagtgagca tccttgtctt gttccagttc 186300
tcagagggaa tgctttcaac ttttccctat tcattattat gttggttgtg ggtttgtcat 186360
tttactttgt catttctgtt agcatcaata cctttttctag caccttccat taaaaaaaat 186420
ctcttaattc cacagccctg tttctctgat tcctcctggt caacattctt tttaaaagtc 186480
ttctacacat ttttttcttc atttccacac ctctcactca ttctttactt cagcctcaat 186540
gtgatgtttg ttctgattca ccaaagctac tcacgaaaag cacaaatatc ctttacatta 186600
taaaatacct tacgaatatt ttattacctt tcaatgcagt agaacactaa ctggctcctt 186660
gcaacacttt gtcgtcctga cattaatttg gggaaattcc cagccattat tatttcaaat 186720
atttcttttg ctttttctc ttctccttct ggtgttccta ttgtacatat gttacaccat 186780
ttgtagttgt cctacagtcc ctggatattt tgtactgttt ttgtccccag tatttgttct 186840
ctttgctttt tagtttttaa gtttctattg ctgtatcctc atgctcagag attctttcct 186900
caactgtgtc cagtctacta agaagcccat caaagtcatt ctttatttct gttatggtgt 186960
ttttgatatc tagcatttct atttcattct ttcttaggat ttccatctgt ttgcttacat 187020
tgtccatgtg ttcttggatg ctatctcctt tatccattag agcccttggc atgttaatca 187080
cagttgtttt aaattcctgg tctgataatt ccaatatccc tgccatattt ggttctgatg 187140
cttgctctgt cttttcaaat gatgtttttg tcttttggta tggtttataa ttttttggca 187200
gttggatgtg atgtatcagg taagtaagcc ccttgtagtg tggggtaagc tgtggggagc 187260
aggaaagcaa tctatagtca tatacttagg tctcagtcct ttagtgagtc tatgcctttg 187320
aactgtgaac ttcagaagtc tttctcagtt tttttcttcc cttttaggtg gaacagaatg 187380

-continued gctagagtgg gatggagttg ggtatttcct tccccccagg tcagttagtt tctgatgata 187440
ccctaggggg ttagactctg attaattagt ttattccggg gaagatcttg ttaagaacag 187500
aattccccgg cctatttcaa aatggttccc tttaccctcc ccctgatgga aacatgaggg 187560
gatttttctc ttaggcttac tgtgggaact tggttgagct cctgagaccc ctaaagtttt 187620
taattatctg gcttgtcagc gctgagtccc cagtaattag tcaattacag ttcaggtgtt 187680
cctccacagc actagttccc atggcagttt ctgctcatga gcatgtcctg ggaagccatg 187740
attccctgta tttgcctctg tctccagtct tgtggatagc agtttgcctt gtgtcttccc 187800
ctctattatg gatccaaaaa gagttgttga ttgttcactc tgttcagctt tttacttgtt 187860
ttgagaatgg agttttgact tctaagatcc ttacctgcaa gaccggaaac cagaagttcc 187920
tgtgttaaga acagactgta gaagatgaaa ggatggagta ttatttttct agagatgcca 187980
caacatacta ccacaaacag agtggcttaa gccaatagaa atgtattctc tcacaattct 188040
ggaggccaga agtaagacat caaggtgtca gcagggccat gctctctctc tgaaaactct 188100
agaggagaat ccttccttgc atcttccagc tctggtggct tctggcattc cttggcttgt 188160
ggaagcacaa ctccagtctc tgcctccctc ttcacatggc ctttccccat gtatcagtgt 188220
ctctgtccaa atcaccctct ccttgctctt agaaagacac catttattgg atttaggatc 188280
caccctagat caagaatgat tcagtcatgg gattcttaac taaccacatc tgcaaagact 188340
ccatttccaa acaaggtcac attaataagt gtgtgtgtgc gggtggtagg gctcaaatat 188400
atctttttga gggatacagt tcaacccact acagcattaa gtaaccaaat taaattttaa 188460
gtgagcagtg gcagggctta tgatgacagt gtatatatga agatttggtg tatgtttcta 188520
tgagagagat tatgagattc gctgatggat ttcatttgga gtgtgacaaa gaacagcatc 188580
aaaaatgact tcgactttta acttgacata ggatgaatag gacttttgat ctgacatagg 188640
atgaatttac tgatctagaa agatgcaagt tttgggggga gaggactatg aagactttcc 188700
ccaattactt taataatata gcatagaatt taagagcaac acctctggag gcaaatagac 188760
ctgggctcac aaataatgtt aacatacctt ggggtatttt acttaatctc cctgggtctt 188820
gggattccca tttgcaaaat gggcataata aaaataatac ctctctcata atattattgg 188880
aatgatttca catgattatg catgtgagct attaatagtc agtggcaaac aggcagtact 188940
tcccctgtaa atcttatcta ttcatctcat tttgaaagga gcctacagag atttggaagg 189000
ccccttcaaa tgcaccattc ttttattctg acatcacttt ggtggattag gaagactgat 189060
gtggcagcag catatagatt agactggggt gggaagagaa ggaggcaggg aacctactaa 189120
gttgtccatt gagagatgtc agtggcatga gaatagtggg gaaagagaaa acagagagga 189180
cgttattgag ggaactgcac aggacctggc aaatgatgca ctgtgagaaa agataaagat 189240
gtctgacttt ctaactctgg aaagttggaa cacagtaact gatgaaagtg gcaaagtgga 189300
agtgtagagt aaccttggga tgagaaaggg gaaggagcat attcagttta gactcaccag 189360
attgaagtac tgacagtata agaaattagg caccaagtag aatcatggca tgcagtaagt 189420
gctccatatc tgaatggttg gtagatctag gtcagtactg tccaatagac atatgagagc 189480
cacaaatgta agccatgggt catttaaatt ttcctagtag ccatattaaa aaaagtagaa 189540
tgaaactaat tttgataata tgttttattt aacctaatat aaccaaaata ctttcattcc 189600
aatatgtaat tgccataaaa tattgattat gttatattct ttttttcagg ctaagttttt 189660
gaaatcccat atgtatttta tacccacagc acatcccaat ttgtactagc catatctcga 189720
gtgctcacta gctgctgtat tggatagtat aattctaggt ggaggtgatt gtcaggcagt 189780
agattatgat aactgcactt cgaaagacag gcatcaatct aaaatcacct gtatggaaga 189840
ggaaaccagg taataggatg aactttgtaa gagagagaat actaaaagag aagggaacct 189900
aagatagaat gggggaacaa ttcattttgc aaaggtttgg tttttccatt agactgccca 189960
gcccctgaaa agaggtgaat tagtaatagt gattcaatgc atgtttttaa catatggacc 190020
tcttggtttt ttaattctac tatttgcaag catcttgttc atgtatttgt ttattgtcca 190080
tctcctcatt accataatgt aaatctgttt tgctcacaat tatatttcca gaataacatc 190140
tctcacacat tagtgctcag taaatgcctg tgagataaaa gtctaatctc taccttcaga 190200
aaatttacaa tatgatgggt aaaaaaccat tacatagagg aaaaatatac taatgataga 190260
ttcatagaga attagattcc tgatgaatga tattgctaag gttgggtcca ggagttcaac 190320
agagagaaag agtcattgat tttggaggag cctagaaata cagaattgaa acatggtcta 190380
tgccttaaat gatggctagc ctttgaatgt atgggaagca aggggaagct ttccaagtag 190440
ggtgaatgac ttatgcaaag gtgtggtgca tgtgaatatt ttagttgcaa tagctattaa 190500
gaaaaagaaa gatatcaaat tgaaaatggt ggccactgaa gtttttcata aggtatgcca 190560
agcaaaactt taaaaatgct atatcaaatg gattgagaga ggagtactgg tgagcagcca 190620
ttgcaattgt ccagaaggca ataaaggttg gactaataag agtgatgcct ttgggggtag 190680
gaggaggaaa gatataagag atgtttgaat aatggccttg gcatattttg atctctattt 190740
ttaaaaagag gctgttattt agcataaatg accttgaagg atgacctaat gagcactgga 190800
tgtttgaatg tgttgctgag gaaaactcca aggttctgaa cttggttgac tgaattatgg 190860
tgccatagac agaaagttcc aaatagcaaa ttgcttttag aggtgaagac tagagaggaa 190920
aatgggttga agtcaaagtg ttggaagata tccacgtgga aatttccagt aagccttcag 190980
atgactaagg gattcagaga atgtaggctc tttccaaatc ttctgttctt tttgcctata 191040
tagaaagtgt ttactttatg tgtttccttg tggctctgtt gattacattt ttatgtgtgg 191100
tttggagctc ctctggcttc agacctgtat ttgttttggg catagttgga gtagagtgct 191160
aacaagctca aggtcatagg tttgatcccc aaaagggcca gttagtttca tggagaggaa 191220
aattgcattc catggttcac agacttgacc cctaatcctg tctgcttgtc tcaaaactat 191280
ctagcattgg tcccaagagg gcccagtgag aaagtgtgag cagttgtgtg cgcaatctat 191340
ttaaactact ggaagaataa ctccaagtgg gtttatctag ttgcttcttc aggaagtttt 191400
gtctgccctc cttcctcaac tcttgggaca gagatcacct tttcagagac aacaccatga 191460
acaaatgcac atgaaactgt catgctcatg tctgcctgca tctgcgttcc tatgttcatt 191520
tacttctcaa gcaaagggca gtgtgagcac ccaggagcgt atagttcttt ggtacaagtg 191580
tctacttgta agtattggag tattatcagt ttgactttga gaactggctt accagtgttg 191640
tacaaaaaag ccctagagag catgaatgtg cccaaaagac tctctaagca aacctttccc 191700
caacagattt tccttatcag actgcttttg cttgcttcgt acttttactg ggaaatataa 191760
gtcaacacag aattcttgtc aattggtcat acaaggatac agcatagaat tctcagtgtt 191820
cttgagaaga atgctggtat ccataaaaca actcctaaac aaacccacag aaggcatctt 191880
ccacacaagt acagagttac cagcacctgc tgggatggca tctaaaatct gttttttttgg 191940
atactgcatt ttcaaaaatc agtcttagag gttctcaaat tgctttttca gttaacagat 192000
ataccctggg tcctacaaga gttaccctga agaggacttg gaataatgct atgcacacac 192060
tgaaagattc aaaataaatc ttcatggctt aaaaaggact tgaaaattat tttcaagttc 192120

-continued actttctcttt cagggaattg gagattgcta caccagggat atttctctta tttggcatta 192180
tggaaaattt tggaggctga gaagtaagag accagaccat caaatcttat ttcattgatt 192240
tctaagacta atagtgatgt cttaaaagaa tatgttatgg aataaatatg actaaaagta 192300
aaaggcagaa taaaattata tgctgatgaa tccagcaaaa ctggttgaaa aattcttagt 192360
gtttggtttg tacacagaca agcaacatac ttatttgcat tgttccttca aattgattac 192420
attgaagata aattatttta acattataaa gggacagcct gaaaatatca aataagtagt 192480
taaaaattat tacatgaaaa ctttgcatgt ctgctggctg ggctgggctg gagtgaagaa 192540
agataaagaa ttatgacaca gtaagaaaat gttagacttg aaatttttac atctgcattg 192600
tggtgcaagg atctgcacta gcacttttta cctgattttt ctggtcagag tcaaattagg 192660
gggaaatgtg gtcagtgtca gaaatgttga gaccatgagt taagagtata tatagaaaac 192720
ggtgtgacac acaccgggac ctgtcaaggg ctgggggct gggggaggga cagcattagg 192780
agaaacacct aatgtagatg atgggttgat aggtgcagta aaccaccatg gcacgtgtat 192840
acctatgtaa caaggctgca cgttctgcac atgtacccca gaacttaaag tataattaaa 192900
aataaaaaat aaaaaaaaga aagaaaatga tgtgacaaag ccaatggaga gaattctact 192960
ttggctatct tagatcctta attaatactc tcattcttaa taatagcaga agtaatgata 193020
ataaaagtaa tagtaaaaat accagaaacc acacaaaaca agagctgata agcagacaag 193080
tgctggacta tgccagtggt ttcatctagc cacagaaaaa ttaaaaaaga tgaaaaaaat 193140
taaattaatg atgagttttc tataaagctt aatttacaca attaaagaat ctgccctttt 193200
ttcttagatt atattcttgc catgttttta aaaaattaat tcattttcag tgatacaatg 193260
gtgatgatag atgatttttt tatttcctta ttttaggcaa ataaagattt tgacacctca 193320
ggttgatttt tctcaatttc tacttttatt ttttgaaatt tcaatatttt gagaaatcta 193380
gaagtttagg aactgttgta tgataatgtt taatccttaa ataataattt gaggcagata 193440
ttgctgttat tatcaaaata agaggaaact aaaccccaca gaagtcattt taatttgtcc 193500
aaagcacata ttagaacatg acacaagccc acatctgcct gatttcagca cttgtttctt 193560
actactatgt aattcctgtt tgtactagtt agggcctagt aaggagagca gaaacccttc 193620
tagaccaggc attttaaaca gagaggattc tttttttttt tttttttttt aagacatctc 193680
gctctgttgc ctagactggg ctgctgggct ggaaagcagt ggcgtgatca cagctcattg 193740
cagccttgac ctcctaggat caagtgatca tcccacctca gcctcttgag tagctgggac 193800
tacaggagcg caccatcaca cccagctttt ttaaaattta tttatttatt tttattttta 193860
ggagagataa ggtctcactc tgttacccat gctggtctcc aactcctgga atcaagcgat 193920
cctcctgcct tgacccccaa aggtgctggg attataggtg tgagccactg tgcacattca 193980
acagagagga tttaatacag atgatggaag agatgagtag ctaaataagg gaggggagtc 194040
aacccagaaa aaacaacatc ctaaaatcac taccatccct atggctagag atactcagag 194100
aggggaaaaa ccatctgcat ggatctaggt ccactagggg aacagaatgc tgcttgcact 194160
gggaggaagg ggttatggag ccaagagctg caagtactgc tgaagacgct gttggaggca 194220
aagagaaaag ggggataata cctggcttct cccttcttct tgtcttttgt cttttgctaa 194280
tgcctcctat tggccaaact tacccagaaa ccagagctca taggtgctga gaaatgtggc 194340
tcattgtgaa aacgagcaaa tcaagggaat gttgggaaat ggatatgaga gcagacaagt 194400
aatcagccag cacattctag cacaaatctg tattaagtta ttccactgta ccttttacta 194460

-continued tagcagtgag gtctagagat accagaggac gcttttcaat attaactatc taagagaatc 194520
tacttggtga tagttgacag atgaggatgt ctctatttcc aattcatctt taaagcagag 194580
tgaggcagaa gaaataaaaa gaaatttggc tctggggtag ccttattttt gagtatttta 194640
gatcatataa gggtggctga atttgaagct ctgaactaaa taggatggag aagcacaatc 194700
ctgggtcgtg tttctttctt actgttttct ccttccctct ctccaggaac aatcacctcc 194760
cacctctgtt tcccttttag agatttgggt ttgggaaaga cagttccata ttcatggggt 194820
ggagtgatag cttcagcgat agcacgtgta tagggacatt tctatgatcc ctgttatccc 194880
ctacatgtcc atttgaaggg agagacccta ctcagggttc tttctgaagg aggtttgcac 194940
ctaagcagga accactgaat taaataagtg aggtggagtt agaaaattat agcacagtta 195000
ctcaattttt aaatctcctc ttaaaaggaa aacctcccta ccaggccaca tttcctactt 195060
tacttgtagt tcaaagtcaa attttacttt tgatgtactg ctgcaattgt ctcaaatcca 195120
atttacatct gctcctgttt ttagtgattg ttttattctt ttacaagcca tctcattcca 195180
tcacagggcg aagaaaagaa catttagaaa ccagatgttg tattaactat aaccattatc 195240
ctttatggga tcccagaggt ttaatctcta tccataaaca ggtgaggaag ataccagctt 195300
tcagctgagc tttacagtta ggatgcttca ctgagaaggg ggcgaaggct ctgccatcca 195360
tctgtcatta tgactcgggg aggctcataa tggatgggta tagcccagca gtttcaaccc 195420
tatcagaccc aaagctctcc tttttataac atatatttta tgatctaccc tttaatgtcc 195480
ctaagtgaaa ttcacagata atatcaacat acacaatttt aacaaaaagc aaaatgatgc 195540
ctgaactgta cataaagtag aaataaaagg aaaaaagttt gtaataaaat aacatgcatt 195600
acaagataga atgcttaggc acaactctcc tagaaaacac acggaagtgg tcagatgttt 195660
atactcgtgg agaatcacgc atgggacagc tgcatgtgcg gactgatgca gatgtggagt 195720
ggaaagattc aaacagcaca attagcattg ccactgatga tgtgattttc taaaacagtg 195780
aaaaagactt ggtaaagttc taccttttct taatttgtat ggtaattgca tccctgaaga 195840
agtcggttta tgttaaaatt gtgcaaaaac actttgagtt tataaaaatt ggagttatat 195900
tccggactta ggtgattata aacaggatta tctcctactt gaaatgtctg gagacctggt 195960
ccatacccaa taaatgtcag aaatgctctc cccagtcatt gcaacagtgc caaatgtctc 196020
ccaaattatc taggaccagc accactccac cctttgggaa tgcttgtgtg ggctgtctaa 196080
gaccactttg gagggcaggg atatgggaat gtttgtctca tggaactcta ggctctaagt 196140
ccacagtttt tctccagaag ccctgattca accatagcac ttgagactac ctcaacttca 196200
ataagctgtc aagagaaaaa tagttggatt gttgccagag gtcttggtaa gattctttat 196260
aatcagcttc cagtttcact taggtgggaa tggtttattc ctagactgtg taagagccaa 196320
tacataactt tcttcatgga ggtatcccga gattggctct atatccctgg gtgttacctg 196380
catagcatga agtactatcc agaactgaca tgcacatgtg gaagaacggc agtggggaat 196440
gacacattat tagatacatt ggttaccgtg cagaaatgct tctttatcct gataatatca 196500
tactcaataa taggtcatca ctcaaaggtg ccattagcca tgtgtctgcc tgtagcgtgt 196560
aaagccaatt ttgaacaaga aagtatcagt cagtattctg agctgtcctc atgcctggat 196620
tgggtgtaag tggtggagta gtaaaagcaa gtgtcttcag acccagattt gatgtcctca 196680
gacccagatt caagccttct ctgctggtct gtgaccttca gtaaactaag taatgtcttt 196740
gagcctccat ttccttatca gtcagtgttt acaatagtgc ctgatgcata ggcttgttgg 196800
aaggatgaat gagataatat aggtaaacca cttggcataa tgactgactc acagtaagtg 196860

-continued ctcagtaaat attaaccacc cttattgttg gagtggtggt aattatctcc aataaagatc 196920
ttacagaaga aaaagatgtt cttttaaaaa aagaggctgt tatttgacgt agatgacctg 196980
gaaggaagat agaattcctc ttagggatag aattggtatt tcctttagga aagaacacct 197040
tttgtacata ttcagtaaca aaaggtgagc cagccctgcc cccaccccca ccactggcaa 197100
agctgggatg gggaaagatt gccctgcata agaatacaat ataattttct tataagttct 197160
ttccaaagga ggggataaag ggtttgatag aaagtggttc ctgggagagt ttgcagaaga 197220
gtggaaaaga tcttgctaag atgacaggag gcacatgagc caccagaaat tccttggatt 197280
catagtaata gtgatgtttg ccattgaaat ggaaggtatt ttctgtcctg tgcttaactc 197340
atccCctttt cattgtttac aaaatcttta gtgaaaggct gtggctagat caccctagtg 197400
tgaatgaaag gagagaggga ttgtctggag tggagcgagg ggagaagtag tacagaacac 197460
catgactata ggaggcaaaa tgctaagagc atgaacaaga catttggagg aagaaggggc 197520
ccgcataatg ttagtcccag ggagattctt ggacattttg agggagcaaa ggtaggaatg 197580
aacgtgagat gggacaccaa tggcacgtga gaaaatatta aagaaaactt tactataatt 197640
tccttaaaac taagtacaaa acttgtgaga ctttttttat atttgggtaa ctttccaaat 197700
agttaatgaa tttttaaaaa atgaaatgag atgcttttaa acgagggaga ttaccaatct 197760
ttataccttg tacttctata aatgctgttg tgaatttgat attcacagta tctattcagt 197820
aaaaaattgg aacgatttat tgaaacaaaa actcaatgct gagagatcac attcttataa 197880
atctcttggt atgggaatgt attagatgcc atttatatat tatgtgcctt atttgatacg 197940
tgtgaacctt ctggcaatag aatattttcc caaccacttt gtgtcaggga ttataagtca 198000
ctgttgggtg acagtgaggg gattttacgt acaactgctt tattgttaat gcatatattg 198060
tacaattcat acatctctta catagctttt gcaagtcctt tgaaacatat ttacttttaa 198120
atagaatctg taaattctat gagatgtctt catttttgtg tgtgattagt tttgtttttc 198180
tgggtatgtt ttcatgttta tttattgcaa tgaccttaat aaaaatggta tataacagta 198240
gaattcttaa ggaatgacac attacaccaa cattatccaa aagaactaat taatcaaaca 198300
tgactaattt taatgtaatt actaaagaaa gatataccat tttattatga cactctagcc 198360
atacattttc aaaatatgct tattaaacag taaatgtaag ataatgattc aattagttac 198420
atttttagaa gtcattagga ttgatattcc tctgccataa gtgaattgaa taataatttc 198480
aaatacaatc agaattaatt taataaaaaa tatgcttttc aactaagaca gatgtaacga 198540
atggccagtc attattttct ggtttcaaag tagcagggga aattaattca gtgtctgtaa 198600
gtttatttat cacacttggc ctataagtgt gataaaaata catgaggcaa aatacatgat 198660
gtaatcccaa ttctcatagt tcattaactc ttttaccaaa aagatctgac atggtatttg 198720
gggcctttat gtaaactgaa tataagctgc gtgatatttg aaaggttttg atattttgaa 198780
tagacatttt catgatacac agacacagat aaaagatgta agtagacagc ttgaggtttc 198840
agagtccctc ctgcagtgtg tttagcagcg ggtacaagat aaatatccaa acaaaatcag 198900
attaagggat taacagaagt gactttgcta tgagttggtg agtggggtca atgggtggct 198960
tgaaagggat tttagagctc tgtttttatt tttcctactt tacatcagtg cattttgggc 199020
aaaataaaat gagtaatgtt tacttttagg cctcagtaat ataaaaaaag gcagattcta 199080
aggattgtgg aaggtcatgt ttttgaaagt gaaaggtaat tcagctccgg ttattaggag 199140
aaactctgtc tccatcttaa ctcatatttc agttgagcag taacatttgg ttttgtgtcc 199200

-continued tctctttttt tttttttact ttaaaaaagc ttggattttt ttccccttga aagaccccat 199260
caaagatagt tgaagaatga ggagagaagg atcatgttta agatccatgt aatcatacat 199320
taagagggaa cacatgggca gggtgtggtg gctcatgcct gtaatcccag caatttggga 199380
ggctgaggcg ggcaaatcac aaggtcagga gtttgagacc aacctggcca acatggtaaa 199440
accccgtctc tattaaaaat ccaaaaaatt agccgggcat agtggtgggt gcctgtaatc 199500
ccagctactc aggaggctga ggcaggagaa tcgcttaaac ccaggaggtg gaggttgcag 199560
tgagccgaga tcatgccact gcactccagc ctgggggaca gtgcgagacc ccatctcaca 199620
aaaaggaaaa aaaaaaagag ggaacacgtg aaatatatgt tttcagtgag gttcctttaa 199680
ttctagagtt tcagcttggt cagccctcta taaaattctg aggcagatac taaaataata 199740
agggctgggt tgggatgggg gcagaataaa gacagcttca aaaatcccct gggcctctgt 199800
cttatctgtg agaggtttct ttaaaaaaca aaagcattgt tccagatagg aattggttat 199860
ttaaattgat atctttatcc tgtaccatat gcacttaaag cttctgacag tcttctctct 199920
tttttaaata gaaattacac aaaaaagata tctatgtatc actttctaat acctaacagg 199980
aaggtcttat aaaatattaa aatagcaata agcaaatatg tactacagga ttaaacacta 200040
gcattgaaaa caaaacaaaa tccaaaacca agaatcaaca acattttcct tttgttgttg 200100 ccccccctacc agatctggac tttatggtct ttgcaaggga ggggcataaa ctttcacaat 200160
tcttctgttt taaaataaat gatgccattg cataaatcag atttatcttt tgaaaatatt 200220
ggtggaaagc catgtgattt gaatggaaag attctttctt ctgaggagag ccaaacaggt 200280
tctgctctaa taaattagca caatctttta agattaaaaa tagcaaaaca ttttaaatag 200340
tctgattata gcttcaacaa gtcaaacata catttctatc tagcctatag ttttaaagag 200400
tctatgtggg tttaacttat tattcctcat tctgatataa aaaaagaaga aaagaaccaa 200460
gtcattttga acattaagaa attcataaag actgtataaa gtaaaaaaaa aaaaaaaaca 200520
aaaacaagaa acaaaaaatc ttcacagatt gttagccatc tctttcaaca atttctcata 200580
aattctttct ttatcagtag ataacccccca tctcataagg aaatactttc caacatttcc 200640
caaatgagat cagtgattgc ttttcatgag agctactgct ctttgagatg tctgggtgaa 200700
gggagaatgt cttctataaa ccagtaaatg ccaaagaata cccaaggggg atttggcaga 200760
agctattttt tgcaggtaaa tctatgtatt ttttctcttt gttcttattt tctccacttg 200820
ctgaatatct gttttagagc agagtgcaca aaaatcaata aggaacttac ttatctttta 200880
aattcttcta tttgcctata agatcttttt tcccgcgttt attctccatg ctcttgatca 200940
agttcagaag attggataat atattgctaa ttttgctaag tttgagagcc aacaaaacaa 201000
tggagccttc taactttaaa aaatttccaa ctcctgcccc tgcacccccca aattcacaat 201060 ttggtgaaca gtacactact tgtgagtgat aaaaagttga aaggtggtgg tggctagata 201120
gacctaatgc tattttatta agccatctat ctatagaatt gttgttttta tactttaaaa 201180
aaatatgtct atgctttctt ttttttcttt ttttcttttt tttttagtca agtactttct 201240
taaagaaaca atagcaccac attggcatag ctggccaaac aataaatggg aaagcaaaat 201300
gtgctacatc ttttattcta agccttctcc caagtgcata aaatagtaac agaaaccctg 201360
gagccacaga gcatgagatg gtttcatcta cacaaacatt gacgttccaa ggagaggaag 201420
gattctcaag ggtggacagg ctttttgttt gtttgtttgt tttttaataa aattttcaag 201480
gaagtgattt cttttcagta ttccattgga tccttagggt gaatgtgtgt gtgtgtgtgt 201540
gtgtgtgtgt gtgtgtgtgt gtctgtgtat gtagggtggg tgttaagaga ttttcatatc 201600
cctagaagag tggattctga tggagagctg cattaacttt ttcaggggaa ctgcctcatc 201660
ttaaaaagtt caaataatac tttaatatta tttggggaag agagaacaga aatttgacct 201720
aagtatccag tatggtcaat taaattggaa ataagcctat gagttgaaag ctcattctta 201780
ccaatgttta ctgttctttt acaaatatct tgaaattgcc tcattcaaga attataaagc 201840
aatctaattc tgaagcaaag cttgtaaagt tttgggttgt gacattttgg ttgctccttt 201900
ctatgaaatc tgagtcattc tgctgtagta tatagtaatc aactgacttc cagggtttgc 201960
atcaatttgt tttctagttt taattcatta aaaaataaaa tagtgaattg gtataatgag 202020
ttattttcaa tttatttata atccagttgg agaggattat gtgttggaaa aagttaagaa 202080
agataatatg gcagtgcatc tttcagcttt cctccttggg ggatttttga ctgtggatag 202140
aattaagtga aggaaataag tcatagacac tcttagaatt atcacatcta actatgacag 202200
aaaacacgtt aagtctgcag aagactgcct ataaagtttt gttgagaggg aataatttta 202260
aaaggtacac actggggaca agaaataaaa agaagtgcca tcttgggaag aggagtccag 202320
tatcttattc cacagaacct gtatgtctgg aaaacaggca gagggcaaaa atgatgtata 202380
gtttctttta catctgtcca tagtgattag aacattgcta agcatgcttg aggtgctcaa 202440
ttcaaataat gttggactga gagttaaaat acttgttgac tgaacaggat tgctggctcc 202500
actaaatggg gccttctttt tgcatatatt cagagatcca gggagtcttt tttttttttt 202560
tcctggcctc tgatccttga ggtgacccag tgggagaaaa actgaagatg ttatttttgt 202620
ttttcatata gactttccaa gaatgtaaaa tatagaattt gcatgaaata atcaagcctg 202680
ggtactttta accaaaaagt tctaaggtga ctagaaagat ctgaatgctg gataattcat 202740
tgttctaatg agaaaatctt gatctgcaga tagggatcat tttctaggct atgatggact 202800
agtacactaa ccagtggact ttcttgatac caattttcag ttgaatggat aaaacacatt 202860
cacagagagc taggggctac ccttctgagc aggcatggga aatttcttgt tgtgatggaa 202920
gtttttgcct ttcaactgga aactctagtc aagcatattt taacaaactt ttaaaaaaat 202980
gtatatacag ctaagaataa gagtaaagtt tgttaaagaa gataactttg tgacttttta 203040
ttagatatta ttttaatatt tcaaattttg gatcactttc cttatattgc ctagaaaaga 203100
aggaatcatt gtgtttttca aaatgaatag aatattattt atagtattaa acgaggtttt 203160
actagatatg tagtaactgc atagaagagt cagtgagtgc taacaaagag taattaattc 203220
ccctttcact ggtagaaatc tctttgtttt tctccttttt cttttccttt ctctcttttc 203280
acttatcttt gtattcataa aaccaaatgc agaattcaaa atcaaattga aaatcaaatg 203340
cttcccacat attttgaaaa gtgttttaag agattgagct gttagctttt aacaactagt 203400
tggccagtta tttggatagc ttcactgaca agaactgaga tgtcaggagc attcaattca 203460
ccaatctcta gctatgctat gaatgggtta tttatagaat tccttgcatc tcagcaactc 203520
aagcgccctg atgttgcacc cttacagcaa cccagggtaa aaaaaatctg aatctttatc 203580
tttttaaacc ttataccacc cctttgaggt aggtagatga catattgccc ccattttgca 203640
gatgaggaaa ctgaggcaca gagaggtgaa gtgacttgcc caaggtcaca cagtggtgag 203700
tccatgacac agctggcaga tgttcatttc ttccatgaga aaaagaaacc aggactgcta 203760
aaattcctag ccttctgctt tttccattcc acagtttcct ctctggactc gccagtccaa 203820
tttgcatcag tggacttttg tgtctgaagt tcctcttgga aggcataact ggggggactt 203880
tgccttcttt cccaaatgga tggtgttttc agtacccttc cccttgtgtc atctttggct 203940

```
ccaggcttcc cctattgttt tgctttcacg tattaccgtt ttggccagac tctttcatat    204000

aacaaactac aaaatagcac cattatacta aaaaacagag ttttacatac tgtttgatat    204060

atcctgtata attgatatgc taaatttaca tagtgctcta tatggaaaaa ataaaaagag    204120

gaaagttact aattaggttg cacattaact catcatttga aggaactctt ttgagttgaa    204180

gaaactttct atgtttaaaa catatgccta aaaatgattg gcctcaaagt tgcaactatt    204240

tgcattattc ttttttgtaa gcatgatgtg gaaaaataaa gctttgtgtc taaaataaaa    204300

tgcatccaac ttatatttgg tacaaatgcc acagatggaa tcttgtgggt tagaattggt    204360

gtgcttcttg acgacttgct gctgcttttg aggaggccaa attcggcaaa tataaaggtt    204420

atgaagggag gtggtgggta tagactaaca agattatcag acactgtaaa acaaacagcc    204480

cgagttgtgt agaaagaagt gcaaataagg aaacaattca taaaccactt agacaaggtt    204540

gctgaatgaa tggctccagc agccaagatt cagagaggaa tttagtgcaa ctggatctat    204600

acaacaccca tgcatttgtg gctcttgaga ggcagggact aagatatata tatatatata    204660

tttttttttt cttttctata gaacattatt gataaaagat caacagcaat ctaccaactc    204720

caggaccatt tttgcaaggt gcaaatcact cctaaagaca atgttggaat gtttacttgt    204780

gtatttcatt gggggaaacg cccatctttt aaatgttatc aaacttattt tttggtaggt    204840

gttccaaagt ttaacaggta actcgtgcag agcaaaggat cctgcggtgg catgtcactc    204900

ttcactcctc aggagggtct tcctacatcc tgtagttctt gtttcctgca ctccctctac    204960

ttgcgttctt caaatgtact tcctataaat aaaggagaaa aagtgacatt aa             205012

<210> SEQ ID NO 11
<211> LENGTH: 70
<212> TYPE: DNA
<213> ORGANISM: Homo sapiens

<400> SEQUENCE: 11

ggcacccacc cgtagaaccg accttgcggg gccttcgccg cacacaagct cgtgtctgtg        60

ggtccgtgtc                                                               70

<210> SEQ ID NO 12
<211> LENGTH: 106
<212> TYPE: DNA
<213> ORGANISM: Homo sapiens

<400> SEQUENCE: 12

gcgcagcgcc ctgtctccca gcctgaggtg cagtgctgca tctctggtca gttgggagtc        60

tgagatgaag cactgtagct caggaagaga gaagttgttc tgcagc                      106

<210> SEQ ID NO 13
<211> LENGTH: 69
<212> TYPE: DNA
<213> ORGANISM: Homo sapiens

<400> SEQUENCE: 13

cagagtgtag cttaacacaa agcacccaac ttacacttag gagatttcaa cttaacttga        60

ccgctctga                                                                69

<210> SEQ ID NO 14
<211> LENGTH: 112
<212> TYPE: DNA
<213> ORGANISM: Homo sapiens

<400> SEQUENCE: 14
```

ggggcaaaga tgactaaaac acttttcctg ccctcgagga gctcacagtc tagtatgtct 60
catcccctac tagactgaag ctccttgagg acagggatgg tcatactcac ct 112

<210> SEQ ID NO 15
<211> LENGTH: 113
<212> TYPE: DNA
<213> ORGANISM: Homo sapiens

<400> SEQUENCE: 15
gccaacggct ggacagcggg caacggaatc ccaaaagcag ctgttgtctc cagagcattc 60
cagctgcgct tggatttcgt cccctgctct cctgcctgag cagcgccctg gcc 113

<210> SEQ ID NO 16
<211> LENGTH: 150
<212> TYPE: DNA
<213> ORGANISM: Homo sapiens

<400> SEQUENCE: 16
aactcttagc ggtggatcac tccactcctg cattgatgaa gaatgcagcc agctgtgaga 60
attaatgtga gttgcaggac acactgatca tcatttcaaa tgcacttgtg actccgtgtt 120
cctcccaggg ctacacctgt ctgagtcatc 150

<210> SEQ ID NO 17
<211> LENGTH: 59
<212> TYPE: DNA
<213> ORGANISM: Homo sapiens

<400> SEQUENCE: 17
gagaaagctc acaagaactg ctaactcatg cccccatgtc taacaacatg gctttctca 59

<210> SEQ ID NO 18
<211> LENGTH: 110
<212> TYPE: DNA
<213> ORGANISM: Homo sapiens

<400> SEQUENCE: 18
gaactttggc cacctggcac tgagaactga attccatagg ctgtgagctc tagcaatgcc 60
ctgtggactc agttctggtg cccggcagtg ctacaacatc aatgccaagg 110

<210> SEQ ID NO 19
<211> LENGTH: 110
<212> TYPE: DNA
<213> ORGANISM: Homo sapiens

<400> SEQUENCE: 19
tgaacatcca ggtctggggc atgaacctgg catacaatgt agatttctgt gttcgttagg 60
caacagctac attgtctgct gggtttcagg ctacctggaa acatgttctc 110

<210> SEQ ID NO 20
<211> LENGTH: 66
<212> TYPE: DNA
<213> ORGANISM: Homo sapiens

<400> SEQUENCE: 20
ggtaaaatgg ctgagtgaag cattggactg taaatctaaa gacaggggtt aggcctcttt 60
ttacca 66

<210> SEQ ID NO 21

<211> LENGTH: 1559
<212> TYPE: DNA
<213> ORGANISM: Homo sapiens
<220> FEATURE:
<221> NAME/KEY: misc_feature
<222> LOCATION: (1437)..(1437)
<223> OTHER INFORMATION: n is a, c, g, or t

<400> SEQUENCE: 21
gctaaaccta gccccaaacc cactccacct tactaccaga caaccttagc caaaccattt 60
acccaaataa agtataggcg atagaaattg aaacctggcg caatagatat agtaccgcaa 120
gggaaagatg aaaaattata accaagcata atatagcaag gactaacccc tataccttct 180
gcataatgaa ttaactagaa ataactttgc aaggagagcc aaagctaaga cccccgaaac 240
cagacgagct acctaagaac agctaaaaga gcacacccgt ctatgtagca aaatagtggg 300
aagatttata ggtagaggcg acaaacctac cgagcctggt gatagctggt tgtccaagat 360
agaatcttag ttcaacttta aatttgccca cagaaccctc taaatcccct tgtaaattta 420
actgttagtc caaagaggaa cagctctttg gacactagga aaaaaccttg tagagagagt 480
aaaaaattta acacccatag taggcctaaa agcagccacc aattaagaaa gcgttcaagc 540
tcaacaccca ctacctaaaa aatcccaaac atataactga actcctcaca cccaattgga 600
ccaatctatc accctataga agaactaatg ttagtataag taacatgaaa acattctcct 660
ccgcataagc ctgcgtcaga ttaaaacact gaactgacaa ttaacagccc aatatctaca 720
atcaaccaac aagtcattat taccctcact gtcaacccaa cacaggcatg ctcataagga 780
aaggttaaaa aaagtaaaag gaactcggca aatcttaccc cgcctgttta ccaaaaacat 840
cacctctagc atcaccagta ttagaggcac cgcctgccca gtgacacatg tttaacggcc 900
gcggtaccct aaccgtgcaa aggtagcata atcacttgtt ccttaaatag ggacctgtat 960
gaatggctcc acgagggttc agctgtctct tacttttaac cagtgaaatt gacctgcccg 1020
tgaagaggcg ggcataacac agcaagacga gaagacccta tggagcttta atttattaat 1080
gcaaacagta cctaacaaac ccacaggtcc taaactacca aacctgcatt aaaaatttcg 1140
gttggggcga cctcggagca gaacccaacc tccgagcagt acatgctaag acttcaccag 1200
tcaaagcgaa ctactatact caattgatcc aataacttga ccaacggaac aagttaccct 1260
agggataaca gcgcaatcct attctagagt ccatatcaac aatagggttt acgacctcga 1320
tgttggatca ggacatcccg atggtgcagc cgctattaaa ggttcgtttg ttcaacgatt 1380
aaagtcctac gtgatctgag ttcagaccgg agtaatccag gtcggtttct atctacnttc 1440
aaattcctcc ctgtacgaaa ggacaagaga aataaggcct acttcacaaa gcgccttccc 1500
ccgtaaatga tatcatctca acttagtatt atacccacac ccacccaaga acagggttt 1559

<210> SEQ ID NO 22
<211> LENGTH: 111
<212> TYPE: DNA
<213> ORGANISM: Homo sapiens

<400> SEQUENCE: 22
ccttttgcct gattccaggc tgaggtagta gtttgtacag tttgagggtc tatgatacca 60
cccggtacag gagataactg tacaggccac tgccttgcca ggaacagcgc g 111

<210> SEQ ID NO 23
<211> LENGTH: 2082
<212> TYPE: DNA
<213> ORGANISM: Homo sapiens

<400> SEQUENCE: 23
atgggttggg cattaggaac ggcctggccc cacaaatcac acaactgggg tgtagaacaa 60
aatggttcca cagatgacac caggctggtc cagggccgat gcaggccaga accccgctgg 120
gaggactccc cagaacaggc actgagctga ggaaaggcag gacacgtggt ctgctaccga 180
ccccaccaga tcttgctggg actctgggca gctccggagt aagagcagca tgctctgcaa 240
cgaagagcta ggtccaagga ccgcaggcgg aggcaggaag tgtcaagatc ccaggttacg 300
gaatggcacc aagtcggtaa ccaaaggaag caacaacccg ggtgttcaag gcagtcgtgc 360
aaggcggcgc gggggcgagg ccgaggccac tccctcccac ttccttgacg ctatttcctg 420
ggaggagccg gagctcgcgg cccggagcca agagattccc agcccagtgc tccaaaatac 480
tcggcctggg ggaggctggt ccgtgagcgt gcgcccggac cgttccgcca tgcatagtgg 540
acccagcact acagcaagcc tggcacgacc tctaaggcgg ttcgcggcaa cgtccgcacg 600
tcggctcgtt ggtctagggg tatgattctc gcttcgggtg cgagaggtcc cgggttcaaa 660
tcccggacga gccctccttt accttttact gagacaagag tgtcttcaag gaataggtta 720
cctgaccagc gctgcaggag gcttgactgt aagtcatcaa tgtacagtaa gctcttttgt 780
ggcaccgcgg tagcagaaag catctcaatc cccagacccg cctggcatgt caggaagaga 840
cgaggcacgc ccagacttgg gcaggtccct ccctttctgc ttcctgactt ccttcctggt 900
gtctcaactc ggccaccaca gcctggtttc gctttgattg acacgcgtca atctatagtt 960
gtggatgaca gtgttcggga gagcccagga actgtcaaaa cttggttctc tgcagtcctg 1020
aaggcactct gtctctttcg gtcactccat ctgacgattg gtgcctgaaa tacacctacg 1080
gtttctggtc agcgtttatc agtggttgga agaacagaac ccctaggaac cctgctgtca 1140
gcacgcagag tgtaaagtct cagatcaagg attcggagaa aggtctctac aggtccctcc 1200
tcgttagtat agtggttggt tgggatgagt cgggttggac ccgtgcggat ccaggaaaac 1260
agcgatcgag gtaaaagtaa tggctgccgt cgtctgccca gcgcgcaatt gtgagtgacc 1320
ttcaccgcta gcgcgcgcca cccaccccac atgaacctgt agggttatgc ccagtctaca 1380
gacgaggaaa ccaagatcca gggaagctga gtcaccggca gagctgggat tacgtctaag 1440
atttgtccag ggggcgagaa ctgcagcgac accatgattt atcatctcca gaaaacaaaa 1500
aaaaaggcct agacacataa aaatggcttc tctgtagagt gagctcaacg agctcaatgt 1560
gattccagtt aaggaattgg gccttaagcc aaatgcgcct aaacgcaact tgcctctcta 1620
ttatttatcc agaggatgaa tttaattcct acgtacatgc gcccacatct cgtcagctgg 1680
tgcctcagag aaatgcgctg acaaatctta aaggtggggc ttcatgacaa aagtccgccc 1740
gttattgctg ctcaacagac ccatcaagtc acgctgttgg acaggcctcg tggcgcaacg 1800
gtagcgcgtc tgactccaga tcagaaggtt gcgtgttcaa atcacgtcgg ggtcaaacaa 1860
aacattgttt tccctaatca aatagaccta cggtgacatt tttcaggata ggaaaaaaaa 1920
aaagcctcct cagtagaagg ataggagggg aatgagacaa atatgaacgt tattcagaag 1980
ttgggtgcag actttcaaca ttatgtgata tatccctgtg gcaaaactgc gcatgtatcc 2040
ctaaggtcta taaaagtaaa aataaattta aaaataaaaa aa 2082

<210> SEQ ID NO 24
<211> LENGTH: 112
<212> TYPE: DNA
<213> ORGANISM: Homo sapiens

<400> SEQUENCE: 24
tctccatcct ccctggggca tcctgtactg agctgccccg aggcccttca tgctgcccag 60
ctcggggcag ctcagtacag gatacctcgg ggtgggagtc agcaggaggt ga 112

<210> SEQ ID NO 25
<211> LENGTH: 2265
<212> TYPE: DNA
<213> ORGANISM: Homo sapiens

<400> SEQUENCE: 25
tgggttaggc attttctgtg cattacctcg ttcatcctta ctacaacctt attaaataga 60
tgtcatcact tctgtatttg cattttacag gcgaggacac aggcttaact cctcaaggcc 120
acggagctga cctttgttag tagcttgagc aagtggggtc tgaagcacac gtgcctgcac 180
ctggcctcag aagtgggact gacacgaggt ttcggttacc atggacctct gtgacctcca 240
tgaccaatct aggttctgga aggggtggtt gggaagccag aatagtcaca gcaagtggaa 300
cagggctagg tggagaccag cgagcctacg acaagaggct ttaggtcata gagggaggtt 360
ttagtagatg agttttatca gtgggcttcg cccacctctt cctaacatct gaccagctgg 420
gctattagtt ttagaaggct gagctgaggc ctgggtgggc caagacatac ttccacagat 480
tgtcttcatc ccactagcca aggtggttga ggacatcaat gaccttcaaa gggaattaac 540
aagtcaaagg aaatggtgtc ctaggtgtca caaatggatg gcttaatcct gataccaggg 600
acaggacata tttgctacat acaaaggatt atatgtaaca aaaatattgg atgtggagtg 660
tgatttaaca aaccccatgg actcatcact tagcccaaga aatggagcat caggagtaac 720
ttgcttttta cctgtgttct tttccccatc cactcctttg cctcctccca tgaggaagca 780
atattttatt tagtttggct tggattggat ttttatatac tttgtcatgt atgtattata 840
cctttaaaca ataaatattg tttagatttg cctggttttg agctctgtaa aaatggtatc 900
atatgtagtt ttctggaact tgctttttat attattattg ttatttttag agacagggtc 960
ttgctgtatc acccaggctg gaacttagtg acaggatcat ggctcactgc agccttgacc 1020
tcccaggctc aagtgatcct ctcgtttcag cctcccgagt agctgggact acatgcatgt 1080
gccacaacac tccactaatt ttttaaattt ttagtagaga caaggtcttg ctatgttgcc 1140
caggcttgga acttgctttt aaacaactcg tcattatgtt tctaacattc acccacgttc 1200
ccgtgtggga ctttgttctt ccattttcac tgttgtatga catcctactg tgctattgta 1260
cagtaggatc tgtacaattg atctattctc tgtcaattat gtgtggattt cttccccagt 1320
ttttggatac tctggctact gccgctatga atattcttat gcatgtcctc ttgtacatgt 1380
cttgtacata tgtgtaagag tttctcatag gtatacaccc aggagtacaa ttgctggctg 1440
tagggtttgt tcagctttgg gagtaaatgc taaattgttt tccaaaatgg ttgtagcagt 1500
tatacattac tggtgagagg gtaaagaatt tttgttgaaa tacatgccct tcaactgttc 1560
acacttaaaa atttttgcca ctctgttggg tatgaaatga tatctcatta gggtctgaat 1620
ttgtattttc ctggttacta agtaggttga gcttcttttc atatgtgcat tgactgtgct 1680
gcttttgtaa aatgaccatt ttggtggggg ctgtattgtt ctatagggtt aactttttct 1740
tcttgatatg taagctttct tttatatttt atatattata tactaaccct ttgttagatt 1800
atttgtcttc attccttatg gttttttttt ttttttttt ttgagacaga gtttcgctct 1860
tgttgcccag gctggagtgc aatggtgcgg tctcggctca ctgcaacctg cgcctcccgg 1920
gttcatgtga ttctcctacc tcagcctccc gagtagttgg gattacaggc atgcgccacc 1980

-continued

```
acacccagca attttgtatt tttagtagac acagggtttc tccatgttgg tcaggctggt   2040

ctcaaactcc cgacctcagg tgatccgccc acctcggcct cccaaagtgc tgggattaca   2100

ggcatgagcc accgcgcctg gcctctcaat tttttaaggt cgttaatatt tttcaataaa   2160

gttaaaaagt tttctgtatt aggatttggt acatcttttg ttatatttag tctaaaataa   2220

tctgtagtat ttattgttat tataaatggt gtctcttaaa agtta                   2265
```